(12) United States Patent
Foreman et al.

(10) Patent No.: US 10,279,180 B2
(45) Date of Patent: May 7, 2019

(54) CARDIAC NEUROMODULATION AND METHODS OF USING SAME

(71) Applicant: The Board of Regents of the University of Oklahoma, Norman, OK (US)

(72) Inventors: Robert D. Foreman, Edmond, OK (US); Jeffrey L. Ardell, Johnson City, TN (US); John A. Armour, Halifax (CA); Michael J. L. DeJongste, CK Haren (NL); Bengt G. S. Linderoth, Solna (SE)

(73) Assignee: The Board of Regents of the University of Oklahoma, Norman, OK (US)

(*) Notice: Subject to any disclaimer, the term of this patent is extended or adjusted under 35 U.S.C. 154(b) by 0 days.

(21) Appl. No.: 15/489,324

(22) Filed: Apr. 17, 2017

(65) Prior Publication Data
US 2017/0216581 A1    Aug. 3, 2017

Related U.S. Application Data

(60) Division of application No. 14/792,401, filed on Jul. 6, 2015, now abandoned, which is a continuation of application No. 12/952,653, filed on Nov. 23, 2010, now Pat. No. 9,072,901, which is a division of application No. 11/287,094, filed on Nov. 23, 2005, now Pat. No. 7,860,563, which is a continuation of application No. 11/266,558, filed on Nov. 3, 2005, (Continued)

(51) Int. Cl.
*A61N 1/36* (2006.01)
*A61N 1/362* (2006.01)
*A61N 1/05* (2006.01)

(52) U.S. Cl.
CPC ........ *A61N 1/36114* (2013.01); *A61N 1/0551* (2013.01); *A61N 1/362* (2013.01); *A61N 1/36117* (2013.01)

(58) Field of Classification Search
None
See application file for complete search history.

(56) References Cited

U.S. PATENT DOCUMENTS

| 3,421,511 A | 1/1969 | Schwartz et al. |
| 3,522,811 A | 8/1970 | Schwartz et al. |

(Continued)

FOREIGN PATENT DOCUMENTS

EP      0688577      12/1995

OTHER PUBLICATIONS

Armour, et al.; "Long-Term Modulation of the Intrinsic Cardiac Nervous System by Spinal Cord Neurons in Normal and Ischemic Hearts," Autonomic Neuroscience: Basic and Clinical (2002), vol. 95, pp. 71-79.

(Continued)

*Primary Examiner* — Kennedy Schaetzle
(74) *Attorney, Agent, or Firm* — Dunlap Codding, P.C.

(57) ABSTRACT

A method of treating heart failure in a patient is disclosed that includes implanting a stimulation device into the identified patient to electrically stimulate the spinal cord, and activating the device to deliver electrical stimulation to the spinal cord.

1 Claim, 47 Drawing Sheets
(4 of 47 Drawing Sheet(s) Filed in Color)

Related U.S. Application Data now Pat. No. 7,769,441, which is a continuation of application No. 10/128,787, filed on Apr. 22, 2002, now abandoned.

(60) Provisional application No. 60/295,028, filed on May 31, 2001, provisional application No. 60/291,681, filed on May 17, 2001, provisional application No. 60/285,176, filed on Apr. 20, 2001.

(56) References Cited

U.S. PATENT DOCUMENTS

| | | |
|---|---|---|
| 3,645,267 A | 2/1972 | Hagfors |
| 3,650,277 A | 3/1972 | Sjostrand et al. |
| 3,796,221 A | 3/1974 | Hagfors |
| 4,044,774 A | 8/1977 | Corbin et al. |
| 4,146,029 A | 3/1979 | Ellinwood, Jr. |
| 4,340,063 A | 7/1982 | Maurer |
| 4,428,378 A | 1/1984 | Anderson et al. |
| 4,458,696 A | 7/1984 | Larimore |
| 4,549,556 A | 10/1985 | Tarjan et al. |
| 4,694,835 A | 9/1987 | Strand |
| 4,903,701 A | 2/1990 | Moore et al. |
| 5,031,618 A | 7/1991 | Mullett |
| 5,058,584 A | 10/1991 | Bourgeois |
| 5,135,004 A | 8/1992 | Adams et al. |
| 5,149,713 A | 9/1992 | Bousquet |
| 5,199,428 A | 4/1993 | Obel et al. |
| 5,220,917 A | 6/1993 | Cammilli et al. |
| 5,255,691 A | 10/1993 | Otten |
| 5,292,336 A | 3/1994 | Spence, Jr. et al. |
| 5,292,338 A | 3/1994 | Bardy |
| 5,330,505 A | 7/1994 | Cohen |
| 5,330,507 A | 7/1994 | Schwartz |
| 5,330,515 A | 7/1994 | Rutecki et al. |
| 5,331,996 A | 7/1994 | Ziehm |
| 5,342,409 A | 8/1994 | Mullett |
| 5,360,441 A | 11/1994 | Oten |
| 5,464,434 A | 11/1995 | Alt |
| 5,496,363 A | 3/1996 | Burgio et al. |
| 5,564,434 A | 10/1996 | Halperin et al. |
| 5,607,418 A | 3/1997 | Arzbaecher |
| 5,700,282 A | 12/1997 | Zabara |
| 5,792,187 A | 8/1998 | Adams |
| 5,817,131 A | 10/1998 | Eisberry et al. |
| 5,824,021 A | 10/1998 | Rise |
| 6,006,134 A | 12/1999 | Hill et al. |
| 6,058,331 A | 5/2000 | King |
| 6,073,048 A | 6/2000 | Kieval et al. |
| 6,124,470 A | 10/2000 | Hartlaub |
| 7,218,964 B2 | 5/2007 | Hill et al. |
| 9,072,901 B2 | 7/2015 | Foreman et al. |
| 2002/0107553 A1* | 8/2002 | Hill ............... A61N 1/36114 607/18 |
| 2002/0143369 A1* | 10/2002 | Hill ............... A61N 1/36114 607/9 |
| 2002/0165586 A1 | 11/2002 | Hill et al. |
| 2003/0004549 A1 | 1/2003 | Hill et al. |

OTHER PUBLICATIONS

Chandler, et al.; "Spinal Inhibitory Effects of Cardiopulmonary Afferent Inputs in Monkeys: Neuronal Processing in High Cervical Segments," J. Neurophysiol. (2002), vol. 87, pp. 1290-1302.
Cardinal et al.; "Spinal Cord Activation Differentially Modulates Ischemic Electrical Responses to Different Stressors in Canine Ventricles," Auton Neurosci (2004) vol. 111, No. 1, pp. 37-47.
Ardell, J.L.; "Intrathoracic Neuronal Regulation of Cardiac Function," Basic and Clinical Neurocardiology, Oxford University Press (2004), pp. 117-153.
International Application No. PCT/US2002/012697 filed Apr. 19, 2002; International Preliminary Examination Report—dated Oct. 4, 2010.
Bilgutay, et al.; "Vagal Tuning a New Concept in the Treatment of Supraventricular Arrhythmias, Angina Pectoris, and Heart Failure," Journal of Thoracic & Cardiovascular Surgery (1968), vol. No. 1, 56, pp. 71-82.
Braunwald, M.D., et al.; "Carotid Sinus Nerve Stimulation in the Treatment of Angina Pectoris and Supraventricular Tachycardia," California Medicine (1970), vol. 112, No. 3, pp. 41-50.
Armour, J.A.; "Instant to Instant Reflex Cardiac Regulation," Cardiology (1976), vol. 61, pp. 309-328.
Schwartz, et al.; "Effect of Dorsal Root Section on the Arrhythmias Associated with Coronary Occlusion," Am. J. Physiol. (1976), vol. 231, No. 3, pp. 923-928.
Blair, et al.; "Responses of Thoracic Spinothalamic Neurons to Intracardiac Injection of Bradykinin in the Monkey," Circ. Res. (1982), vol. 51, No. 1, pp. 83-94.
Ammons, et al.; "Effects of Intracardiac Bradykinin on T2-T5 Medial Spinothalamic Cells," Am. J. Physoiol. (1985), vol. 249, 2 Pt 2, pp. R147-R152.
Blair, et al.; "Activation of Feline Spinal Neurones by Potentiated Ventricular Contractions and Other Mechanical Cardiac Stimuli," J. Physiol. (1988), vol. 404, pp. 649-667.
Schwartz, et al.; "Autonomic Mechanisms and Sudden Death New Insights from Analysis of Baroreceptor Reflexes in Conscious Dogs with and without a Myocardial Infarction," Circulation (1988), vol. 78, No. 4, pp. 969-979.
Hobbs, et al.; "Cardiac and Abdominal Vagal Afferent Inhibition of Primate T9-S1 Spinothalamic Cells," Am. J. Physiol. (1989), vol. 257 (4 Pt 2), pp. R889-R895.
Butler, et al.; "Cardiac Responses to Electrical Stimulation of Discrete Loci in Canine Atrial and Ventricular Ganglionated Plexi.," American Physiological Society (1990), vol. 259, pp. H1365-H1373.
Hull, et al.; "Heart Rate Variability Before and After Myocardial Infarction in Conscious Dogs at High and Low Risk for Sudden Death," JACC (1990), vol. 16, No. 4, pp. 978-985.
Armour, J.A.; "Intrinsic Cardiac Neurons," Journal of Cardiovascular Electrophysiology (1991), vol. 2, No. 4, pp. 331-341.
Chandler, et al.; "Effects of Vagal Afferent Stimulation on Cervical Spinothalamic Tract Neurons in Monkeys," Pain (1991), vol. 44, No. 1, pp. 81-87.
Linderoth, et al; "Effects of Sympathectomy on Skin and Muscle Microcirculation During Dorsal Column Stimulation: Animal Studies," Neurosurgery (1991), vol. 29, No. 6, pp. 874-879.
Vanoli et al.; "Vagal Stimulation and Prevention of Sudden Death in Conscious Dogs with a Healed Myocardial Infarction," Circ. Res. (1991), vol. 68, No. 5, pp. 1471-1481.
Cardinal, et al.; "Distinct Activation Patterns of Idioventricular Rhythms and Sympathetically-Induced Ventricular Tachycardias in Dogs With Atrioventricular Block," PACE (1992), vol. 15, pp. 1300-1306.
Fu, et al.; "Vagal Afferent Fibers Excite Upper Cervical Neurons and Inhibit Activity of Lumbar Spinal Cord Neurons in the Rat," Pain (1992), vol. 51, No. 1, pp. 91-100.
Hobbs, et al.; "Evidence that C1 and C2 Propriospinal Neurons Mediate the Inhibitory Effects of Viscerosomatic Spinal Afferent Input on Primate Spinothalamic Tract Neurons," J. Neurophysiol. (1992), No. 67, No. 4, p. 852-860.
Chandler, et al.; "A Mechanism of Cardiac Pain Suppression by Spinal Cord Stimulation: Implications for Patients with Angina Pectoris," European Heart Journal (1993), vol. 14, No. 1, p. 96-105.
Hobbs, et al.; "Segmental Organization of Visceral and Somatic Input onto C3-T6 Spinothalamic Tract Cells of the Monkey," Journal of Neurophysiology (1992), vol. 68, No. 5, pp. 1575-1588.
Huang et al.; "Effects of Transient Coronary Artery Occlusion on Canine Intrinsic Cardiac Neuronal Activity," Integrative Physiological and Behavioral Science (1993), vol. 28, No. 1, pp. 5-21.
Adamson, et al.; "Unexpected Interaction Between β-Adrenergic Blockade and Heart Rate Variability Before and After Myocardial Infarction a Longitudinal Study in Dogs at High and Low Risk for Sudden Death," Circulation (1994), vol. 90, No. 2, pp. 976-982.
Ardell, et al.; "Structure and Function of Mammalian Intrinsic Cardiac Neurons," Neurocardiology, edited by Armour, J.A. and Ardell, J.L., New York: Oxford University Press, 1994, pp. 95-114.

(56) References Cited

OTHER PUBLICATIONS

Armour, J.A.; "Peripheral Autonomic Neurnal Interactions in Cardiac Regulation," Neurocardiology, edited by Armour, J.A. and Ardell, J.L., New York: Oxford University Press (1994), pp. 219-244.
Foreman, R.D.; "Spinal Cord Neuronal Regulation of the Cardiovascular System," Neurocardiology, edited by Armour, J.A. and Ardell, J.L., New York: Oxford University Press (1994), pp. 245-276.
Hull, et al.; "Exercise Training Confers Anticipatory Protection From Sudden Death During Acute Myocardial Ischemia," Circulation (1994), vol. 89, pp. 548-552.
Linderoth, et al.; "Sympathetic Mediation of Peripheral Vasodilation Induced by Spinal Cord Stimulation: Animal Studies of the Role of Cholinergic and Adrenergic Receptor Subtypes," Neurosurgery (1994), vol. 35, No. 4, pp. 711-719.
Yuan, et al.; "Gross and Microscopic Anatomy of the Canine Intrinsic Cardiac Nervous System," The Anatomical Record (1994), vol. 239, pp. 75-87.
Armour, J.A.: "Canine Intrinsic Cardiac Neurons Involved in Cardiac Regulation Possess a1,a2,b1 and b2 Adrenoreceptors," Can. J. Physiol. Pharmacol. (1996), vol. 13, pp. 277-284.
Cardinal, et al.; "Reduced Capacity of Cardiac Efferent Sympathetic Neurons to Release Noradrenaline and Modify Cardiac Function in Tachycardia-Induced Canine Heart Failure," Can. J. Physiol. Pharmacol. (1996), vol. 74, pp. 1070-1078.
Chandler, et al.; "Vagal, Sympathetic and Somatic Sensory Inputs to Upper Cervical (C1-C3) Spinothalamic Tract Neurons in Monkeys," J. Neurophysiol. (1996), vol. 76, No. 4, pp. 2555-2567.
Zhang, J., et al.; "Thoracic Visceral Inputs Use Upper Cervical Segments to Inhibit Lumbar Spinal Neurons in Rats," Brain Research (1996) vol. 709, pp. 337-342.
Armour, et al.; "Gross and Microscopic Anatomy of the Human Intrinsic Cardiac Nervous System," The Anatomical Record (1997), vol. 247, pp. 289-298.
Croom, et al.; "Cutaneous Vasodilation During Dorsal col. Stimulation is Mediated by Dorsal Roots and CGRP," American Physiological Society (1997), vol. 272, pp. H950-H957.
Hautvast, et al.; "Spinal Cord Stimulation in Chronic Intractable Angina Pectoris: A Randomized, Controlled Efficacy Study," Am. Heart J. (1998), vol. 136, No. 6, pp. 1114-1120.
Schwartz, et al.; "Autonomic Mechanisms and Sudden Death. New Insights From Analysis of Baroreceptor Reflexes in Conscious Dogs with and without Myocardial Infarction," Circulation (1998), vol. 78, pp. 969-979.
Barron, et al.; "Spinal Integration of Antidromic Mediated Cutaneous Vasodilation During Dorsal Spinal Cord Stimulation in the Rat," Neuroscience Letters (1999), vol. 260, No. 3, pp. 173-176.
Foreman, R.D.; "Mechanisms of Cardiac Pain," Annu. Rev. Physiol (1999), vol. 61, pp. 143-167.
Linderoth, et al.; "Physiology of Spinal Cord Stimulation: Review and Update," Neuromodulation (1999), vol. 2, No. 3, pp. 150-164.
Qin, et al.; "Chemical Activation of Cervical Cell Bodies: Effects on Responses to Colorectal Distension in Lumbosacral Spinal Cord of Rats," J. Neurophysiol. (1999), vol. 82, No. 6, pp. 3423-3433.
Chandler, et al.; "Intrapericardiac Injections of Algogenic Chemicals Excite Primate C1-C2 Spinothalamic Tract Neurons," Am. J. Physiol. Regul. Integr. Comp. Physiol. (2000), vol. 279, No. 2, pp. R560-R568.
Foreman, et al.; "Modulation of Intrinsic Cardiac Neurons by Spinal Cord Stimulation: Implications for Therapeutic Use in Angina Pectoris," Cardiov. Res. (2000), vol. 47, No. 367-375.
Hopkins, et al.; "Pathology of Intrinsic Cardiac Neurons From Ischemic Human Hearts," Anatomical Record (2000), vol. 259, pp. 424-436.
Kember, et al.; "A Periodic Stochastic Resonance in a Hysteretic Population of Cardiac Neurons," The American Physical Society (2000), vol. 61, No. 2, pp. 1816-1824.
Meyerson, et al,; "Spinal Cord Stimulation," Bonica's Management of Pain, edited by Loeser JD. Lippincott, (2000), pp. 1857-1876.
Ardell, J.L.; "Neurohumoral Control of Cardiac Function," Heart Physiology and Pathophysiology Academic Press (2001), pp. 45-59.
Farrell, et al.; "Angiotensin II Modulates Catecholamine Release into Interstitial Fluid of Canine Ventricle In Vivo," Am. J. Physiol. Heart Circ. Physiol. (2001) vol. 281, pp. H813-H822.
Kingma et al.; "Neuromodulation Therapy Does Not Influence Blood Flow Distribution or Left-Ventricular Dynamics During Acute Myocardial Ischemia," Autonomic Neuroscience: Basic & Clinical (2001), vol. 91, pp. 47-54.
Tanaka, et al.; "Low Intensity Spinal Cord Stimulation May Induce Cutaneous Vasodilation Via CGRP Release," Brain Research (2001), vol. 896, Nos. 1-2, pp. 183-187.
Qin, et al.; "Responses and Afferent Pathways of Superficial and Deeper c(1)-c(2) Spinal Cells to Intrapericardial Algogenic Chemicals in Rats," American Physiological Society (2001), vol. 85, No. 4, pp. 1522-1532.

\* cited by examiner

FIG. 8B
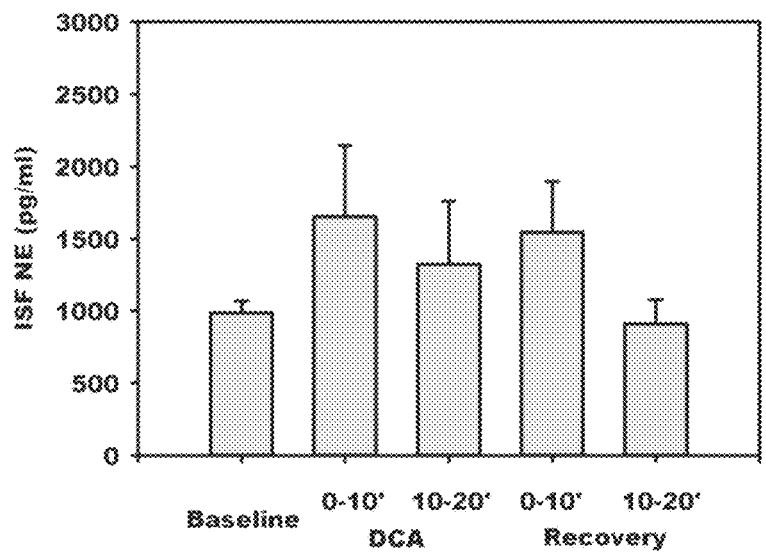
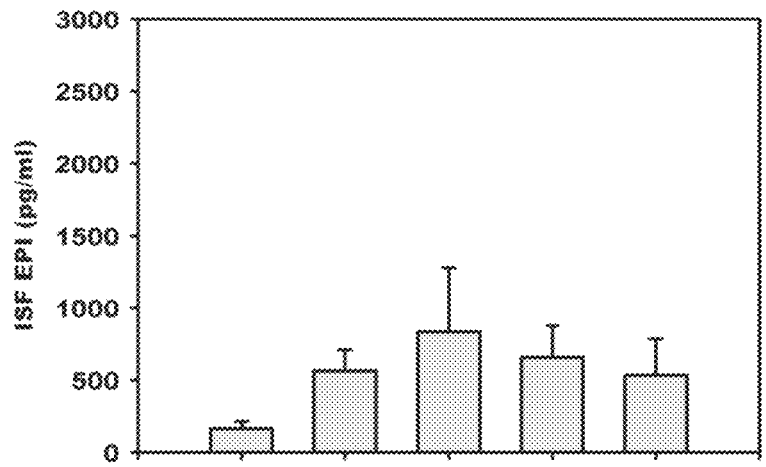

FIG. 11
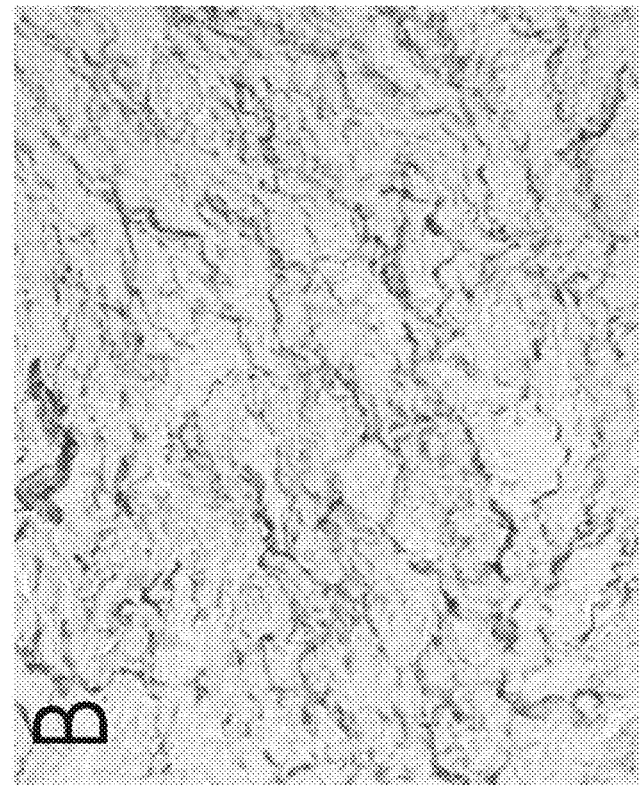
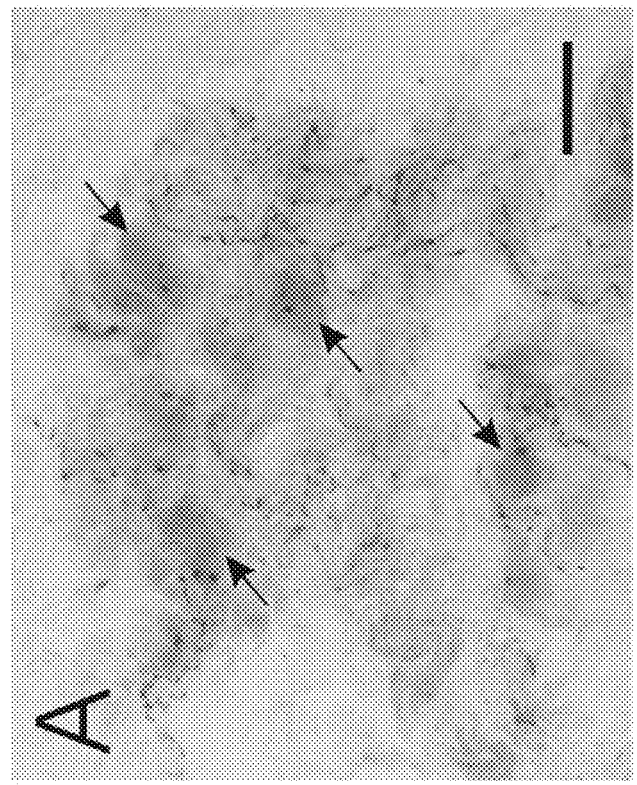

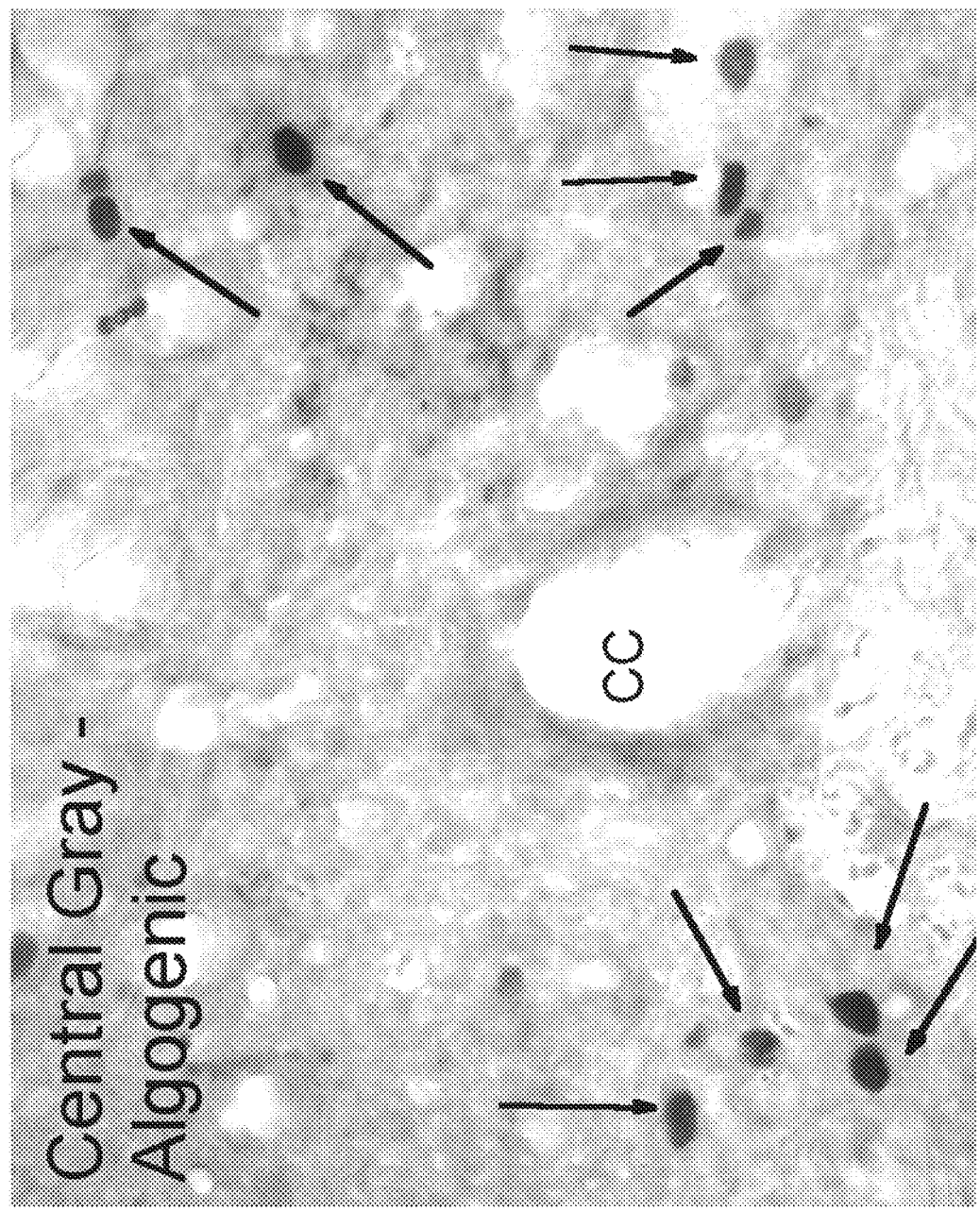
FIG. 17 CONTD.

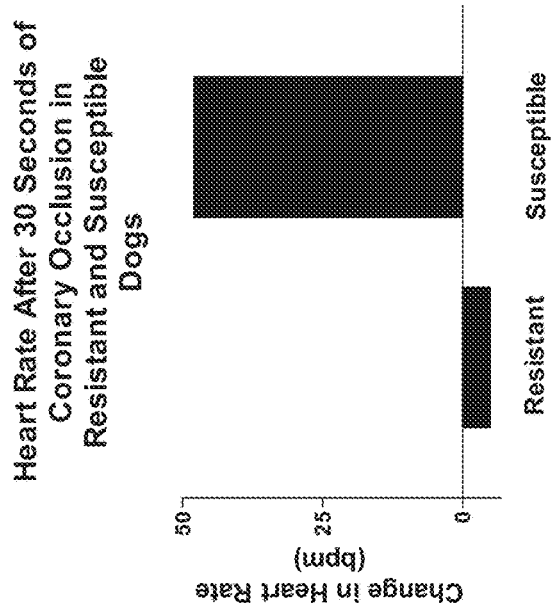
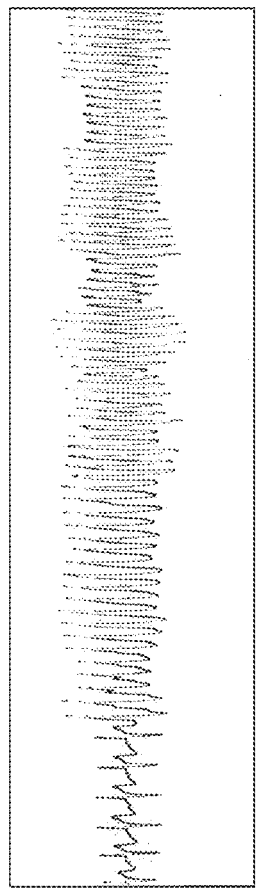
FIG. 25

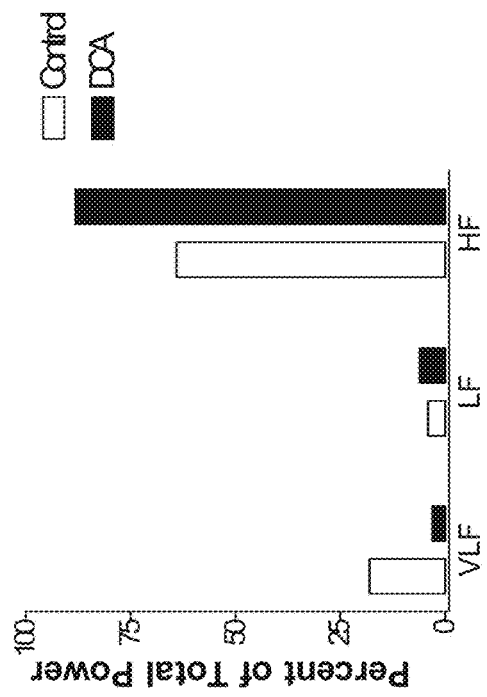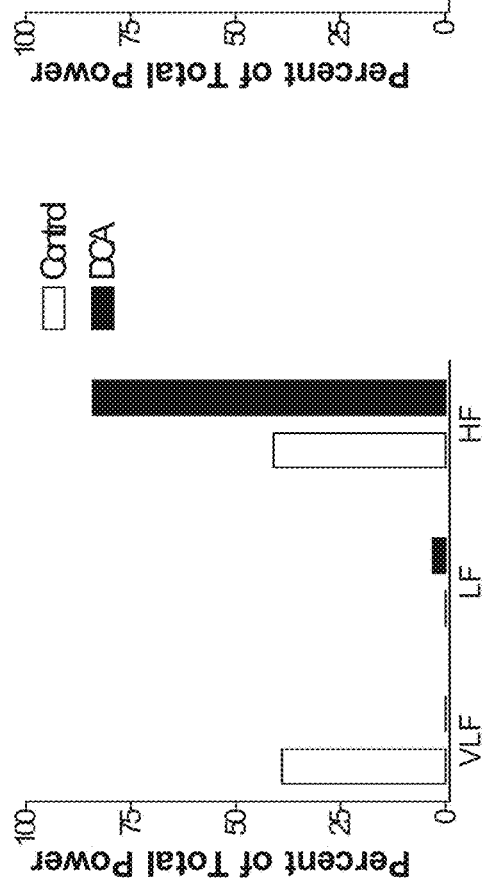
FIG. 28

CARDIAC NEUROMODULATION AND METHODS OF USING SAME

CROSS-REFERENCE TO RELATED APPLICATIONS/INCORPORATION BY REFERENCE STATEMENT

This application is a divisional of U.S. Ser. No. 14/792,401, filed Jul. 6, 2015, now abandoned; which is a continuation of U.S. Ser. No. 12/952,653, filed on Nov. 23, 2010, now U.S. Pat. No. 9,072,901, issued Jul. 7, 2015; which is a divisional of U.S. Ser. No. 11/287,094, filed on Nov. 23, 2005, now U.S. Pat. No. 7,860,563, issued on Dec. 28, 2010; which is a continuation of U.S. Ser. No. 11/266,558, filed on Nov. 3, 2005, now U.S. Pat. No. 7,769,441, issued on Aug. 3, 2010; which is a continuation of U.S. Ser. No. 10/128,787, filed on Apr. 22, 2002, now abandoned; which claims priority under 35 USC § 119(e) of U.S. Provisional Application Ser. No. 60/295,028, filed on May 31, 2001; U.S. Provisional Application Ser. No. 60/291,681, filed on May 17, 2001; and U.S. Provisional Application Ser. No. 60/285,176, filed on Apr. 20, 2001. The entire contents of each of the above-referenced patents and patent applications are hereby expressly incorporated herein by reference.

BACKGROUND

Recently, the emergence of novel views of the anatomic pathways and neural mechanisms involved in the regional control of the heart have led to the presently claimed and disclosed intrinsic cardiac nervous system modalities and treatments. In fact, it has been determined that a level of processing occurs that permits independent intrinsic cardiac as well as intrathoracic extracardiac and central spinal integration of afferent and efferent autonomic influences, and local neural coordination without necessarily involving the higher brain centers. This knowledge has led to the development of the present disclosure. Lathrop and Spooner [24] have postulated that a "hierarchy of control mechanisms among these different elements, and that they interact as a system of autonomous efferent feedback loops rather than simply as relay stations subservient to central command." Indeed, disruption of neuronal circuitry leads to numerous cardiac pathologies. Neuronal interactions that occur within this circuitry or hierarchy modulate different regions of both healthy and diseased hearts. Thus, the knowledge of this circuitry and methodologies of modulating this circuitry (as disclosed and claimed herein) have allowed for the development and treatment of cardiac pathologies using novel therapeutic approaches to ameliorate specific cardiac pathologies.

Regional control of cardiac function is dependent upon the coordination of activity generated by neurons within intrathoracic autonomic ganglia and the central nervous system. The hierarchy of nested feedback loops therein provides precise beat-to-beat control of regional cardiac function. Contrary to classical teaching, studies undertaken and disclosed in the present specification utilizing electrophysiological and neuropharmacological techniques applied from the level of whole organ to that of neurons recorded in vitro indicate that intrathoracic autonomic ganglia act in a manner greater than simple relay stations for autonomic efferent neuronal control of the heart. It has been determined that within this hierarchy of intrathoracic ganglia and nerve interconnections, complex processing takes place that involves spatial and temporal summation of sensory inputs, preganglionic inputs from central neurons and intrathoracic ganglionic reflexes activated by local cardiopulmonary sensory inputs. The activity of neurons within intrathoracic autonomic ganglia is likewise modulated by circulating hormones, chief among them being circulating catecholamines and angiotensin II.

The progressive development of cardiac disease is associated with maladaptation of these neurohumoral control mechanisms. Recent data indicate that conventional therapy of cardiac diseases such as myocardial ischemia and heart failure exert their beneficial effects not only on cardiomyocytes directly, but indirectly via the intrinsic cardiac nervous system. The present disclosure of the complex processing that occurs within the intrathoracic nervous system, as well as between peripheral and central neurons, will provide a basis for understanding the role that the cardiac nervous system plays in regulating not only the normal heart, but the diseased heart. Information derived from research and experimentation of this complex neuronal hierarchy provides for novel therapeutic approaches for the effective treatment of cardiac dysfunction including protection of cardiac myocytes and stabilization of myocardial electrical activity by targeting various populations of neurons regulating regional cardiac behavior.

Varying elements within the cardiac neuronal hierarchy exert more influence over regional cardiac function than has been traditionally understood. For example, it is now well recognized that the cardiac nervous system is fundamental to the management of heart failure. As such, this nervous system represents a novel and previously unrecognized target for the treatment of heart failure. Control of regional cardiac function is dependent upon intrinsic properties of the cardiac electrical and mechanical tissues as modulated by neural inputs arising from neurons in the intrathoracic autonomic ganglia, spinal cord and brainstem. Disruptions in neural inputs to the heart or alterations in the cardiac interstitial milieu can be associated with deleterious cardiac structural remodeling and, as a consequence, cardiac dysfunction. In the most extreme case, this becomes evident in congestive heart failure. Excessive activation of the intrathoracic cardiac efferent nervous system, as with myocardial ischemia, can evoke ventricular dysrhythmias involving changes within the cardiac nervous system in addition to alterations in cardiomyocyte ion channel function. Maladaptation of neurohumoral control mechanisms can likewise adversely remodel the cardiac extracellular matrix.

The conventional treatment for reducing the frequency and intensity of angina pectoris resulting from myocardial ischemia is anti-ischemic therapy. These therapies are usually based upon restoring the balance between myocardial oxygen supply and myocardial oxygen demand. Pharmacological agents and revascularization procedures (CABG and PTCA) are conventional treatments for such disease states. Yet there are a significant number of patients that do not experience adequate relief of their anginal symptoms with these treatments or are poor candidates for these therapies. Thus, alternative approaches utilizing direct electrical activation of neural elements within the spinal cord have been devised, with the resultant modulation of the intrathoracic neurohumoral milieu thereby eliciting anti-ischemic, antiarryhtymic, and anti-anginal effects.

A disturbance of the fine balance within the whole cardiac neuraxis can result in dramatic changes in cardiac efferent neuronal outflow. Experimental studies have been performed to demonstrate that pathological processes can change the integrative behavior of the cardiac neuraxis. These changes occur when cardiac sensory neurites are activated intensely and for long periods, as when cardiac tissue becomes damaged during regional ventricular ischemia. On the other hand, central processing of cardiac sensory output may become deranged leading to conflicting signals that interfere with the maintenance of cardiac function. This has led to the proposed scheme that the hierarchy of cardiac neurons interacts effectively if there is an appropriate balance therein.

Under normal, physiological conditions stimuli applied to the heart do not elicit marked changes in cardiac efferent neuronal activity because central neurons can suppress excessive cardiac sensory information processing. Information has been obtained to support the conclusion that, in the hierarchy of cardiac control, activation of spinal neuronal circuits modulates the intrathoracic cardiac nervous system. Experimental studies have shown that activation of the dorsal columns at the T1-T2 segments significantly reduces the activity generated by the intrinsic cardiac neurons in their basal conditions as well as when activated in the presence of focal ventricular ischemia induced by occluding the left coronary artery. Not only does dorsal column activation modulate the intrinsic cardiac nervous system, but it also modifies the activity of spinal neurons within the T3-T4 segments. In addition, experimental evidence indicates that the central nervous system maintains a tonic inhibitory influence over intrathoracic cardiopulmonary-cardiac reflexes. One of the present inventors has also shown that reflexes mediated through the middle cervical ganglion are increased after decentralization. Based on this evidence, it is postulated that disease processes change the balance between the central and peripheral neuronal processing of cardiac sensory information. Thus, use of electrical currents to activate spinal neuronal circuits can reverse or halt disease processes of the heart preconditioning the heart— i.e., applying electrical activation prior to disease—also is contemplated as a means to pro-actively treat a patient with high susceptibility to cardiac pathologies including arrhythmias.

Within the hierarchy for cardiac control, neurons of the upper cervical segments modulate information processing in the spinal neurons of the upper thoracic segments. In human studies, spinal cord stimulation of the C1-C2 spinal segments relieved the pain symptoms in patients with chronic refractory angina pectoris. Experimental studies in support of the present disclosure have shown that spinal cord activation of the upper cervical segments of the spinal cord suppressed the activity of spinal neurons in T3-T4 segments. Furthermore, chemical stimulation with glutamate of cells in the C1-C2 segments also reduced upper thoracic spinal neuronal activity. The upper cervical region is intriguing because it is positioned between supraspinal nuclei and spinal circuitry. Neurons in C1-C2 could serve as a filter, an integrator, or as a relay for afferent information, since these neurons receive inputs from vagal afferents from the heart.

Very little information has been published to address underlying mechanisms explaining how central and peripheral cardiac neurons process cardiac sensory information and interact in the maintenance of adequate cardiac output. The present disclosure shows that disease processes change the balance between the central and peripheral neuronal processing so involved. For instance, when the activity generated by cardiac sensory neurons becomes excessive (such as during focal ventricular ischemia), cardiac function is profoundly affected, cardiac myocyte protection is reduced and arrhythmias are increased. A disturbance of the fine balance within the whole cardiac neuraxis results in dramatic changes in cardiac efferent neuronal outflow. Over the past 30 years, the anatomy and function of the peripheral cardiac nervous system has been studied, focusing during the last decade on its intrinsic cardiac component. The classical view of the autonomic nervous system presumes that its intrinsic cardiac component acts solely as a parasympathetic efferent neuronal relay station in which medullary preganglionic neurons synapse with parasympathetic efferent postganglionic neurons therein. In such a concept, the latter neurons project to end effectors on the heart with little or no integrative capabilities occurring therein. Similarly, intrathoracic extracardiac sympathetic ganglia have been thought to act solely as efferent relay stations for sympathetic efferent projections to the heart. As the present disclosure shows, neural control of regional cardiac function resides in the network of nested feedback loops made up of the intrinsic cardiac nervous system, extracardiac intrathoracic autonomic ganglia, the spinal cord and brainstem. Within this hierarchy, the intrinsic cardiac nervous system functions as a distributive processor at the level of the target organ. Thus, the intrinsic cardiac nervous system plays an important role in the functioning of the heart and in its diseased pathologies. This novel information thereafter leads to numerous methodologies (some of which are claimed and disclosed herein for the treatment, preconditioning and/or quenching of disease pathologies through the use of spinal cord stimulation.

Experimental studies have also shown that pathological processes can change the integrative behavior of the cardiac neuraxis. These changes occur when populations of cardiac sensory neurites are activated intensely and for long periods of time when local cardiac tissue becomes damaged during, for instance, regional ventricular ischemia. Thus, under normal, physiological conditions stimuli applied to the heart do not elicit marked changes in cardiac efferent neuronal activity because central neurons suppress cardiac sensory information processing. On the other hand, central processing of cardiac sensory output may become deranged during excessive inputs leading to conflicting signals that interfere with the maintenance of cardiac function. This has led to the novel concept that the hierarchy of cardiac neurons interact effectively if there is an appropriate balance therein. Fundamental to this hierarchy is its component on the target organ—the intrinsic cardiac nervous system and its influence on the heart.

Consistent coherence of activity generated by differing populations of neurons is indicative of principal and direct synaptic interconnections between them or, conversely, the sharing by such neurons of common inputs. Such relationships have been identified among medullary and spinal cord sympathetic efferent preganglionic neurons, as well as among different populations of sympathetic efferent preganglionic neurons. Different populations of neurons, distributed spatially within the intrinsic cardiac nervous system, respond to cardiac perturbations in a coordinate fashion. If neurons in one part of this neuronal network respond to inputs from a single region of the heart, such as the mechanosensory neurites associated with a right ventricular ventral papillary muscle, then the potential for imbalance within the different populations of neurons regulating various cardiac regions might occur and, thus, its neurons display little coherence of activity. In other words, relatively low levels of specific inputs on a spatial scale to the intrinsic cardiac nervous system result in low coherence among its various neuronal components. On the other hand, excessive input to this spatially distributed nervous system would destabilize it, leading to cardiac arrhythmia formation, etc.

Thus it is an object of the present disclosure to use the identification of the intrinsic cardiac nervous system along with the experimental data and results to provide methodologies utilizing spinal cord stimulation for the (1) treatment of cardiac disease pathologies; (2) communication between an external point and the intrinsic cardiac nervous system; (3) preconditioning of the intrinsic cardiac nervous system in order to promote a protective effect against cardiac disease pathologies; and (4) quenching aberrant neuronal activity occurring within the intrinsic cardiac nervous system.

This and numerous other objects of the present disclosure will be appreciated in light of the present specification, drawings, and claims.

BRIEF DESCRIPTION OF THE SEVERAL VIEWS OF THE DRAWINGS

The patent or application file contains at least one drawing executed in color. Copies of this patent or patent application publication with color drawings will be provided by the Office upon request and payment of the necessary fee.

FIGS. 8A-8C show ISF, aorta and coronary sinus norepinephrine (NE) and epinephrine (EPI) levels in response to stellate stimulation (4 Hz), angiotensin II (ANG II) infusion (100 μM, 1 ml/min) into the blood supply for the Right Atrial Ganglionated Plexus (RAGP) and Dorsal Cord Activation (DCA, 50 Hz, 200 μsec, 90% motor threshold). ISF fluids were sampled using the microdialysis techniques summarized in Aim 3.

FIG. 11 shows photomicrographs showing CGRP-immunoreactive nerve fibers in a dog intracardiac ganglion (panel A) and PGP 9.5-immunoreactive nerve fibers in dog sinoatrial node (panel B). The chromogen was VIP in A and diaminobenzadine in B (both from Vector). Both panels are at the same magnification. Scale bar=50 µm.

FIG. 25 shows stratification of ventricular fibrillation risk in a susceptible dog. Left panel illustrates induction of ventricular fibrillation during exercise and myocardial ischemia test. As shown in right panel, susceptible dogs are characterized by a tachycardic response to acute myocardial ischemia that is uncontrolled and leads to VF. Resistant dogs have an increase in heart rate within 15 seconds of coronary occlusion, but have strong vagal reflexes that reduce heart rate within 30 seconds of the occlusion as illustrated in the right panel.

FIG. 28 shows heart rate variability was computed from 25 minutes of continuous resting ECG with spectral densities computed using a fast Fourier transformation. High frequency variation in heart rate is thought to predominantly arise from vagal input to the SA node, while lower frequency bands (VLF, LF) are thought to arise predominantly from sympathetic activity. DCA effects were examined on two different days following 4 days of stimulation lasting for 4 hours.

DETAILED DESCRIPTION

Figure 1:
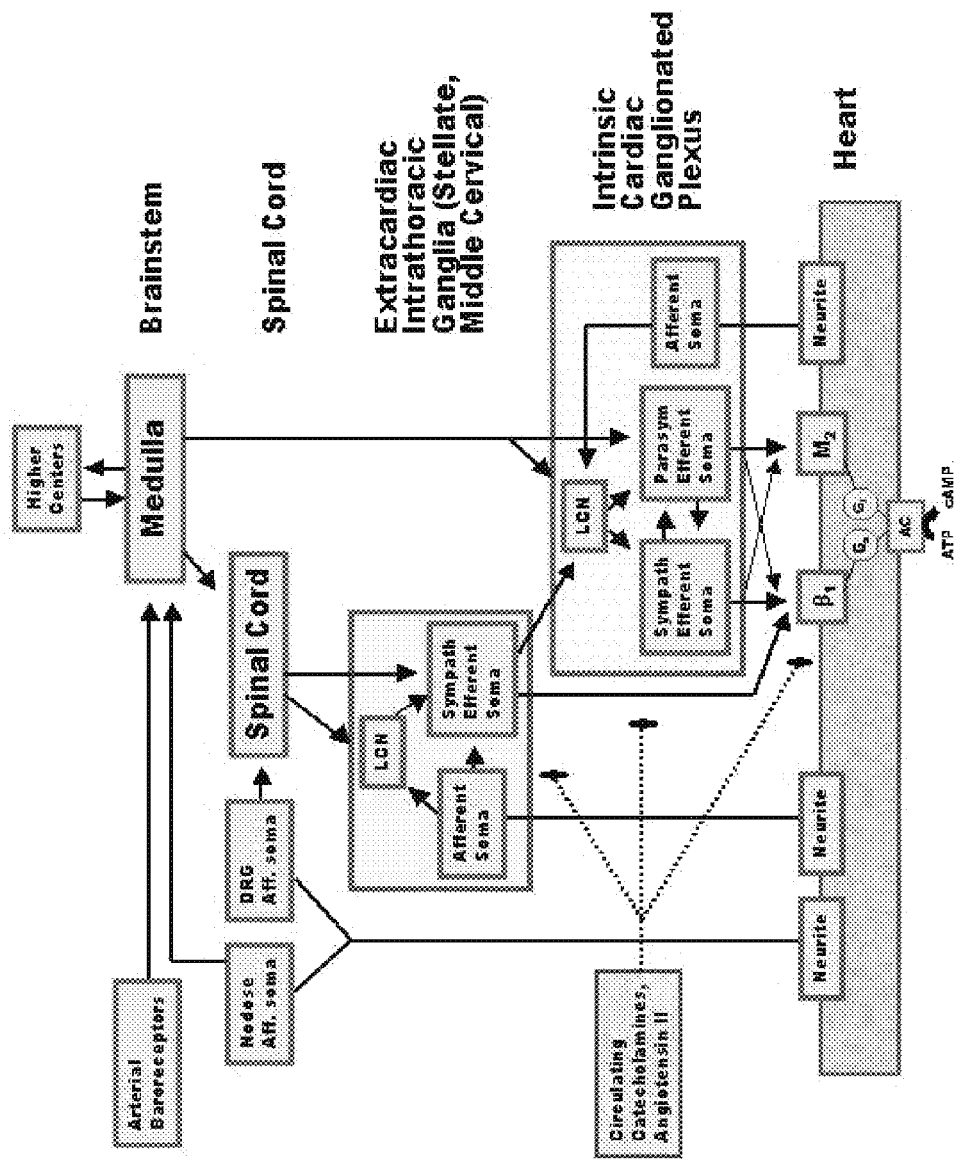
FIG. 1 is a schematic of the neural interactions occurring within the intrathoracic autonomic ganglia and between the peripheral networks and the central nervous system. Within the intrinsic cardiac ganglia are included sympathetic (Sympath) and parasympathetic (Parasym) efferent neurons, local circuit neurons (LCN) and afferent neurons. Contained within the extracardiac intrathoracic ganglia are sympathetic efferent neurons, local circuit neurons and afferent neurons. These intrinsic cardiac and extracardiac networks form separate and distinct nested feedback loops that act in concert with CNS feedback loops involving the spinal cord and medulla to regulate cardiac function on a beat to beat basis. These nerve networks are also influenced by circulating humoral factors including catecholamines (catechol) and angiotensin II (ANG II). Aff., afferent; DRG, dorsal root ganglia; $G_s$, stimulatory guanine nucleotide binding protein; $G_i$, inhibitory guanine nucleotide binding protein; AC, adenylate cyclase; $\beta_1$—beta-1 adrenergic receptor; $M_2$—muscarinic receptor.

Before explaining at least one embodiment of the present disclosure in detail, it is to be understood that the present disclosure is not limited in its application to the details of construction and the arrangements of the components set forth in the following description of illustrated in the drawings. The present disclosure is capable of other embodiments or of being practiced or carried out in various ways. Also, it is to be understood that the phraseology and terminology employed herein is for purpose of description and should not be regarded as limiting.

The present disclosure encompasses the concept of an intrinsic cardiac nervous system and the ability to stimulate this intrinsic cardiac nervous through the use of SCS or DCA. The stimulation of this intrinsic cardiac nervous system results in the ability to easily and with minimal invasiveness, treat cardiac pathologies either pre-, during, or post-symptom.

The present disclosure provides a method for protecting cardiac function and reducing the impact of ischemia on the heart. This methodology includes the steps of: (1) providing a stimulator capable of generating a predetermined electrical signal; (2) placing the stimulator adjacent a neural structure capable of carrying the predetermined electrical signal from the neural structure to the intrinsic cardiac nervous system; and (3) activating the stimulator for a predetermined period of time to generate the predetermined electrical signal to protect cardiac function and reduce the impact of ischemia on the heart. In an alternate embodiment of this method, the neural structure is a spinal cord.

The present disclosure further provides a method for treating an animal having a cardiac pathology by protecting cardiac function and reducing the impact of ischemia on the heart. This methodology includes the steps of: (1) providing a stimulator capable of generating a predetermined electrical signal; (2) placing the stimulator adjacent a neural structure capable of carrying the predetermined electrical signal from the neural structure to at least one of the intrinsic cardiac nervous system and the heart; and (3) activating the stimulator for a predetermined period of time to generate the predetermined electrical signal to modulate at least one of the intrinsic cardiac nervous system and the heart, and thereby protecting at least one of the intrinsic cardiac nervous system and the heart to treat the cardiac pathology. In an alternate embodiment of this methodology, the neural structure is a spinal cord.

The present disclosure also provides a method for electrically communicating with at least one of an intrinsic cardiac nervous system and a heart. This methodology includes the steps of: (1) providing a stimulator capable of generating a predetermined electrical signal; (2) placing the stimulator adjacent a neural structure capable of carrying the predetermined electrical signal from the neural structure to at least one of the intrinsic cardiac nervous system and the heart; and (3) activating the stimulator for a predetermined period of time to generate the predetermined electrical signal to communicate with at least one of the intrinsic cardiac nervous system and the heart. In an alternate embodiment of this methodology, the neural structure is a spinal cord.

Additionally, the present disclosure encompasses a method of modulating electrical neuronal and humoral responses of at least one of an intrinsic cardiac nervous system and a heart. This methodology includes the steps of: (1) providing a stimulator capable of generating a predetermined electrical signal; (2) placing the stimulator adjacent a neural structure capable of carrying the predetermined electrical signal from the neural structure to at least one of the intrinsic cardiac nervous system and the heart; and (3) activating the stimulator for a predetermined period of time to thereby generate the predetermined electrical signal to modulate the electrical neuronal and humoral response of at least of the intrinsic cardiac nervous system and the heart. In an alternate embodiment of this methodology, the neural structure is a spinal cord.

Furthermore, the present disclosure also calls for a method of activating spinal cord neurons to induce a conformational change in an intrinsic cardiac nervous system. This methodology includes the steps of: (1) providing a stimulator capable of generating a predetermined electrical signal; (2) placing the stimulator adjacent a spinal cord to carry the predetermined electrical signal from the spinal cord to an intrinsic cardiac nervous system; and (3) activating the stimulator for a predetermined period of time to thereby generate the predetermined electrical signal to thereby activate spinal cord neurons in proximity of the stimulator so as to induce a conformational change in the intrinsic cardiac nervous system. In an alternate embodiment of this methodology, the neural structure is a spinal cord.

The present disclosure also provides for a method for the prolonged activation of spinal cord neurons to induce a conformational change in an intrinsic cardiac nervous system. This methodology includes the steps of: (1) providing a stimulator capable of generating a predetermined electrical signal; (2) placing the stimulator adjacent a spinal cord to carry the predetermined electrical signal from the spinal cord to an intrinsic cardiac nervous system; and (3) activating the stimulator for a predetermined period of time to thereby generate the predetermined electrical signal to thereby activate spinal cord neurons in proximity of the stimulator so as to induce a conformational change in the intrinsic cardiac nervous system wherein the activation effects persist for a period of time extending beyond the activation of the stimulator. In an alternate embodiment of this methodology, the neural structure is a spinal cord.

Additionally, the present disclosure includes a method for transiently nullifying neuronal activation of an intrinsic cardiac nervous system by myocardial ischemia. This methodology includes the steps of: (1) providing a stimulator capable of generating a predetermined electrical signal; (2) placing the stimulator adjacent a neural structure capable of carrying the predetermined electrical signal from the neural structure to the intrinsic cardiac nervous system; and (3) activating the stimulator for a predetermined period of time to thereby generate the predetermined electrical signal to transiently nullify neuronal activation of an intrinsic cardiac nervous system by myocardial ischemia. In an alternate embodiment of this methodology, the neural structure is a spinal cord.

The present disclosure also provides for a method for prolonged nullification of neuronal activation of an intrinsic cardiac nervous system by myocardial ischemia. This methodology includes the steps of: (1) providing a stimulator capable of generating a predetermined electrical signal; (2) placing the stimulator adjacent a neural structure capable of carrying the predetermined electrical signal from the neural structure to the intrinsic cardiac nervous system; and (3) activating the stimulator for a predetermined period of time to thereby generate the predetermined electrical signal to nullify the neuronal activation of the intrinsic cardiac nervous system by myocardial ischemia for a prolonged period of time extending beyond stimulator activation. In an alternate embodiment the neural structure is a spinal cord.

The present disclosure also includes a method for transiently suppressing neuronal activation of an intrinsic cardiac nervous system by myocardial ischemia. This methodology includes the steps of: (1) providing a stimulator capable of generating a predetermined electrical signal; (2) placing the stimulator adjacent a neural structure capable of carrying the predetermined electrical signal from the neural structure to the intrinsic cardiac nervous system; and (3) activating the stimulator for a predetermined period of time to thereby generate the predetermined electrical signal to transiently suppress the neuronal activation of the intrinsic cardiac nervous system by myocardial ischemia. In an alternate embodiment of the present methodology, the neural structure is a spinal cord.

The present disclosure includes a method for prolonged suppression of neuronal activation of an intrinsic cardiac nervous system by myocardial ischemia. This methodology includes the steps of: (1) providing a stimulator capable of generating a predetermined electrical signal; (2) placing the stimulator adjacent a neural structure capable of carrying the predetermined electrical signal from the neural structure to the intrinsic cardiac nervous system; and (3) activating the stimulator for a predetermined period of time to thereby generate the predetermined electrical signal to suppress the neuronal activation of the intrinsic cardiac nervous system by myocardial ischemia for a prolonged period of time extending beyond stimulator activation. In an alternate embodiment of this methodology, the neural structure is a spinal cord.

The intrinsic cardiac nervous system has been classically considered to contain only parasympathetic efferent postganglionic neurons that receive inputs from medullary parasympathetic efferent preganglionic neurons. As such, intrinsic cardiac ganglia have been viewed as simple relay stations and major autonomic neuronal control of the heart was believed to reside solely in the brainstem and spinal cord. However, the data supporting the present disclosure indicate that centripetal as well as centrifugal processing occurs within the mammalian intrathoracic nervous system (i.e., the intrinsic cardiac nervous system). This involves afferent neurons, local circuit neurons (i.e., neurons that interconnect neurons within one ganglion and neurons in different intrathoracic ganglia), as well as sympathetic and parasympathetic efferent postganglionic neurons.

The intrinsic cardiac nervous system consists of multiple aggregates of neurons and associated neural interconnections, localized to discrete atrial and ventricular regions. Among these distinct ganglionated plexi, preferential control of specific cardiac functions has been identified. For example, right atrial ganglionated plexus neurons have been associated with primary, but not exclusive, control of SA nodal function and inferior vena cava-inferior atrial ganglionated plexus neurons primarily, but not exclusively, with control of AV nodal function. One population of intrinsic cardiac neurons, the parasympathetic postganglionic ones, receives direct input from medullary parasympathetic preganglionic neurons. Another population, adrenergic efferent ones [8,9], receives input from more centrally located neurons in intrathoracic ganglia and the spinal cord. The fact that ventricular sensory neurites continue to influence the activity generated by neurons on the heart following chronic decentralization of the intrinsic cardiac nervous system indicates that the somata of afferent neurons, some of which project axons to central neurons, are located within the intrinsic cardiac nervous system. This concept has received anatomical confirmation. Functional data also indicate that the intrinsic cardiac nervous system contains local circuit neurons interconnecting intrinsic cardiac afferent with efferent neurons.

Sub-populations of right atrial neurons that receive afferent inputs from sensory neurites in both ventricles are responsive to local mechanical stimuli and the nitric oxide donor nitroprusside. Neurons in at least one ganglionated plexus locus were activated by epicardial application of veratridine, bradykinin, the $\beta_1$-adrenoceptor agonist prenaterol or the excitatory amino acid glutamate. Epicardial application of angiotensin II, the selective $\beta_2$-adrenoceptor agonist terbutaline or selective $\alpha_1$- or $\alpha_2$-adrenoceptor agonists elicited inconsistent neuronal responses. The activity generated by both populations of atrial neurons studied over 5 minute periods during basal states displayed periodic coupled behavior (cross correlation coefficients of activities that reached, on average, 0.88±0.03; range 0.71-1) for 15-30 seconds periods of time. These periods of coupled activity occurred every 30-50 second during basal states, as well as when neuronal activity was enhanced by chemical activation of their ventricular sensory inputs. It has been observed that neurons throughout one intrinsic cardiac ganglionated plexus receive inputs from mechano- and chemo-sensory neurites located in both ventricles. That such neurons respond to multiple chemical stimuli, including those liberated from adjacent adrenergic efferent nerve terminals, indicates the complexity of the integrative processing of information that occurs within the intrinsic cardiac nervous system. Thus, the interdependent activity displayed by populations of neurons in different regions of one intrinsic cardiac ganglionated plexus, responding as they do to multiple cardiac sensory inputs, forms the basis for integrated regional cardiac control.

Recent anatomical and functional data indicate the presence of the multiple neuronal subtypes within intrathoracic extracardiac and intrinsic cardiac ganglia. Within this neuronal hierarchy, the intrinsic cardiac nervous system functions as a distributive processor at the level of the target organ. The redundancy of function and non-coupled behavior displayed by neurons in intrathoracic extracardiac and intrinsic cardiac ganglia minimizes the dependency for such control on a single population of peripheral autonomic neurons. In this regard, network interactions that occur within the intrinsic cardiac nervous system to integrate parasympathetic and sympathetic efferent outflow to the heart do so in coordination with intrathoracic extracardiac neurons that process afferent information from multiple sites in the heart during each cardiac cycle. As no consistent coherence of activity generated has been identified among neurons in intrinsic cardiac and intrathoracic extracardiac ganglia, different populations of neurons, distributed spatially within the intrathoracic cardiac nervous system, respond to cardiac perturbations in a coordinate fashion. If neurons in one part of this neuronal network respond solely to inputs from a single region of the heart, such as the mechanosensory neurites associated with a right ventricular ventral papillary muscle, then the potential for imbalance within the different populations of neurons regulating various cardiac regions might occur. A relatively low level of inputs on a spatial scale to the intrinsic cardiac nervous system would result in low coherence among its components. In contrast, excessive input to this spatially distributed nervous system would destabilize it, leading to cardiac arrhythmia formation, etc.

Regional control of cardiac function is dependent upon the coordination of activity generated by neurons within intrathoracic autonomic ganglia and the central nervous system. The hierarchy of nested feedback loops therein provides precise beat-to-beat control of regional cardiac function. Contrary to classical teaching, intrathoracic autonomic ganglia act as more than simple relay stations for autonomic efferent neuronal control of the heart. Within the hierarchy of intrathoracic ganglia and nerve interconnections, complex processing takes place that involves spatial and temporal summation of sensory inputs, preganglionic inputs from central neurons and intrathoracic ganglionic reflexes activated by local cardiopulmonary sensory inputs. The activity of neurons within intrathoracic autonomic ganglia is likewise modulated by circulating hormones, chief among them being circulating catecholamines and angiotensin II.

The progressive development of cardiac disease is associated with maladaptation of these neurohumoral control mechanisms. Differences exist in autonomic control of the heart before any overt cardiovascular disease occurs and such differences critically influence the outcome at the time of ischemic heart disease onset. Differential remodeling of the cardiac neuron hierarchy (central and peripheral) for reflex control of the heart occurs in animals susceptible verses resistant to development of ventricular fibrillation during the evolution of chronic myocardial ischemia/infarction. Understanding neuronal reorganization/remodeling that occurs within the peripheral autonomic nervous system and the interactions that occur between this neural remodeling and the remodeling of the myocardium leads to the novel approaches as presently disclosed and claimed for anti-arrhythmia therapy and also to therapies directed at ischemic heart disease and protection of the heart.

With respect to neural control of the heart, the intrathoracic ganglia and their interconnections form the final common pathway for autonomic modulation of cardiac function. Data summarized and presented herein indicates in support of the present disclosure that intrathoracic autonomic ganglia contain a heterogeneous population of cell types including afferent, efferent and local circuit neurons. Yet, as a group, the intrathoracic reflexes mediated within these peripheral autonomic ganglia function in a coordinated fashion with central neurons located in the spinal cord, brainstem and supraspinal regions to regulate cardiac output on a beat to beat basis.

Afferent Neurons

Cardiac Afferent Neurons.

Sensory afferent neurons provide the autonomic nervous system with information about blood pressure, blood volume, blood gases as well as the mechanical and chemical milieu of the heart. For sensory inputs from cardiopulmonary regions, the nodose and dorsal root ganglia are classically recognized as providing sensory inputs to the brainstem and spinal cord respectively. Data indicates that intrathoracic extracardiac (i.e., stellate and middle cervical ganglia) and intrinsic cardiac ganglia also contain afferent neurons whose sensory neurites lie variously within the heart, lungs and great thoracic vessels. Additional sensory inputs for the control of cardiac autonomic neurons arise from baroreceptors and chemoreceptors located along the aortic arch, carotid sinus and carotid bodies as well as from other afferent neural elements within the CNS, especially the hypothalamus.

Nodose Ganglia Afferent Neurons.

The nodose receive cardiac afferent inputs from sensory neurites located in atrial and ventricular tissues. These sensory neurites preferentially sense chemical stimuli, with a few responding to mechanical stimuli or both modalities. The response characteristics to induced stimuli are likewise divergent with mechanical stimuli exerting short-lived effects, while the augmentation in activity elicited by chemical stimuli far outlasts the applied stimulus. While inputs from these receptors contribute to overall cardiovascular regulation, they are not normally perceived.

Dorsal Root Ganglia (DRG) Afferent Neurons.

The cell bodies of DRG afferent neurons, receiving input from cardiac sensory neurites, are located in $C_6$-$T_6$ dorsal root ganglia. The sensory neurites of most of these afferent neurons transduce chemical and mechanical stimuli. The inputs from this subpopulation of cardiac afferent neurons subserve normal cardiovascular regulation, as well as nociception when excessively activated.

Intrathoracic Afferent Neurons.

Functional and anatomical data indicate that intrathoracic autonomic ganglia contain afferent soma. The sensory neurites associated with these afferent neurons are variously located in atrial, ventricular, major vascular and pulmonary tissues. Most are responsive to mechanical and chemical stimuli. These afferent neurons continue to influence intrathoracic efferent postganglionic outflows to the heart even after long-term decentralization of intrathoracic ganglia. Such intrathoracic afferent neurons provide inputs to the intrathoracic short-loop feedback control circuits that involve intrinsic cardiac and intrathoracic extracardiac neurons. These intrathoracic neural circuits, acting in concert with CNS mediated reflexes, dynamically control regional cardiac function throughout each cardiac cycle to maintain electrical stability of the heart and protect the myocytes.

Aortic and Carotid Artery Baroreflexes.

Stretch receptors, sensitive to changes in vessel size, are found on thoracic and cervical arteries, being concentrated on the aortic arch and the carotid sinus. They provide inputs to neurons within the medulla and spinal cord proportional to systemic arterial blood pressure. Inputs from these sensory neurites course centrally in the IX and X cranial nerves to synapse with neurons located in the nucleus of the medullary solitary tract. Via multi-synaptic connections, these afferent inputs modulate the activity of cardiac parasympathetic efferent preganglionic neurons located primarily in the nucleus ambiguus. They also influence sympathetic efferent neuronal outflow to the heart via brainstem projections to the intermediolateral (IML) region of the spinal cord. The baroreflex so involved represents a negative feedback system that modulates cardiac function and peripheral vascular tone in response to everyday stressors.

Efferent Neurons

Sympathetic Efferent Neurons.

The somata of sympathetic preganglionic efferent preganglionic neurons which regulate the heart are located within the intermediolateral (IML) cell column of the spinal cord, projecting axons via the rami T1-T5 to synapse with sympathetic postganglionic neurons contained within various intrathoracic extracardiac and intrinsic cardiac ganglia. Activation of these sympathetic efferent projections augments heart rate, changes patterns and speed of impulse conduction through the electrical system of the heart and increases contractile force in atrial and ventricular tissues. Sympathetic efferent postganglionic somata that project axons to various cardiac effector tissues are localized in intrathoracic extracardiac and intrinsic cardiac ganglia. Classically, the somata of sympathetic efferent postganglionic neurons that innervate the heart have been thought to be restricted to the stellate ganglia. However, cardiac sympathetic efferent postganglionic soma have also been identified in thoracic middle cervical, mediastinal and intrinsic cardiac ganglia. A subpopulation of intrinsic cardiac neurons express the catecholaminergic phenotype, these neurons thus contain the necessary enzymes to convert L-DOPA to dopamine and norepinephrine. The intrinsic cardiac nervous system also contains a separate population of small intensely fluorescent (SIF) cells that display tyrosine hydrolyase immunoreactivity. Some of these projects to adjacent principal intrinsic cardiac neurons.

Parasympathetic Efferent Neurons.

The somata of cardiac parasympathetic efferent preganglionic neurons within the brainstem are located primarily within the nucleus ambiguous, with lesser numbers being located in the dorsal motor nucleus and regions in between. Axons from these preganglionic soma projects via the X cranial nerve to synapse with parasympathetic efferent postganglionic neurons located within various intrinsic cardiac ganglia (see hereinafter below). Activation of parasympathetic efferent neurons depresses heart rate, slows the speed of impulse conduction through the heart, induces major suppression of atrial muscle contractile force and evokes negative inotropic effects on ventricular contractile force.

Local Circuit Neurons

A subpopulation of neurons contained within extracardiac and intrinsic cardiac intrathoracic autonomic ganglia function to interconnect neurons within individual ganglia and between neurons in separate intrathoracic ganglia; these are called local circuit neurons. Preliminary data indicate that these neurons are involved in processing of afferent information to coordinate sympathetic and parasympathetic efferent outflows to cardiac effector sites. Interactions within this neuron population form the substrate for generation of the basal activity within peripheral autonomic ganglia, especially when intrathoracic ganglia are disconnected from the influence of central neurons.

Organization of the Intrinsic Cardiac Nervous System

The cardiac nervous system consists of distinct ganglia clusters that function in an interdependent manner to modulate regional cardiac function. To date, eight separate ganglia clusters have been identified within the canine intrinsic nervous system, five associated with atrial tissues and three with ventricular tissue.

The five atrial ganglionated plexuses include: 1) the right atrial ganglionated plexus localized in fatty tissue on the ventral surface of the common right pulmonary vein complex; 2) the inferior vena cava-inferior atrial ganglionated plexus located on the inferior right atrium adjacent to the inferior vena cava; 3) the dorsal atrial ganglionated plexus located on the dorsal surface of the atria between the common pulmonary veins, immediately caudal to the right pulmonary artery; 4) the ventral left atrial ganglionated plexus contained within fat on the caudal-ventral aspect of the left atrium adjacent to the AV groove; and 5) the posterior atrial ganglionated plexus.

The three major ventricular ganglionated plexi are: 1) the right lateral ventricular ganglionated plexus located adjacent to the origin of the right marginal artery; 2) the left lateral ventricular ganglionated plexus located adjacent to the origin of the left marginal artery; and 3) the cranial medial ventricular ganglionated plexus located in fatty tissues surrounding the base of the aorta and main pulmonary artery. Of these eight clusters of ganglia, functions have been primarily ascribed to five of them: neurons in the right atrial and posterior atrial ganglionated plexus have been shown to exert preferential control over the sinoatrial node; those in inferior vena cava-inferior atrial ganglia exert predominant control over inferior atrial and atrioventricular conductile tissues. Neurons in dorsal atrial and cranial medial ventricular ganglia are principal modulators of contractile tissue.

Neurohumoral Interactions Contributing to Cardiac Control

FIG. 1 is a graphical representation of the neurohumoral interactions involved in control of cardiac function. Data indicates that a hierarchy of peripheral autonomic neurons functions interdependently via nested feedback loops to regulate cardiac function on a beat-to-beat basis. FIG. 1, therefore, summarizes the concept of neural control of the heart as mediated by intrathoracic extracardiac and intracardiac neurons which are continuously influenced by descending projections from higher centers in the spinal cord, brainstem, and suprabulbar regions. Each successive synaptic relay point within this autonomic outflow, from the brainstem to the heart, is in turn influenced by afferent feedback from various cardiopulmonary and vascular afferent receptors. Accumulating evidence suggests that there may be at least four functionally distinct neuronal types within the intrinsic cardiac nerve plexus; parasympathetic postganglionic efferent neurons, local circuit neurons, adrenergic postganglionic efferent neurons and afferent neurons. Local circuit and cardiac afferent neurons also lie within intrathoracic extracardiac ganglia, along with the sympathetic postganglionic neurons.

With respect to intrathoracic autonomic ganglia, cholinergic and adrenergic efferent neurons in these ganglia represent the output elements that project axons to cardiac electrical and mechanical tissues. Local circuit neurons interconnect adjacent neurons within one ganglion or link neurons in separate clusters of intrathoracic ganglia. These interneurons are involved in coordination of neuronal activity within these peripheral autonomic ganglia, thereby providing the underlying inputs necessary for the maintenance of basal autonomic neuronal discharge. Intrathoracic afferent neurons provide mechanosensitive and chemosensitive inputs from cardiopulmonary regions directly to intrinsic cardiac and extracardiac neurons, forming the basis of the intrathoracic neural feedback system. Superimposed on activities generated by neurons in peripheral autonomic ganglia are efferent inputs from preganglionic neurons in the brainstem and spinal cord that together exert tonic influences on regional cardiac tone. CNS preganglionic inputs are, in turn, influenced by inputs from higher centers in the central nervous system and by afferent feedback from central and peripheral sensory afferent neurons.

Interactions Among Peripheral Autonomic Neurons

Cardiac performance is modulated by both sympathetic and parasympathetic efferent neuronal inputs. The induced change in any regional cardiac function ultimately depends upon the intrinsic characteristics of the cardiac end-effector being innervated, the level of efferent activity from the CNS to the periphery and interactions occurring within peripheral autonomic ganglia and at the respective cardiac end-effectors.

Interactions at the Organ Level.

Anatomical and functional studies indicate that sympathetic and parasympathetic efferent postganglionic nerve endings lie in close proximity to each other in the target tissues. Interactions among sympathetic and parasympathetic efferent projections to the heart involve pre- and postjunctional mechanisms at the end-effectors in cardiac tissue. Post-junctional interactions involve differential modulation of adenylate cyclase via G-protein coupled receptor systems (FIG. 1). Catecholamines, released from sympathetic efferent projections or derived from the circulation, influence myocardial tissues by binding primarily to $\beta_1$ and $\beta_2$-adrenoceptors. Myocardial $\beta$ adrenergic receptors are coupled to and stimulate adenylate cyclase via stimulatory guanine nucleotide binding protein ($G_s$). Acetylcholine, released from parasympathetic efferent postganglionic neurons, binds to cardiomyocyte $M_2$ muscarinic receptors which, in turn, are coupled to and inhibit adenylate cyclase via inhibitory guanine nucleotide binding protein ($G_i$). The interactions between these two receptor-coupled systems at the adenylate cyclase level ultimately determine the rate of formation of cAMP and thereby myocyte second messenger function. The neural interactions that occur at cardiac end-effectors involve primarily modulation of neurotransmitter release from pre-junctional synaptic terminals. Neural release of the principal mediators norepinephrine and acetylcholine, along with the co-release of various neuropeptides (e.g. NPY and VIP) act on specific receptors associated with sympathetic or parasympathetic efferent axon terminals. These mechanisms act to modulate subsequent neurotransmitter release.

Interactions within the ICN.

Various lines of evidence indicate that peripheral sites that are separate from the end-effectors contribute to mediating sympathetic-parasympathetic interactions for the control of regional cardiac function. Stimulating parasympathetic and/or sympathetic efferent projections to the heart activates subpopulations of intrinsic cardiac neurons. These extrinsic autonomic projections converge on separate aggregates of intrinsic cardiac neurons, each of which exhibit preferential control over regional cardiac function. With respect to control of chronotropic function, surgical disruption of the right atrial ganglionated plexus eliminates direct vagal projections to the sinoatrial node. Sympathetic efferent neuronal control of chronotropic function and the vagal inhibition of the sinus tachycardia produced by cardiac sympathetic efferent neurons are maintained. These residual sympathetic-parasympathetic efferent neuronal interactions occur at the level of the heart and are prejunctional to the sinoatrial node. As shown herein, these residual interactions occur within the intrinsic cardiac nervous system. Whether such intraganglionic autonomic interactions play correspondingly roles in modulation of dromotropic and inotropic function has yet to be determined.

Intraganglionic interactions within the intrinsic cardiac nervous system depend in large part on common shared afferent inputs and/or interconnections mediated via local circuit neurons. In order to evaluate these interactions, separate populations of neurons were recorded in the ventral right atrial ganglionated plexus (RAGP) in basal states and during discrete mechanical and chemical stimuli of ventricular neurites. In basal states, the coherence of activity generated by the two populations of RAGP neurons fluctuated with a periodicity of 30-50 s and with an average peak coherence of 0.88±0.03. Coherence was increased in conjunction with the enhanced neuronal activity evoked during exposure of ventricular sensory inputs to mechanical and chemical (nitroprusside, veratridine, bradykinin, adrenergic agonists or glutamate) stimuli. The interdependent activity displayed by the population of neurons in different regions of one intrinsic cardiac ganglionated plexus, depending as they do on multiple cardiac sensory inputs, forms the basis for coordination of regional cardiac function within the intrinsic cardiac nervous system.

Interactions within the Intrathoracic Nervous System.

Coordination of autonomic outflows from intrathoracic neurons to cardiomyocytes depends to a large extent on sharing of inputs from higher centers along with interactions among and between various peripheral ganglia. Interactions within and between intrathoracic ganglia involve local circuit neurons (see herein above). Activities generated by neurons in intrinsic cardiac ganglia demonstrate no consistent short-term relationship to neurons in extracardiac ganglia. However, the sharing of cardiopulmonary afferent information acting through both intrathoracic and brain stem/spinal cord feedback loops permits an overall coordination of effector control. Together, these nested feedback control systems allow for a redundancy in neural control of the heart while at the same time maintaining the flexibility to differentially modulate regional cardiac function.

Electrophysiology of Intrinsic Cardiac Ganglia

In Vivo Studies.

Cardiac neurons generate spontaneous activity in situ, frequently exhibiting activity that is temporally related to the cardiac or respiratory cycles. Of the neurons that displayed cardiac-related activity, many are affected by mechano- or chemosensory inputs from the heart. Trains of electrical stimuli delivered to axons in the T1-T5 ventral roots activate a substantial population of stellate and middle cervical neurons. These data indicate a convergence of preganglionic inputs onto the extracardiac postganglionic soma, reflective of a functional amplification of such sensory input. In contrast, trains of electrical stimuli delivered to the vago-sympathetic trunks or stellate ganglia activate a much smaller population of intrinsic cardiac neurons. Moreover, few intrinsic cardiac neurons are activated after a fixed latency when extracardiac efferent neurons that innervate the heart are stimulated electrically, a finding indicative of monosynaptic interconnections to such neurons. These data indicate that, in contradistinction to extracardiac ganglia, substantial spatial and temporal summation of inputs are required to modify the activity generated by neurons on the heart. Intrinsic cardiac neurons generate low level activity in such a state consistent with a nerve network that functions as a "low pass filter", thereby minimizing the potential for imbalances within autonomic efferent neuronal inputs to the heart, a process which by itself could be arrhythmogenic.

In Vitro Studies.

Intrinsic cardiac ganglia contain a heterogeneous population of neurons. An intracellular recording from isolated whole mount aggregates of intrinsic cardiac ganglia indicates that complex neural interactions occur within the heart. Studies on aggregates of intrinsic cardiac ganglia derived from different species further indicate that the resting membrane potentials of these neurons is approximately −60 mV, with relatively low input resistances and thresholds for the generation of action potential being approximately 20 mV more positive than the resting membrane potential. These properties are consistent with neurons functioning with low excitability. No evidence for ramp-like pacemaker activities has been found within mammalian intrinsic cardiac neurons in vitro. Thus spontaneous activity generated by such neurons in vivo likely reflects underlying cell-cell interactions. For orthodromic stimulation there is substantial dispersion in time of the evoked excitatory postsynaptic potentials (EPSP's) generated by a given intrinsic cardiac neuron, indicative of polysynaptic inputs to neurons within the intrinsic cardiac nervous system. After the generation of action potentials, prolonged afterhyperpolarizations are produced by these cells, an additional factor which limits the excitability of intrinsic cardiac neurons in situ. Chronic disruptions of nerve inputs to these ganglia evoke changes in membrane properties which may result in increased excitability within the ganglionated plexus.

Intracellular recordings from isolated aggregates of intrinsic cardiac ganglia have identified both cholinergic and non-cholinergic synaptic mechanisms coexisting within intrinsic cardiac ganglia. In rats and pigs only fast excitatory postsynaptic potentials are displayed by intrinsic cardiac neurons in response to orthodromic stimulation of closely adjacent intraganglionic axons. These postsynaptic potentials are substantially attenuated, but not completely eliminated, by nicotinic cholinergic blockade. In the dog, orthodromic stimulation of presynaptic fibers in these nerves elicits fast and slow postsynaptic potentials within intrinsic cardiac neurons. Fast excitatory postsynaptic potentials are mediated by cholinergic nicotinic receptors, while the slow excitatory and slow inhibitory potentials are mediated by cholinergic muscarinic receptors. In the pig direct application of norepinephrine modifies the properties of about 25% of identified intrinsic cardiac neurons. These data indicate that intrinsic cardiac neurons possess muscarinic cholinergic, nicotinic cholinergic as well as adrenergic receptors. As detailed hereinafter, many other putative neurotransmitters likewise modify electrical events of intrinsic cardiac neurons. These neurochemicals may play important roles in the modulation of intrinsic cardiac neuronal activity.

In summary, intrathoracic autonomic ganglia do not function as obligatory synaptic stations for autonomic efferent neuronal input to the heart. Instead, they are capable of complex signal integration involving afferent, local circuit as well as parasympathetic and sympathetic efferent neurons. While the physiological properties of extracardiac autonomic ganglia tend to amplify CNS and afferent feedback inputs, those of the intrinsic cardiac nervous system act to limit cardiac excitability. As such, the final common pathway of cardiac control—the intrinsic cardiac nervous system—appears to function as a "low pass" filter to minimize transient neuronal imbalances arising from separate sympathetic and parasympathetic efferent neuronal inputs to the heart. In conjunction with this local afferent feedback mechanism, neurons in intrathoracic ganglia also mediate local cardio-cardiac reflexes at sites separate from those on the heart and the CNS. The synaptic events underlying such intraganglionic interactions involve multiple neurotransmitters that interact with various neuronal receptors to exert rapid acting neuronal membrane conductance and/or longer-term modulation of synapses within the intrinsic cardiac nervous system.

Synaptic Mechanisms Associated with Neurons in Intrathoracic Autonomic Ganglia

Cholinergic Mechanisms.

Synaptic transmission in autonomic ganglia principally involves the release of acetylcholine by presynaptic terminals and subsequent binding of that neurotransmitter to nicotinic cholinergic receptors on postganglionic neurons. In mammals this synaptic junction is not obligatory, indicating that a significant convergence of inputs may be necessary to evoke postganglionic neuronal activity. Thus the potential for synaptic integration exists within intrathoracic autonomic ganglia. Nicotinic and muscarinic cholinergic receptors have been associated with intrathoracic autonomic neurons. Furthermore, blockade of nicotinic receptors attenuates, but does not eliminate, activity generated by the intrinsic cardiac neurons. Muscarinic blockade attenuates excitatory and inhibitory synaptic function within intrinsic cardiac ganglia as well. These sets of data indicate that acetylcholine exerts both mediator and modulator effects at synapses within intrathoracic autonomic ganglia.

Application of nicotine to intrathoracic autonomic neurons can alter their activity and induce concomitant changes in regional cardiac function, whether the neurons are located in extracardiac or intrinsic cardiac ganglia. Nicotinic activation of intrinsic cardiac neurons evokes a biphasic cardiac response, with initial suppression in regional cardiac function being followed by augmentation. Acute decentralization of intrathoracic ganglia from the CNS attenuates, but does not eliminate, such effects. In time, following chronic decentralization of intrathoracic ganglia including those on the heart as with cardiac transplantation, peripheral nerve networks remodel to sustain cardiac function. For cholinergic receptor systems, the remodeling primarily involves augmentation of excitatory influences mediated by muscarinic receptors.

Non-Cholinergic Mechanisms.

Blockade of nicotinic cholinergic receptors attenuates, but does not eliminate, the activity generated by neurons within the intrathoracic autonomic ganglia. These data indicate that non-nicotinic putative neurotransmitters act as mediators for synaptic transmission within the intrathoracic neuronal system. Anatomical and physiological studies have identified multiple putative neurotransmitters in association with the mammalian intrinsic cardiac ganglia which include purinergic agonists, catecholamines, angiotensin II, calcitonin gene-related peptide, neuropeptide Y, substance P, neurokinins, endothelin and vasoactive intestinal peptide. Many of these putative neurochemicals arise from neurons whose cell bodies are located in stellate, middle cervical or mediastinal ganglia, while others may be synthesized by neurons intrinsic to the heart. Direct application of various neurotransmitters adjacent to neurons in intrinsic cardiac ganglia modifies the activities they generated, often resulting in concomitant changes in cardiac pacemaker and/or contractile behavior.

Intrinsic cardiac ganglia contain a heterogeneous population of neurons that utilize cholinergic and non-cholinergic synapses to control intraganglionic, interganglionic and nerve effector organ cell activities. Some of these neurotransmitters subserve short duration synaptic actions (e.g., acetylcholine) while others modulate pre- and/or post-synaptic function over longer periods of time (e.g., neuropeptide Y).

Neural Remodeling in the Heart Associated with Myocardial Ischemia

Myocardial ischemia and infarction can induce substantial changes in the intrathoracic nerve networks and their reflex control of regional cardiac function. Chen and coworkers [(41;42;122)] have recently proposed the sprouting hypothesis of sudden cardiac death: namely, "Myocardial Ischemia results in nerve injury, followed by sympathetic nerve sprouting and regional myocardial hyperinnervation. The coupling between augmented sympathetic nerve sprouting with electrical remodeled myocardium results in VT, VF and SCD." The results of these studies and others have indicated that the evolution of cardiac pathologies may be associated with a heterogeneous distribution of efferent projections to cardiac end-effectors. Myocardial ischemia may also alter the neurochemical profile of that innervation; e.g., expression of vasoactive intestinal polypeptide and calcitonin gene-related peptide are enhanced in sympathetic neurons after myocardial infarction. Finally, the evolution of cardiac pathology can be associated with disruptions of the intrinsic cardiac nervous system and its ability to process afferent information. Such changes compromise the abilities of the peripheral nerve networks to maintain homogeneity for reflex control of regional cardiac function. This neural remodeling, when coupled with the ischemic-induced heterogeneous electrical remodeling of cardiac myocytes, creates a synergistic substrate for arrhythmias and sudden cardiac death.

Interactions Between CNS and Intrathoracic Neuronal Networks: Implications for Treatment of Myocardial Ischemia and Angina Pectoris Myocardial ischemia reflects an imbalance in the supply: demand balance within the heart with resultant activation of cardiac afferent neurons and, as a consequence, the perception of symptoms (i.e., angina pectoris). In addition to such nociceptive responses, activating cardiac afferent neurons can elicit autonomic and somatic reflexes. Pharmacological, surgical and angioplasty therapies are commonly used to improve symptoms and cardiac function in patients exhibiting angina pectoris. While these treatments are usually successful, some patients still suffer from cardiac pain following these procedures. Recently, epidural stimulation of the spinal cord (SCS or Dorsal Cord Activation, DCA) has been suggested as an alternative to bypass surgery in high-risk patients. With DCA, high frequency, low intensity electrical stimuli are delivered to the dorsal aspect of the T1-T3 segments of the thoracic spinal cord. This therapy decreases the frequency and intensity of anginal episodes. DCA reduces the magnitude and duration of ST segment alteration during exercise stress in patients with cardiac disease, improves myocardial lactate metabolism and increases workload tolerance. The mechanisms whereby this mode of therapy produces such beneficial effects are, to date, poorly understood and although used extensively in Europe, are not a standard of practice within the United States.

Figure 2:
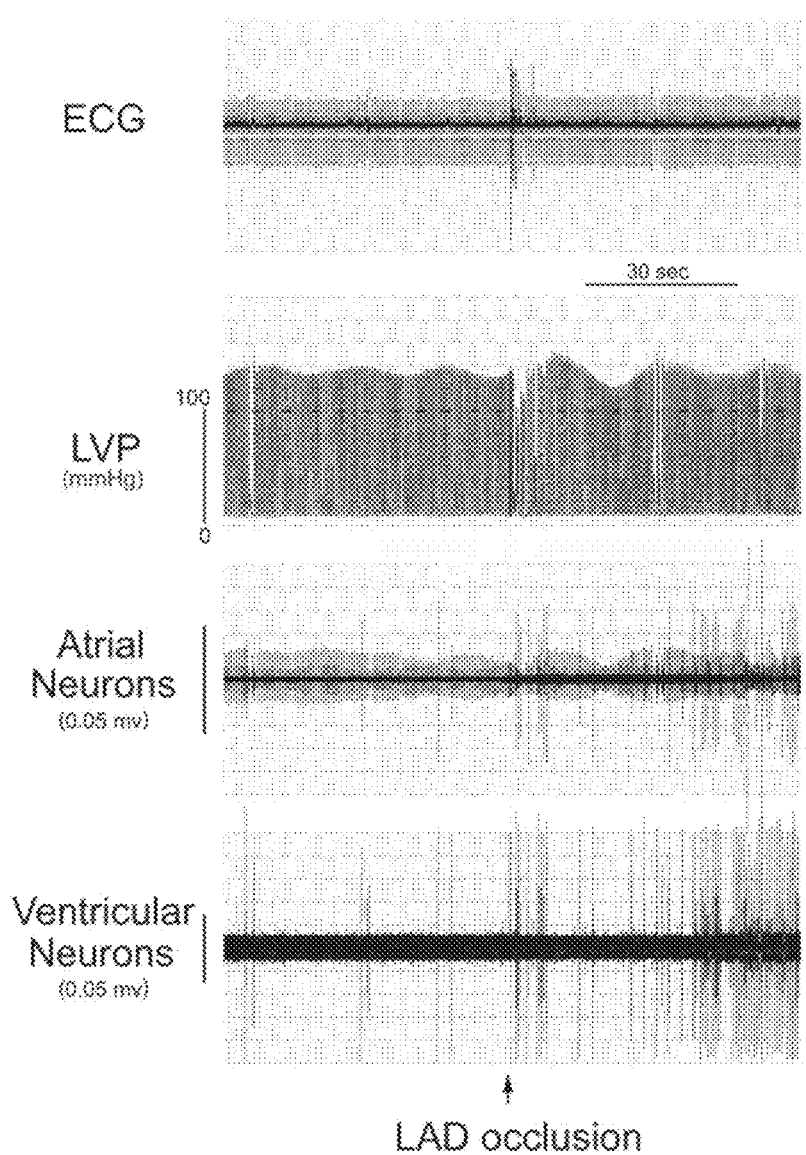
FIG. 2 shows chronotropic (ECG), inotropic (LVP, Left vent. pressure) and neuronal responses recorded simultaneously in atrial (right atrial ganglionated plexus; RAGP) and ventricular (cranial medial ganglionated plexus; CMVGP) intrinsic cardiac neurons before and during transient occlusion of the left anterior descending coronary artery. Note the enhanced activity in both ganglionated plexi, with the ventricular ganglionated plexus being more affected.
Figure 3:
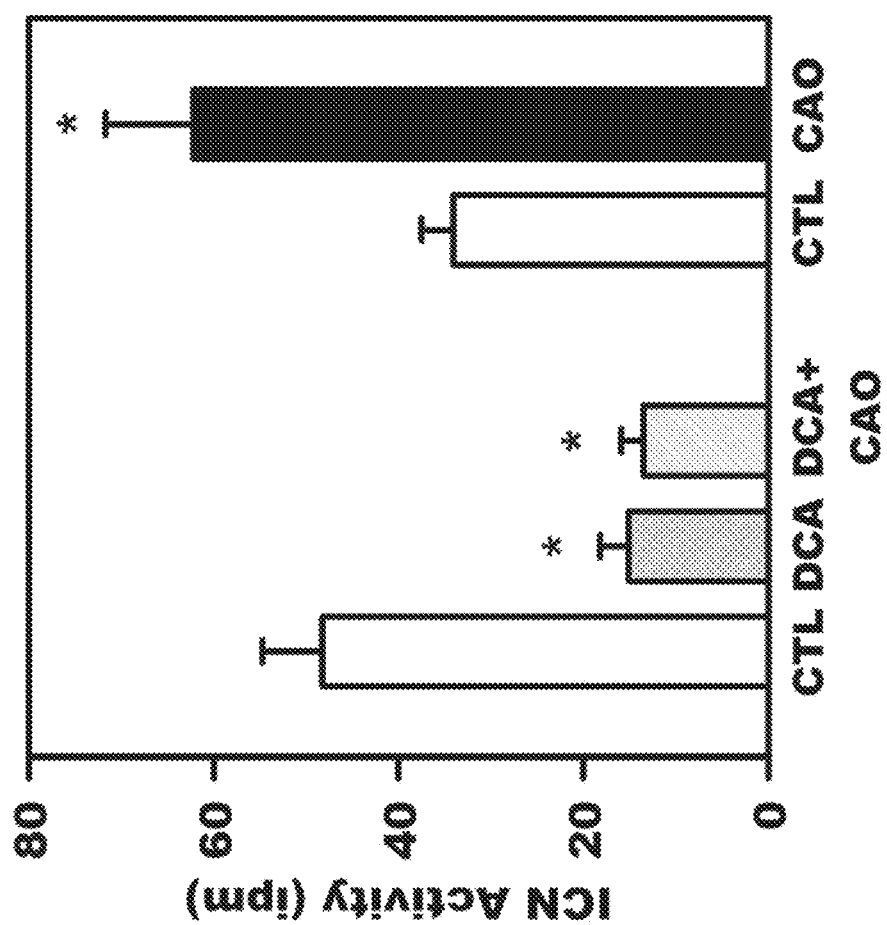
FIG. 3 is a graphical representation of the change in intrinsic cardiac neuronal activity induced by transient occlusion of the left anterior descending artery (CAO) and/or dorsal cord activation (DCA) at 90% Motor Threshold.
Figure 4:
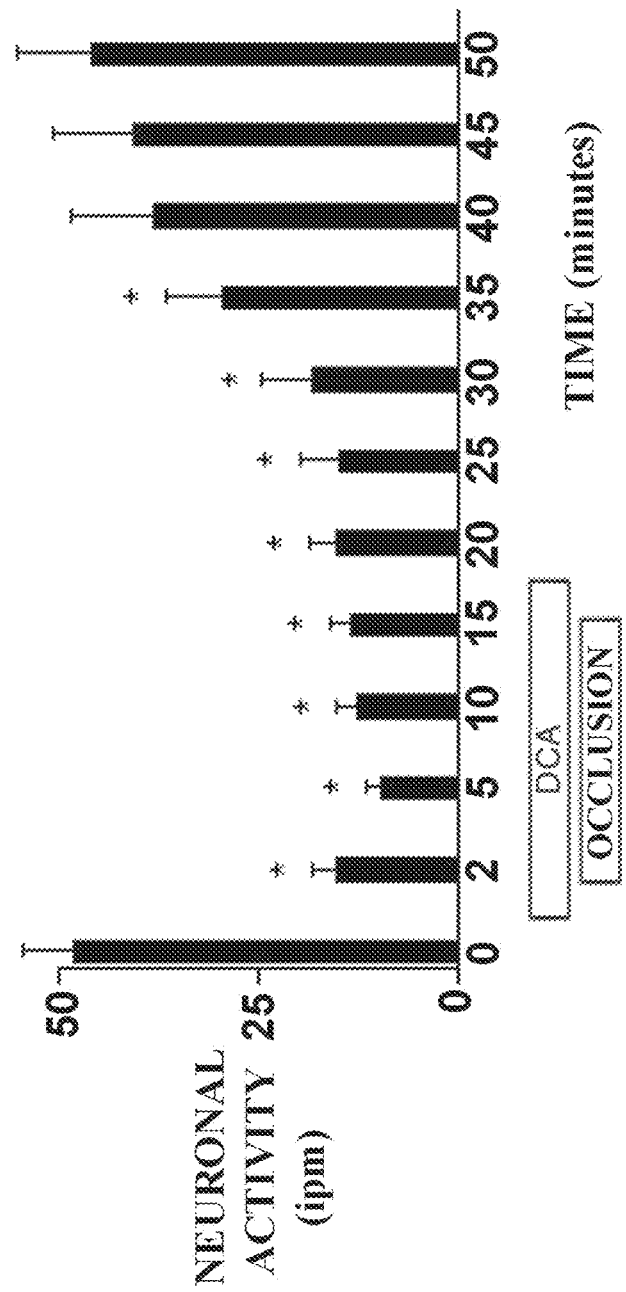
FIG. 4 is a graphical representation of long-term effects (memory) on intrinsic cardiac neuronal activity induced by short-term DCA. Following bilateral transection of the ansae subclavia, DCA no longer affected activity within the intrinsic cardiac nervous system.

Since intrathoracic cardiac neurons have been found to play important modulatory roles in cardiac regulation, the use of DCA and its effects on the activity generated by intrinsic cardiac neurons has been studied and is at least one component of the present disclosure. Transient cardiac ventricular ischemia increases the activities generated by intrathoracic ganglia, including those on the heart. Excessive focal activation of intrathoracic neural circuits can induce cardiac dysrhythmias, even in normally perfused hearts. DCA results in an immediate suppression in intrinsic cardiac neuronal activity. A neuro-suppressor effect imposed in the intrinsic cardiac nervous system occurs whether DCA is applied immediately before, during or after coronary artery occlusion (FIGS. 2 and 3). Furthermore, the suppression of intrinsic cardiac neuronal activity persists even after cessation of DCA (FIG. 4). That transection of the ansae subclavia eliminated these effects indicates that they primarily involve the sympathetic nervous system.

The synaptic mechanisms and specific pathways mediating these responses likely involve both sympathetic afferent and efferent neurons. Dorsal cord activation excites sensory afferent fibers antidromically such that endorphins or neuropeptides such as calcitonin gene-related peptide or substance P are locally released in the intrinsic cardiac ganglia and myocardium. Opiates and neuropeptides can also influence intrinsic cardiac neurons (see herein-above). Spinal cord stimulation also suppresses intrinsic cardiac adrenergic as well as local circuit neurons as the result of altered sympathetic efferent preganglionic neuronal activity. It is also known that activation of sympathetic efferent preganglionic axons suppresses many intrathoracic reflexes that are involved in cardiac regulation. Thus these neuro-suppressor effects appear to be due, in part, to activation of inhibitory synapses within intrathoracic ganglia. Recent clinical experience with DCA highlights the dynamic interactions that can occur between central and intrathoracic neurons, demonstrating the potential for effective clinical treatment of cardiac pathology via modulation of the intrathoracic nervous system or the intrinsic cardiac nervous system.

Coordination of Activities within and Between Ganglia of the Intrinsic Cardiac Nervous System FIGS. 2-4 summarize the induced changes in intrinsic cardiac nerve activity produced by transient coronary artery occlusion (CAO) and their modulation by descending projections from the T1-T3 segments of the spinal cord. Note the augmentation in activity within the atrial and ventricular neurons (FIG. 2) produced by CAO is attenuated by electrical stimulation of the dorsal aspects of the T1-T3 segments of the spinal cord (FIG. 3, DCA; Dorsal Cord Activation). The suppression of activity induced by DCA on the intrinsic cardiac neuronal activity is maintained long after the termination of spinal cord stimulation (FIG. 4).

Figure 5:
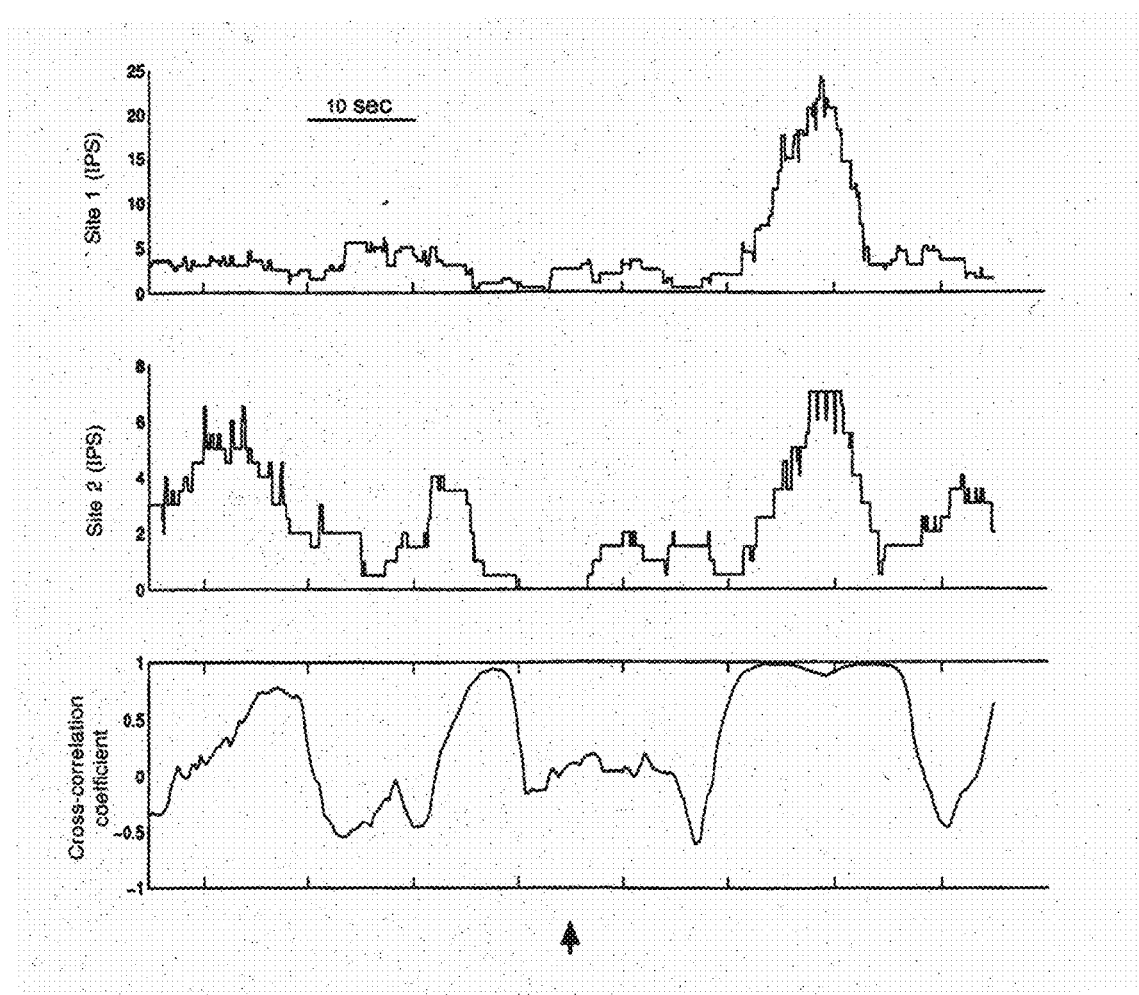
FIG. 5 shows activity generated by two different populations of intrinsic cardiac neurons contained within the right atrial ganglionated plexus. Arrow indicates application of veratridine to the epicardium of the left ventricle. At baseline, note the cycling of activity with a periodicity of 20 seconds. In the unstressed condition, this bursting is usually associated with increased coordination of activity between the two populations of neurons (see bottom trace). When an afferent stress is imposed to the ICN, as with application of epicardial veratridine, activity increased in both sites and the coherence of activity generated by these two populations of neurons approached unity.

As shown in FIG. 5, activity generated by two different populations of intrinsic cardiac neurons contained within the right atrial ganglionated plexus. Arrow indicates application of veratridine to the epicardium of the left ventricle. At baseline, note the cycling of activity with a periodicity of 20 seconds. In the unstressed condition, this bursting is usually associated with increased coordination of activity between the two populations of neurons (see bottom trace). When an afferent stress is imposed to the ICN, as with application of epicardial veratridine, activity increased in both sites and the coherence of activity generated by these two populations of neurons approached unity.

Figure 6:
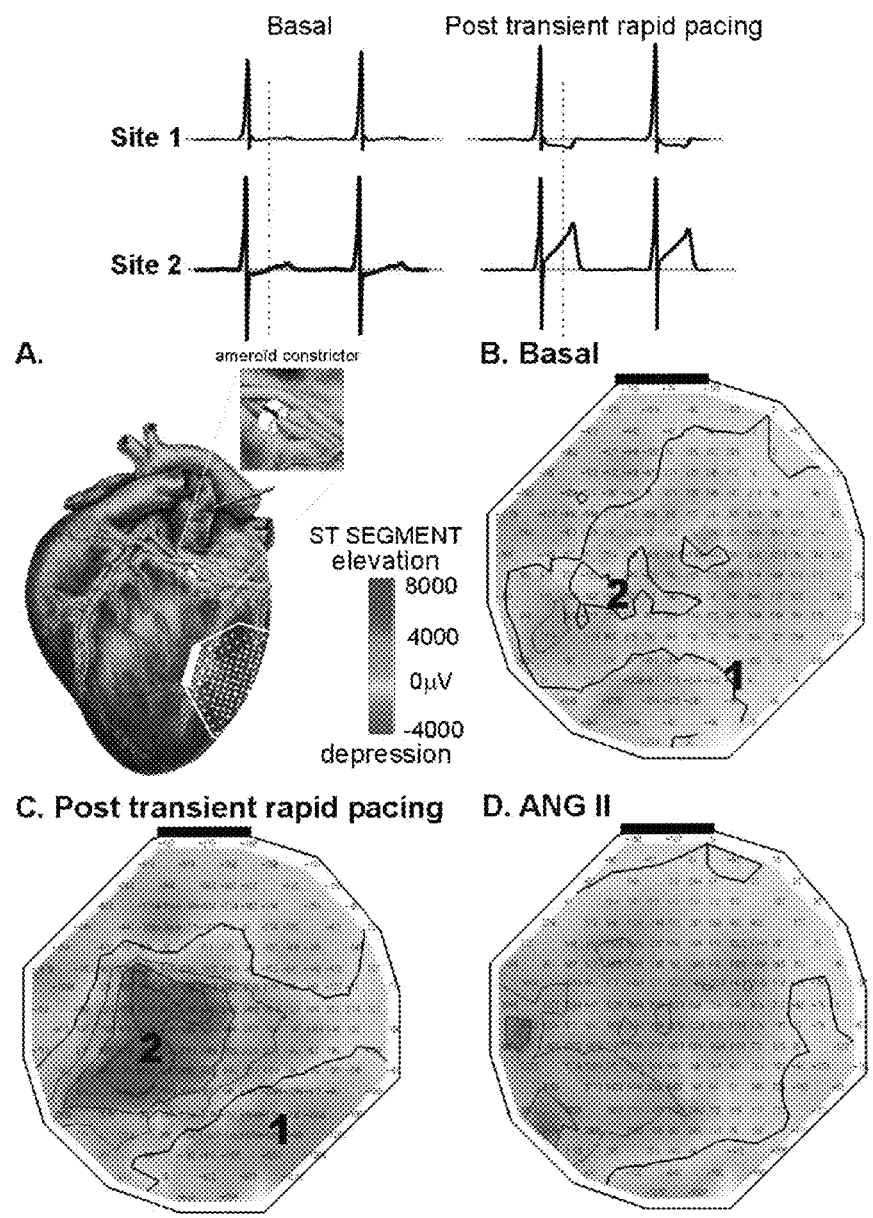
FIG. 6 shows that chronic myocardial ischemia is induced by placement of an ameroid constrictor on the left circumflex (LCx) artery 4 weeks previously (panel A). Under basal conditions, electrograms display slight ST segment displacement (panel B). Transient rapid ventricular pacing (240/min for 1 min), used to increase myocardial $O_2$ demand, precipitates ischemic episodes. In the first beats following rapid pacing, ST segment displacement is inhomogeneously augmented in the LCx territory. Marked ST segment depression (−2 to −6 mV) occurs in some areas, whereas ST elevation (+2 to +15 mV) develops in others (panel C). ST segment changes were also induced by ANG II when administered to RAGP neurons via the right coronary artery proximal to branching of the SA node artery (40 μg/min for 2 min). Note that the ST changes, induced by ANG II, occurred at the apical margin of the plaque electrode, i.e., at the periphery of the LCx territory (Panel D). In contrast, the changes induced by transient rapid pacing occurred at a more central location in the LCx territory (panel C).
Figure 7:
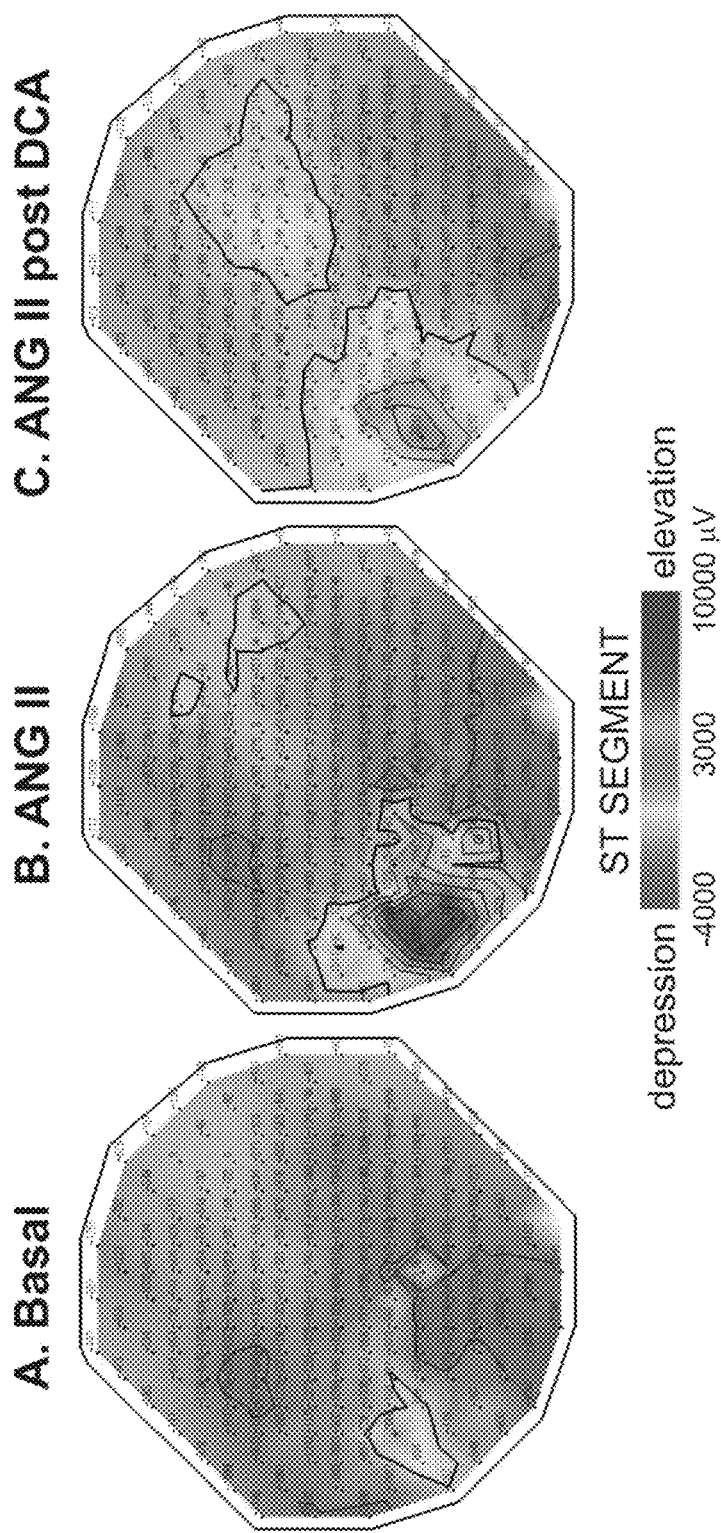
FIG. 7 shows ST segment changes were induced by angiotensin II (ANG II) administered to RAGP neurons via the right coronary artery proximal to branching of the SA node artery (40 μg/min for 2 min). Note that the ST changes occurred at the apical margin of the plaque electrode (panel B). Thus, the ST segment changes are caused by direct or indirect activation of ganglionated plexus neurons that project efferent axons to the specific ventricular areas in which the changes occurred. Moreover, the ANG II effects are attenuated by DCA (panel C), showing that such ventricular events can be influenced by interactions between intrinsic cardiac and spinal neurons.

Functional Remodeling of the Intrinsic Cardiac Nervous System in Response to Chronic Myocardial Ischemia FIGS. 6 and 7 summarize the changes induced in baseline electrophysiology and in the neural control of cardiac electrical function in response to chronic myocardial ischemia produced by chronic placement of an ameroid constrictor on the left circumflex artery. This constrictor produces a progressive occlusion of the artery with induction of collateral blood vessels and does not produce muscle necrosis or scar formation.

Figure 8A:
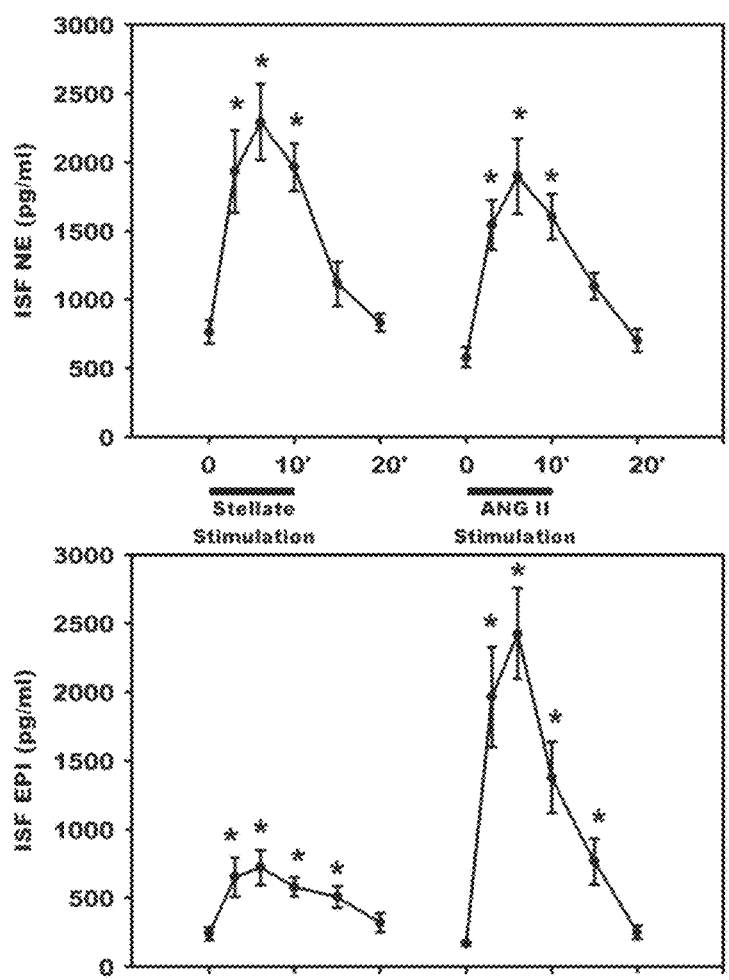
Figure 8C:
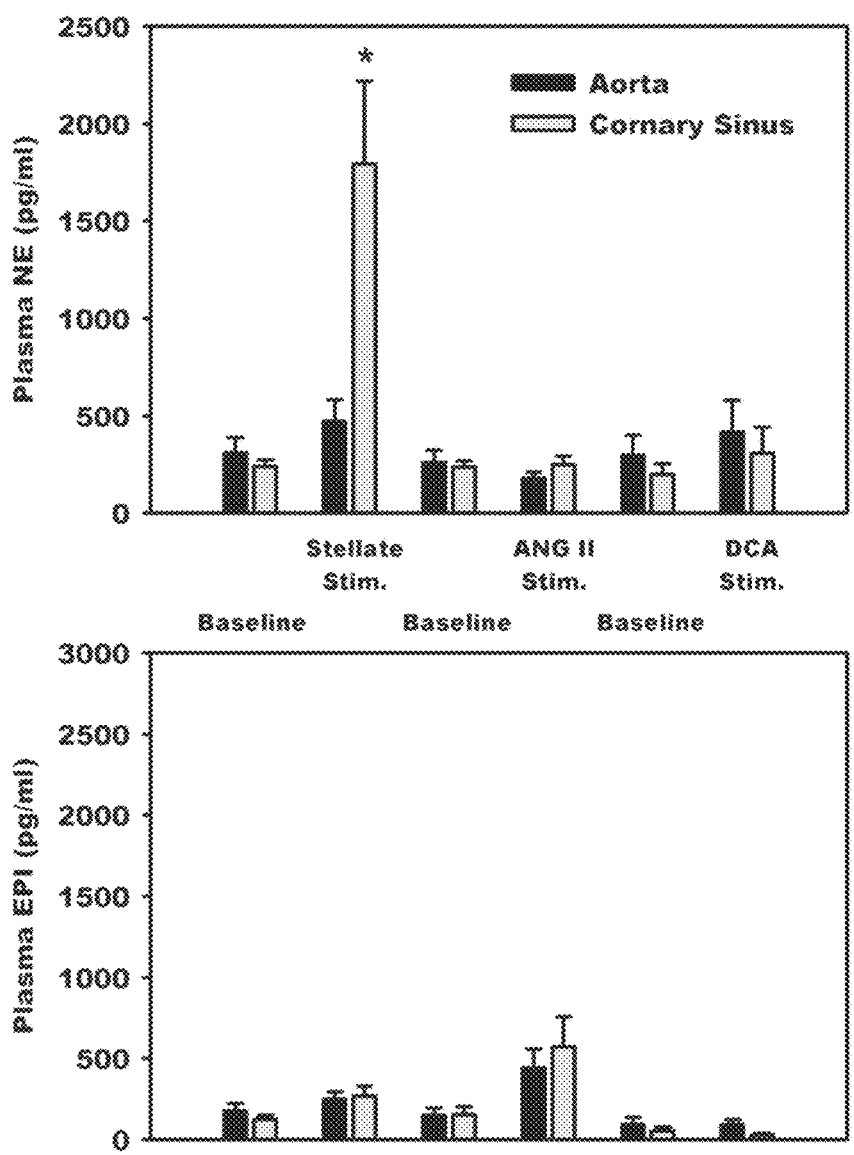

Differential Control of Neurotransmitter Release within the Cardiac Interstitium Exogenous administration of ANG II into the blood supply for the right atrial ganglionated plexus increased NE concentration in the cardiac interstitial fluid (ISF) to the same extent as achieved during electrical stimulation of the stellate ganglia (FIG. 8A) in the anesthetized dog. LV dP/dt correlated with ISF NE release. However, NE spillover into the coronary sinus occurred only during sympathetic efferent neuronal stimulation (FIG. 8C). ISF EPI levels increased moderately with stellate stimulation and to levels equal to NE release with ANG II stimulation. This differential release of catecholamines from cardiac nerves occurred in spite of a 40-fold higher NE compared to EPI content in the dog LV myocardium (237±33 vs. 6.4±1.0 ng/g). Neither stellate nor ANG II stimulation evoked EPI spillover into the coronary sinus. Dorsal cord activation (FIG. 8B) evoked a release of EPI into the ISF equivalent to stellate stimulation, but with only a modest increase in ISF NE. These data illustrate the potential for differential neural release of catecholamines within the heart depending on how efferent outflows are activated and underscore the importance of simultaneous measurements of ISF and transcardiac release in evaluation of the neural control of regional cardiac function.

Electrophysiological Properties of In Vitro Cardiac Ganglia

Figure 9:
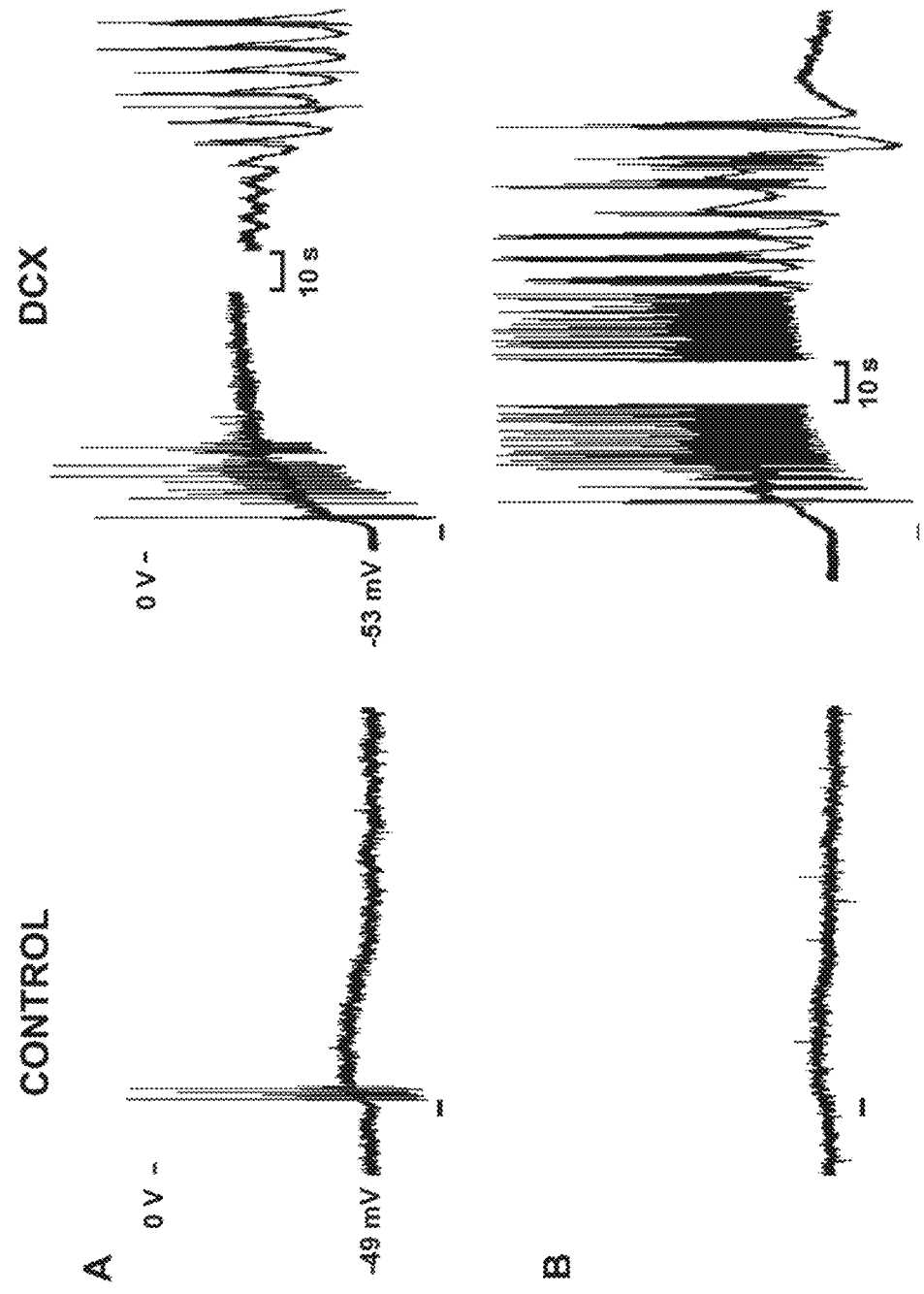
FIG. 9 shows the effects of acetylcholine (ACh) on canine intrinsic cardiac neurons obtained from sham control (CONTROL) and from hearts where all extracardiac nerve connections to the heart were interrupted 3 weeks previously (DCX). The horizontal bar under the traces indicates application of a 10 ms pulse of ACh (1 mM) from the tip of a pipette placed near the ganglion. A, CONTROL. ACh depolarized a control intrinsic cardiac neuron, evoking a short burst of APs at the start of depolarization. DCX. ACh depolarized the chronically decentralized neuron more than the control one, evoking a longer lasting burst of APs. During the repolarization phase, the membrane potential began to oscillate with APs being discharged on oscillatory peaks. B. Hexamethonium (100 μM for 5 min in perfusate) reduced the amplitude of ACh-induced depolarization relative to the control state; no APs were generated. DCX. Hexamethonium reduced the amplitude of ACh-induced depolarization; AP discharge was facilitated during plateau phase of response. The bursting of activity is reflective of the enhanced muscarinic receptor-mediated responses of these neurons.
Figure 10:
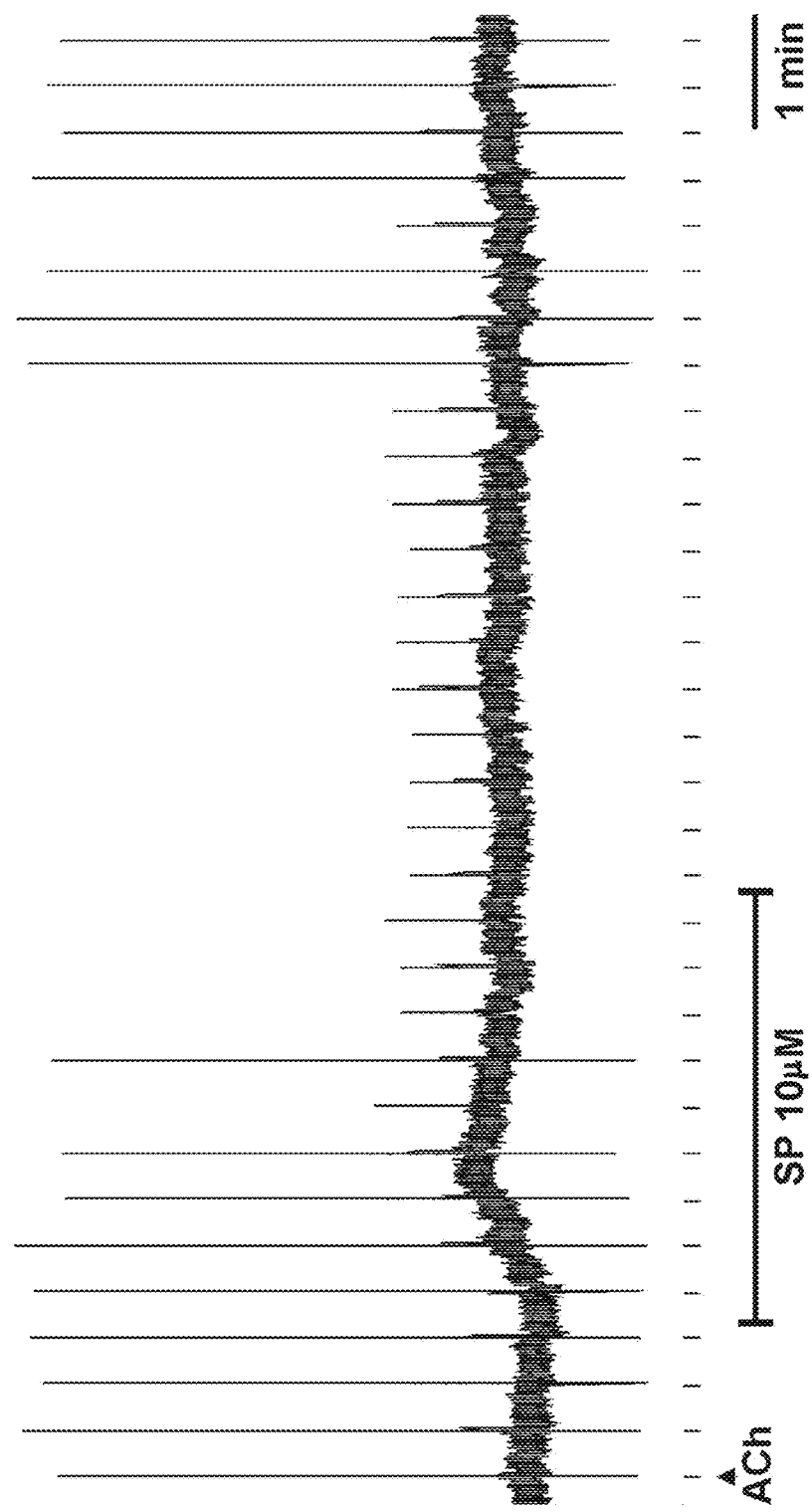
FIG. 10 shows inhibition of ACh-evoked responses by substance P (SP). Top trace shows intracellular recording from an intracardiac neuron and bottom marks indicate times when 28 ms puffs of ACh (10 mM) were given by local pressure injection. Local application of ACh evoked action potentials. These ACh evoked potentials were blocked during bath application of 10 µM substance P (see horizontal bar).

Disruption of nerve projections to or within the intrinsic cardiac nervous (ICN) system is associated with alterations in the passive and active properties of the cardiac neurons. chronic interruption of the extrinsic nerve inputs to the ICN has been shown to produce changes in membrane properties that lead to increased network excitability within this ganglionated plexus. Intrinsic cardiac neurons remain responsive to cholinergic synaptic inputs. The cholinergic receptor systems are differentially affected by disruption of nerve inputs to the ICN, with muscarinic responsiveness being enhanced (FIG. 9). Non-cholinergic neurotransmitters can modulate the activity of these neurons. FIG. 10 illustrates the interaction between acetylcholine and the peptide, substance P.

Quantification of the Innervation Profile for the Canine Heart

Data indicate that the progression of cardiac disease is associated with myocyte and neural remodeling. The neural remodeling likely includes degenerative and regenerative aspects. The net result is the potential for heterogeneous innervation to various regions of the heart. Chen et al. have therefore proposed the "nerve sprouting hypothesis of sudden cardiac death". As illustrated in FIG. 11 by using immunohistochemical techniques, characterization of innervation density (panel B) and types of fibers (panel A) within ganglia and cardiac tissues has been accomplished.

Interactions within the intrinsic cardiac nervous system depend in large part on common shared afferent inputs and/or interconnections mediated via local circuit neurons. The degree of coordination between aggregates of intrinsic cardiac neurons is influenced by proximity and the activation state of afferent inputs. In basal states, the degree of coherence of activity within a single cardiac ganglia waxes and wanes with a periodicity of approximately 20-30 sec. In response to enhanced neuronal activity, evoked during activation of their associated sensory inputs, that coherence increases. For neurons contained within different intrinsic cardiac ganglia, lesser degrees of coherence of basal activity between them, but this coherence increases during stimulation of afferent inputs owing to common shared inputs between them.

There are two distinct classes of sensory input affecting ICN activity: a phasic input, whose influence is short-lived and subserves rapid feedback processes within the ICN and a dynamic input whose influence is determined by the context/history of its activation and whose influence on ICN activity is long-lived. Mechano-sensitive neurites subserve the phasic inputs and chemo-sensitive neurites subserve the neural "memory".

Myocardial ischemia and infarction induce substantial changes in the intrathoracic nerve networks and their reflex control of regional cardiac function including protection and stabilization of electrical activity of the heart. Chronic myocardial ischemia induces a heterogeneous distribution of efferent projections to cardiac end-effectors. Heterogeneous distribution of sympathetic fibers to the left ventricle results in similar heterogeneous release of catecholamines into the interstitial space during stimulation of the efferent nerves. Myocardial ischemia alters the neurochemical profile of that innervation, with differential increases in neuropeptide content within subsets of neurons contained within the intrinsic cardiac nervous system. The evolution of cardiac pathology is associated with disruptions of the intrinsic cardiac nervous system and its ability to process afferent information and such changes are more evident in the CMVPG than the RAGP intrinsic cardiac ganglia. Animals that exhibit indices of higher vagal tone (higher baroreflex sensitivity and higher heart rate variability) demonstrate lesser degrees of ischemic-induced neural remodeling.

DCA can exert long-term modulation of the activities within the intrinsic cardiac nervous system. While initial studies indicate that catecholamines are released in response to DCA, it is anticipated that DCA also will activate sensory afferent fibers antidromically such that endorphins or neuropeptides such as calcitonin gene-related peptide or substance P are locally released in the intrinsic cardiac ganglia and myocardium. Opiates and neuropeptides can also influence the intrinsic cardiac neurons. DCA also suppresses intrinsic cardiac adrenergic as well as local circuit neurons via altered sympathetic efferent preganglionic neuronal input. Activation of sympathetic efferent preganglionic axons suppresses many intrathoracic reflexes that are involved in cardiac regulation. Thus these neuro-suppressor effects may be due, in part, to activation of inhibitory synapses within intrinsic ganglia.

Heterogeneous alterations within the intrinsic cardiac ganglia or at the end-terminus of the autonomic innervation to the ischemic myocardium are major contributors to the increased incidence of sudden cardiac death in patients with coronary artery disease. Chronic DCA ameliorates ischemia-induced remodeling within the intrinsic cardiac nervous system and thereby reduces the heterogeneous neural substrate that predisposes the susceptible animals to ventricular arrhythmias and sudden cardiac death.

Control of regional cardiac electrical and mechanical function is dependent upon varied neural inputs from intrathoracic autonomic ganglia, the spinal cord and brainstem, as well as by circulating neurohumoral agents. Neural control of the heart is dependent upon the coordination of activity generated by neurons within intrathoracic autonomic ganglia and the CNS. The hierarchy of nested feedback loops therein provides precise beat-to-beat control over regional cardiac function. Within the hierarchy of intrathoracic ganglia and nerve interconnections, complex processing takes place that involves the summation of preganglionic inputs from central neurons with those derived from cardiopulmonary sensory inputs.

Excessive activation of the intrathoracic cardiac efferent nervous system can provoke cardiac arrhythmias, as can myocardial ischemia. These maladaptations likely involve changes within the cardiac nervous system in addition to alterations in cardiomyocyte function. Differential adaptations of cardiomyocyte ion channels (e.g., IK and ICa) and intercellular connections during the progression of cardiac disease have been termed "electrical remodeling." Recent data indicates that neurohumoral control mechanisms likewise reorganize during progression into certain cardiac diseases and are referred to as "neurohumoral remodeling."

Changes in autonomic outflow accompany and influence the progression of cardiac disease. Sympathetic efferent neuronal activation contributes to sudden cardiac death in patients with ischemic as well as non-ischemic heart disease. The ATRAMI study demonstrates that baroreflex sensitivity and heart rate variability predict risk for cardiovascular mortality and myocardial infarction. Electrical stimulation of vagal efferent neurons suppresses the tendency to ventricular fibrillation formation in dogs with depressed vagal reflex activity as measured by baroreflex sensitivity. Yet, pharmacological agents that increase vagal efferent neuronal tone, such as a low-dose scopolamine, do not confer similar degrees of protection.

The mechanism(s) whereby activation of sympathetic efferent neurons and/or withdrawal of parasympathetic efferent neuronal tone increase the risk for sudden death are not clear. However, post-infarction heterogeneous remodeling of cardiac innervation, including extracardiac sympathetic and intrinsic cardiac efferent neural elements, likely contributes to the resultant cardiac electrical instability. The present disclosure outlines the evolution of neural remodeling associated with chronic myocardial ischemia and infarction and thus provides a stepping off point for the development of treatments for cardiac pathologies utilizing SCS or DCA.

After decades of progress, improvement in the management of cardiac arrhythmias appears to have leveled off. The problem of sudden cardiac death occurring as the result of an initial arrhythmic event has not been addressed (except perhaps through palliative public health strategies which include public access defibrillators, PAD). This state of affairs is due, in part, to the fact that key pieces of information regarding cardiac arrhythmia formation are still missing, including the ability to identify the apparently normal individual at risk before an event occurs. While changes in myocardial electrical events have been well characterized in the diseased heart, information concerning the complex neuronal organization regulating cardiac rhythm remains limited. The comprehensive present disclosure which includes the knowledge of the complex processing which occurs within the intrathoracic nervous system, as well as between peripheral and central cardiovascular neurons, provides a basis for understanding the role that the cardiac nervous system plays in regulating the electrical behavior of not only the normal heart, but the diseased heart as well, thus providing for novel therapeutic approaches for the effective treatment of cardiac arrhythmias, sudden cardiac death or syncope of cardiac origin by targeting discrete populations of neurons regulating regional cardiac behavior.

Control of regional cardiac function is dependent upon properties intrinsic to cardiac electrical and mechanical tissues as modulated by neuronal reflexes arising at the level of the intrinsic cardiac and intrathoracic extracardiac nervous systems, in addition to well-known spinal cord and brainstem reflexes. The proper function of this cardiac neuronal hierarchy is ultimately dependent on ongoing cardiovascular sensory and spinal cord neuronal inputs. The synergism of function within the cardiac autonomic hierarchy and cardiac myocytes results in a finely balanced, rapidly responsive control system that is continuously being upgraded to maintain adequate cardiac output. As outlined hereinabove, the intrinsic cardiac ganglia form the principal final common pathway for autonomic modulation of regional cardiac function. Maintenance of cardiac output depends not only on the Frank-Starling mechanism and circulating catecholamines, but also on inputs from this nervous system. Disruptions of the sensory inputs to the hierarchy of autonomic neurons regulating the heart due to alterations in the mechanical and/or chemical milieu of the heart can be associated with compromised control of the heart.

Anatomy and Function of the Intrathoracic Cardiac Nervous System (Intrinsic Cardiac Nervous System)

Divergent populations of cardiac neurons within different intrathoracic ganglia interact on an ongoing basis to maintain adequate cardiac output, requiring little ongoing input from spinal cord neurons. neurons in this hierarchy interact to regulate normal cardiac function on a beat-to-beat basis. The development of novel strategies to manage cardiac disease necessitates not only a thorough understanding of the processing of information arising from cardiac and major intrathoracic vascular sensory neurites, but also inputs from central neurons. Neurons in the spinal control exert preferential control over such intrathoracic neuronal processing of cardiac sensory information.

Human studies have shown that stimulation of the dorsal T1-T2 segments of the spinal cord suppresses angina pectoris (sensory information arising from the heart) without masking awareness of acute myocardial ischemic episodes. The mechanisms whereby activation of the dorsal aspect of the cranial thoracic spinal cord produces improved cardiac function and reduces symptoms of the ischemic myocardium are not currently understood. The experiments and resulting data from the present disclosure show that the anti-anginal and cardiac stabilization effects of such spinal cord modulation are mediated via stabilization of the intrathoracic nervous system, especially its intrinsic cardiac component. Neural control of cardiac function resides in the network of nested feedback loops made up of the intrinsic cardiac nervous system, extracardiac intrathoracic autonomic ganglia, the spinal cord and brainstem. Within this hierarchy, the intrinsic cardiac nervous system functions as a distributive processor at the level of the target organ. The redundancy of function and non-coupled behavior displayed by neurons in intrathoracic extracardiac and intrinsic cardiac ganglia minimizes the dependency for such control on a single population of peripheral autonomic neurons. On the other hand, network interactions occurring within the intrinsic cardiac nervous system integrate parasympathetic and sympathetic efferent outflow with cardiovascular afferent feedback to modify cardiac rate and regional contractile force throughout each cardiac cycle. Thus, neural control of cardiac function resides in the network of nested feedback loops made up of the intrinsic cardiac nervous system as well as the extracardiac intrathoracic nervous system, spinal cord and brainstem (FIG. 1).

The redundancy of function and non-coupled behavior displayed by neurons in intrathoracic extracardiac and intrinsic cardiac ganglia minimizes the dependency for such control on a single population of peripheral autonomic neurons. Furthermore, network interactions occurring within the intrinsic cardiac nervous system integrate parasympathetic and sympathetic efferent outflow with afferent feedback to modify cardiac rate and regional contractile force throughout each cardiac cycle.

The Intrinsic Cardiac Nervous System

The intrinsic cardiac nervous system has been classically considered to contain only parasympathetic efferent postganglionic neurons that receive inputs from medullary parasympathetic efferent preganglionic neurons. As such, intrinsic cardiac ganglia are viewed as simple relay stations and major autonomic neuronal control of the heart is purported to reside solely in the brainstem and spinal cord. However, current data indicates that centripetal as well as centrifugal processing occurs within the mammalian intrathoracic nervous system. This involves afferent neurons, local circuit neurons (i.e., neurons that interconnect neurons within one ganglion and neurons in different intrathoracic ganglia), as well as sympathetic and parasympathetic efferent postganglionic neurons. The divergent populations of neurons within the intrinsic cardiac nervous are influenced by spinal cord neurons on an ongoing basis in the maintenance of adequate cardiac output. FIG. 1 provides an outline for the putative types of neurons and their interconnectivity within the cardiac neuronal hierarchy.

The development of novel therapeutic strategies to manage abnormal cardiac states necessitates a thorough understanding of not only of the processing of information arising from sensory neurites in various regions of the heart and great thoracic vessels, but how spinal control neurons exert preferential control over the intrathoracic cardiac nervous system with particular reference to its target organ. Similarly, intrathoracic extracardiac sympathetic ganglia have been thought to act solely as efferent relay stations for sympathetic efferent projections to the heart. However, recent anatomical and functional data indicate the presence of the multiple neuronal subtypes within the intrinsic cardiac nervous system. The intrathoracic nervous system, including its intrinsic cardiac component, is made up of different neuronal subtypes. These include afferent, local circuit as well as adrenergic and cholinergic efferent postganglionic neurons. These neurons form the intrathoracic component of the central and peripheral neuronal feedback loops that regulate regional cardiodynamics on a beat-to-beat basis.

The intrinsic cardiac nervous system consists of multiple aggregates of neurons and associated neural interconnections, localized to discrete atrial and ventricular regions. Among these distinct ganglionated plexuses, preferential control of specific cardiac functions has been identified. For example, right atrial ganglionated plexus (RAGP) neurons have been associated with primary, but not exclusive, control of SA nodal function and inferior vena cava-inferior atrial ganglionated plexus neurons primarily, but not exclusively, with control of AV nodal function. One population of intrinsic cardiac neurons, the parasympathetic postganglionic ones, receives direct inputs from medullary parasympathetic preganglionic neurons. Another population, adrenergic efferent ones, receives inputs from more centrally located neurons in intrathoracic ganglia and the spinal cord. That ventricular sensory neurites continue to influence the activity generated by neurons on the heart following chronic decentralization of the intrinsic cardiac nervous system has been interpreted as indicating that the somata of afferent neurons are located within the intrinsic cardiac nervous system, some of which project axons to central neurons. This latter concept has received anatomical confirmation. Intrinsic local circuit neurons interconnect cardiac afferent to efferent neurons that innervate each region of the heart.

The Intrathoracic Extracardiac Nervous System

Neurons in intrathoracic ganglia, including those on the heart, receive constant inputs not only from spinal cord neurons, but also from cardiac afferent neurons to modulate cardiac efferent neurons. The activity generated by most intrinsic cardiac neurons increases markedly in the presence of focal ventricular ischemia. Furthermore, excessive activation of limited populations of intrinsic cardiac neurons induces cardiac dysrhythmias that lead to ventricular fibrillation, even in normally perfused hearts. Therapies that act to stabilize such heterogeneous evoked activities within cardiac reflex control circuits have obvious clinical importance. Proper information exchange among the intrathoracic components of the cardiac nervous system act in concert to stabilize the electrical and mechanical behavior of the heart, particularly in the presence of focal ventricular ischemia. Thus, use of SCS or DCA is a means to stabilize the heart prior or post ischemia. An object of the present disclosure is to provide such treatment methodologies.

Consistent coherence of activity generated by differing populations of neurons is indicative of principal, direct synaptic interconnections between them or, conversely, the sharing by such neurons of common inputs. Such relationships have been identified among medullary and spinal cord sympathetic efferent preganglionic neurons, as well as among different populations of sympathetic efferent preganglionic neurons. Different populations of neurons, distributed spatially within the intrathoracic cardiac nervous system, respond to cardiac perturbations in a coordinate fashion. If neurons in one part of this neuronal network respond to inputs from a single region of the heart, such as the mechanosensory neurites associated with a right ventricular ventral papillary muscle, then the potential for imbalance within the different populations of neurons regulating various cardiac regions might occur and, thus, its neurons would display little coherence of activity. In other words, relatively low levels of specific inputs on a spatial scale to the intrathoracic cardiac nervous system would result in low coherence among its various neuronal components. On the other hand, excessive input to this spatially distributed nervous system would destabilize it, leading to cardiac arrhythmia formation, etc.

Interactions Among Intrathoracic Extracardiac and Intrinsic Cardiac Neurons

One must know how neurons in intrinsic cardiac versus intrathoracic extracardiac ganglia interact to regulate regional contractile function in order to understand not only the complexity of cardiac control, but also how the cardiac neuroaxis can be targeted therapeutically to manage specific cardiac disease entities. Over the past 30 years studies of the anatomy and function of the peripheral cardiac nervous system have taken place, focusing during the last decade on its intrinsic cardiac component. The classical view of the autonomic nervous system presumes that its intrinsic cardiac component comprises a parasympathetic efferent neuronal relay station in which medullary preganglionic neurons synapse with parasympathetic efferent postganglionic neurons therein. In such a concept, the latter neurons project to end effectors on the heart with little or no integrative capabilities occurring therein. Similarly, intrathoracic paravertebral ganglia have been thought to represent synaptic stations for sympathetic efferent postganglionic neurons controlling the heart.

The intrinsic cardiac nervous system functions, according to the present disclosure, as a distributive processor at the level of the target organ. The redundancy of function and non-coupled behavior displayed by neurons within intrathoracic extracardiac and intrinsic cardiac ganglia minimizes the dependency for such control on a single population of peripheral autonomic neurons. In that regard, network interactions occurring at the level of the heart integrate parasympathetic and sympathetic efferent inputs with local afferent feedback to modify cardiac rate and regional contractile force throughout each cardiac cycle. A recent editorial by David Lathrop and Pete Spooner of the NIH highlights the potential clinical relevance of altered processing of information by these populations of neurons such that a lack of coordination of data exchange within the cardiac neuronal axis may lead to the genesis of cardiac arrhythmias. Hence the importance of determining how neurons in intrathoracic extracardiac and intrinsic cardiac ganglia interact in the maintenance of adequate cardiac output.

The different populations of neurons distributed spatially within the intrathoracic cardiac nervous system respond to cardiac perturbations in a complex fashion. Neurons in intrathoracic extracardiac ganglia do not respond to cardiac perturbations in a fashion similar to that displayed by intrinsic cardiac ones. Consistent coherence of activity generated by differing populations of neurons has been identified among medullary and spinal cord sympathetic efferent preganglionic neurons, as well as among different populations of sympathetic efferent preganglionic neurons. A relatively low level of inputs on a spatial scale to one population of intrathoracic cardiac neurons results in low coherence among its components. In contrast, excessive input to this spatially distributed nervous system destabilizes it, leading for instance to cardiac arrhythmia formation. Since neurons in one part of the intrathoracic neuronal network respond solely to inputs from a single region of the heart, such as from mechanosensory neurites in a right ventricular ventral papillary muscle, then the potential for imbalance within the different populations of neurons in various levels of the intrathoracic neuronal hierarchy arises.

Ultimately, the outflows of efferent neuronal signals to the various regions of the heart depend to a large extent on the direct or indirect inputs they receive from cardiac and major intrathoracic vascular sensory neurites in addition to pulmonary mechanosensory neurites. The redundancy of function and non-coupled behavior displayed by neurons in intrathoracic extracardiac and intrinsic cardiac ganglia minimizes the dependency for regional cardiac control on a single population of intrathoracic neurons. This may be particularly relevant with respect to supporting the output of the ischemic heart. In that regard, network interactions occurring among intrathoracic extracardiac and intrinsic cardiac neurons secondary to inputs from cardiovascular afferent neurons involve local circuit neurons feeding information foreword to cardiac parasympathetic and sympathetic efferent neurons. These network interactions are under the constant influence of spinal cord neurons Cardiac Afferent Neurons Overview of Cardiac Sensory Neuronal Transduction.

It has been known for some time that cardiac sensory neurites (nerve endings) are associated with somata located in ganglia relatively distant from the heart, nodose and dorsal root ganglia. It has recently become evident that cardiac sensory neurites are also associated with somata located in intrathoracic ganglia, including those on the heart. The relative distance between these sensory neurites and their associated somata represents a major determinant of their function. The somata of many cardiac afferent neurons located near to or on the target organ display high frequency (phasic) activity that directly affects target organ efferent neurons (TABLE I). In this manner, high fidelity information content can exert rapid control over efferent neurons adjacent to or on the heart that modulate regional contractility. In contrast, cardiac afferent neuronal somata located relatively distant from their sensory neurites (i.e., in nodose or dorsal root ganglia) are, of necessity, involved in longer latency influences on second order neurons in the cardiac neuroaxis. These relatively distant cardiac afferent neurons, as such, are involved in relatively long latency cardio-cardiac reflexes, being spatially removed from the target organ they display memory. A division of cardiac sensory neuronal function into two broad, functional categories can be based on spatially derived cardiac sensory transduction (TABLE I). It should be noted that some cardiac sensory neurons within dorsal root ganglia generate high frequency phasic activity, particularly when their sensory neurites are exposed to increasing concentrations of local chemicals.

That two broad categories of cardiac afferent neurons exist (TABLE I) indicates unique transduction capabilities such that cardiac information provided to second order cardiac neuroaxis neurons depends not only on the location of their sensory neurites, but on the location of their somata. The sensory information transduced by fast responding cardiac afferent neurons, impinging as it does directly on cardiac motor neurons, is one of the primary determinants of the input function to cardiac efferent neurons that coordinate regional cardiac behavior. Fast responding cardiac sensory neurons normally generate relatively high frequency (10-100 Hz) activity patterns reflective of regional cardiodynamics. Slow responding cardiac afferent neurons generally transduce alterations primarily in the local chemical milieu and, thus, by their nature are generally not responsive to regional alterations that occur on a short time scale. During physiological states, they generate tonic activity at lower frequencies (0.1-1 Hz).

TABLE I

Cardiac afferent neuronal function

| Fast responding afferent neurons | Slow responding afferent neurons |
|---|---|
| Mechanosensory specific | Multimodal (mechanical/chemical) |
| Activity related to local mechanical events | Not responsive to instantaneous events |
| High frequency, phasic (non-tonic) activity | Tonic, low frequency activity |
| High fidelity signals | Noisy signals that limit resolution |
| Noise free transduction | Requires noise for signal transduction |
| Limited memory | Memory capability (affected by past events) |
| Soma located primarily on or near the heart | Soma primarily in ganglia distant from the heart |
| Primarily inputs to short control loops | Primarily inputs to longer control loops |

The sensory neurites associated with intrinsic afferent neuronal somata are located in atrial and ventricular tissues, as well as the adventitia of major coronary arteries. The sensory neurites associated with the somata of afferent neurons in intrathoracic extracardiac ganglia are concentrated in the same cardiac regions, in addition to being found around the origins of vena cava and on the thoracic aorta. Cardiovascular afferent neurons within the thorax provide feed-forward information to efferent neurons in intrathoracic ganglia, some via local circuit neurons. Those in the nodose ganglion influence medullary nucleus tractus solatarius neurons, while those in dorsal root ganglia influence spinal cord neurons. As discussed hereinabove, the varied transduction properties displayed by cardiac afferent neurons in nodose, dorsal root and intrathoracic ganglia reflect to a considerable extent the anatomical location of their somata, i.e., the distance between their somata and associated sensory neurites. Cardiac afferent neurons with somata close to or on the heart influence cardiac efferent neurons to initiate short-loop reflexes with short latencies of activation while those located in nodose ganglia initiate longer latency reflexes. That is why cardiac afferent neurons in intrathoracic ganglia display different transduction capabilities than those in dorsal root and nodose ganglia.

Afferent axons arising from cardiac or intrathoracic vascular sensory neurites vary in diameter (degree of myelination), according to the location of the cardiopulmonary nerve in which they course. For instance, most aortic mechanosensory neurites are associated with Ad axons, most of which are located in the intrathoracic dorsal cardiopulmonary nerve. Many ventricular sensory neurites are associated with c class axons. On the other hand, carotid artery mechanosensory neurites associated with afferent axons are divisible into the A🅂 and C fiber categories, each population displaying unique transduction properties.

Function.

The majority of cardiac sensory neurons, particularly those located distant from the heart, generate sporadic, low frequency activity. As the activity generated by the most cardiac afferent neurons is of low frequency (i.e., 0.01-0.1 Hz), information content cannot reside in the interspike intervals of activity. Rather, it resides primarily in their average activity over time unless their activity becomes entrained to cardiodynamics in the presence of increased sensory neurite chemical milieu. Information transduced by multimodal sensory neurites associated with each axon connected to individual cardiac afferent neuronal somata also depends on their cardiac spatial distribution. Arrays of atrial sensory neurites are concentrated in the region of the sinoatrial node (right atrium) and the dorsal aspects of both atria, others are scattered throughout the rest of the atria. Ventricular sensory neurites are concentrated in the outflow tracts of the two ventricles as well as the right and left ventricular papillary muscles. Another concentration of sensory neurites is located in the adventitia on the inner arch of the thoracic aorta.

Intrathoracic cardiac afferent neurons influence (via intrathoracic local circuit neurons) cardiac efferent postganglionic neurons with latencies as short as 40 milliseconds. Nodose ganglion cardiac afferent neurons influence cardiac parasympathetic efferent preganglionic neurons in the medulla via short latency reflexes (75 ms) as well. On the other hand, dorsal root ganglion cardiac afferent neurons influence sympathetic efferent postganglionic neurons via longer latency (100-500 ms) reflexes. Thus, the differing populations of cardiac sensory neurons located at each level of the cardiac neuroaxis not only displaying unique transduction characteristics, but subserve cardio-cardiac reflexes that of necessity differ in latency and form.

Nodose Ganglion Afferent Neurons.

Figure 12:
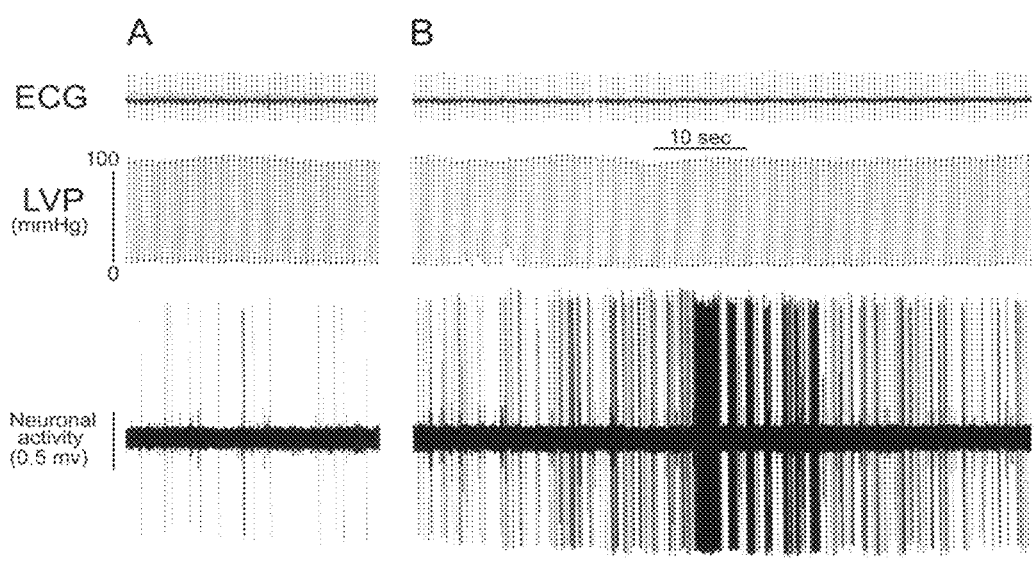
FIG. 12 shows enhancement of the activity generated by a canine nodose ganglion afferent neuron following application of the long acting adenosine agonist CPA (via a 1 cm×1 cm pledget) to the ventral left ventricular epicardium (between panels A & B). Monitored cardiac variables were not affected by this intervention. Panel B was obtained 1 minute after terminating CPA application.

Using neuroanatomical tracing techniques, about 500 somata associated with cardiac sensory neurites have been identified throughout the right and left nodose ganglia. Their axons belong to the A🅂 and c classes, as defined by Erlanger and Gasser. Histochemical evidence indicates that the somata of nodose ganglion afferent neurons express receptors for a variety of neurochemicals, including adenosine, bradykinin and substance P receptors. Most of these cardiac afferent neurons transduce multiple chemicals, including purinergic agents such as adenosine (FIG. 12). Few nodose ganglion cardiac sensory neurons solely transduce alterations in the mechanical milieu of the heart.

Doral Root Ganglion Afferent Neurons.

Despite the widely held opinion that the majority of cardiac afferent neurons are located primarily in left-sided dorsal root ganglia, anatomic evidence indicates that cardiac afferent neurons are distributed relatively equally among right and left dorsal root ganglia from the C6 to the T6 levels of the spinal cord. Afferent neuronal somata lie scattered predominantly, but not exclusively, around the centrally located axons in these ganglia. Over 500 cardiac sensory neurons have been identified anatomically in canine dorsal root ganglia from the $T_1$ to the $T_3$ levels of the spinal cord, ganglia containing up to 50 cardiac afferent neuronal somata. The axons connecting cardiac sensory neurites with somata in dorsal root ganglia belong to the Ad or c classes of axons, each having little bearing on their sensory transduction capabilities.

Intrathoracic Extracardiac Ganglion Afferent Neurons.

Functional evidence indicates the presence of cardiac sensory neuronal somata in stellate, middle cervical and mediastinal ganglia. Axons connecting atrial or ventricular mechanosensory neurites with somata in extracardiac ganglia belong in the Ad class of axons. Those connecting intrathoracic vascular mechanosensory neuritis with somata in intrathoracic extracardiac ganglia belong to Ad class of axons as well. On the other hand, ventricular endocardial mechanosensory neurites connected with somata in intrathoracic ganglia belong to c class axons. Cardiac and aortic chemosensory neurites connected with somata in intrathoracic ganglia also belong to Ad class axons.

Intrinsic Cardiac Ganglion Afferent Neurons.

Unipolar neurons are located throughout atrial and ventricular intrinsic cardiac ganglionated plexuses. Based on anatomical and functional data, the somata of some intrinsic cardiac afferent neurons project axons centrally; the remainder interacting directly with other intrinsic cardiac neurons exclusive of central neuronal inputs. Sensory neurites associated with intrinsic cardiac afferent neurons are located in all four chambers of the heart (particularly in the cranial aspect of the ventricles) are multimodal in nature (transduce mechanical and chemical stimuli). Unfortunately, little is currently known of their transduction capabilities.

Cardiac afferent neurons with sensory neurites located primarily in the atria and the outflow tracts of the ventricles or major intrathoracic vessels initiate short, intermediate and relatively long duration cardiovascular-cardiac reflexes, depending on their multimodal transduction capabilities.

Intrathoracic Extracardiac and Intrinsic Cardiac Ganglionic Interactions

Cardiac sensory input to the multiple nested feedback loops within the intrathoracic cardiac neuronal axis displaying redundancy of function and non-coupled behavior within the different anatomical levels of this hierarchy (FIG. 1) to minimize dependency of regional cardiac control on a single population of neurons. The different populations of cardiac afferent neurons, being capable of transducing multiple stimuli, forms the basis for integrated control of cardiac efferent neurons affecting regional cardiac function. Such control resides from the level of target organ to that of the central nervous system. As mentioned hereinabove, neurons in intrathoracic extracardiac and intrinsic cardiac ganglia exhibit differential reflex control over regional cardiac function that depends in large part on the varied anatomy and function of afferent neurons providing information about the cardiac milieu. This concept is based on the observation that intrathoracic extracardiac and intrinsic cardiac neurons display redundancy of function and non-coupled behavior (FIG. 13), such non-coupled behavior minimizing cardiac dependency on a single population of intrathoracic neurons. Intrathoracic reflexes can exert considerable influence over regional cardiodynamic behavior (11).

Intrathoracic cardiac afferent neurons are multimodal in nature (i.e., responsive to local mechanical and chemical stimuli), transducing a host of chemicals that include ion channel modifying agents (i.e., veratridine; c.f., FIG. 13), $\beta_1$- or $\beta_2$-adrenoceptor agonists, $\alpha_1$- or $\alpha_2$-adrenoceptor agonists, excitatory amino acids, or peptides (c.f., angiotensin II, bradykinin or substance P). The activity generated by populations of intrinsic cardiac local circuit neurons display, as a consequence of such sensory inputs, periodically occurring coupled behavior (cross correlation coefficients of activities that reach, on average, 0.88±0.03; range 0.71-1) for 15-30 seconds periods of time. This coupled activity occurs every 30-50 seconds during basal states, as well as when cardiac afferent neuronal inputs to this neuronal hierarchy increase in response to alterations in the ventricular chemical milieu.

On the other hand, neurons in intrathoracic extracardiac (middle cervical or stellate) and intrinsic cardiac ganglia do not display such function, despite the fact that neurons in intrathoracic extracardiac and intrinsic cardiac ganglia receive inputs from cardiac mechanosensory and chemosensory neurites. That is due in part because neurons in intrathoracic extracardiac ganglia receive many inputs mechanosensory neurites located on the inner arch of the aorta. That some of these neurons are still influenced by cardiac sensory inputs when decentralized from central neurons indicates that intrathoracic cardiac afferent neurons can influence the intrathoracic neuronal hierarchy independent of central neuronal inputs.

Figure 13:
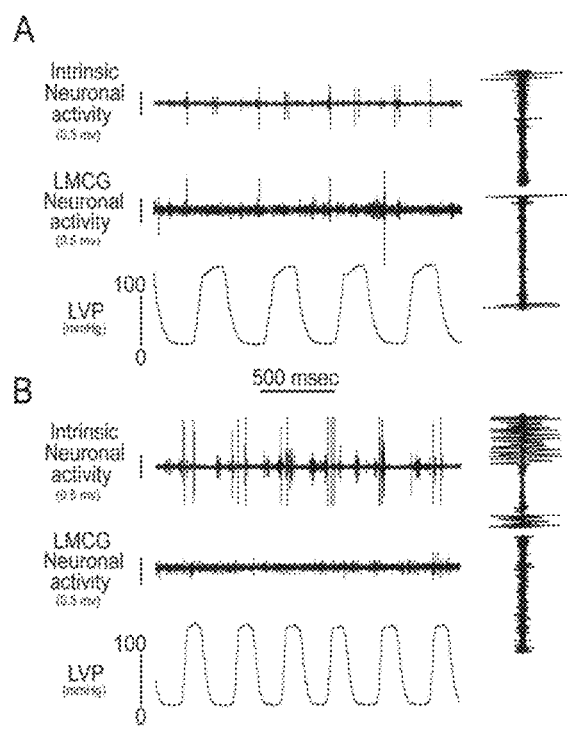
FIG. 13 shows simultaneous recordings of activity generated by intrinsic cardiac (above) and intrathoracic extracardiac (left middle cervical ganglion-LMCG) neurons concomitant with left ventricular sensory inputs induced by epiacrdial application of veratridine. The right hand panels denote XY plots of each activity versus pressure. Note that enhancement of their ventricular sensory inputs depicted in panel B activated one population while suppressing the other. Activities occurred during specific phases of the cardiac cycle (XY plots).

Neurons in intrathoracic extracardiac and intrinsic cardiac ganglia exhibit non-coupled behavior, even when they are mutually entrained to cardiac events by cardiovascular afferent feedback (FIG. 13). This shows a redundancy of cardioregulatory control exerted by the different populations of intrathoracic neurons. That these different populations respond differently to similar cardiac interventions indicates the selective nature of the feedback mechanisms extant in different 'levels' of the intrathoracic neuronal hierarchy FIG. 1. This also implies minimal reliance at any time on one population of peripheral autonomic neurons for the control of regional cardiac behavior. The selective influence exerted by each population of intrathoracic (intrinsic and extrinsic) neurons on regional cardiac function depends in large part on the nature and content of their inputs from cardiac and intrathoracic vascular sensory neurites. Since the sensory information transduced by most cardiac sensory neurons is in the 0.1 Hz range, it is unlikely that meaningful data is represented by interspike intervals during physiological states as such relatively low frequency activity is not coherent. The fact that most of the sensory information they receive is of low frequency content implies that their responsiveness is dependent primarily on average activity rather than instant-to-instant activity change (interspike intervals). Coherent (rhythmic) activity is generated by limited populations of cardiac sensory neurons such as those in dorsal root ganglia. Indeed, excessive sensory neuronal input to spinal cord neurons in the ischemic state may act to destabilize cardiac neuronal hierarchical control of cardiac electrical behavior.

Intrathoracic Synapses

Direct application of neurochemical agonists or selective antagonists has been used to survey receptor subtypes associated with neurons within the intrathoracic cardiac nervous system and to characterize the functional differences of neurons within its various ganglia. Chemical stimulation of specific intrathoracic neurons with low doses of chemicals such as nicotine, neuropeptides, catecholamines, amino acids and purinergic agents can induce changes in their activity. When neuronal changes so induced are of sufficient magnitude, alterations in cardiac pacemaker, conductive and regional contractile function occur. The cardiac responses so induced reflect activation of specific populations of neurons in intrathoracic extracardiac or intrinsic cardiac ganglia as similar application of such neurochemicals to intracardiac axons of passage does not effect neuronal activity or cardiodynamics. In agreement with that, transection of all extrinsic neuronal inputs to the intrathoracic nervous system (acute decentralization) attenuates cardiac responses so elicited. This data indicates the importance of the connectivity of neurons within the thorax with central ones in mediating cardio-cardiac reflexes.

Cholinergic Mechanisms:

Synaptic transmission in cardiac autonomic ganglia has been thought to be principally involved in the release of acetylcholine by presynaptic terminals and subsequent binding of that neurotransmitter to nicotinic cholinergic receptors on postganglionic neurons. In mammals this synaptic junction is not obligatory, indicating that a significant convergence of inputs may be necessary to evoke postganglionic activity. Nicotinic and muscarinic cholinergic agonists and antagonists modify intrinsic cardiac neurons in vitro and in vivo, as well as neurons in intrathoracic extracardiac ganglia. Local application of nicotine to intrinsic cardiac or intrathoracic extracardiac neurons induces alterations in cardiac rate and regional contractile function. Activation of intrinsic cardiac neurons with nicotine induces either augmenter or depressor cardiac effects, depending on the population of neurons so affected. Blockade of nicotinic receptors attenuates, but does not eliminate, these cardiac reflexes. Muscarinic cholinergic blockade attenuates synaptic function within intrathoracic ganglia, as well, indicating that acetylcholine exerts both mediator and modulator effects at synaptic junctions within intrathoracic ganglia.

Noncholinergic Mechanisms:

Blockade of nicotinic cholinergic receptors attenuates, but does not eliminate synaptic transmission within intrathoracic ganglia indicating that non-nicotinic synapses act as primary mediators of synaptic transmission within the intrathoracic nervous system. Anatomical and physiological studies have identified multiple putative neurotransmitters in association with neuronal somata in mammalian intrathoracic extracardiac and intrinsic cardiac ganglia. These chemicals include purinergic agents (adenosine and ATP), alpha- and beta-adrenergic agonists, angiotensin II, bradykinin, calcitonin gene-related peptide, neuropeptide Y, histamine, serotonin, substance P and vasoactive intestinal peptide as well as excitatory and inhibitory amino acids. Many of these putative neurotransmitters arise from neurons whose cell bodies are intrathoracic extracardiac (stellate and middle cervical) ganglia, while other may be synthesized by neurons intrinsic to the heart. Direct application of various putative neurotransmitters adjacent to neurons in intrinsic cardiac or intrathoracic extracardiac ganglia modifies cardiac pacemaker and contractile activities. Such responses presumably reflect varied receptor mediated activation of adjacent neurons and their associated dendrites since when identical concentrations of these neurochemicals are applied directly to intracardiac axons of passage neuronal activity and cardiac indices remain unaffected.

Thus, when taken together, synapses interconnecting intrathoracic afferent, local circuit and efferent neurons utilize a host of neurochemicals in the regulation of regional cardiodynamics, even when disconnected from the influence of central neurons.

Memory Function within the Intrathoracic Nervous System

Cardiovascular-cardiac reflexes exert long-term control over cardiodynamics, including those initiated solely within the intrathoracic neuronal hierarchy. Intrathoracic cardio-cardiac reflexes display different latencies of activation in as much as intrathoracic cardiac afferent neurons influence local circuit neurons in ganglia at different levels of the thorax (intrinsic cardiac, mediastinal, middle cervical and stellate ganglia) following different latencies. The differing populations of cardiac afferent neurons that initiate these varied intrathoracic reflexes display unique transduction characteristics that are suited to the cardio-cardiac reflexes that they sub serve. For instance, intrathoracic cardio-cardiac reflexes have latencies as short as 40 ms, whereas those involving spinal cord neurons have latencies that exceed 450 milliseconds. Thus, the relative distance between cardiac sensory neurites and neuronal somata is a significant determinant of cardio-cardiac reflex latencies they initiate.

Inherent in this issue is the fact that intrathoracic neurons involved have two types of memory: (1) The first type involves non-computational memory displayed by cardiac chemosensory neurons, in as much as the previous status of their transduction behavior is a major determinant of their responsiveness to a chemical stimulus. The slowly varying, long-term transduction capabilities exhibited by cardiac chemosensory neurites is characteristic of passive memory. (2) The second type of memory displayed in the intrathoracic nervous system is represented by active processing of sensory inputs from: (i) cardiovascular afferent neurons and (ii) central efferent preganglionic neurons. This computational memory resides in the network interactions that are dependent on intrathoracic local circuit neurons. Their state dependent memory represents hysteretic computation of cardiovascular sensory information that, along with inputs from central neurons, exerts ongoing control over cardiac efferent neurons. Such computation ability is necessary if a population of neurons is to simultaneously process information arising from many sources—an important characteristic of the intrathoracic nervous system. The presence of such complex information processing within the intrathoracic autonomic nervous system has led to the discovery that this nervous system functions as a distributive processor of centripetal and centrifugal information arising from and going to the heart that, of necessity, requires state-dependent memory.

Memory Displayed by Slow Responding Cardiac Afferent Neurons.

Most of the cardiac afferent neuronal somata located near or on the target organ transduce high frequency (phasic) information directly to target organ efferent neurons that control regional contractile behavior. In this manner, high fidelity information content can exert rapid control over cardiac efferent neurons coordinating regional contractile patterns. On the other hand, the cardiac sensory neurites located anatomically distant from their associated somata (i.e., in nodose and dorsal root ganglia) take longer to influence second order neurons (c.f., neurons in the CNS). These latter cardiac afferent neurons are involved in relatively long latency cardio-cardiac reflexes. Presumably because of that function (lack of necessary short term influences), for the most part they display relatively long term memory function since they transduce slowly varying chemical signals. It should be noted that some intermediary cardiac afferent neurons also generate tonic activity, only generating high frequency, phasic activity when exposed to increasing concentrations of chemicals reflective of their multimodal transduction properties. The passive memory function displayed by these slow responding cardiac sensory neurons resides in the state dependent properties of their cardiac chemosensory neurites. This is also indicative of the fact that chemical excitation of these afferent neurons remains long after removal of the stimulus—yet another form of memory.

Local Circuit Neuronal Memory Function.

It has been postulated that active memory resides in the multi-synaptic processing of cardiac sensory information that takes place within the intrathoracic neuronal hierarchy. This is particular relevant with respect to the processing of cardiopulmonary sensory information by intrathoracic local circuit neurons. It has been determined that memory is displayed by remodeled intrathoracic local circuit neurons following chronic removal of their central neuronal inputs. Short duration (10 msec.) cardiopulmonary sensory inputs to neurons in chronically decentralized intrathoracic ganglia results in the activation of local circuit neurons therein for up to 2 seconds. Such data indicates a memory capacity that lasts for a number of cardiac cycles subsequent to sensory inputs arising during one cardiac cycle.

As there is little direct relationship between sensory inputs and output in the intrathoracic cardiac nervous system, its local circuit neurons act to compute state-dependent information on a beat-to-beat basis. This permits inputs from multiple sources (peripheral cardiovascular afferent neurons and spinal cord efferent neurons) to influence restricted cardiac efferent neuronal outputs to the heart in an efficient manner and over time. Thus, one function of intrathoracic local circuit neurons is key to understanding hysteretic information processing (memory) since their capacity to compute relatively minor sensory input alterations without adapting out represents an important characteristic of this neuronal hierarchy. In such a scenario, local circuit neurons function to reduce 'noise' to ensure restricted (not excessive) output in the presence of multiple sensory inputs.

This processing of cardiovascular sensory information by intrathoracic local circuit neurons accounts for the stability of the control exerted over regional cardiac function during relatively prolonged period of time in normal cardiovascular states. On the one hand, simple state switching among excitatory versus inhibitory neurons in this population would generate oscillatory behavior such as occurs among excitatory and inhibitory neurons in the spinal cord. This would, in fact, lead to instability of function since computational analysis would become deranged and noise reduction capabilities would be lost. On the other, memory function associated with intrathoracic local circuit neurons, driven by ongoing cardiac sensory inputs, ensures stable control over cardiac efferent neuronal outputs. For that reason, hysteretic memory related to the active processing of cardiac sensory information is important for the ultimate stability of cardiac efferent neuronal control.

Current data indicates that passive memory resides in cardiac sensory transduction and active memory in the processing of that information by local circuit neurons within the intrathoracic neuronal hierarchy. Control based memory residing in intrathoracic extracardiac and intrinsic cardiac local circuit neuronal interactions, driven as they are by cardiovascular sensory inputs; it is not a passive process. Neurons in chronically decentralized intrathoracic ganglia also display hysteretic memory. In the situation where there is a loss of inputs from central neurons, 100 millisecond long bursts of sensory information (such as arise from aortic mechanosensory neurites during each cardiac cycle) affect local circuit neurons for up to 3 seconds after their discontinuance. That period of time is sufficient for the next five or six cardiac cycles to be generated.

Thus, events in one cardiac cycle influence regional cardiac behavior throughout a few subsequent cardiac cycles via fed-foreword reflexes residing solely within the intrathoracic nervous system. By utilizing such fed-foreward reflexes, the intrinsic cardiac nervous system can be pre-conditioned through the use of SCS or DCA to thereby "override" quench neuronal signals which would place the heart into a diseased state. Such pre-conditioning may take the form of constant SCS or DCA stimulation; and/or long pulses of SCS or DCA stimulation followed by short or long resting periods. In this manner the intrinsic cardiac nervous system is pre-conditioned to resist ischemic neuronal overloading.

Focal Ventricular Ischemia

Myocardial Ischemia.

The importance of the processing of sensory information arising from the ischemic myocardium by the intrathoracic cardiac nervous system in the maintenance of adequate cardiac output is only now beginning to be appreciated by those of ordinary skill in the art. One of the major challenges to neurocardiology is understanding the response characteristics of each component of the cardiac neuronal hierarchy to myocardial ischemia so that focused neurocardiological strategies can be devised to stabilize cardiac function in such a state. For that reason, one of the objects of the present disclosure is to remodel the heart using SCS or DCA stimulation to combat remodeling that occurs within the intrathoracic cardiac nervous system in the presence of focal ventricular ischemia. The selective nature of the responses elicited by each component of the intrathoracic neuronal hierarchy to myocardial ischemia depends on how each population is affected by the content of their altered cardiac sensory inputs. Neuronal interactions in diseased states are relevant given the fact that pharmacological agents proven for use in treating heart failure (i.e., beta-adrenoceptor or angiotensin II receptor blocking agents) target not only cardiomyocytes directly, but also indirectly by altering their inputs from cardiac efferent neurons secondary to altering the intrathoracic neuronal interactions.

Data also indicates that the cardiac neuronal hierarchy becomes obtunded by a variety of interventions, including multiple transmural laser 'revascularization' therapy or heart failure. Intrathoracic neuronal function also remodels in the presence of focal ventricular ischemia. Given the fact that certain populations of intrathoracic neurons, when activated, can induce ventricular fibrillation even in the normally perfused heart, therapy directed at the intrinsic cardiac nervous system, whether pharmacological or surgical in nature, or through use of SCS or DCA stimulation are of benefit in managing the ischemic heart and one of its sequellae—ventricular arrhythmias.

Activation of the dorsal columns of the cranial thoracic spinal cord results in a suppression of the activity generated by neurons not only on the target organ, but also in middle cervical and stellate ganglia. It is known that neurons in middle cervical and stellate ganglia are under the constant influence of spinal cord neurons such that following their decentralization the activity generated by many of the latter increased upon removal of such control. Furthermore, removal of spinal cord inputs to the intrathoracic extracardiac nervous system results in enhancement of many intrathoracic extracardiac cardio-cardiac reflexes. It has also been shown that excessive activation of spinal cord neurons suppresses the intrinsic cardiac nervous system, i.e., preconditioning the intrinsic cardiac nervous system.

Heart failure has been considered to be primarily a hemodynamic disorder. Only recently has the importance of neurohumoral mechanisms that act to maintain adequate cardiac output in the presence of heart failure become appreciated, particularly with respect to arrhythmia formation. This recognition and other clinically relevant findings have forced a reappraisal of neuronal mechanisms involved in regulating the ischemic myocardium.

Upper cervical neuronal modulation of upper thoracic cell activity and interactions within and between upper cervical and upper thoracic spinal neurons involved in this processing have been examined. More specifically, these experiments have determined that different populations of neurons within and between segments of the spinal cord exhibit coherence and correlation of activity and may, on occasion, act independently. It has been determined that neurons in the upper cervical (C1-C2) spinal cord are organized to process cardiac sensory information and coordinate the interactions between the C1-C2 and the T3-T4 spinal neurons, to thereby determine autonomic outflow to the intrinsic cardiac nervous system. Coupling of neuronal processing fluctuates within and between two cell populations during increased cardiac sensory stimulation. In the present application it is shown that chemical activation of upper cervical neurons modulates the stimulus locked and long lasting responses of thoracic spinal cord neurons to myocardial algogenic chemical stimuli. It has also been demonstrated that cardiac sensory information arising via thoracic sympathetic afferent activity ascends in the spinal cord via propriospinal neurons to influence neurons in the upper cervical spinal cord. In addition, vagal sensory inputs excite neurons in upper cervical spinal segments. Thus, the upper cervical spinal cord is an area that processes cardiac sensory information transduced by afferent somata in nodose and dorsal root ganglia. Based on these experiments and data, it was determined that, within the hierarchy of control that regulates cardiac function (FIG. 1), neurons in C1-C2 spinal cord process cardiac sensory information to coordinate the interactions within and between C1-C2 and T3-T4 spinal neurons and thereby determine autonomic outflow to the intrinsic cardiac nervous system.

Well-established evidence links the autonomic nervous system to life-threatening arrhythmias and cardiovascular mortality. The autonomic imbalance of increased sympathetic activity and reduced vagal activity increases the likelihood for ventricular fibrillation during myocardial ischemia. Clinical studies using various markers of impaired vagal activity support the experimental evidence that this type of autonomic imbalance increases cardiovascular risk. Disease processes may change the balance between the central and peripheral neurons involved in such regulation. For instance, when the activity generated by cardiac sensory neurons becomes abnormal, cardiac function can be affected profoundly. Therefore, a disturbance of the fine balance within the cardiac neuraxis will produce dramatic changes in cardiac efferent neuronal outflow. Within the hierarchy of central neurons that control the heart, complex sensory processing involves spatial and temporal summation of cardiac sensory inputs to affect central preganglionic autonomic efferent neurons that modulate autonomic efferent postganglionic activity, as well as intrathoracic ganglionic reflexes and the intrinsic cardiac nervous system. Experimental studies, as discussed herein, show that pathological processes can change the integrative behavior of the central cardiac neuraxis. For example, arrhythmias generated by occlusion of the coronary artery are significantly decreased after transection of upper thoracic dorsal roots. This observation indicates that the spinal cord receives and processes information that is generated during an ischemic episode. Furthermore, spinal neurons of the upper thoracic segments are sensitive to changes associated with arrhythmias. These changes can occur when cardiac sensory neurites are activated intensely and for long periods when cardiac tissue becomes damaged during regional ventricular ischemia.

Information Processing of Spinal Neurons—Single Cell Analysis

Sympathetic afferents from the heart convey noxious and mechanical, presumably innocuous, information via the dorsal roots primarily in the upper thoracic segments. We herein show that both centrally projecting as well as non-projecting neurons respond to noxious stimuli applied to the heart. We also demonstrate that chemical stimulation of cardiac nociceptors produces either a stimulus-locked or long lasting evoked response of superficial and deep spinal neurons of the upper thoracic spinal cord.

The classical concept of acute cardiac nociception is based on a serial neuronal system that transmits information from cardiac afferents to spinal neurons. The transfer of information is mediated by classical neurotransmitters, such as excitatory amino acids, that lead to membrane potential changes within a time span of milliseconds to seconds. Thus, nociceptive stimulation of cardiac afferents evokes discharge rates of spinal neurons that increase as long as the nociceptors are stimulated. It is generally assumed that impulses of spinal neurons responding to cardiac stimuli constitute a simple renewal process with a very high number of degrees of freedom. Electrophysiological studies show that nociceptive responses of spinal neurons are the basis of mean discharge rates of single neurons. It was further shown that discharge rates are often correlated in a generally linear manner to the intensity of noxious stimulation and antinociception is consequently defined as a reduction in discharge rates of nociceptive neurons.

Multiple Cell Analysis

Under normal, physiological conditions stimuli applied to the heart do not elicit marked changes in cardiac efferent neuronal activity because central neurons suppress excessive cardiac sensory information processing. In the hierarchy of cardiac control, activation of spinal neuronal circuits modulates the intrathoracic cardiac nervous system. Activation of the dorsal columns at the T1-T2 segments significantly reduces the activity generated by the intrinsic cardiac neurons in their basal conditions as well as when activated in the presence of focal ventricular ischemia induced by occluding the left coronary artery. Not only does dorsal column activation modulate the intrinsic cardiac nervous system, but it also modifies the activity of spinal neurons within the T3-T4 segments. In addition, the central nervous system maintains a tonic inhibitory influence over intrathoracic cardiopulmonary-cardiac reflexes. Reflexes mediated through the middle cervical ganglion are increased after decentralization. Thus, disease processes change the balance between the central and peripheral neuronal processing of cardiac sensory information. For instance, when the activity generated by cardiac sensory neurons becomes excessive, e.g., during focal ventricular ischemia, cardiac function can be profoundly affected. Thus, a disturbance of the fine balance within the cardiac neuraxis results in dramatic changes in cardiac efferent neuronal activity. Nests of neural networks in the hierarchy of cardiac control, therefore, appear to interact effectively when an appropriate balance is achieved therein.

Upper Cervical Modulation of the Thoracic Spinal Cord and Heart

Within the hierarchy for cardiac control, neurons of the upper cervical segments modulate information processing in the spinal neurons of the upper thoracic segments. In human studies, spinal cord stimulation of the C1-C2 spinal segments relieves pain symptoms in patients with chronic refractory angina pectoris. Experimental studies disclosed and discussed herein show that spinal cord activation of the upper cervical segments of the spinal cord suppresses the activity of spinal neurons in T3-T4 segments. Furthermore, chemical stimulation with glutamate of cells in the C1-C2 segments also reduces upper thoracic spinal neuronal activity and that chemical stimulation of C1-C2 cells suppresses the activity of lumbosacral spinal neurons. It is especially important to note that this suppression of lumbosacral neuronal activity is sustained even after the spinal cord is transected at the spinomedullary junction. Glutamate was chosen as the stimulant because it only activates cell bodies but not the axons passing through the upper cervical segments.

Neuroanatomy of High Cervical Neurons

Little information about descending pathways that originate from C1-C2 segments is available, but anatomical studies provide some evidence for a subpopulation of C1-C2 cells that are involved in propriospinal modulation of spinal sensory neurons. Horseradish peroxidase (HRP) injection into the thalamus of cats labeled cells in the lateral cervical nucleus; however, a subpopulation of cells in the medial part of this nucleus was unlabeled, and axons of these unlabeled cells appear to descend to caudal spinal segments. Others in the art have confirmed those descending projections by injecting HRP in the C8-T5 segments of one monkey and finding labeled cells in the lateral cervical nucleus and in the C1-C2 gray matter. Furthermore, another group skilled in the art has shown in cats that neurons in the medial portion of the lateral cervical nucleus respond to noxious stimuli. In addition, spinal sensory neurons in upper cervical segments receive noxious inputs from large areas of the body and thus, may project to more caudal spinal segments, as well as to the thalamus. Indeed, it has been proposed that the lateral spinal nucleus, which extends down the entire spinal cord, may participate in inhibition of efferent nerve activity in rats. The data as presently disclosed also shows that after selective spinal transections in rats supported the concept that spinal inhibitory effects in sensory neurons utilize upper cervical segments.

Spinal Relay for Vagal Inputs

A very interesting finding is the differential processing of cardiac vagal afferent information in the cervical and thoracic spinal cord. Electrical and chemical stimulation of vagal afferent fibers primarily excites neurons of the C1, C2 segments. It should be pointed out that these cervical cells also receive input that was carried to the thoracic spinal cord via the sympathetic afferents. However, the vagal information elicits larger evoked responses. In contrast to excitation of upper cervical spinal neurons, vagal input from the cardiopulmonary region generally reduces neuronal activity in sensory cells of rats, cats and monkeys in segments below C3; vagal facilitation of responses to noxious inputs are reported only at low stimulus intensities. Antinociceptive effects of vagal stimulation also are found in the tail-flick response in rats, and vagotomy attenuates opioid-mediated and stress-induced analgesia.

Disruption of the C1-C2 neurons with the excitotoxin, ibotenic acid, eliminates the suppressor effects on thoracic spinal neurons with vagal stimulation. Vagal suppression of evoked activity of thoracic spinal neurons resulting from intrapericardial injections of algogenic chemicals is attenuated or eliminated after ibotenic acid was placed on the dorsal surface of the C1-C2 spinal segments.

Neurons in the upper cervical (C1-C2) and upper thoracic (T3-T4) spinal cord process cardiac sensory information to coordinate the interactions within and between these populations of spinal cord neurons and thereby modulate efferent neurons that regulate regional cardiac function. Specifically, neurons in C1-C2 spinal cord process cardiac sensory information to coordinate the interactions within and between C1-C2 and T3-T4 spinal neurons and thereby determine autonomic outflow to the intrinsic cardiac nervous system.

Simultaneous Recordings of Two Neurons

Figure 14:
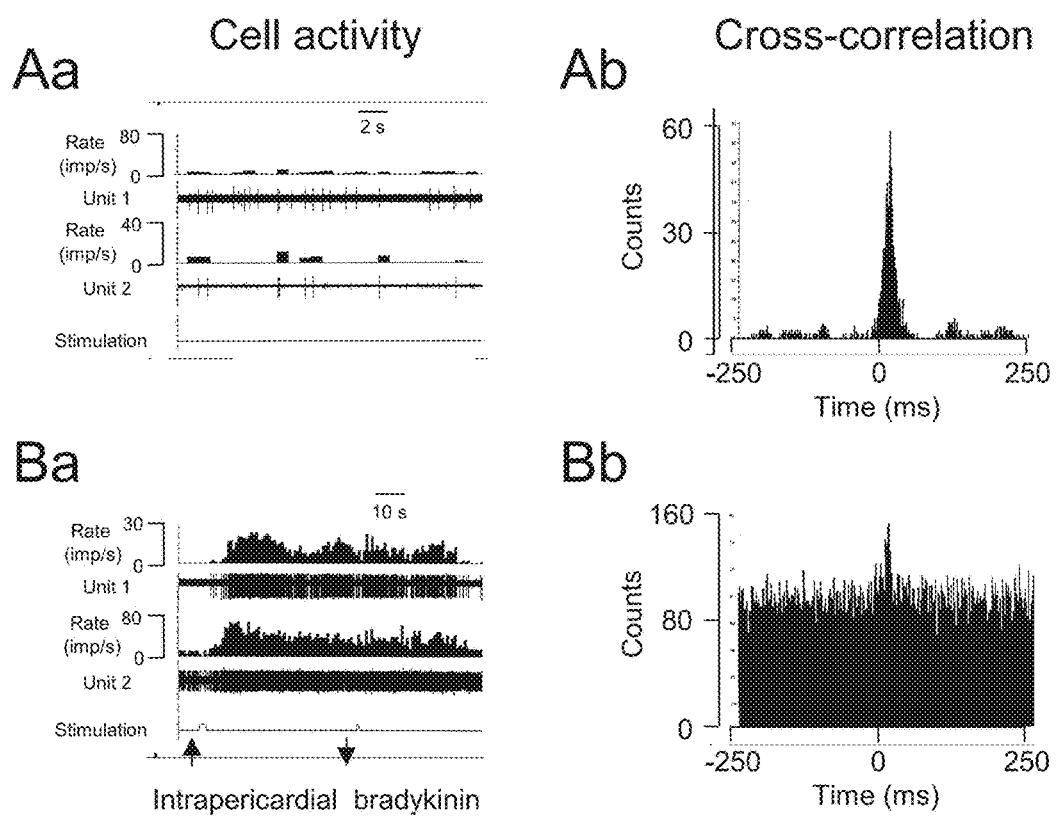
FIG. 14 shows examples of two different pairs of spinal neurons in the T3 spinal segment. Aa is background activity recorded from deeper (Unit 1; lamina V-VII) and superficial (Unit 2; lamina I-II) neurons. Ab is the cross-correlogram of the background activity. Central peaks centered around 0 delay represent the action potentials that occur from one neuron shortly before (negative delays) or after an action potential occurs in the other neuron. Ba is activity from superficial (Unit 1; lamina I-II) and deeper (Unit 2; lamina V-VII) neurons evoked by an injection of bradykinin into the pericardial sac. Bb is the cross-correlogram of the evoked activity. The upper tracings are discharge rate in impulses/sec (imp/s) and lower tracings (Unit) are the raw records of the extracellular action potentials. The arrows represent the injection (upward) and removal of bradykinin. The characteristics of the cross-correlograms were similar to those described by Sandkuhler et al.

Different populations of neurons within and between segments of the spinal cord exhibit coherence and correlation of activity and may, on occasion, act as independent units. Valuable data was gathered by recording from two cells simultaneously by using two microelectrodes. FIG. 14 demonstrates simultaneous recordings of two cells and particularly indicates the correlation of two cells in the T3 segment of the spinal cord.

Noxious Chemical Stimulation of the Heart—Responses of T3-T4 and C1-C2 Neurons.

Figure 15:
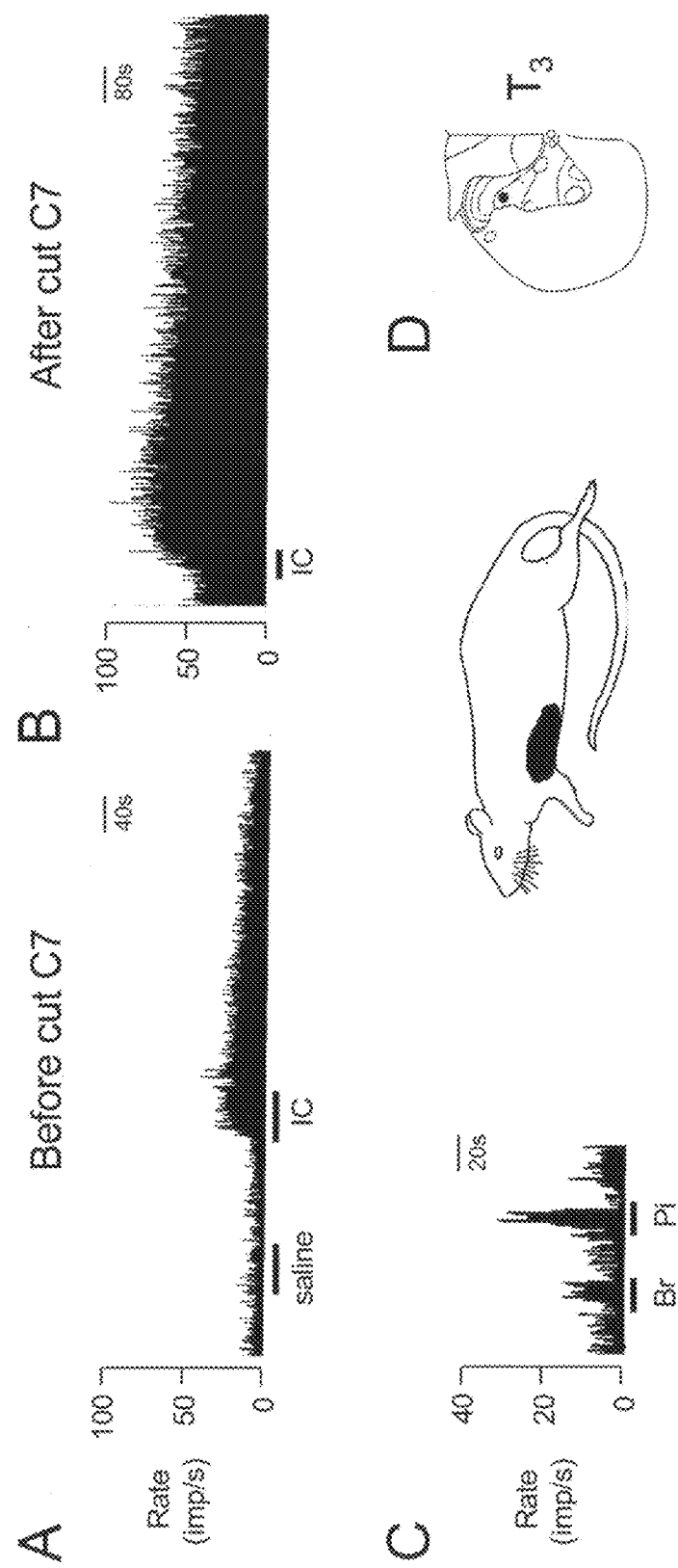
FIG. 15 shows responses of a T3 spinal neuron to visceral and somatic stimulation. A&B: responses of the cell to saline (A) and to intrapericardial injections of algogenic chemicals before (A) and after (B) the spinal cord was transected at the C7 segment. C: responses of brushing hair (Br) and pinching (Pi) the skin in the somatic field represented by the ellipse on the rat figurine. D: the black dot marks the location of the recording site for this cell.

A typical example of an upper thoracic cell responding to somatic and noxious chemical stimulation of the heart is shown in FIG. 15. The chemical evoked responses also show tonic activity descending from upper cervical and supraspinal regions. The evidence of tonic modulation supports the conclusion that there is a hierarchy of control or modulation from the upper cervical spinal cord (FIG. 1). Intrapericardial injections of algogenic chemicals generally increase the activity of T3-T4 spinal neurons, but the activity appears to decrease in a few cells. Intrapericardial injections also increased the average activity of 50% of the $C_1$-$C_2$ spinal neurons from 8.1±1.3 imp/s to 21.6±2.6 imp/s. Mechanical stimulation of the somatic fields on the chest and forelimbs activated afferent fibers that converged onto the T3-T4 spinal neurons; whereas, the input from somatic afferent fibers converging onto C1-C2 neurons was from receptive fields in the neck and jaw regions.

Cell Response to Coronary Artery Occlusion

Figure 16:
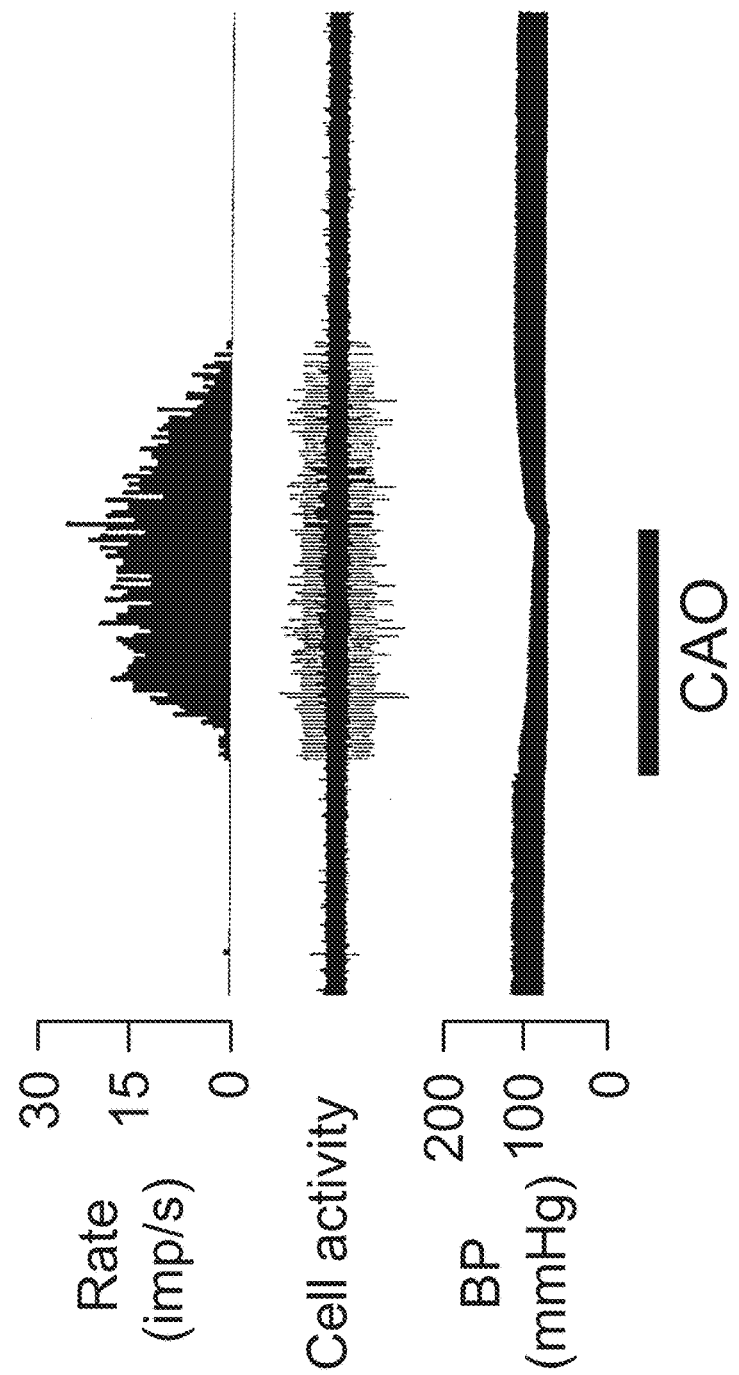
FIG. 16 shows response of T3 deeper spinal neuron to occlusion of the left coronary artery (CAO). The top trace is the rate of cell discharges in impulses/sec (imp/s). The second trace shows the raw tracing of the individual extracellular action potentials (Cell Activity). The third trace is blood pressure in mmHg. The horizontal bar represents the stimulus period for CAO. The occlusion was sustained for one minute.

Chemical stimulation of the heart using algogenic chemical stimulation of cardiac afferents provides a global method for activating cardiac afferents. The effects of coronary artery occlusion on upper cervical and upper thoracic cell activity is included herein because it specifically provides a means of activating nociceptive afferents in regional areas of the heart and clearly demonstrates that SCS or DCA stimulation has a preconditioning or protective effect on the heart thereby dampening neuronal activity of the intrinsic cardiac nervous system. Such an effect leads or lends itself to therapeutic SCS or DCA stimulation of the intrinsic cardiac nervous system to prevent and/or lessen the effects of cardiac pathologies. FIG. 16 demonstrates that the left coronary artery can be occluded and thereby produce a response in a T3 spinal neuron.

Neurochemistry

Figure 17:
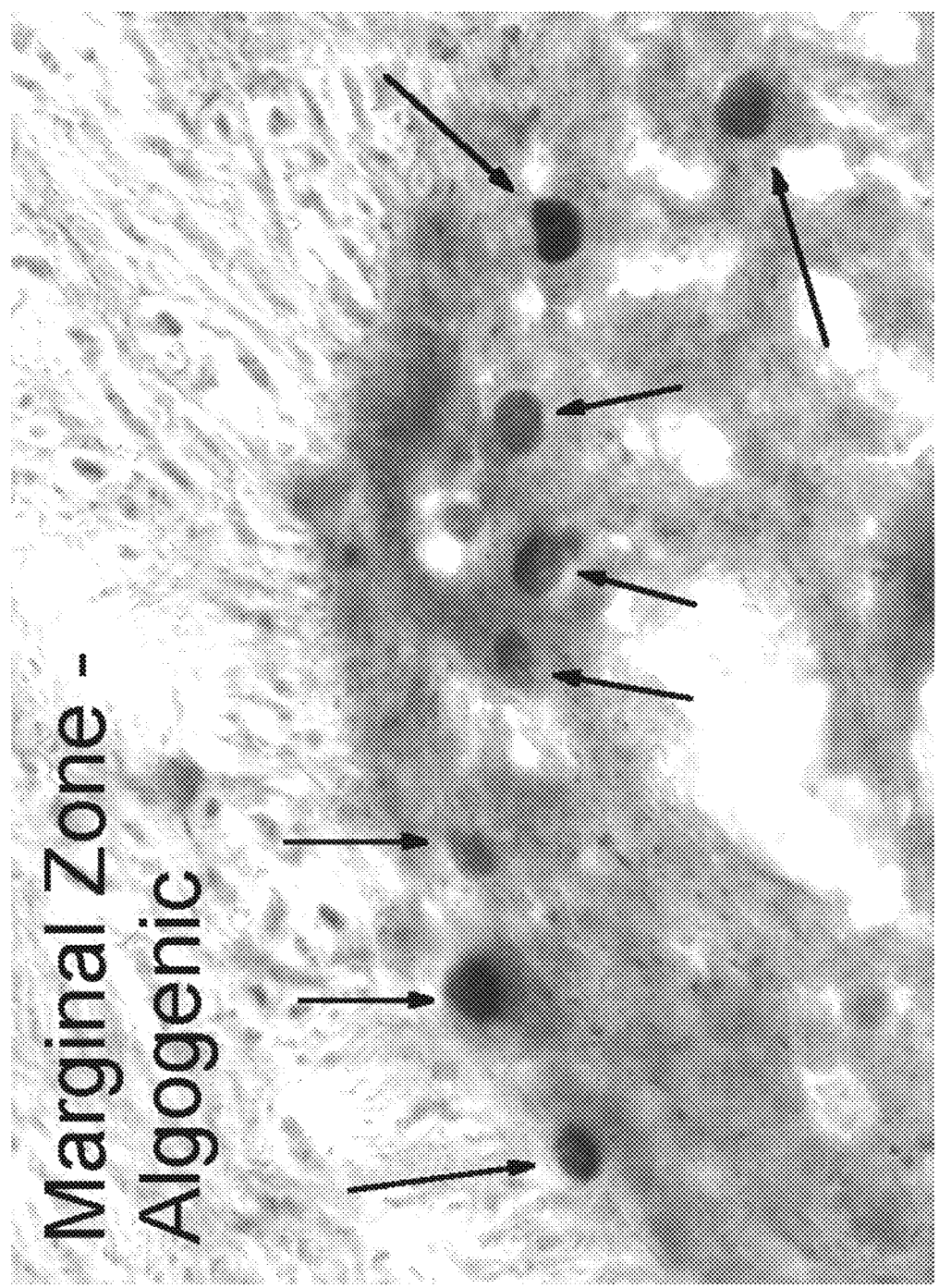
FIG. 17 shows intrapericardial infusion of algogenic chemicals caused intense c-fos immunoreactivity in the nuclei of T3-T4 neurons (arrows) in the marginal zone (left photo) and central gray region (right photo; cc—central canal).

Experiments were performed to show changes in c-fos expression in the upper thoracic segments in response to activation of cardiac afferents by injecting algogenic chemicals into the pericardial sac (FIG. 17). In the resting conditions, very little c-fos was expressed in the T3-T4 segments and the little c-fos that was expressed appeared in the more superficial laminae (I-III) rather than in the deeper laminae, where cells are activated by stimulation of cardiac afferent fibers. In another experiment, an intra pericardial infusion of normal saline did not cause any additional expression of c-fos. These results show that very few neuronal sites are activated by either the surgical procedures or the infusion of a solution which does not activate the cardiac afferent fibers. Heart rate and mean blood pressure did not change during these infusions. In contrast, the intrapericardial infusion of algogenic chemicals produced greater c-fos expression in the supercial laminae and laminae surrounding the central canal V-VII (FIG. 17). This data simulates a process (angina and the activation of cardiac nociceptive sympathetic afferent fibers) that most likely occurs for an extended time period. This data is provided to demonstrate that these techniques represent a reproducible approach to simulate cardiac pathologies and that the use of SCS or DCA stimulation to modulate the intrinsic cardiac nervous system can significantly impact the progression or effecti of such cardiac pathologies.

Effects of Vagal Stimulation on c-Fos Expression in C1-C2 Neurons

Figure 18:
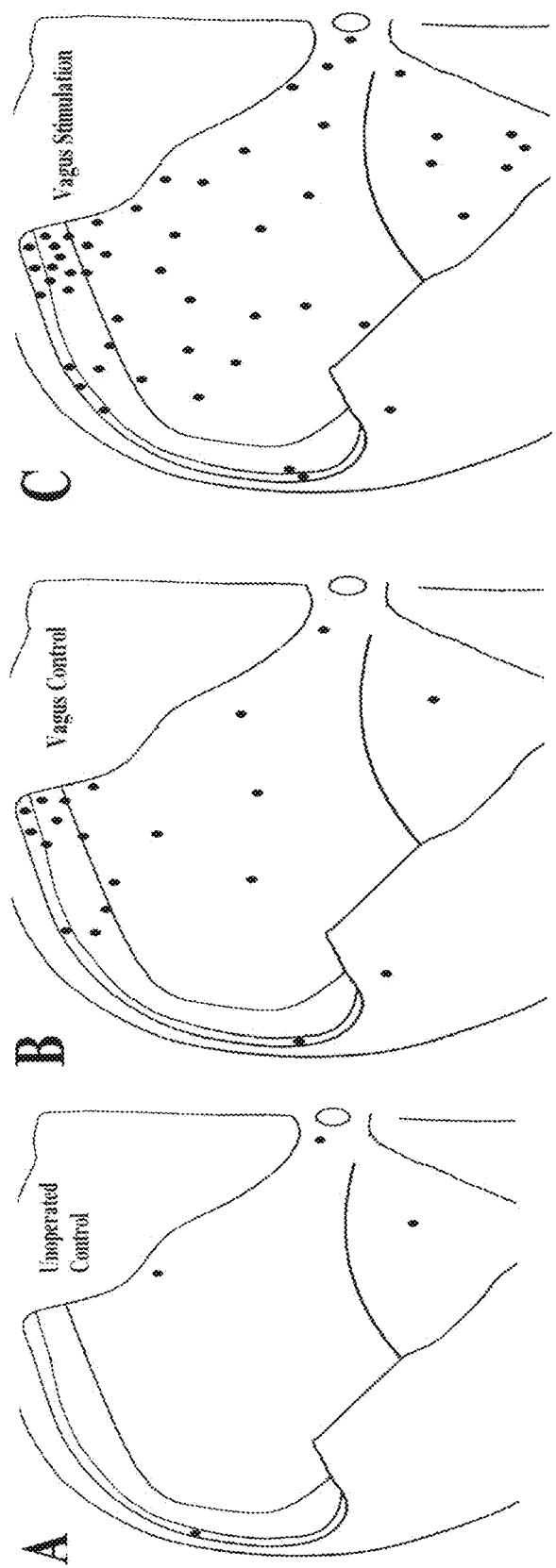
FIG. 18 shows distribution of c-fos immunoreactive (IR) neurons/100 µm in the C1 spinal segment following (A)—unoperated control, (B)—Vagal crush, (C)—Vagal stimulation. Following stimulation of the vagus, c-fos IR neurons (black dots) were abundant in the medial marginal zone and substantia gelatinosa. C-fos IR neurons also were located throughout the nucleus proprius, along the marginal zone, in the ventral horn, and central gray region.

In order to determine whether input from the vagus would activate C1-C2 neurons, c-fos immunohistochemical studies following vagal electrical stimulation were performed. Three groups have been evaluated: unoperated controls, rats with the vagus nerve crushed for 2 hrs, and rats with the vagus nerve stimulated with the following parameters: (20 Hz, 30 V, 0.2 ms, 5 min on, 5 min off for 1 hr. Abundant c-fos immunoreactive neurons were found in the superficial dorsal horn (marginal zone, substantia gelatinosa), nucleus proprius, central gray region (area X), and ventral horn (FIG. 18).

C1 Modulation of Upper Thoracic Cell Activity

Originally, it was assumed that supraspinal pathways are necessary for descending inhibitory effects of visceral afferents on sensory neurons. However, evidence shows that in rats that high cervical neurons can mediate inhibitory effects of cardiopulmonary spinal input in lumbar spinothalamic tract (STT) and dorsal horn (DH) neurons. Thus, it appears that the upper cervical segments play an important role in the hierarchy that controls the efferent outflow to the intrathoracic and intrinsic cardiac nervous system. Based on this knowledge and evidence from previous studies, we conclude that cell bodies located in the gray matter of C1-C2 spinal segments can modulate nociceptive cardiac-evoked activity of spinal neurons in the upper thoracic spinal cord. The effects of glutamate activation of cell bodies in the upper cervical spinal cord on the activity of cells in the T3-T4 spinal cord evoked by injections of bradykinin (BK) into the pericardial sac have been examined. Others have used Glutamate to activate cell bodies in the cervical spinal cord in the art. Glutamate (1M) was absorbed onto filter paper pledgets (2×2 mm) and was placed on the dorsal surface of the C1-C2 segments. Saline control pledgets were applied at the same sites before and after glutamate. Saline did not elicit any responses.

Chemical Stimulation of C1-C2 Cells Before and after Rostral C1 Transection

Figure 19:
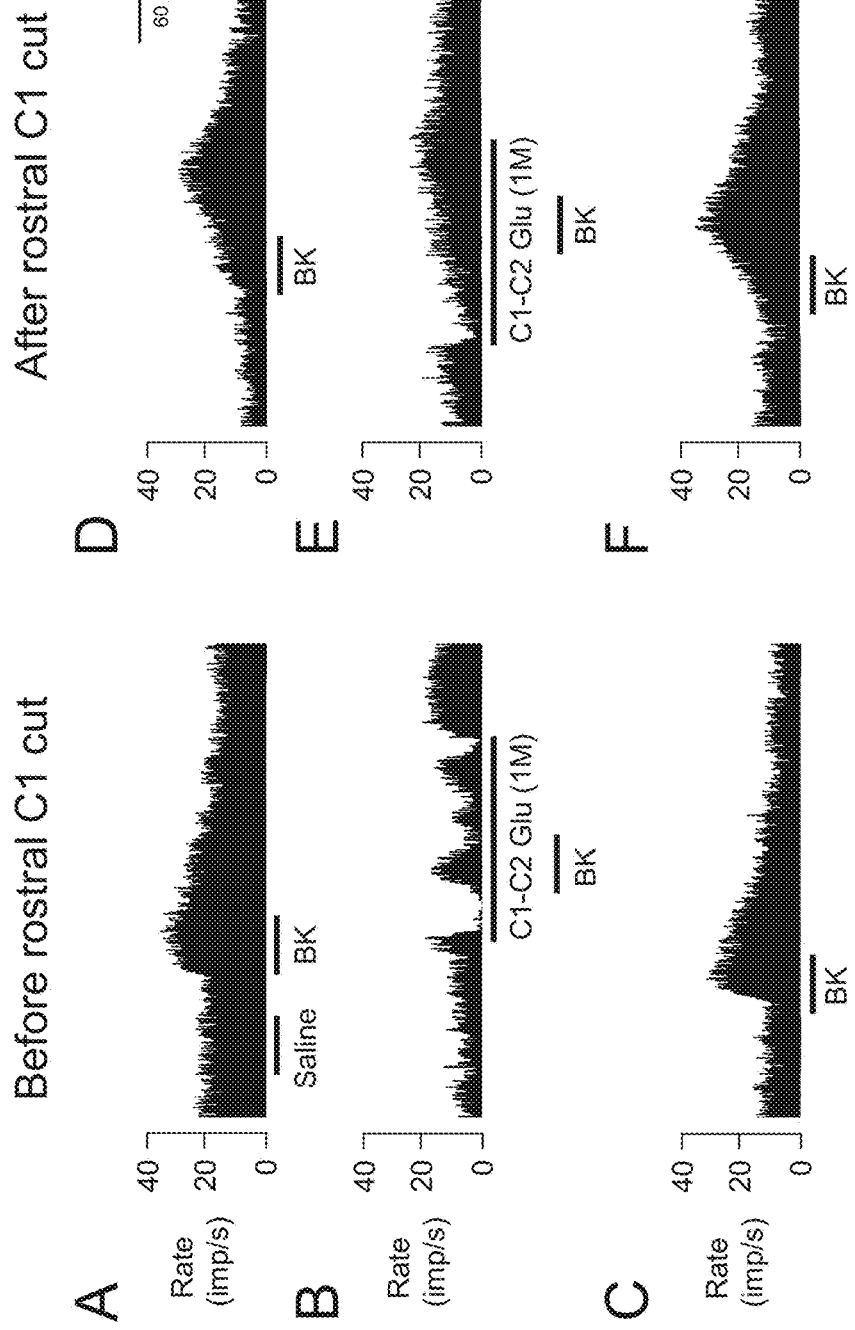
FIG. 19 shows responses of T3 cell to chemical stimulation of glutamate before and after rostral C1 spinal transection. The responses were evoked by intrapericardial injections of bradykinin (BK). Saline was used as the control. Pledgets of glutamate placed on the C1-C2 dorsal spinal cord (B) decreased the discharge rate of the cell for the three minute period it was applied. The background activity recovered after glutamate was removed. After the rostral C1 cut, BK still increased the discharge rate of the thoracic STT cell (D) although the BK response characteristics changed. The presence of glutamate attenuated this response (E). The increased rate of discharge to BK injections was again observed when glutamate was removed (F). In each panel, action potentials were recorded on a rate histogram.

The evoked activity of one T3 cell to glutamate is shown before (panels A-C of FIG. 19) and after rostral C1 (panels D-F of FIG. 19) transections. These transections demonstrate that supraspinal pathways are not necessary to elicit the effects from C1 cell activation. Chemical stimulation of the C1 cell bodies with glutamate suppresses the evoked responses of the T3 cell to algogenic chemical stimulation of cardiac afferent fibers. Cells in the upper cervical segments serve as an important relay in the hierarchy of cardiac control that modulates the activity of cells in thoracic segments.

Neuroanatomy and Immunohistochemistry

Figure 20:
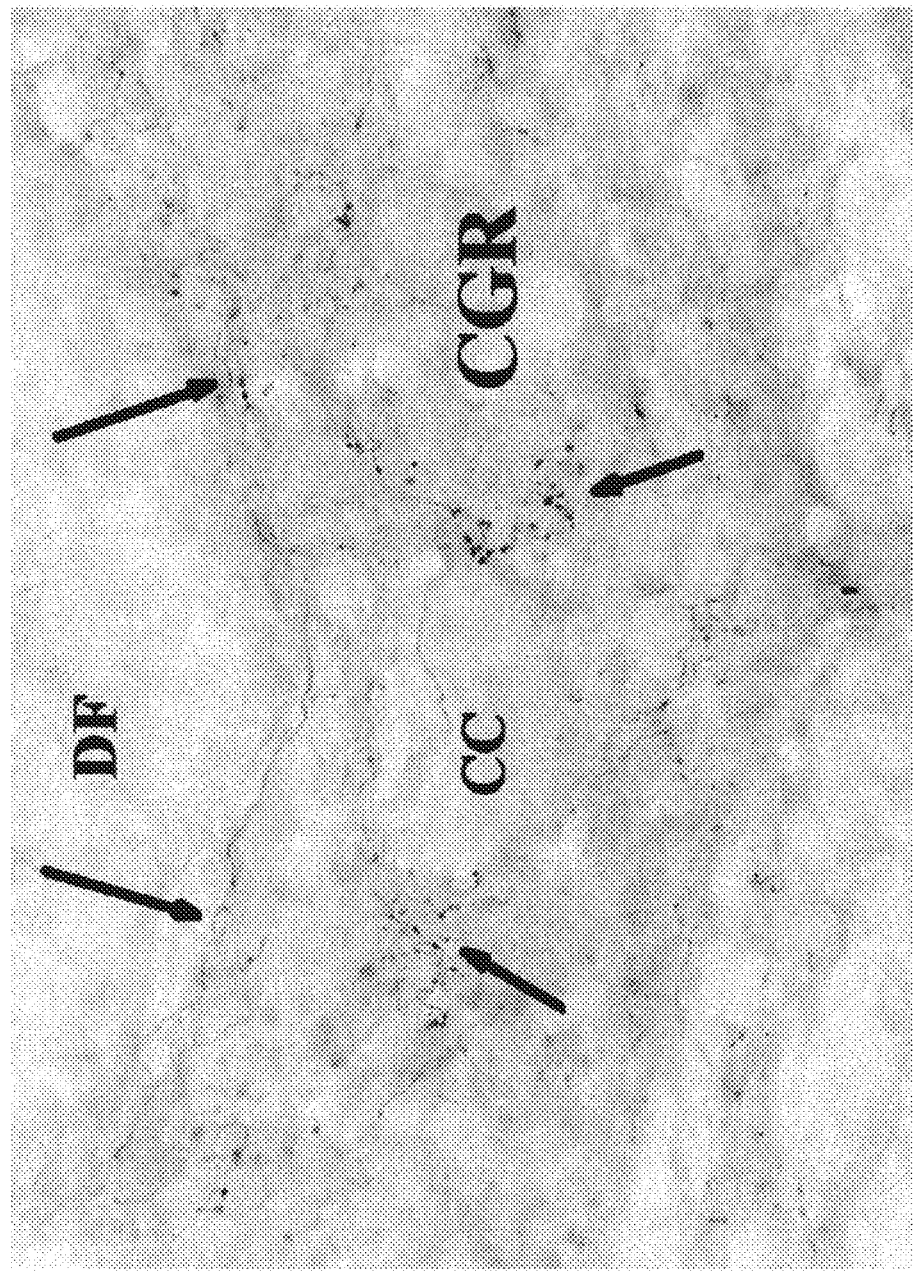
FIG. 20 shows anterogradely labeled fibers (arrows) with PHAL were abundant in the T3-T4 central gray region (area X; photograph on right; cc=central canal). The lateral portion of the central gray region contains the intermediomedial (IMM) cell nucleus where some preganglionic sympathetic neuronal cell bodies reside. Abundant PHAL immunoreactive fibers also were found in the superficial dorsal horn and nucleus proprius (photograph on left) in the T3-T4 segments.
Figure 21:
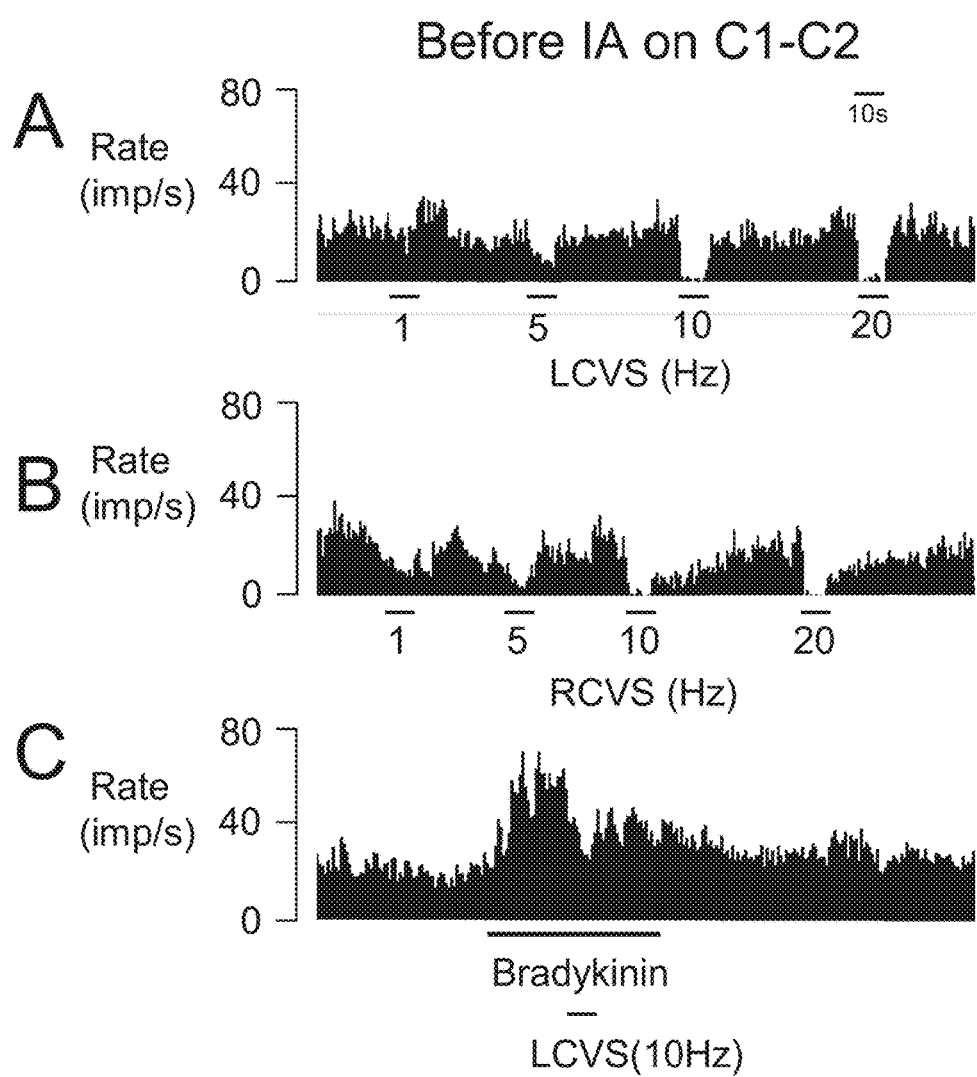
FIG. 21 shows effects of vagal afferent stimulation on the background activity and evoked activity of a T3 neuron before ibotenic acid was placed on the dorsal C1-C2 spinal cord. Electrical stimulation of the left cervical vagus (A: LCVS; {30 V, 0.1 ms} ipsilateral to the cell) right cervical vagus (B; RCVS; contralateral) at different frequencies. Vagal stimulation reduced the discharge rate of the evoked response to noxious stimulation of the cardiac afferents intrapericardial injections of bradykinin (C). IA; ibotenic acid. The short horizontal bars represent the period of vagal stimulation, the long horizontal bar represents the bradykinin injection and the numbers indicate the frequencies tested.

Retrograde tracing was used to detect upper cervical neurons with propriospinal projections to the lumbosacral spinal segments in the rat. Termination sites of the upper cervical propriospinal neurons in the gray matter of the upper thoracic segments are shown in FIG. 20. Termination sites of the thoracic propriospinal neurons in the upper cervical segments are also shown in FIG. 21. Using PHA-L an anterograde study has been performed from the C1-C2 segments in the rat. PHA-L was injected into the C1-C2 segments and rats survived 12-24 hours. Anterogradely labeled fibers were identified in the nucleus proprius as far as the upper thoracic segments. PHAL moves by fast transport, degrades rapidly, and is picked up by fibers of passage. The results shown in FIG. 20 indicate the feasibility of anterograde tracing from upper cervical segments.

Vagal Modulation of T3-T4 Neurons Via the C1-C2 Segments

Electrical Stimulation of the Vagus

Electrical stimulation of the vagal afferents, in general, suppresses the activity of the upper thoracic spinal neurons (FIG. 21). Electrical and chemical stimulation of vagal afferents excites upper cervical spinal neurons.

Chemical Disruption of the C1-C2 Neurons

Figure 22:
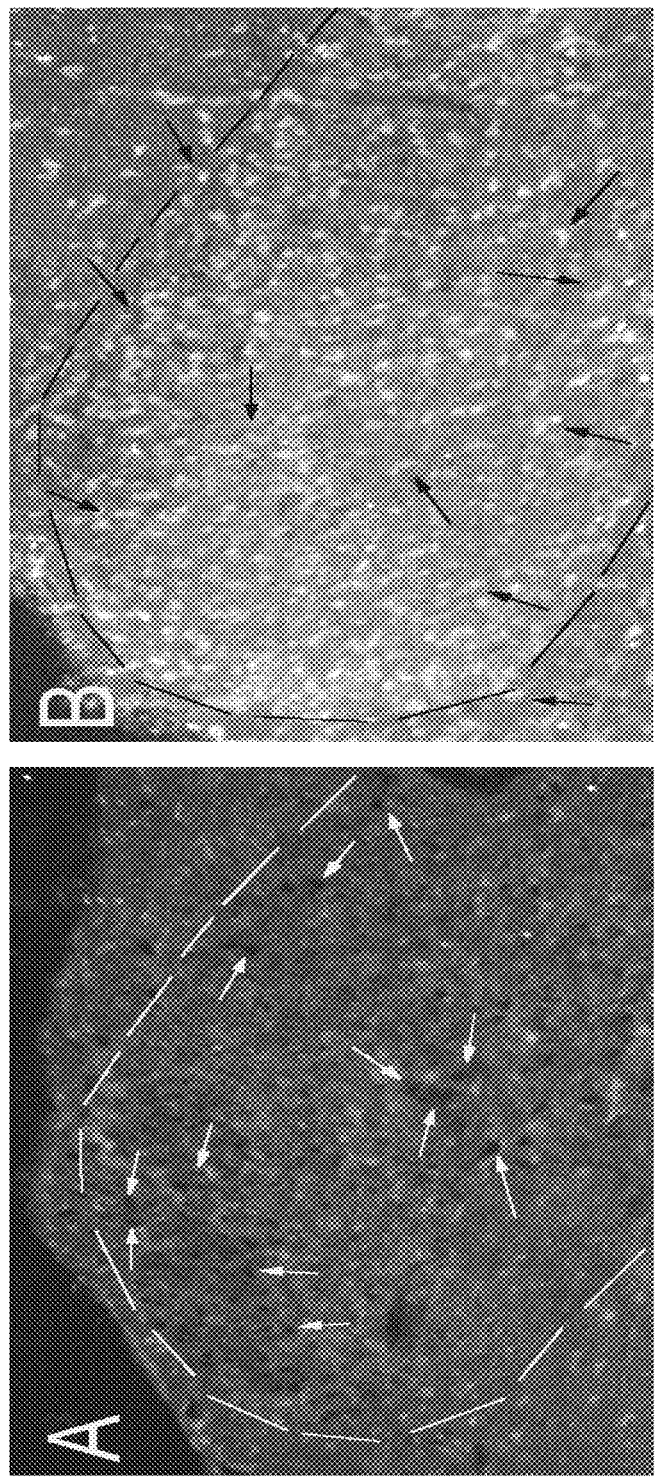
FIG. 22 shows vehicle (A) or ibotenic acid (B) was placed via pledget on the dorsal surface of the C1-C2 spinal segments for 2 hrs. After 14-16 hrs, rats were perfused with fixative and the medulla, C1-2, C3-5 segments were processed for annexin fluorescence histochemistry. Photomicrographs are from the C1 dorsal horn and the gray matter is outlined. Very little annexin staining was observed in control tissue sections (A) or in the medulla and C3-5 segments from ibotenic acid treated rats. White arrows point to unlabeled (black) cells in the dorsal horn. In rats treated with ibotenic acid (B), many annexin positive (white) cells were observed (arrows). Annexin binding indicates cells with energy impairment and/or undergoing apotosis. Annexin belongs to a family of proteins that bind acidic phospholipids, particularly phosphotidylserine (PS). PS is assymetically distributed in the cell membrane by the enzyme, aminophospholipid translocase. Following energy impairment, PS distributes to the outer cell leaflet and annexin binding illustrates cells with PS on the outside of the cell.

Chemical disruption of the C1-C2 spinal neurons alters the effects of stimulation of the cardiac afferent input on the regulation of information processing in the cervical and thoracic spinal cord. In order to produce chemical disruption of cells, ibotenic acid was chosen because it is an excitotoxin that has been used effectively in previous studies. Ibotenic acid is a structurally rigid glutamate analog that destroys neuronal perikarya, but spares axons and non-neuronal cells. After ibotenic acid is injected into a nucleus or applied to the surface of the spinal cord, the cells in the region are initially excited and then enter a phase of depolarization block. FIG. 22 shows that ibotenic acid applied to the dorsal surface of the C1-C2 spinal segments causes energy impairment and/or apoptosis of cells located beneath the surface of these segments. The advantage of this methodology is that the neuronal relays in the C1-C2 segments can be disrupted without interrupting the axons that pass through this region.

Vagal Effects after Chemical Disruption of C1-C2 Cell Bodies

At least part of the vagal inhibitory effects of the upper thoracic neurons depends on the C1-C2 relay. Approximately 20 min. after ibotenic acid was placed on the spinal cord, the inhibitory effects to vagal stimulation observed in FIG. 22 were eliminated. These results indicate that at least part of the vagal inhibitory pathway is dependent on an intact relay in the C1-C2 segments.

Using high frequency, low intensity electrical stimulation of the dorsal aspect of the T1-T2 spinal cord, the modulatory effects on the final common integrator of cardiac function, the intrinsic cardiac nervous system, have been determined. Dorsal cord activation by itself decreases basal intrinsic cardiac neuronal activity by 77%. This suppression of neuronal activity persisted for 30-45 minutes after terminating the dorsal cord stimulation. When LAD occlusion was initiated during dorsal cord activation, neuronal activity remained suppressed. Thus, use of SCS or DCA cord stimulation to precondition and/or remodel the neuronal activity of the intrinsic cardiac nervous system has been shown.

Figure 23:
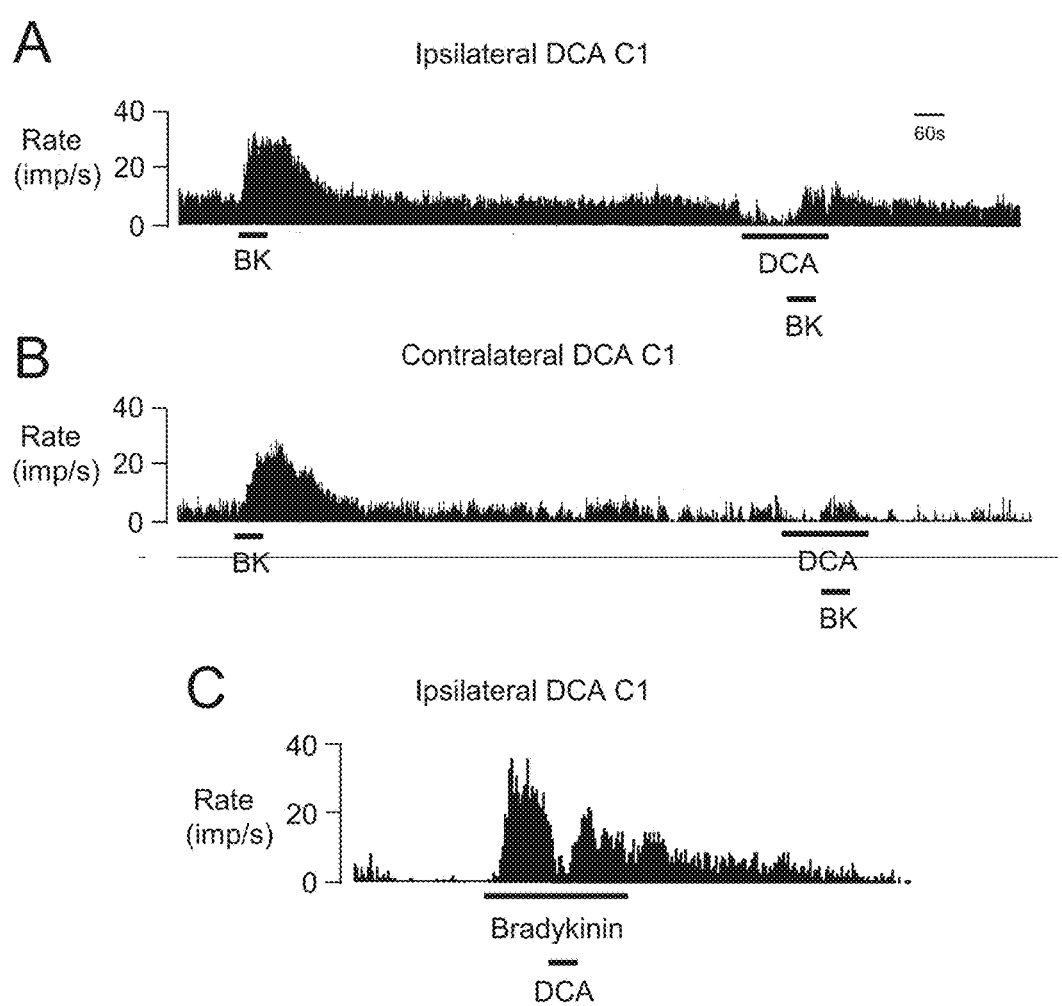
FIG. 23 shows responses of T3 cell to intrapericardial injections of bradykinin (BK) before and after dorsal cord activation. Electrical stimulation (250 uA, 0.25 us and 50 Hz) of the ipsilateral (A) or contralateral (B) C1-C2 dorsal columns applied prior to intrapericardial injections of BK markedly reduced the evoked responses. C: dorsal cord activation during the evoked response to BK also reduced the cell activity. Horizontal lines are the period of the stimulus.

Thus, dorsal cord activation suppresses intrinsic cardiac neuronal activity in both normally perfused and ischemic hearts and dorsal cord activation suppresses the activity of upper thoracic spinothalamic tract neurons evoked by chemical stimulation of cardiac afferents. Dorsal cord activation or SCS can modulate the activity of cells in central nervous system and the intrinsic cardiac nervous system. Dorsal cord activation can be used at either the thoracic or the cervical levels. The cervical segments are particularly interesting, because this is a key region for hierarchical control, and dorsal cord activation of the upper cervical segments has been used to relieve the symptoms in patients with chronic refractory angina pectoris. Dorsal cord activation of the upper cervical segments suppresses the responses of a T3 spinal neuron evoked by algogenic chemical stimulation of the cardiac afferents is shown in FIG. 23.

Chemical stimulation of the upper cervical cell bodies suppresses upper thoracic cell responses to nociceptive (chemical) and non-nociceptive (mechanical) input. In contrast, chemical stimulation of the upper thoracic cell bodies excites the upper cervical spinal neurons. Furthermore, the responses to nociceptive and non-nociceptive stimuli are enhanced. Inactivation of the upper cervical cell bodies eliminates the suppression of spontaneous and evoked activity of the upper thoracic neurons. In fact, the nociceptive and non-nociceptive responses are facilitated because elimination of the upper cervical spinal neurons reduces the tonic inhibition that continually impinges on the upper thoracic spinal neurons. Elimination of the upper thoracic cell bodies does not have an appreciable effect on the spontaneous activity and the evoked responses of the upper cervical spinal neurons, because vagal input produces larger responses of the upper cervical neurons than do the inputs that originate from sympathetic afferents.

Vagotomy also changes the modulation of spontaneous activity and nociceptor evoked responses of C1-C2 and T3-T4 spinal neurons. Inactivation of C1-C2 cell bodies eliminates vagal effects of chemical and mechanical stimulation on the activity of the upper thoracic neurons. Vagotomy also eliminates the nociceptive and non-nociceptive responses of the C1-C2 spinal neurons after elimination of input from the T3-T4 spinal neurons. C-fos expression at the upper thoracic segments increases after C1-C2 ablation before and after activation of the vagal afferents, because the cells of the upper cervical segments tonically suppress cell activity in the upper thoracic spinal cord. Perturbations change the correlation characteristics of the pairs of neurons. In addition, the responses of the individual neurons, which are recorded simultaneously, change their response characteristics independently after the interventions are made. The cfos expression does not change in the cervical segments because of the disruption of the cells by ibotenic acids that participate in producing the suppression of thoracic activity.

In anterograde tracing studies with PHAL, a clearer picture of the reciprocal innervation between the C1-C2 and T3-T4 segments is seen.

The experiments were designed in order to study the activity and responses of individual cells (192) as well as pairs (96) of cells. Results indicate that coronary artery occlusion evokes responses in the C1-C2 and T3-T4 neurons. That ischemic responses differ from the algogenic chemical responses because chemical stimulation provides a global activation of the afferents; whereas, coronary artery occlusion limits the stimulus to a specific region of the heart. Since vagal input provided the strongest input to the C1-C2 neurons and sympathetic afferents provided the excitatory inputs to T3-T4 neurons, different patterns of activity are demonstrated. Since activation of the vagus excites C1-C2 cells and suppresses the activity of T3-T4 cells, vagotomy reduced the responses of upper cervical neurons but enhances upper thoracic responses to coronary artery occlusion. Coronary artery occlusions will increase the number of cells filled with c-fos expression in both C1-C2 and T3-T4 spinal segments.

The experiments were also designed to study the activity and responses of individual cells (384) as well as pairs (192) of cells to address information processing of the effects of algogenic chemical stimulation and coronary artery occlusion before and after the cells of C1-C2 are disrupted using ibotenic acid. Dorsal cord activation of the T1-T2 or C1-C2 segments suppresses the evoked T3-T4 cell activity to algogenic chemical stimulation and coronary artery occlusion. Since disruption of cells with ibotenic acid reduces or eliminates vagal suppression of the evoked activity of the T3-T4 cells, inhibitory effects of dorsal cord activation are reduced or eliminated, because synaptic activity occurs in the same segments that are stimulated electrically with dorsal cord activation. Disruption of C1-C2 cells with ibotenic acid might reduce the effectiveness of T1-T2 dorsal cord activation on the evoked responses of T3-T4 spinal neurons due to the vasodilator effects of dorsal cord activation being eliminated when the spinal cord was transected at least four to six segments rostral to the site of stimulation. Dorsal cord activation changes the correlation of cell activity in the pairs of cells. These changes are responsible for the suppressed activity of the intrinsic cardiac nerve activity. Dorsal cord activation generates patterns of activity in the spinal neurons that act to stabilize the activity generated by the intrinsic cardiac neurons.

Algogenic chemical stimulation evokes short lasting and long lasting excitatory as well as inhibitory responses of the C1-C2 and T3-T4 neurons. If two neurons recorded simultaneously receive common input from algogenic chemical stimulation of cardiac afferents, they have more synchronous action potentials than statistically expected, and their cross-correlation function correspondingly shows a sharp central peak (i.e., when the mutual delay is at zero). However, the central peak is widened to a variable extent when several neuronal connections are interposed between the locus of common input and the neurons from which the activity is recorded. There are stronger correlations in pairs of neurons when one neuron is in the superficial dorsal horn and the other one is in the deeper dorsal horn. Experiments have shown that latency to the onset of the evoked response of superficial cell to algogenic chemical stimulation of cardiac afferents is shorter than the latency to the onset of the evoked response in a deeper cell. This difference in the latency suggests that the superficial neurons serve as an interneuron between the input from the primary afferents and the activation of the deeper cells. Since vagal input provided the strongest input to the C1-C2 neurons and the sympathetic afferents provided the excitatory inputs to the T3-T4 neurons, different patterns of activity have been demonstrated. Since activation of the vagus excites C1-C2 cells and suppresses the activity of T3-T4 cells, vagotomy will reduce the responses of the upper cervical but enhance upper thoracic responses to nociceptive algogenic chemical stimulation. No effects occurred using saline controls. With respect to mechanical studies, some of the cells discharge in response to the premature ventricular contraction. Some of the bursts occur early in the compensatory phase, but more commonly the burst is associated with the potentiated contraction. Cells were analyzed individually and as pairs. Vagotomy does not prevent responses of the neurons to chemical stimulation, but most likely modulates some of the mechanical responses. Chemical stimulation increases the number of cells filled with c-fos expression in both the upper cervical and upper thoracic spinal segments. After bilateral vagotomy, a decreased number of cells with c-fos, but the number of thoracic spinal cells with c-fos increases because vagal activation of upper cervical neurons suppresses the activity in thoracic neurons. As shown in FIG. 18, cells located in specific regions of these segments were found.

Chemical stimulation of the upper cervical cell bodies suppresses upper thoracic cell responses to nociceptive (chemical) and non-nociceptive (mechanical) input. In contrast, chemical stimulation of the upper thoracic cell bodies excites the upper cervical spinal neurons. Furthermore the responses to nociceptive and non-nociceptive stimuli are enhanced. Inactivation of the upper cervical cell bodies eliminates the suppression of spontaneous and evoked activity of the upper thoracic neurons. In fact, the nociceptive and non-nociceptive responses are facilitated because elimination of the upper cervical spinal neurons reduces the tonic inhibition that continually impinges on the upper thoracic spinal neurons. Elimination of the upper thoracic cell bodies does not have much effect on the spontaneous activity and the evoked responses of the upper cervical spinal neurons because vagal input produces larger responses of the upper cervical neurons than do the inputs that originate from sympathetic afferents. Vagotomy changes the modulation of spontaneous activity and nociceptor evoked responses of C1-C2 and T3-T4 spinal neurons. Inactivation of C1-C2 cell bodies eliminates vagal effects of chemical and mechanical stimulation on the activity of the upper thoracic neurons. Vagotomy also eliminates the nociceptive and non-nociceptive responses of the C1-C2 spinal neurons after elimination of input from the T3-T4 spinal neurons. C-fos expression at the upper thoracic segments increases after C1-C2 ablation before and after activation of the vagal afferents, because the cells of the upper cervical segments tonically suppress cell activity in the upper thoracic spinal cord. The perturbations change the correlation characteristics of the pairs of neurons. In addition, the responses of the individual neurons, but recorded simultaneously, change their response characteristics independently after the interventions are made. The cfos expression is not changed in the cervical segments because of the disruption of the cells by ibotenic acids that participate in producing the suppression of thoracic activity. Anterograde tracing studies with PHAL, have shown that a clearer picture of the reciprocal innervation between the C1-C2 and T3-T4 segments is obtained.

Differential remodeling of the peripheral and central cardiac nervous hierarchy and its nerve-cardiac myocyte junction in the presence of a healed myocardial infarction specifically as related to the genesis of ventricular fibrillation occurs. Tests utilize a well-defined canine model of ventricular fibrillation that combines three elements relevant to the genesis of malignant arrhythmias in man: a healed myocardial infarction, acute myocardial ischemia, and physiologically elevated sympathetic efferent neuronal activity have shown that differential remodeling is at least partially responsible for cardiac pathologies. Test also reveal and demonstrate that SCS or DCA stimulation of the intrinsic cardiac nervous system has a preconditioning effect pre-remodeling and a quenching effect post re-modeling. Based on an "exercise and ischemia test", animals in this model separate into two groups: 1) animals that develop ventricular fibrillation and are thereby classified "susceptible" to fibrillation; and 2) dogs that don't develop sustained ventricular tachycardia/fibrillation and are thus defined as "resistant". Thus, differential remodeling of the cardiac neuron hierarchy (central and peripheral) for reflex control of the heart occurs in susceptible versus resistant animals.

Autonomic Nervous System and Sudden Death after Myocardial Infarction.

A canine model of lethal ventricular arrhythmias developed in 1978 has been used to elaborate the mechanisms of sudden death after myocardial infarction (MI). In this model, animals with a chronic anterior wall infarction undergo a sub-maximal exercise stress test, culminating in transient total occlusion of the circumflex coronary artery for 2 minutes. During that 2-minute period of transient myocardial ischemia, 40% of the dogs develop ventricular fibrillation (VF); the remaining animals do not generate sustained ventricular arrhythmias. This model produces clinically relevant information by incorporating a healed anterior MI in the setting of elevated sympathetic efferent neuronal tone (induced by exercise), coupled with acute, regional myocardial ischemia distant from the original infarction. This model was developed to duplicate the clinical situation of a patient with multi-vessel coronary artery disease who begins sub-maximal exertion in the convalescent phase of an uncomplicated MI, patients who then develop transient myocardial ischemia. In the dog model, those destined to develop VF display persistent tachycardia in response to transient, acute myocardial ischemia. In contrast, VF resistant animals have been found to possess active vagal reflexes that control heart rate during the ischemic event. Thus, this model produces two distinct groups of animals, based on the occurrence of VF, that have very different characteristics of autonomic control of heart rate.

This model gives rise to the data that non-invasive markers of cardiac vagal reflexes predict risk for sudden death after myocardial infarction. This is shown through baroreflex sensitivity (BRS) data relating a rise in systolic blood pressure to RR interval slowing was prospectively tested prior to exercise and the induction of myocardial ischemia to predict outcomes. BRS was reduced in chronic MI dogs destined to develop VF during exercise and acute, regional myocardial ischemia. Interestingly, BRS was lower before MI in dogs that either died after coronary artery ligation or developed VF within 30 days of acute MI during exercise. Clinical conformation of these results has been published and shows that BRS was lower in patients who subsequently died suddenly after their first myocardial infarction. Results establish that autonomic markers add critical predictive information to the sudden death risk profile after MI. Baroreflex sensitivity measurements provide one index of the cardiac parasympathetic nervous system. Heart rate variability (HRV) quantifies cardiac autonomic interactions by measuring the impact of vagally mediated respiratory sinus arrhythmia via beat-to-beat RR interval variability derived from resting ECG recordings. It is shown herein dogs at high risk for sudden death had low variability measurements, suggesting low tonic vagal input to the heart. Tonic autonomic activity was influenced significantly by MI and recovered only in dogs at low risk for sudden death. In contrast, dogs at high risk for sudden death displayed little recovery during the first 30 days following MI. This persistent blunting of vagal tone was associated with a high risk for VF during exercise and myocardial ischemia. These experiments provide evidence that autonomic control of heart rate remodels during the progression of coronary artery disease.

If depression of vagal efferent neuronal tone to the heart and, as a consequence, cardiovascular reflexes are important for the development of lethal ventricular arrhythmias, does augmentation of cardiac vagal efferent neuronal activity prevent sudden cardiac death in such a model? This issue was addressed using the Schwartz and Stone model of sudden death by electrically stimulating the vagus nerve by means of chronically implanted electrodes. When the vago-sympathetic trunk was electrically stimulated during exercise initiated at the onset of coronary artery occlusion, the incidence of VF was prevented in over 80% of high-risk dogs tested. This effect was largely independent of the heart rate reduction associated with vagal activation. Furthermore, augmentation of tonic vagal activity by daily exercise training prevented VF in 100% of the high-risk dogs, either in the presence or absence of acute myocardial infarction. Finally, left stellate ganglionectomy was effective in reducing VF in these high-risk animals. Thus, abnormal autonomic control of the infarcted heart associated with sympathetic efferent neuronal dominance and weak vagal input, results in ventricular electrically instability that increases the risk for sudden cardiac death.

Remodeling of the Cardiac Neuronal Hierarchy after Myocardial Infarction.

What comprises the cardiac neuronal hierarchy and why is it important for the management of cardiac arrhythmias in chronically infracted hearts? Neurons in intrathoracic extracardiac and intrinsic cardiac ganglia have long been thought to act as simple efferent information relay stations involving one synapse, for instance in paravertebral sympathetic ganglia or parasympathetic ganglia on the heart. Recently, this concept has been extended in recognition of the fact that cardiovascular afferent information is also processed within the intrathoracic nervous system, including its component intrinsic to the heart. Neurons in intrathoracic ganglia, including those on the heart, receive constant inputs from spinal cord neurons to modulate their behavior. They also receive sensory inputs from cardiac afferent neurons on an ongoing basis. That is why the activity generated by most intrinsic cardiac neurons increases markedly in the presence increased sensory inputs arising from the ischemic myocardium. Indeed, excessive activation of limited populations of intrinsic cardiac neurons induced cardiac dysrhythmias that lead to ventricular fibrillation. Thus, therapies that act to stabilize heterogeneous evoked activities within cardiac reflex control circuits such, as the SCS or DCA stimulation of the intrinsic cardiac nervous system of the present disclosure, has obvious clinical importance.

Proper information exchange among the intrathoracic components of the cardiac nervous system act in concert to stabilize the electrical and mechanical behavior of the heart, particularly in the presence of focal ventricular ischemia. Different populations of neurons, distributed spatially within the intrathoracic cardiac nervous system, respond to cardiac perturbations in a coordinate fashion. If neurons in one part of this neuronal axis respond to inputs from a single region of the heart, such as the mechanosensory neurites associated with a right ventricular ventral papillary muscle, then the potential for imbalance within the different populations of neurons regulating various cardiac regions occurs and, thus, its neurons display little coherence of activity. On the other hand, relatively low levels of specific inputs on a spatial scale to the intrathoracic cardiac nervous system results in low basal coherence among its various neuronal components, thereby acting to stabilize cardiac regulation. Alternatively, excessive input to the spatially distributed intrathoracic nervous system destabilizes cardiac electrical behavior, leading to cardiac arrhythmia formation. Intrathoracic extracardiac and intrinsic cardiac neurons receive tonic inputs not only from cardiac and major intrathoracic vascular sensory neurites, but also from spinal cord neurons in the integration of efferent neuronal inputs to the heart.

Chronic Ventricular Ischemia and the Cardiac Neuronal Hierarchy

Figure 24:
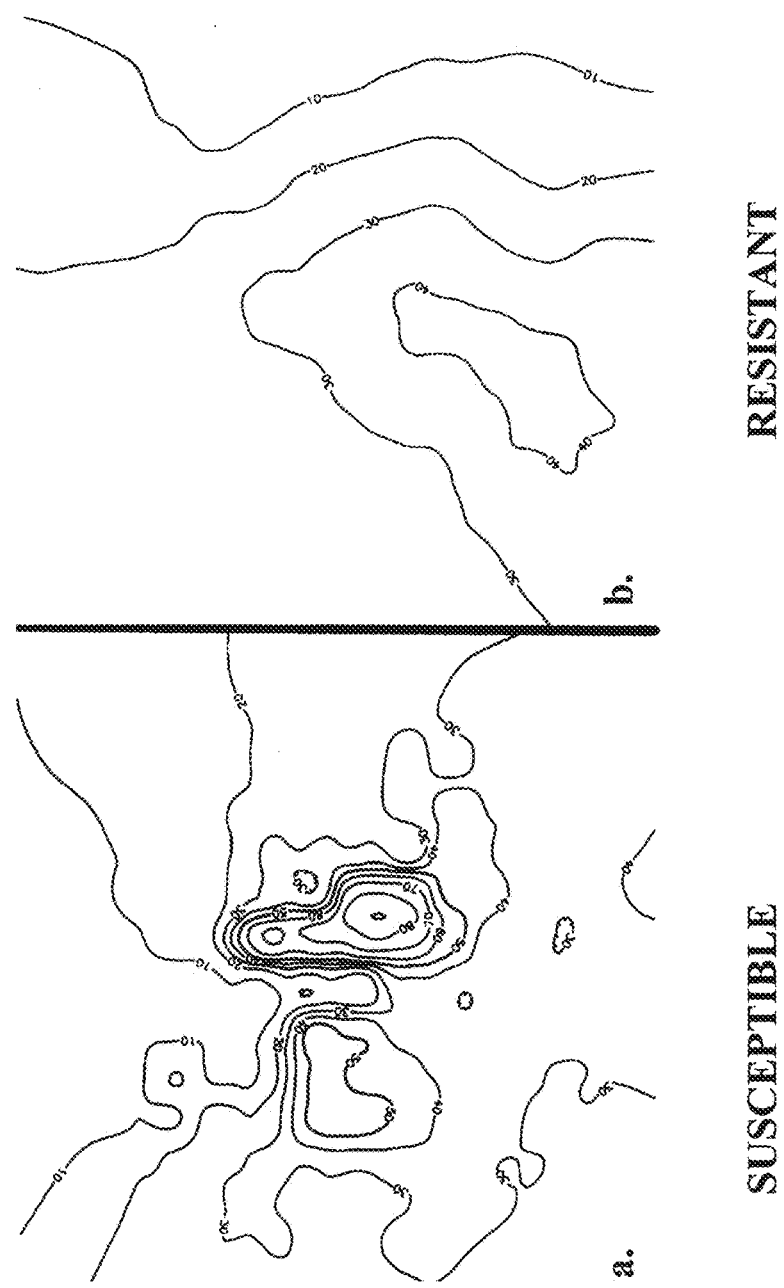
FIG. 24 shows epicardial conduction mapping across the anterior myocardial infarction in a susceptible dog (panel a) and a resistant dog (panel b) with normal left ventricular function. The longest time for epicardial electrical activation was about 80 milliseconds in susceptible dogs. This is in contrast to resistant dogs in which the longest time for epicardial activation was about 40 milliseconds.

The infarct matrix is important in determining risk for VF in the Schwartz and Stone model discussed hereinabove. This is illustrated by data showing epicardial conduction mapping across the infarct zone in high and low risk dogs. It has been found that conduction delays are much more profound across the infarct zone in high-risk dogs (>85 millisecond) compared with low risk animals (FIG. 24). High-risk dogs exhibit "mottled" myocardial infarcts that are electrophysiologically unstable, with electrical activation waves persisting as long as 85 milliseconds after epicardial electrical activation terminates. This matrix reflects a very large surface area for the development and sustaining of reentrant arrhythmias, which lead to VF in high-risk dogs. When ventricular function is normal, very fast VT leading to VF arises from a purely reentrant mechanism. Components that contribute to development of a mottled infarct include autonomic characteristics of dogs before MI. Baroreflex sensitivity is lower in dogs destined to die after MI or develop VF during the exercise and myocardial ischemia test. Using a marker derived of both baroreflex sensitivity and spectral analysis of heart rate variability, dogs at high risk for post-MI sudden death were identified with high sensitivity and specificity. These findings indicate that innate differences in cardiac autonomic control that can be identified before the development of overt cardiac disease may determine post-MI sudden death. Furthermore, autonomic differences before MI influence the type of infarct that develops with the LAD ligation in this model. This underscores the importance of understanding the hierarchy of autonomic control of the heart and how abnormalities contribute to the pathophysiology of cardiac disease (FIG. 1).

The importance of the peripheral cardiac nervous system in the maintenance of normal cardiac output can be appreciated from the present disclosure. The selective nature of the responses elicited by each component of the intrathoracic neuronal hierarchy to myocardial ischemia depends on how each population of peripheral autonomic neurons is affected, as well as the nature and content of their sensory inputs. That ischemia sensitive cardiac afferent neurons in nodose and dorsal root ganglia influence the behavior of central autonomic neurons which, in turn, modify cardiovascular autonomic efferent preganglionic neurons represents yet another level of this regulatory hierarchy.

Myocardial Ischemia.

Recent anatomical and functional data indicate the presence of the multiple neuronal subtypes within intrathoracic extracardiac and intrinsic cardiac ganglia. Its intrinsic cardiac component functions as a distributive processor at the level of the target organ. The redundancy of function and non-coupled behavior displayed by neurons within intrathoracic extracardiac and intrinsic cardiac ganglia minimizes the dependency for such control on a single population of peripheral autonomic neurons. In that regard, network interactions occurring at the level of the heart integrate parasympathetic and sympathetic efferent inputs with local afferent feedback to modify cardiac rate and regional contractile force throughout each cardiac cycle. A recent editorial by David Lathrop and Pete Spooner of the NIH highlights the potential clinical relevance of altered processing of information by these populations of neurons such that a lack of coordination of data exchange within the cardiac neuronal axis may lead to the genesis of cardiac arrhythmias.

Interactions Among Neurons in the Cardiac Neuronal Hierarchy.

The different populations of neurons distributed spatially within the intrathoracic cardiac nervous system respond to cardiac perturbations in a complex fashion. For instance, neurons in intrathoracic extracardiac ganglia do not respond to cardiac perturbations in a similar fashion as intrinsic cardiac ones. Consistent coherence of activity generated by differing populations of neurons has been identified among medullary and spinal cord sympathetic efferent preganglionic neurons, as well as among different populations of sympathetic efferent preganglionic neurons. If neurons in one part of the intrathoracic neuronal network respond solely to inputs from a single region of the heart, then the potential for imbalance within the different populations of neurons in various levels of the intrathoracic neuronal hierarchy might occur. A relatively low level of inputs on a spatial scale to populations of intrathoracic cardiac neurons would result in a low basal coherence among its components and stabilize that system. In contrast, excessive input to this spatially distributed nervous system would destabilize it, leading for instance to cardiac arrhythmia formation.

Arterial reflexes can become blunted during the evolution of heart disease. Focal ventricular ischemia is known to alter cardio-cardiac reflexes. Furthermore, ischemia induced liberation of chemicals such as adenosine or hydroxyl radicals within the affected myocardium can suppress ventricular myocyte electrical and contractile behavior. On the other hand, locally released adenosine or hydroxyl radicals can influence the cardiac nervous system via excitation of its afferent neuronal components. Thus, when devising a therapy to modify the outcome of myocardial ischemia one must consider not only altered cardiac myocyte behavior, but autonomic neuronal alterations. A brief summary of some of the issues concerning autonomic neuronal control of the ischemic myocardium is presented below, including its importance in one sequellae of myocardial ischemia—ventricular arrhythmia formation.

Symptomatology.

The somata of isolated afferent neurons are sensitive to adenosine. ATP and, to a lesser extent, adenosine influence sensory neurites of dorsal root ganglion neurons. The importance of adenosine in the genesis of cardiac pain became evident when Christer Sylvén and his colleagues administered adenosine into the blood stream of patients with diseased coronary arteries. Indeed, the symptoms induced by adenosine in these patients mimicked those that they experienced during effort. These data are in accord with the fact that dorsal root ganglion purine cardiac afferent neurons play an important role in the genesis of pain and that the ventricular sensory neurites of these neurons become non-responsive to ischemia in the presence of adenosine receptor blockade.

Cardiovascular Reflexes Secondary to Myocardial Ischemia.

Alterations in heart rate secondary to ventricular ischemia can be due, in part, to altered neural control of cardiac pacemaker cells. Myocardial ischemia can be attended by not only by tachycardia, but also by bradycardia.

Most ventricular sensory neurites associated with nodose ganglion cardiac afferent neurons are sensitive to purinergic agents. Activation of a sufficient population of nodose ganglion afferent neurons by exposing their sensory neurites to purinergic agents can result in the induction of bradycardia via medullary reflexes. Bradycardia can also be induced when sufficient populations of intrinsic cardiac neurons projecting axons to medullary neurons are activated by purinergic agents. In contrast, activation of cardiac sensory neurites associated with dorsal root ganglion neurons with adenosine results in the reflex excitation of sympathetic efferent neurons that innervate the heart. The details of the various reflex responses induced when specific populations of cardiac afferent neurons in nodose as opposed to dorsal root ganglia are modified by local ischemia remain to be fully elucidated. Coordination of autonomic outflows to the heart depends to a large extent upon the sharing of inputs from higher centers concomitant with interactions among neurons in various intrathoracic ganglia. That sharing of cardiac afferent information occurs within the intrathoracic and brainstem/spinal cord feedback loops of FIG. 1 allows for overall coordination of cardiac function.

Cardiac Arrhythmias.

Another sequel of myocardial ischemia is the development of cardiac arrhythmias. As neurons from the level of the insular cortex to the intrinsic cardiac nervous system can be involved in the genesis of cardiac arrhythmias, it is important to recognize that such neurons can induce untoward cardiac electrical events in the presence of myocardial ischemia. For instance, activation of a relatively minor population of intrinsic cardiac neurons in anesthetized canine preparations by exogenous application of an alpha- or beta-adrenoceptor agonist, endothelin I or angiotensin II can induce ventricular dysrhythmias or even fibrillation. DCA and SCS do reduce or ameliorate these effects.

Neural Substrates for Arrhythmia Formation in Ischemia.

The selective nature of the responses elicited by each component of the cardiac neuronal hierarchy to focal, ventricular ischemia depends on how each population of neurons within this autonomic neuronal hierarchy is affected and that depends in large part on the nature and content of their ventricular sensory inputs. It also depends, in part, on any alteration in ventricular efferent postganglionic axon function secondary to their presence within the ischemic zone.

Cardiac Afferent Neurons.

The chemical milieu of the sensory neurites associated with intrinsic cardiac afferent neurons also change when the blood flow in a coronary artery is compromised. Locally liberated adenosine, ATP, oxygen free radicals and peptides can affect the sensory neurites associated with afferent neuronal somata in nodose, dorsal root or intrathoracic ganglia. Oxygen free radicals also affect the functional integrity of ventricular nerves. The quantities of purinergic agents liberated into the local blood stream and pericardial fluid, increases during ventricular ischemia, as peptides or hydrogen peroxide can affect the activity generated by intrathoracic and central cardiac afferent neurons in an indirect fashion as chemicals accumulated in myocardial tissues and pericardial fluid modify their sensory neurites. When coronary arterial blood flow is restored, during the reperfusion phase various metabolites that accumulate upstream can influence intrinsic cardiac neurons and their sensory neurites supplied by that blood even more.

That ischemia sensitive cardiac afferent neurons in relatively distant (nodose and dorsal root) ganglia versus the somata of cardiac afferent neurons relatively closer to the affected tissue (intrathoracic extracardiac and intrinsic cardiac afferent neurons) influence the behavior of cardiac efferent postganglionic neurons via central and intrathoracic local circuit neurons represents yet another issue of importance within this regulatory hierarchy (FIG. 1). Alterations in heart rate secondary to ventricular ischemia activation of cardiac afferent neurons results in altered neural control of cardiac pacemaker cells. Thus, myocardial ischemia can be attended by tachycardia or bradycardia. Activation of a sufficient population of nodose ganglion afferent neurons by exposing their sensory neurites to a variety of chemicals that are liberated by the ischemic myocardium results in the induction of bradycardia via medullary reflexes. In contrast, excitation of the cardiac sensory neurites associated with dorsal root ganglion neurons by chemicals such as adenosine results induces the reflex excitation of sympathetic efferent neurons that innervate the heart.

Intrinsic Cardiac Neurons.

Intrinsic cardiac neurons are modified by myocardial ischemia in two fashions: one direct and the other indirect. Transient occlusion of the coronary arterial blood supply to a population of intrinsic cardiac neurons directly affects the function of their somata and/or dendrites. Presumably a lack of energy substrates normally available to them via their local arterial blood supply accounts in part for their altered behavior, as well as the fact that they are bathed by local products of ischemia such as oxygen free radicals and purinergic agents. Each major intrinsic cardiac ganglionated plexus on human or dog hearts is perfused by two or more arterial branches arising from different major coronary arteries. Intrinsic cardiac neurons and cardiomyocytes are affected by hypoxia. Myocardial ischemia of short duration affects not only cardiac myocyte function, but also the capacity of intrinsic cardiac neurons to respond to their sensory inputs. Metabolites accumulating locally when the regional coronary arterial blood supply of intrinsic cardiac neurons is compromised also influence the somata and dendrites of such neurons in a direct manner. Thus, regional ventricular ischemia influences the cardiac neuronal hierarchy in a number of ways, depending on whether the arterial blood supply affected by the arterial lesion directly affects the somata and dendrites of somata therein or indirectly via affecting sensory neurites in the infarct zone.

Data indicate that adaptations occur within the cardiac neuronal hierarchy in the presence of acute, focal ventricular ischemia. The cardiac nervous system remodels during chronic ischemic/infarction to maintain control over regional cardiac dynamics.

Figure 26:
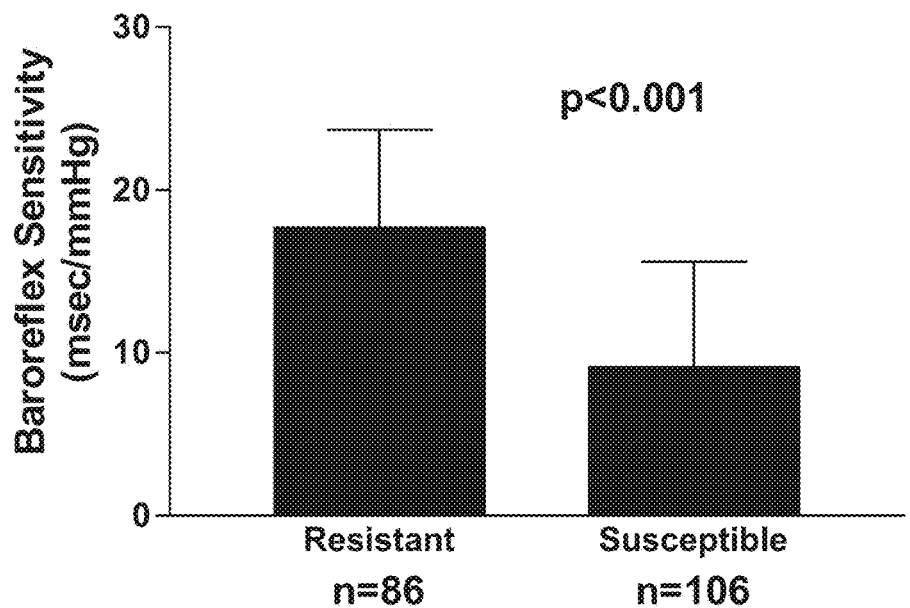
FIG. 26 shows the heart rate slowing in response to systemic hypertension (phenylephrine induced) quantifies baroreflex sensitivity.

Myocardial infarction is induced by ligation of the left anterior descending coronary artery in an open chest procedure during surgical anesthesia. The circumflex coronary artery is instrumented with a pneumatic occluder so that reversible myocardial ischemia can be induced at a later time. After 30 days of recovery, dogs have autonomic tests performed including baroreflex sensitivity (Sleight phenylephrine method) and heart rate variability (time and frequency domain). Then animals run on a treadmill using a protocol in which workload (belt speed and elevation) are increased every 3 minutes. Once heart rate reaches 210 beats per minute the circumflex occluder is inflated for 2 minutes, the first minute the dogs continue to run on the treadmill and the treadmill is stopped for the last minute. Forty percent of the post-MI animals develop ventricular fibrillation (VF) during the 2 minutes of coronary occlusion. The other 60% do not have sustained ventricular arrhythmias. An example of the arrhythmia that susceptible dogs develop is illustrated in FIG. 25. This observation indicates that reflex vagal activation is relatively weak in susceptible dogs and thus leads to ventricular electrical instability and even ventricular fibrillation. This indication was further tested by measuring baroreflex sensitivity during activation of cardiac vagal fibers by means of high pressure baroreflex testing. Relating the heart rate slowing in response to systemic hypertension (phenylephrine induced) quantifies baroreflex sensitivity (FIG. 26). It was found that baroreflex sensitivity was depressed in susceptible dogs compared with resistant animals and the baroreflex was an accurate predictor of the outcome of the exercise and ischemia test (Table II).

TABLE II

| Resistant | Susceptible |
| --- | --- |
| Strong vagal reflexes | Weak vagal reflexes |
| High baroreflex sensitivity | Low baroreflex sensitivity |
| High heart rate variability | Low heart rate variability |
| Transmural scar | Mottled scar |
| No late potentials | +late potentials |

These findings were clinically validated in the multicenter trial called ATRIAMI in which baroreflex sensitivity was found to be an independent risk factor for post-MI sudden cardiac death. Subsequently, the indication that weak vagal reflexes was responsible for susceptible dogs developing VF was tested using electrical stimuli delivered to vagal efferent preganglionic axons to augment cardiac vagal control. Vagal stimulation was started at the time of coronary artery occlusion and continued until the occluder was released. Vagal stimulation prevented VF in over 80% of the susceptible dogs. Even during subsequent exercise testing in which vagal stimulation was coupled with atrial pacing to maintain heart rate at control levels, VF was prevented in about 50% of the animals. Therefore, electrical stimulation of cardiac vagal efferent neurons prevents ventricular electrical instability that develops during exercise and transient myocardial ischemia in susceptible dogs.

Figure 27:
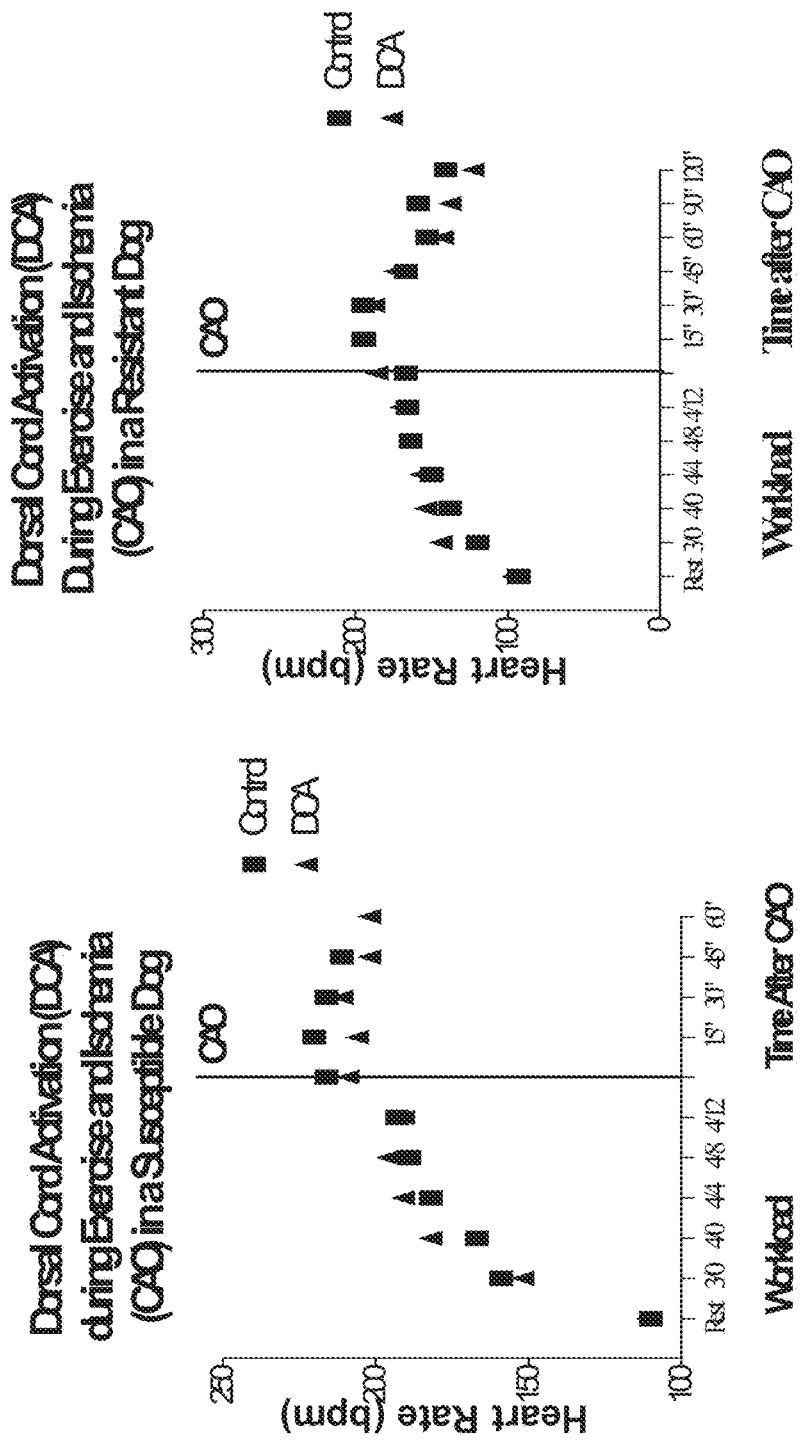
FIG. 27 shows chronotropic response to graded increases in treadmill exercise. Once heart rate reaches 210 beats per minute the circumflex occluder is inflated for 2 minutes, the first minute the dogs continue to run on the treadmill and the treadmill is stopped for the last minute. While concurrent DCA minimally affected heart rate responses in the resistant dog (right panel), in the susceptible dog DCA reduced the heart rate during the ischemic period (left panel).

One susceptible and one resistant dog were implanted with a spinal cord stimulator and allowed to recover for 7 days. Control exercise and ischemia testing and heart rate variability were studied prior to and during dorsal cord activation (DCA, 50 Hz, 200 μs, 90% motor threshold). The stimulator was activated for 4 hours daily for 4 days; then testing was repeated with the stimulator on. FIG. 27 shows the chronotropic response to graded increases in treadmill exercise. Once heart rate reaches 210 beats per minute the circumflex occluder is inflated for 2 minutes, the first minute the dogs continue to run on the treadmill and the treadmill is stopped for the last minute. While concurrent DCA minimally affected heart rate responses in the resistant dog (right panel), in the susceptible dog DCA reduced the heart rate during the ischemic period (left panel).

Spinal Cord Influences on Neural Control of Chronotropic Function

Figure 29:
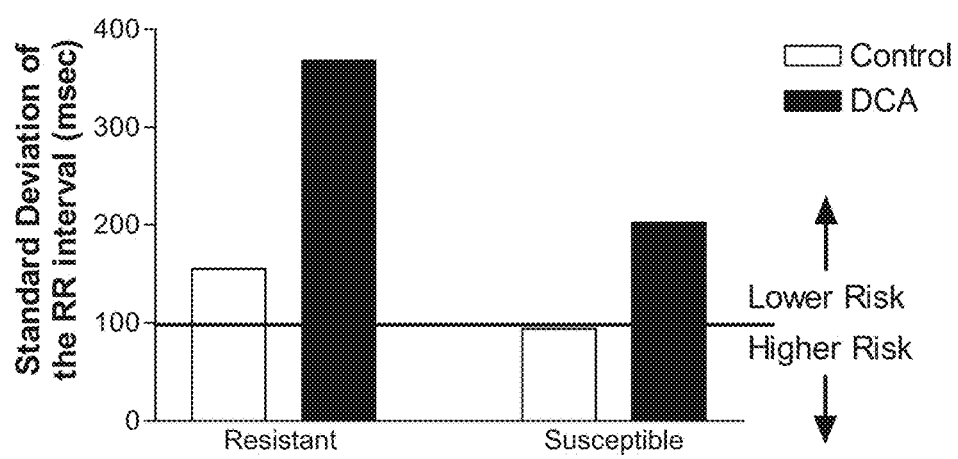
FIG. 29 shows dorsal cord activation increased the standard deviation of the RR intervals in both resistant and susceptible dogs, again suggesting that cardiac autonomic neuronal activity shifted toward efferent vagal control. Standard deviation of the RR interval values below 100 milliseconds predicts high risk for ventricular fibrillation during exercise and ischemia.

Both spectral analysis (FIG. 28) and time domain analysis (FIG. 29) of heart rate variability indicate that spinal cord stimulation via DCA augments parasympathetic nervous system activity to the heart.

It is very difficult to predict how central and intrathoracic autonomic neurons involved in cardiac regulation remodel to sustain cardiac output in the presence of chronic, regional ventricular infarction. Data indicate, however, that the cardiac neuronal hierarchy becomes obtunded by a variety of interventions, including chronic regional ventricular injury.

Information Processing within the Intrinsic Cardiac Nervous System and its Control of Regional Cardiac Function.

Myocardial ischemia and infarction induce substantial changes in the intrathoracic nerve networks and their reflex control of regional cardiac function. Chronic myocardial infarction/ischemia induces a heterogeneous distribution of efferent projections to cardiac end-effectors. Myocardial infarction/ischemia alters the neurochemical profile of that innervation, with differential increases in neuropeptide content within subsets of neurons contained within the intrinsic cardiac nervous system. The evolution of cardiac pathology is associated with disruptions of the intrinsic cardiac nervous system and its ability to process afferent information and such changes will be more evident in the CMVPG than the RAGP intrinsic cardiac ganglia. Animals that exhibit indices of higher vagal tone (higher baroreflex sensitivity and higher heart rate variability) demonstrate lesser degrees of ischemic/infarct-induced neural remodeling.

The Functional Connectivity of Intrinsic Cardiac and Intrathoracic Extracardiac Neurons in Normal and Acutely Ischemic Hearts.

Little direct functional interconnectivity exists among intrinsic cardiac neurons and their intrathoracic extracardiac counterparts. Independent function as such indicates that little reliance on one such population normally occurs when regulating regional cardiac function; i.e., dysfunction of one population occurs without a major loss of regional cardiac control. Significant alterations in the cardiac milieu, such as occurs during acute, focal ventricular ischemia, induces greater coherence of activity among populations of intrathoracic and intrathoracic extracardiac neurons.

Chronic myocardial ischemia induces a heterogeneous distribution of efferent projections to cardiac end-effectors. We anticipate that this heterogeneous distribution of sympathetic fibers to the left ventricle results in similar heterogeneous release of catecholamines and neuropeptides into the interstitial space during stimulation of the efferent nerves. Finally, animals that exhibit indices of higher vagal tone (higher baroreflex sensitivity and higher heart rate variability) demonstrate lesser degrees of ischemic/infarct-induced remodeling of the efferent outflow of the left ventricle.

Activation of the dorsal columns of the cranial thoracic spinal cord suppresses the activity generated by neurons not only on the target organ, but also in middle cervical and stellate ganglia. It is known that neurons in these ganglia are under the constant influence of spinal cord neurons such that following their decentralization their activity increases (i.e., spinal cord neurons exert tonic suppression of their function). Removal of spinal cord inputs to the intrathoracic nervous system enhances many intrathoracic cardio-cardiac reflexes is tied to the principle and thus excessive activation of spinal cord neurons suppress the intrinsic cardiac nervous system.

Heterogeneous alterations within the intrinsic cardiac ganglia or at the end-terminus of the autonomic innervation to the ischemic myocardium are major contributors to the increased incidence of sudden cardiac death in patients with coronary artery disease. The increased incidence of sudden death often result from lack of protection of the myocytes and instability of the cardiac electrical system. Chronic DCA ameliorate ischemia-induced remodeling within the intrinsic cardiac nervous and thereby reduces the heterogeneous neural substrate that predisposes the susceptible animals to ventricular arrhythmias and sudden cardiac death.

Heart failure has traditionally been considered to be primarily a hemodynamic disorder. The importance of neurohumoral mechanisms that act to maintain adequate cardiac output in the presence of ventricular ischemia is apparent. This recognition has forced a reappraisal of neuronal mechanisms involved in regulating the ischemic myocardium leading to the development of the present disclosure.

Spinal cord-peripheral neural interactions and modulation of peripheral nerve function in the ischemic heart. Dorsal column activation stabilizes the intrinsic cardiac nervous system in acute myocardial ischemia experiments were conducted. The purpose of these experiments was to determine if dorsal column activation (DCA) induces long-term effects on the intrinsic nervous system, the final common integrator of cardiac function, particularly in the presence of myocardial ischemia. Methods: Activity generated by right atrial neurons was recorded in 10 anesthetized dogs during basal states, and during 15 min occlusions of the LAD coronary artery, with and without background DCA. For DCA, dorsal T1-T4 spinal segments were stimulated for 17 min. at 90% of motor threshold (50 Hz; 0.2 ms duration). For combined effects, the coronary occlusion commenced 1 min into DCA. Results: Ischemia-induced excitatory effects on the intrinsic cardiac nervous system were suppressed (−76%) during DCA and for approximately 20 min after DCA termination. Conclusions: DCA suppresses basal activity within the intrinsic cardiac nervous system and prevents the ischemia-induced activation of these peripheral neural networks. This stabilization of intrinsic cardiac neuronal function, induced by higher elements of the neural hierarchy for cardiac control, is maintained for prolonged periods post-stimulation and is reflective of the neural memory of these processes. These long-term effects may partially explain the prolonged effects patients with angina experience not only during DCA, but also for a time thereafter.

Figure 30:
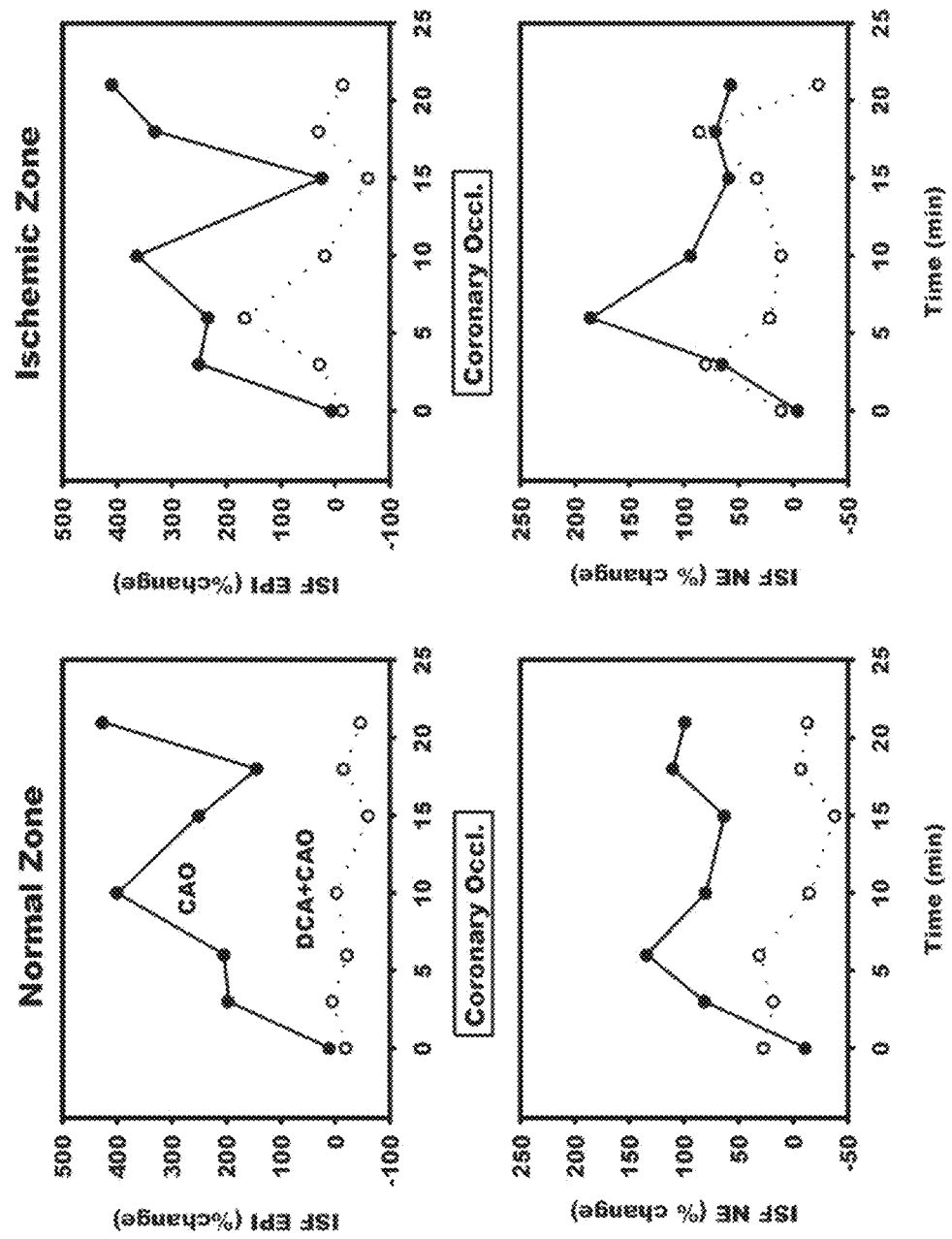
FIG. 30 shows percent change is ISF NE and EPI in response to sole coronary artery occlusion (CAO, solid lines) and CAO in the presence of DCA (CAO+DCA, dotted lines). Left panels show data from normally perfused left ventricular regions. Right panels show data from the ischemic zone. Time 0 is pre-occlusion baseline; CAO is on for 15 min.

Coronary artery occlusion induces differential catecholamine release in the normal and ischemic myocardium. (FIG. 30, solid line). The purpose of this study was to determine if transient coronary occlusion differentially effects norepinephrine (NE) and epinephrine (EPI) release into the canine ventricular interstitial space (ISF). Methods: In anesthetized dogs, left ventricular ISF samples were collected by microdialysis during 15 min occlusions of the circumflex coronary artery. Results: Coronary artery occlusion (CAO) induced a biphasic response in ISF catecholamine release, with ISF EPI increased 400% and ISF NE increased 150% in both the normal and ischemic myocardium. By 15 min of CAO, ISF catecholamines returned towards baseline. ISF EPI, and to a lesser extent NE, increased upon reperfusion. Conclusions: Coronary artery occlusion evokes a differential release of catecholamines, primarily reflected in the neuronal release of epinephrine. Neuronal release of catecholamines into the ISF, associated with coronary artery occlusion onset and reperfusion, is reflective of reflex interactions among peripheral and central components of the cardiac neural hierarchy in response to the ischemic stress.

Doral column activation stabilizes peripheral adrenergic function in acute myocardial ischemia. The purpose of this study was to determine whether DCA modulates NE and EPI release into the canine ISF in both normal hearts and those exposed to transient myocardial ischemia. Methods: In anesthetized dogs, left ventricular ISF samples were collected by microdialysis during electrical stimulation (50 Hz, 0.2 ms) of the dorsal T1-T4 segments of the spinal cord at an intensity of 90% of motor threshold with and without concurrent 15 min occlusions of the circumflex coronary artery. Results: ISF EPI doubled by 10 min and tripled by 20 min of DCA (239 to 935 pg/ml, respectively). ISF EPI remained twice baseline 20 min post-DCA. DCA increased left ventricular NE by 43% (890 to 1273 pg/ml); ISF NE returned to baseline values 20 min post-DCA. Heart rate and left ventricular inotropic function were not affected by DCA. When 15 min CAO was instituted during DCA (FIG. 30, dotted lines), ischemia induced changes in ISF EPI and NE were obtunded (FIG. 30, solid lines), both at the onset of occlusion and during reperfusion. Conclusions: DCA evokes differential release of catecholamines, primarily reflecting neuronal release of epinephrine. Evoked release of catecholamines into the ventricular interstitium persists for a considerable period of time post-DCA. Pre-existing DCA suppresses the release of catecholamines by intrathoracic adrenergic neurons reflexly-induced by transient myocardial ischemia. The long-term DCA effects on myocardial catecholamine release may account, in part, for the fact that this form of therapy produces clinical benefit to patients with angina pectoris not only during its application, but for a time thereafter.

Spinal Cord-Peripheral Neuronal Interactions Modify Myocardial Electrical Stability. Dorsal Column Activation Reduces Ventricular Fibrillation Accompanying Acute Myocardial Ischemia.

Figure 31:
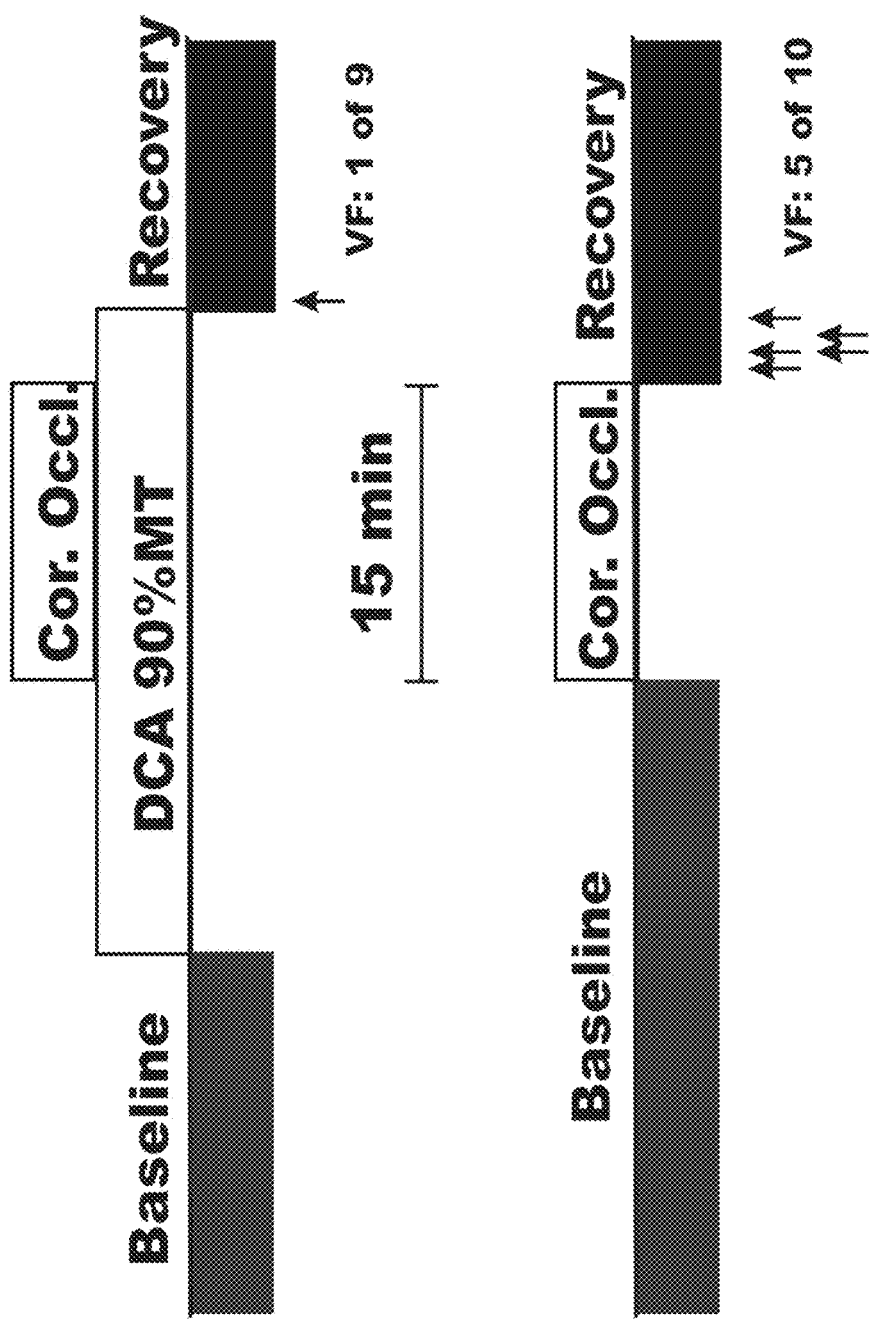
FIG. 31 shows effects of DCA on induction of ventricular fibrillation (VF) associated with 15 min coronary artery occlusion and reperfusion. Arrows indicate time point for onset of VF. With coronary artery occlusion, VF was induced in 50% of the animals; when VF occurred, it was within 6 min of reperfusion onset. With pre-existing DCA, coronary artery occlusion induced VF in only 1 of 9 animals (1 min post DCA; 7 min post-occlusion).

The purpose of this study was to determine if the stabilization of peripheral neural function exerted by DCA reduces the potential for ventricular fibrillation induction in acute myocardial ischemia. Methods: Under anesthesia, atrial and ventricular electrograms were recorded during basal states, and during 15 min occlusions of the proximal circumflex artery with and without pre-existing DCA. DCA involved electrical stimulation (50 Hz, 0.2 ms) of the dorsal T1-T4 segments of the spinal cord at an intensity of 90% of motor threshold for 36 min, with coronary artery occlusion commencing 15 min into DCA (FIG. 31). Results: Coronary artery occlusion induced ventricular fibrillation (VF) in 5 of 10 dogs, with VF occurring within 6 min of reperfusion (FIG. 31 arrows). With pre-existing DCA, coronary artery occlusion induced VF in 1 of 9 dogs, the VF occurring after terminating DCA. Conclusions: DCA stabilizes efferent neuronal outflows for cardiac control and obtunds the ischemia-induced reflex activation of cardiac neural networks. Such stabilization of neural function reduces the substrate for induction of lethal arrhythmias during acute myocardial ischemia and, in particular, the subsequent reperfusion period.

Dorsal column activation stabilizes ischemic myocardial electrical dysfunction. The purpose of this study was to determine whether DCA modulates electrical imbalance within the chronically ischemic ventricle. Methods: An ameroid constrictor was implanted around the left circumflex coronary artery to gradually occlude that vessel. Four weeks later, under general anesthesia multiple ventricular unipolar electrograms were recorded in the normal and ischemic left ventricle during basal states and when ANG II (40 µg/min; 1 minute) was administered to right atrial neurons before and after DCA. Results: ANG II increased the area and magnitude of regional ST segment changes in the ischemic ventricle. ANG II induced minimal changes in the electrical behavior of the normal myocardium. DCA (50 Hz, 0.2 ms, 0.32 mA for 15 min) modified ischemic indices, even suppressing regional ventricular ST segment abnormalities previously induced by ANG II. Conclusions: DCA suppresses ischemia induced ventricular electrical disturbances. This may occur, in part, via stabilizing intrathoracic adrenergic neurons that modulate the ischemic ventricle.

Processing of cardiac sensory information by neurons in the upper thoracic (T3-T4) spinal cord. Chemical activation of cardiac receptors differentially affects activity of superficial and deeper spinal neurons in rats. The purpose of this study was to evaluate responses of superficial (depth <300 µm) versus deeper thoracic spinal neurons to chemical stimulation of cardiac afferent neurons and to determine if descending central neuronal inputs modulate these effects. Methods: Extracellular potentials of single T3-T4 neurons were recorded in pentobarbital anesthetized, paralyzed and ventilated male rats. A catheter was placed in the pericardial sac to administer 0.2 ml of an algogenic chemical mixture that contained adenosine ($10^{-3}$M), bradykinin, histamine, serotonin, and prostaglandin $E_2$ ($10^{-5}$ M). Results: Intrapericardial chemicals elicited responses in 27% of the superficial neurons and in 47% of the deeper neurons. All superficial neurons that responded to cardiac afferents were excited. Of the deeper neurons, approximately 80% were excited, 15% were inhibited and 5% showed excitation-inhibition. Spontaneous activity of superficial neurons with short-lasting excitatory responses was significantly lower than that of deeper neurons ($P<0.05$). After cervical spinal transection, spontaneous activity generated by superficial and deeper neurons increased significantly, as did responses to chemical activation of cardiac afferents neurons. Conclusions: Chemical stimulation of cardiac afferent neurons excites superficial T3-T4 spinal neurons; deeper neurons exhibit multiple patterns of responses. These data further indicate that thoracic spinal neurons that process cardiac nociceptive information are tonically inhibited by higher center neurons.

Descending modulation of thoracic cardiac nociceptive transmission by upper cervical spinal neurons. The purpose of this study was to examine effects of stimulating upper cervical spinal neurons on spontaneous and evoked activity of thoracic spinal sensory neurons that responded to noxious cardiac stimuli. Methods: Extracellular potentials of single T3 neurons were recorded in pentobarbital anesthetized male rats. A catheter was placed in the pericardial sac to administer bradykinin ($10^{-5}$M, 0.2 ml, 1 min) as a noxious cardiac stimulus and saline as control. A glutamate pledget (1 M, 1-3 min) was placed on the surface of C1-C2 segments to chemically activate upper cervical spinal neurons. Results: In 77% of the T3 neurons tested, glutamate at C1-C2 inhibited spontaneous activity and/or excitatory responses to intrapericardial bradykinin. After transection at the rostral C1 spinal cord, excitatory amino acid (glutamate) excitation of C1-C2 neurons still reduced the spontaneous activity of T3 neurons, as well as excitatory inputs from cardiac sensory neurons. Conclusions: Chemical activation of C1-C2 spinal neurons evokes a descending inhibition in thoracic spinal cord cardiac neurons during basal states as well as in the presence of noxious cardiac stimuli. Furthermore, modulation of cranial thoracic neurons by upper cervical spinal neurons does not require supraspinal connectivity.

Figure 32:
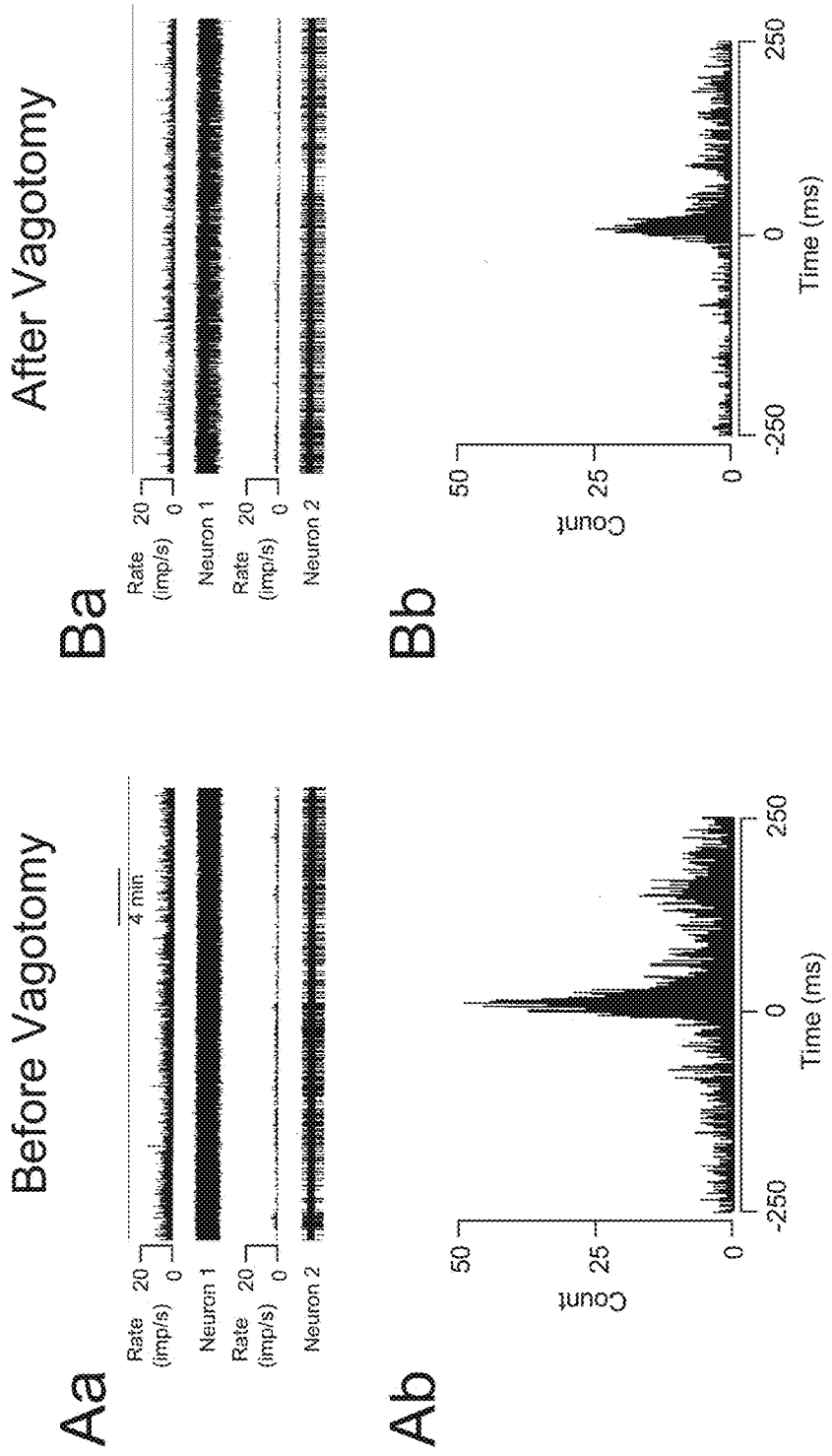
FIG. 32 shows examples of the activity generated by a pair of superficial spinal neurons in the T3 spinal segment. Aa is basal activity recorded simultaneously from the neuron pair with intact neuraxis and Ba is basal activity after vagotomy. With the neuraxis intact, the cross-correlogram of the basal activity between these two neurons showed a central peak centered around 0 delay and a second smaller peak occurred approximately 150 ms after the central peak. Following bilateral vagotomy, the central peak was reduced and the secondary peak eliminated. Upper tracings represent discharge rate (impulses/sec; imp/s) and lower tracings (Unit) extracellular action potentials.

Interdependence of cardiac sensory information processing by neurons in the upper thoracic (T3-T4) spinal cord. The purpose of these studies was to evaluate the coordination of activity among upper thoracic neurons that process cardiac sensory inputs. To date, we have evaluated the correlation of spontaneous and evoked activity of 15 pairs of T3 spinal neurons. Included is FIG. 32 that demonstrates the ability to simultaneously record the activity generated by two cells in the T3 segment of the spinal cord, both before and after their multisynaptic vagal inputs was disrupted. In this case, vagotomy changed correlation among their function. In another pair of T3 neurons, their activity recorded simultaneously demonstrated that they exhibited coordination of activity approximately 130 ms from time 0, a feature that disappeared after placing glutamate on the C1-C2 segments of the dorsal spinal cord (not shown). In that case, background activity was similar before and after glutamate application. This data indicate that coordination of activity among T3 neurons can be modified by cardiac afferent inputs or following activation of descending pathways. These novel data indicate that different populations of neurons distributed spatially within and among thoracic and upper cervical spinal cord segments respond to cardiac sensory inputs in a coordinate fashion. These results also demonstrate the contributions that vagal afferent neurons make to the coordination of activity among cervical and thoracic spinal neurons; their cardiac component representing an important transducer of myocardial ischemic events to central neurons.

Figure 33:
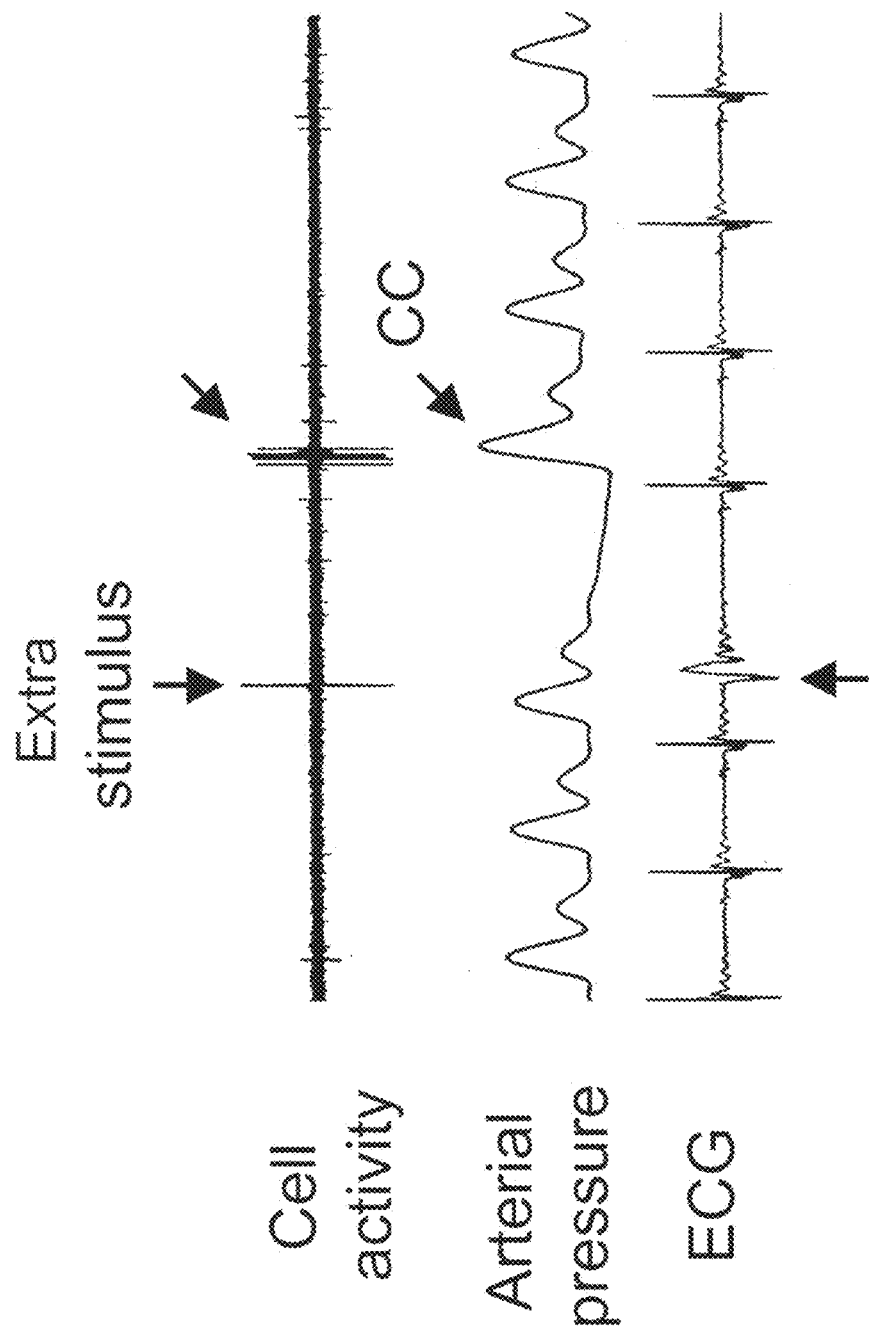
FIG. 33 shows responses of a T3 spinal neuron to an electrically induced premature ventricular contraction. The extra stimulus was delivered at the arrow in the top trace. This stimulus produced a premature ventricular contraction that was followed by a compensatory contraction (CC in middle trace). The $2^{nd}$ arrow in the top trace points out the burst of neuronal activity following the extra stimulus that was associated with the potentiated beat. The arrow in the bottom trace indicates electrical activity associated with the electrical stimulus. The ECG was recorded from lead II.

Mechanical activation of spinal neurons using programmed ventricular arrhythmias. Data demonstrating the feasibility of recording the responses of spinal neurons to premature ventricular contractions and compensatory beats. To generate these events, an electrical stimulus was applied through a pair of stainless steel electrodes that were inserted in the free wall of the left ventricle. FIG. 33 shows that the T3 deeper spinal neuron responded with a burst of activity during the compensatory beat. However, the cell was unresponsive to mechanical events associated with normal beats. The results demonstrate that we are able to record the activity of cells in response to the effects of administering an extra stimulus electrically.

Without the present specification, one of ordinary skill in the art would not have appreciated or known to use SCS or DCA stimulation as a means to (1) electrically influence the intrinsic cardiac nervous system to protect cardiac myocytes from initial ischemic damage or from being further damaged during subsequent ischemic episodes; and (2) preserve the electrical stability of the intrinsic cardiac nervous system and the heart itself prior, during, or post an ischemic episode. As such, the present disclosure would be non-obvious in light of the prior art showing the use of SCS stimulation for the treatment of angina. In fact, those of ordinary skill in the art that SCS alleviated widely and traditionally believe angina pain by either changing blood flow within ischemic or non-ischemic myocardium or modifying left ventricular (LV) pressure-volume dynamics. As the following experiments show, however, SCS does not alter these blood parameters—rather, SCS influences and effects the modulation of neuronal activity within the intrinsic cardiac nervous system. Thus, use of SCS to treat, modify, protect, and influence neuronal activity within the intrinsic cardiac nervous system is a novel and non-obvious approach to the pre- and post-treatment of an ischemic heart.

In the first series of experiments, it is shown that (1) SCS modifies the capacity of the intrinsic cardiac nervous system to generate electrical activity; (2) SCS suppresses the excitatory effects that local myocardial ischemia exerts on the neurons of the intrinsic cardiac nervous system; and (3) SCS does not change heart indices such as blood pressure. Thus, the underlying principle that SCS can and does stimulate and provoke an effect in the intrinsic cardiac nervous system is shown and demonstrated.

Electrical stimulation of the dorsal aspect of the upper thoracic spinal cord is used increasingly to treat patients with severe angina pectoris refractory to conventional therapeutic strategies. Clinical studies show that spinal cord stimulation (SCS) is a safe adjunct therapy for cardiac patients, producing anti-anginal as well as anti-ischemic effects. The effects of SCS on the final common integrator of cardiac function, the intrinsic cardiac nervous system, were studied during basal states as well as during transient (2 min) myocardial ischemia. Activity generated by intrinsic cardiac neurons was recorded in 9 anesthetized dogs in the absence and presence of myocardial ischemia before, during and after stimulating the dorsal T1-T2 segments of the spinal cord at 66 and 90% of motor threshold using epidural bipolar electrodes (50 Hz; 0.2 ms; parameters within the therapeutic range used in humans). The SCS suppressed activity generated by intrinsic cardiac neurons. No concomitant change in monitored cardiovascular indices was detected. Neuronal activity increased during transient ventricular ischemia (46%), as well as during the early reperfusion period (68% compared to control). Despite that, activity was suppressed during both states by SCS.

Thus, SCS modifies the capacity of intrinsic cardiac neurons to generate activity. SCS also acts to suppress the excitatory effects that local myocardial ischemia exerts on such neurons. Since no significant changes in monitored cardiovascular indices were observed during SCS, it is concluded that modulation of the intrinsic cardiac nervous system might contribute to the therapeutic effects of SCS in patients with angina pectoris.

Introduction

Patients who suffer from severe angina pectoris following coronary artery revascularization or whose clinical status render them inappropriate candidates for such a procedure can obtain relief from their angina by spinal cord stimulation (SCS) (Jessurun et al., 1997; Schoebel et al., 1997). High frequency, low intensity electrical stimuli delivered to the dorsal aspect of the $T_1$-$T_2$ thoracic spinal cord suppresses the pain associated with myocardial ischemia without affecting awareness of the symptoms from a possible myocardial infarction (Anderson et al., 1994; Eliasson et al., 1996; Hautvast et al., 1998; Sanderson et al., 1994). Application of SCS does not appear to induce any adverse effects in patients experiencing transient ischemia of the myocardium (Sanderson et al., 1992), patients retain their capacity to sense angina during increased workload (Mannheimer et al., 1993).

The effects of SCS have been attributed to improved myocardial perfusion and/or alterations in the oxygen demand and supply ratio as reflected in a reduction in stress-induced alterations in the ST segment of the ECG (Sanderson et al., 1992). Spinal cord stimulation also improves myocardial lactate metabolism (Mannheimer et al., 1993). Spinal cord stimulation has recently been suggested as an adjunct to coronary artery bypass surgery in high-risk patients (Mannheimer et al., 1998).

Spinal cord stimulation has been shown to influence information processing within the central nervous system (Chandler et al., 1193; Yakhnitsa et al., 1999). This treatment modality has also been demonstrated to influence peripheral blood flow (Augustinsson et al., 1995; Augustinsson et al., 1997; Linderoth et al., 1991; Linderoth et al., 1994; Croom et al., 1997). In order to understand the mechanisms underlying SCS in cardiac control, we studied the effects of SCS upon the intrinsic cardiac nervous system. Intrinsic cardiac neurons receive constant inputs from spinal cord neurons to regulate regional cardiac function on a beat-to-beat basis (NAMES). Transient regional ventricular ischemia markedly increases the activity generated by intrinsic cardiac neurons (Huang et al., 1993). Furthermore, excessive activation of limited populations of intrinsic cardiac neurons induces cardiac dysrhythmias, even in normally perfused hearts (Huang et al., 1994).

The experiments and data detailed hereinbelow show that SCS, applied with clinically employed electrical stimulation parameters, modifies the activity generated by intrinsic cardiac neurons in situ. SCS does not change cardiac dynamics. Effects of SCS on intrinsic cardiac neural activity were characterized during coronary arterial occlusion as well as during the subsequent reperfusion period and it was determined that SCS modifies intrinsic cardiac neuronal function in the presence of myocardial ischemia. These experiments show that SCS influences the behavior of intrinsic cardiac neurons markedly, changes that are involved in the clinically observed effects of SCS during acute myocardial ischemia.

Methods

Animal Preparation

Experiments performed in the present study were approved by the Institutional Animal Care and Use Committee of the OUHSC and followed the guidelines outlined by the International Association for the Study of Pain and in the NIH Guide for the Care and Use of Laboratory Animals (National Academy Press, Washington, D.C., 1996). Nine adult male dogs of mixed breed weighing between 15 and 25 kg were used. Animals were kept under standard laboratory conditions in a light-cycled environment (12 h/12 h) with free access to water at all times and to food at regular intervals. For the duration of the surgery, dogs were first anesthetized with sodium thiopental (20 mg/kg, i.v.) and maintained with sodium thiopental administered in boluses (5 mg/kg i.v.) to effect every 5-10 min. Animals were intubated and then artificially ventilated using a Harvard respirator (Palm Springs, Calif.). After the surgical preparation was completed, anesthesia was changed to alpha chloralose. An initial bolus dose of alpha chloralose (75 mg/kg, i.v.) was administered, with repeat doses (20 mg/kg) given as required during the remainder of the experiment. The level of anesthesia was checked throughout each experiment by observing pupil reaction, monitoring jaw tension and squeezing a hindpaw to determine if blood pressure and heart rate changed. This anesthetic regimen has been demonstrated to produce adequate anesthesia without suppressing autonomic neural responses (Gagliardi et al., 1988). Electrodes inserted into the forelimbs and the left hind limb were connected to an Astro-Med, Inc. (West Warwick, R.I.) model MT 9500 eight channel rectilinear recorder to monitor a modified Lead II electrocardiogram.

Implantation of Spinal Cord Stimulation Electrodes

After induction of anesthesia, animals were placed in the prone position and the epidural space of the mid-thoracic spinal column was penetrated percutaneously with a Touhy needle using A-P fluoroscopy and loss-of-resistance technique, as is routinely done in the clinic. A four-pole catheter (Medtronic QUAD Plus Model 3888; Medtronic Inc., Minneapolis, Minn.) was introduced through the cannula and its tip was advanced to the $T_1$ level of the spinal column and placed slightly to the left of the midline (Augustinsson et al., 1995). The two poles of this stimulating lead chosen for subsequent use (inter-electrode distance of 1.5 cm) were placed at the level of the $T_1$ and $T_4$ vertebrae. Final placement was aided by delivering electrical current to induce motor responses using the rostral or caudal poles as cathodes, respectively. Rostral stimulation just above motor threshold resulted in proximal forepaw and/or shoulder muscle contractions while caudal electrode stimulation induced contractions in the lower trunk. Once the appropriate electrode positions were obtained, the lead was fixed to the intraspinous ligaments with a suture surrounding a Silicone protective sleeve. Extension wires were tunneled subcutaneously to the ventral surface of the animal where they were connected to a stimulator. Motor responses were rechecked after the animal had been turned to the supine position to make sure the electrodes had not moved during this maneuver and to establish the appropriate stimulus intensities for the subsequent SCS.

Cardiac Instrumentation

After placing the animal on its back, a bilateral thoracotomy was made in the fifth intercostal space to expose the heart. The subclavian ansae on both sides of the thorax were exposed and silk ligatures were placed around them so that each could be easily sectioned later in the experiments to decentralize the intrinsic cardiac nervous system. The ventral pericardium was incised and retracted laterally to expose the heart and the ventral right atrial deposit of fat containing the ventral component of the right atrial ganglionated plexus. Neurons in this ganglionated plexus are representative of those found in the various intrinsic cardiac ganglionated plexuses (Gagliardi et al., 1988).

Left atrial chamber pressure was measured via a PE-50 catheter inserted directly into the left atrial chamber via its appendage. Left ventricular chamber pressure was monitored via a Cordis (Miami, Fla.) #6 French pigtail catheter, which was inserted into that chamber through a femoral artery. Systemic arterial pressure was measured using a Cordis #7 French catheter placed in the descending aorta via the other femoral artery. These catheters were attached to Bentley (Irvine, Calif.) Trantec model 800 transducers.

Neuronal Recording

Activity generated by ventral right atrial neurons was recorded in situ, as has been done in previous studies (Gagliardi et al., 1988). To minimize epicardial motion during each cardiac beat, a circular ring of stiff wire was placed gently on the fatty epicardial tissue overlying the ventral surface of the right atrium containing the right atrial ganglionated plexus. A tungsten microelectrode (30-40 µm diameter and exposed tip of 1 µm; impedance of 9-11 M at 1000 Hz), mounted on a micromanipulator, was lowered into this fat using a microdrive. Exploration was done by driving the electrode tip through this tissue beginning at the surface of this fat, penetrating to regions adjacent to cardiac musculature. Proximity to the atrial musculature was indicated by increases in the amplitude of the ECG artifact. The indifferent electrode was attached to mediastinal connective tissue adjacent to the heart. Signals recorded via the electrode were led to a CWE BMA-831 differential preamplifier with a high impedance head stage (bandpass filters set at 300 Hz and 10 kHz), and were processed by a signal conditioner (bandpass 100 Hz-2 kHz). Signals were amplified further via a Princeton Applied Research (Princeton, N.J.) battery driven amplifier (300 Hz-2 kHz) and were displayed on an Astro-Med, Inc. (West Warwick, R.I.) MT 9500 8 channel rectilinear recorder along with the cardiovascular variables described above. Data were stored via a Vetter (Rebesburg, Pa.) M3000A digital tape system for later analysis. Action potentials generated by neurons in one site of a right atrial ganglionated plexus were recorded using extracellular recording electrodes, individual units being identified by their amplitudes and configurations. As established previously (Armour et al., 1990), extracellular action potentials so generated are derived from somata and/or dendrites rather than axons of passage. Amplitudes of identified action potentials varied by less than 25 µV over several minutes. Each potential retained the same configuration over time. Action potentials recorded in a given locus with the same configuration and amplitude (±25 µV) were considered to be generated by a single unit.

Protocols

Five different protocols were employed in each animal (cf. FIG. 34) The order in which each protocol was applied was randomized among animals.

Protocol A—Spinal Cord Stimulation

The parameters used to electrically stimulate the thoracic spinal cord were similar to those used clinically. Stimuli were delivered to the dorsal aspect of the thoracic spinal cord via a Grass model S48 stimulator connected to the quadripolar electrode via a stimulus isolation unit (Grass model CCU1) via, a constant current unit (Grass SIU1). With the animal placed in the supine position for all subsequent experimentation, the current intensity used to evoke detectable skeletal muscle motor responses was determined as the motor threshold (MT). Stimuli (50 Hz and 0.2 ms duration) were delivered at two intensities (66 and 90% of MT). An intensity of 66% of MT has been shown to recruit low threshold, rapidly conducting axons (A-beta), whereas higher, intensity stimuli (90%) activate fast A-delta fibers as well as the other axonal populations (Croom et al., 1997; Linderoth et al., 1991). The current measured at MT varied among animals likely because of the varied anatomy of the thoracic spinal space among animals. The stimulus intensity was found to vary between 30 and 50 µA when current was set to 66% of MT. When the stimulus current was 90% of MT, it varied between 80 and 210 µA among different animals. The MT was rechecked periodically and remained stable over time in individual animals. With respect to protocol A, cardiac indices and intrinsic cardiac neural activity were monitored immediately before, during and for 30-45 s after 4 ruin of SCS at 90% of MT (FIG. 34 (A)).

Protocol B—Regional Ventricular Ischemia

A silk (3-0) ligature was placed around the left anterior descending coronary artery and another around the circumflex coronary artery, approximately 1 cm from their respective origins. Each ligature was led through a short segment of polyethylene tubing in order to occlude these arteries later in the experiments while leaving the arterial blood supply (right coronary and sinoatrial arteries) patent to the ventral right atrial neurons that were being investigated. Fur protocol B, cardiac indices and neuronal activity were monitored before, during and immediately after occluding the two coronary arteries concurrently for 2 min (FIG. 34(B)).

Protocols C, D and E in which SCS and Regional Ventricular Ischemia were Combined The effects of 2 min of myocardial ischemia on intrinsic cardiac neuronal activity and regional cardiac indices were studied in the presence of SCS (at 90% of MT for 4 min) applied at different times during the myocardial ischemia. Protocol C: The spinal cord was stimulated for 4 min and the 2 min of coronary artery occlusion began 1 min after the onset of the SCS (in the middle of the SCS; Foreman FIG. 1C). Protocol D: Spinal cord stimulation was initiated 1 min after coronary artery occlusion began (staged occlusion with overlapping stimulation) (FIG. 34(D)). Protocol E: In this protocol, spinal cord stimulation began immediately after finishing 2 min of coronary artery occlusion (FIG. 34(E)). The order in which each of these protocols was applied was randomized among dogs.

After all of the protocols described above were completed, the right and left subclavian ansae were sectioned in five of the dogs, thereby eliminating spinal cord afferent and efferent communications with neurons in intrathoracic ganglia. After this maneuver, the five SCS and transient coronary occlusion protocols described above were repeated.

Data Analysis

Individual action potentials, which maintained their configurations over time, were analyzed. Activity generated by the somata and/or dendrites of neurons within the right atrial ganglionated plexus was averaged during successive 30-s periods before, during and after each intervention. At the same time, heart rate, left ventricular wall (intramyocardial) and chamber systolic pressures were measured, as was aortic pressure. Neuronal activity and cardiovascular indices recorded immediately before each intervention and during the steady state response to an intervention were averaged and presented as means±S. E. M. Fluctuations in the amplitude of action potentials generated by a unit varied by less than 50 μV over several minutes, action potentials retaining the same configurations over time. Thus, action potentials recorded in a given locus with the same configuration and amplitude (±50 μV) were considered to be generated by a single unit. Action potentials with signal-to-noise ratios greater than 3:1 were analyzed. The threshold for neuronal activity changes was taken as a change of more than 20% from baseline values. Neuronal activity responses elicited by each intervention were evaluated by comparing activity generated immediately before each intervention with data obtained at the point of maximum change during the intervention. Data were expressed as means±S. E. M. Oneway ANOVA and paired t-test with Bonferroni correction for multiple tests was used for statistical analysis. A significance value of $P<0.05$ was used for these determinations.

Results

Identification of Active Sites

Action potentials were identified in 1-3 loci within the ventral right atrial ganglionated plexus of each animal. Based on the different amplitudes and configurations of the recorded action potentials within these loci, ongoing activity was generated by an average of 5.1±0.9 (range 3-9) neurons. Identified neurons generated, on average, 496±112 impulses per minute (ipm) during control conditions throughout the duration of these experiments. Multiple neurons at each identified active site generated action potentials that were altered in a similar fashion by each of the different interventions tested.

(Protocol A) Effects of Spinal Cord Stimulation

Only the effects of SCS employed at 90% of MT are presented herein since 66% MT elicited minimal changes in the activity generated by the intrinsic cardiac neurons. The average activity generated by identified right atrial neurons in all animals (n=9) fell from 496±112 to 1501±71 ipm (P<0.01) during SCS at 90% MT (FIG. 34(A)). Neuronal activity remained depressed for 10-20 s after SCS ceased (142±61 ipm), returning to control levels by about 1 min after cessation of stimulation (FIG. 35(A)). SCS did not change monitored cardiac indices overall. For instance, SCS did not change heart rate (155±8 vs. 159±8 beats per minute) or left ventricular chamber systolic 124±8 vs. 131±8 mmHg) and diastolic pressures. SCS did not change aortic pressure (124±8/99±6 vs. 122±5/95±4 mmHg).

Figure 35:
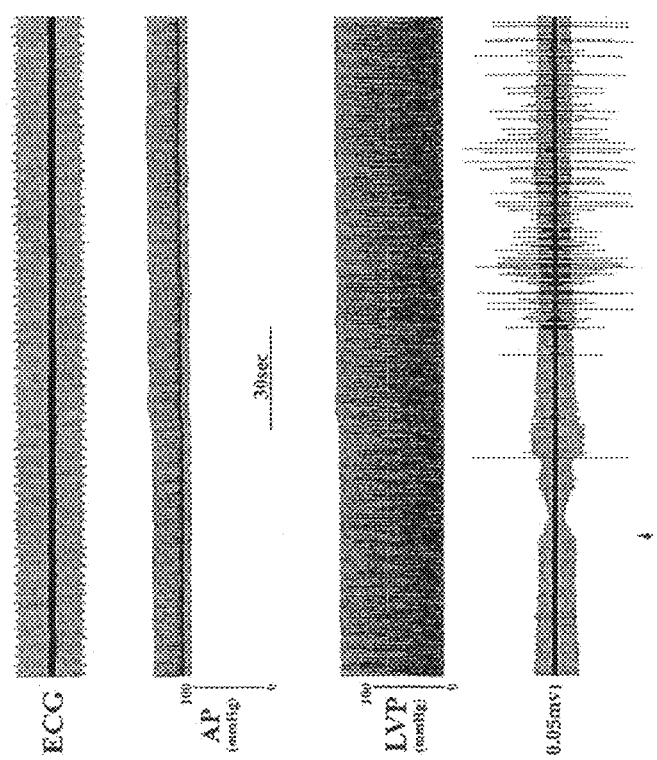
FIG. 35 shows the initiation of coronary artery occlusion (arrow below) resulting in an increase in the activity generated by right atrial neurons (individual units identified by action potentials greater than the small atrial electrogram artifacts). From above down are the ECG, aortic pressure (AP), left ventricular chamber pressure (LVP) and neuronal activity. Horizontal timing bar=30 s.

FIG. 35. shows initiation of coronary artery occlusion (arrow below) resulted in an increase in the activity generated by right atrial neurons (individual units identified by action potentials greater than the small atrial electrogram artifacts). From above down are the ECG, aortic pressure (AP), left ventricular chamber pressure (LVP) and neuronal activity. Horizontal timing bar=30 s.

(Protocol B) Effects of Transient Myodcardial Ischemia

When ventricular ischemia was induced by occluding both the left anterior descending and circumflex coronary arteries for 2 min in neurally intact preparations, the activity generated by right atrial neurons increased in each animal (FIG. 35). Neuronal activity increased, on average, by 46% (370±126 to 539±91 ipm; P<0.01) (FIGS. 35(B) and (C)) despite the fact that the blood supply of identified neurons was unaffected. Neuronal activity remained elevated immediately after reperfusion began (621±175 ipm, +68% compared to control values; P<0.05). Monitored cardiac indices did not change significantly during the 2 min of coronary artery occlusion or during the reperfusion period. For instance, heart rate was similar at the end of ventricular ischemia episodes (140±10 beats per minute) as before these episodes began (142±9 beats per minute). Even though left ventricular chamber systolic pressure underwent minor reductions in a few instances, this index remained unchanged overall (121±6 vs. 121±6 mmHg). Left ventricular diastolic pressure and aortic pressures were also unaffected. No serious dysrhythmias were induced during the brief periods of coronary artery occlusion. During the early reperfusion phase, minor S-T segment elevation and terminal QRS slurring was evident in each animal.

SCS Modulated Responses to Transient Myocardial Ischemia

Figure 34:
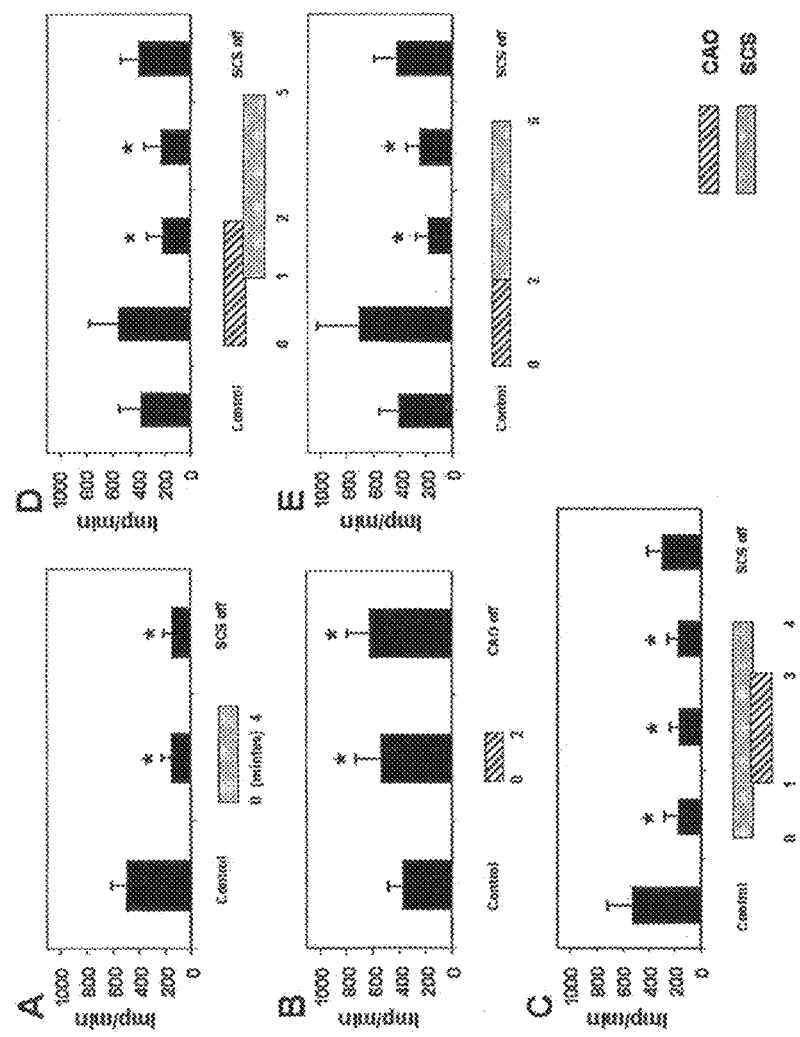
FIG. 34 shows the average neuronal activity data derived from all animals during each of the five protocols utilized in this study. When SCS was applied alone (A) neuronal activity was suppressed, a change which persisted for a short time after terminating the SCS (SCS off). (B) Coronary artery occlusion (CAO) enhanced neuronal activity. (C) SCS suppressed neuronal activity before, during and after coronary artery occlusion. Data obtained for the other protocols (SCS and CAO) are presented in panels D and E. * Represents data which was significantly different from control values ($P<0.05$).

Neuronal activity was not enhanced by coronary artery occlusion induced in the presence of SCS, irrespective of whether SCS was applied during (FIGS. 34 c and 34(D)) or immediately after (Foreman FIG. 1E) the ischemic period. Monitored cardiovascular variables did not change significantly when the combined coronary artery occlusion and SCS protocols were instituted.

(Protocol C) Occlusion in the Middle of Stimulation

Figure 36:
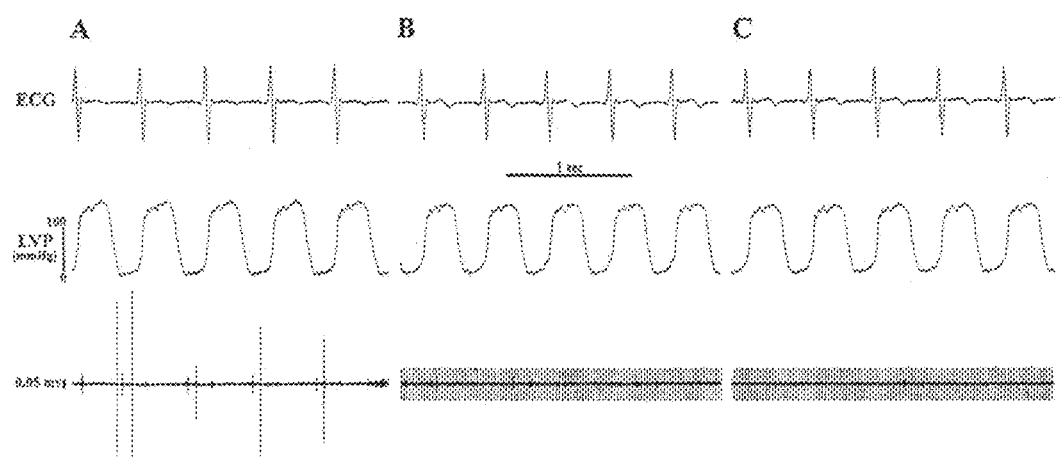
FIG. 36 shows the influence of SCS on the ECG, left ventricular chamber pressure (LVP=145 mmHg) and intrinsic cardiac neuronal activity (lowest line) before and during coronary artery occlusion. (A) Multiple neurons generated action potentials, represented by their differing heights, at a rate of 132 impulses per minute (ipm) during control states. (B) Once SCS was initiated (note stimulus artifacts in the neuronal tracing), neuronal activity decreased to 34 imps/min (no activity generated during the record). ECG alterations were induced thereby. (C) Neuronal activity continued at the rate (39 imp) in the presence of SCS even though coronary artery occlusion had been maintained for over 1.5 min.

When the 2-min period of myocardial ischemia occurred in the middle of the SCS (1 min after SCS began), the neurosuppressor effects of SCS persisted during the ischemic period (FIG. 36). For instance, intrinsic cardiac neuronal activity was reduced from that of control states (511±197 ipm) during SCS (169±99 ipm, P<0.01 compared to control), neuronal activity remaining suppressed when the stimulation occurred in conjunction with the occlusion (164±74, P<0.01 compared to control; FIG. 34-C). Suppression of neuronal activity persisted after terminating the occlusion while the SCS was maintained (166±84 ipm, P<0.01 compared to control). Only after discontinuing the SCS did neuronal activity gradually return to control values.

(Protocol D) Occlusion Overlapped by Stimulation

During this protocol (FIG. 34(D)), the activity generated by intrinsic cardiac neuronal activity was enhanced by 42% (388±155 to 555±211 ipm; P<0.01) during the initial coronary artery occlusion period. When SCS was applied 1 min after the occlusion began, neuronal activity was suppressed by 46% (activity of 211±134 ipm) even though the myocardial ischemia persisted (Fig. CC-C). In this protocol, neuronal activity remained suppressed during the reperfusion period (227±134 ipm) while the SCS persisted neuronal activity returned to control values only after SCS ceased (394±142 ipm).

FIG. 36 shows the influence of SCS on the ECG, left ventricular chamber pressure (LVP=145 mmHg) and intrinsic cardiac neuronal activity (lowest line) before and during coronary artery occlusion. (A) Multiple neurons generated action potentials, represented by their differing heights, at a rate of 132 impulses per minute (ipm) during control states. (B) Once SCS was initiated (note stimulus artifacts in the neuronal tracing), neuronal activity decreased to 34 imps/min (no activity generated during the record). ECG alterations were induced thereby. (C) Neuronal activity continued at that rate (39 ipm) in the presence of SCS even though coronary artery occlusion had been maintained for over 1.5 min.

(Protocol E) Occlusion Followed by Stimulation

In this protocol (FIG. 34(E)), coronary artery occlusion alone enhanced neuronal activity (403±150 to 701±315 ipm; P<0.01). When SCS was started immediately following termination of 2 min of coronary occlusion (that is during the early reperfusion period), neuronal activity fell to 173±295 ipm (P<0.01 compared to the ischemia period). Neuronal activity remained suppressed throughout this stimulation period, being 244±98 ipm (P<0.01 compared to control values) after 4 min of SCS. This is in distinct contrast to the finding that neuronal activity remained elevated (~70% of control values) during the early reperfusion period immediately after SCS was terminated (FIG. 34(B)).

Acute Decentralization

After all of the experimental protocols described above were completed, the spinal cord was stimulated in 5 animals at 90% of MT before and after sectioning the right and left ventral and dorsal subclavian ansae. After surgically disconnecting intrinsic cardiac neurons from the spinal cord neurons, ongoing neuronal activity decreased from 378±34 to 162±72 ipm (P<0.01). SCS did not modify the activity generated by identified intrinsic cardiac neurons thereafter (162±72 vs. 147±61 ipm); nor did SCS affect recorded cardiac indices.

Discussion

Results of the present experiments demonstrate that the activity generated by intrinsic cardiac neurons is modulated when the dorsal aspect of the thoracic spinal is stimulated electrically. That suppression of the ongoing activity generated by intrinsic cardiac neurons induced by SCS persisted for at least 30 s following termination of 4 min of SCS shows that the effects of this intervention last beyond the stimulation period. Interruption of afferent and efferent nerves traveling in the subclavian ansae eliminated the suppressor effects that SCS exerted on intrinsic cardiac neurons. These data show that the influence of spinal cord neurons on the intrinsic cardiac nervous system occur primarily via axons coursing in the intrathoracic sympathetic nervous system.

Based on results obtained when SCS was applied to the lumbosacral spinal cord, both sympathetic afferent and efferent fibers contribute to the suppression of intrinsic cardiac activity so identified. Four minutes of SCS at 66% of MT was much less effective in suppressing neuronal activity than when the spinal cord was stimulated at 90% of MT. Spinal cord stimulation at 90% MT antidromically activates sensory afferent fibers that release calcitonin gene-related peptide (CGRP) from their afferent terminals, an action that may be dependent on the presence of nitric oxide; such local release of CGRP from sensory afferent nerve terminals produces vasodilation of the rat hind paw (Croom et al., 1997). It is known that endorphins are released into the coronary circulation of humans during SCS (Eliasson et al., 1991). The release of neuropeptides by antidromic activation of sensory neurites (Croom et al., 1997) acts to change the activity generated by intrinsic cardiac neurons (Armour et al., 1993).

Activation of sympathetic efferent preganglionic axons suppresses many intrathoracic reflexes that are involved in cardiac regulation (Armour et al., 1985) as well as the activity generated by populations of neurons within intrathoracic extracardiac (Armour, 1986) and intrinsic cardiac (NAMES) ganglia, thereby reducing the capacity of intrathoracic sympathetic efferent neurons to influence cardiodynamics (Butler et al., 1988). This effect may in part be due to activating inhibitory synapses within intrathoracic ganglia, including those on the heart such as occurs when intracranial pressure raises (Murphy et al., 1995). Such suppression of neuronal activity has been demonstrated in sympathetic efferent neurons controlling the peripheral vasculature as well (Linderoth et al., 1991; Linderoth, Fedorcsak et al., 1991).

As has been shown previously (Huang et al., 1993), the activity generated by right atrial neurons increased in the presence of regional ventricular ischemia (FIG. 35), remaining elevated during the early reperfusion phase (FIG. 34(B)). This information and knowledge has clinical relevance since excessive activation of limited populations of intrinsic cardiac neurons can lead to the induction of ventricular arrhythmias (Huang et al., 1994) or even ventricular fibrillation (Armour, 1999). Application of SCS before and during the induction of transient coronary artery occlusion prevented ischemia-induced changes in neuronal activity (FIG. 36), including that identified during the reperfusion period (FIG. 34(C)). In other words, although intrinsic cardiac neuronal activity was enhanced during regional ventricular ischemia, SCS returned intrinsic cardiac neuronal activity to base line levels during these ischemic episodes. It is important to note that the two coronary arteries that were occluded did not supply arterial blood to identified right atrial ventral neurons (Huang et al., 1993). The transient periods of regional ventricular ischemia were of short enough duration to induce minor or no alterations in recorded cardiac variables. Thus, the effects of transient coronary artery occlusion on intrinsic cardiac neuronal activity are the result of altered inputs to intrinsic cardiac neurons arising from distant ischemia-sensitive afferent neurites. SCS was effective in reducing such inputs. These neurosuppressor effects occurred whether SCS was applied immediately before or during coronary artery occlusion, or during the early reperfusion phase (FIG. 34). These data support the notion that SCS suppresses intrinsic cardiac neurons responsiveness to regional ventricular ischemia as well as during the subsequent reperfusion period.

The data obtained in this study are in accord with clinical findings indicating that improvement of cardiac function and symptoms can occur when SCS is applied to patients with angina pectoris (deJongste et al., 1994). Since modification of the intrinsic cardiac nervous system can lead to alterations in ventricular regional flow (Kingma et al., 1994), perhaps some of the responses elicited by SCS involved subtle changes in the redistribution of coronary artery blood flow given that no detectable changes in cardiodynamics were identified with the methods used in these experiments. Thus, the effects that SCS induces in a clinical setting reside, in part, in the capacity of such therapy to stabilize this final common regulator, even in the presence of ventricular ischemia. Since the intrinsic cardiac nervous system receives inputs arising from cardiac sensory nenrites as well as from central neurons (Murphy et al., 1995), SCS may exert multiple effects on this local neuronal circuitry. Heterogeneous activation of intrinsic cardiac neurons destabilizes cardiac neuronal regulation that, in turn, leads to the genesis of ventricular tachydysrhythmias (Huang et al., 1994). Data obtained in the present experiments indicated that SCS reduces the excitability of intrinsic cardiac neurons, even in the presence of ventricular ischemia and, as such, may help to stabilize cardiac function.

In summary, electrical stimulation of the thoracic spinal cord influences the function of the final common neuronal regulator of cardiac function, the intrinsic cardiac nervous system, even in the presence of myocardial ischemic challenge. Thus, SCS acts in part to protect the heart from some of the deleterious consequences resulting from myocardial ischemia via altering the function of the intrinsic cardiac nervous system.

As stated previously, electrical stimulation of the dorsal aspect of the upper thoracic spinal cord is used to treat patients with angina pectoris refractory to conventional therapeutic strategies. The purpose of the following described experiments was to determine whether spinal cord stimulation SCS in dogs affects regional myocardial blood flow and left-ventricular LV function before and during transient obstruction of the left anterior descending coronary artery LAD. In anesthetized dogs, regional myocardial blood flow distribution was determined using radiolabeled microspheres and left-ventricular function was measured by impedance-derived pressure-volume loops. SCS was accomplished by stimulating the dorsal T1-T2 segments of the spinal cord using epidural bipolar electrodes at 90% of motor threshold MT 50 Hz, 0.2-ms duration. Effects of 5-min SCS were assessed under basal conditions and during 4-min occlusion of the LAD.

In summary, SCS alone evoked no change in regional myocardial blood flow or cardiovascular indices. Transient LAD occlusion significantly diminished blood flow within ischemic, but not in non-ischemic myocardial tissue. Left ventricular pressure-volume loops were shifted rightward during LAD occlusion. Cardiac indices were altered similarly during LAD occlusion and concurrent SCS. Thus, SCS does not influence the distribution of blood flow within the non-ischemic or ischemic myocardium. Nor does it modify LV pressure-volume dynamics in the anesthetized experimental preparation.

Introduction

The majority of patients with angina pectoris secondary to coronary artery disease can be adequately controlled with medication and revascularization procedures. However, a subset of patients exists with chronic angina that is refractory to these standard treatment strategies. Neuromodulation therapy has been advocated as an adjunct therapy for patients with chronic refractory angina pectoris (DeJongste, Hautvast et al., 1994; Mannheimer et al., 1985) or even as an alternative to coronary artery bypass grafting CABG in high-risk patients (Mannheimer et al., 1998) to improve the clinical response to ischemia. With regard to safety concerns, electrical stimulation of the dorsal aspect of the spinal cord SCS does not mask anginal symptoms elicited during acute myocardial infarction (Anderson et al., 1994; Sanderson et al., 1994). Furthermore, SCS appears to have anti-ischemic properties as demonstrated during exercise stress testing (DeJongste, Hautvast et al., 1994; Sanderson et al., 1994; Hautvast et al., 1994), ambulatory ECG monitoring (DeJongste et al., 1994; Hautvast et al., 1997), and rapid right atrial pacing (Mannheimer et al, 1993; Sanderson et al., 1994).

Chauhan et al. 1994 showed that the velocity of coronary arterial blood flow of patients with either CAD measured in the left main artery with stenosis >50% in the right coronary artery or syndrome X changed when transcutaneous electrical nerve stimulation TENS; 150 Hz at 300 ms, 10-60 mA is applied for 5 min. In agreement with that, other reports indicate that SCS can increase myocardial blood flow in low-flow regions, possibly related to recruitment of coronary collateral vessels and a decrease in flow in normally perfused myocardium (Mobilia et al., 1998). Other contrary studies indicate, however, that SCS does not improve blood flow within the ischemic myocardium of patients with significant coronary artery disease or syndrome X even though it reduces ST-segment alterations (De Landesheere et al., 1992; Sanderson et al., 1996; Jessurun et al., 1998; Norrsell et al., 1998). Furthermore, at least one study has indicated that SCS does not alter total coronary blood flow in patients undergoing dipyramidole stress testing (Hautvast et al., 1996).

In light of these divergent clinical findings, examination of the influence of SCS on the distribution of regional myocardial blood flow utilizing radiolabeled microsphere technique (Baer et al., 1984) and LV chamber dynamics utilizing the conductance catheter technique (Baan et al., 1984) in canine hearts was undertaken. As has been indicated in the previously discussed experiments hereinabove, SCS does not alter cardiac indices (Foreman et al., 2000). Thus, the effects of altered cardiac workload on regional ventricular flow elicited during SCS were expected to be minimal. For that reason, the effects of SCS on the distribution of blood flow in the acutely ischemic myocardium were also examined. The duration of ischemic period was brief in order that cardiac indices return to normal values after terminating regional myocardial ischemia. The results obtained from these disclosed experiments indicate that SCS does not affect regional myocardial blood supply or LV dynamics in the normally perfused myocardium. Furthermore, SCS does not alter blood flow within a ventricular ischemic zone; nor does it affect the ischemia-induced rightward shift of the LV pressure-volume relationship.

Materials and Methods

Animal Preparation

The experiments performed in the present study were performed in accordance with the Guide to the Care and Use of Experimental Animals set up by the Canadian Council on Animal Care and under the regulations of the Animal Care Committee at Laval University. Adult mongrel dogs of either sex, weighing between 20 and 25 kg, were used. Dogs were tranquilized with diazepam 1 mg/kg, i.v. and fentanyl 20 mg/kg, i.v. and then anesthetized with sodium pentobarbital 25 mg/kg, i.v. Noxious stimuli were applied occasionally to a paw throughout the experiments to ascertain the adequacy of the anesthesia. Repeat doses of pentobarbital 5 mg/kg, i.v. were administered throughout the experiments as required. Dogs were intubated and mechanically ventilated with a mixture of oxygen 25% and room air 75%, maintaining an end-expiratory pressure of 5-7 cm $H_2O$ to prevent atelectasis. Respiratory rate and tidal volume were adjusted to maintain arterial blood gases within physiological values. Body temperature was monitored and kept between 37.58 C and 38.58 C by a water-jacketed Micro-Temp heating unit Zimmer, Dover, Ohio, USA.

Spinal Cord Stimulation

Implantation of the Spinal Cord Stimulation Electrodes

After the animal was placed in the prone position, the epidural space was entered with a Touhy needle via a small skin incision in the lower thoracic region. A four-pole lead Medtronic QUAD Plus Model 3888; Medtronic, Minneapolis, Minn. was advanced rostrally in the epidural space to the upper thoracic level under anterior-posterior fluoroscopy and positioned slightly to the left of midline according to current clinical practice (DeJongste et al., 1994). The most cranial pole of the lead was positioned at the T1 level. Electrical current was delivered via the rostral and caudal poles to verify their functional positioning. Increasing stimulus intensity via the rostral pole as cathode to motor threshold intensity MT-induced muscle contractions in the proximal forepaw and shoulder. Stimulation with the caudal pole as cathode at MT activated thoracic paravertebral muscles, resulting in a twisting movement of the trunk. When a satisfactory electrode position was obtained, the lead, protected by a silicon sleeve, was fixed to the interspinous ligament and then connected to an external stimulator.

Threshold Determination for Spinal Cord Stimulation

The animal was shifted to the decubitus position for the remainder of the experiment and MT was then reestablished. SCS was delivered via the indwelling electrode connected to a Grass S48 Stimulator Grass Instruments, Quincy, Mass., USA via a stimulus isolation unit Grass SIU 5B and a constant current generator GrassrCCU1A. The parameters used to stimulate the spinal cord were 50 Hz and 0.2-ms duration; these values are the same as those used previously to reduce neuronal activity of intrinsic cardiac neurons in anesthetized dogs (Foreman et al., 2000). Stimulation intensity was 90% of that evoking a motor response and corresponds to the maximum used in patients (Chandler et al., 1993; Anderson et al., 1994). The current intensity used for SCS at 90% of MT, varied between 0.16 and 0.72 mA mean: 0.44 mA among animals. The most rostral and caudal poles were chosen as cathode and anode, respectively, so that the entire spinal cord area used for angina therapy in humans would be stimulated.

CardioVascular Instrumentation

Both femoral arteries and the right femoral vein were exposed and cannulated with 8F vascular introducers. Cordis, Miami, Fla., USA. A 7F 12-electrode conductance catheter with Pigtail and vascular port Cordis, Roden, The Netherlands was advanced into the LV chamber via the left femoral artery. Pressure transducers were connected to the vascular port of the conductance catheter and to a fluid-filled catheter Cordis a4 placed in the descending aorta. A femoral vein catheter was used for periodic drug injections and for fluid replacement therapy physiological saline. Surface needle electrodes were positioned to record a standard lead II electrocardiogram. Analog data were displayed on an Astro Med model MT-9500 polygraph and stored directly on a computer hard disk at a sampling rate of 333 samples/channel using the AxoScope data acquisition software Axon Instruments, Foster City, Calif., USA. Total LV pressure-volume loops were determined from changes in the electrical impedance measured by the summed volumes using a signal conditioner-processor Leycom Model Sigma-5, Oegstgeest, The Netherlands, as described previously (Baan et al., 1984). A computer analysis system Conduct-PC, Cardiodynamics, Leiden, The Netherlands was used to assess LV pressure-volume loops.

Placement of Coronary Artery Occluder

Under fluoroscopy, a modified right Judkins catheter 8F, Cordis, USA was advanced to the left coronary ostium. Thereafter, a balloon catheter was advanced into the left anterior descending LAD coronary artery. The position of the balloon catheter was verified by injection of contrast medium Hexabrix 320, Malinckrodt Medical, Pointe-Claire, CAN into the left main coronary artery, visualized in the left anterior oblique position. A baseline coronary artery angiogram was obtained to confirm positioning of the balloon in the ventral descending coronary artery about 2 cm from its origin.

Experimental Protocol

Surgical preparation and angiographic balloon catheter placement were followed by a 30-min stabilization period. Regional blood flow and LV dynamics were obtained at: 1 baseline C1; 2 during 5-min SCS; 3 return to steady-state conditions C2; 4 4 min of LAD occlusion CO; 5 return to steady-state conditions C3; and 6 5-min SCS during which time blood flow in the LAD was stopped for 4 minutes. The experimental protocol was always begun with interventions 1 and 2 since the initial goal was to assess the effects of SCS on myocardial blood supply and LV dynamics. SCS and coronary occlusion were performed twice in each animal. Four dogs underwent the following protocol sequence baseline-SCS; baseline-LAD occlusion; baseline-SCS/LAD occlusion. In another four dogs, the protocol sequence was altered baseline-SCS; baseline-SCS/LAD occlusion; baseline-LAD occlusion. Blood flow in the LAD was totally obstructed by inflating the angiocatheter balloon ns8 to a pressure of 8 atm Inde-flator Plus 20, ACS, Tomecula, Calif., USA for 4 min. Completeness of coronary obstruction was confirmed by injection of contrast medium under fluoroscopy. At least 10 min elapsed between each intervention to stabilize the experimental preparation. The time during which the coronary artery was occluded 4 min was of sufficient duration to alter regional dynamics cf., the pressure-volume relationship, yet result in a return to control values upon restoration of coronary artery blood flow.

Measurement of Regional Myocardial Blood Flow

Regional blood flow distribution was determined using the radioactive microsphere technique (Baer et al., 1984). Six different radiolabeled microspheres Sn, Sr, Nb, Sc, Ce, In, each with a diameter of 15 mm, were obtained from NEN Boston, Mass., USA. Immediately prior to injection, the microsphere suspension was agitated in a vortex mixer for 2 min. Each injection comprised 1.6–3=106 microspheres administered into the LV chamber as a bolus over 15-20 s and flushed with 15 ml of warmed saline. For each microsphere injection, a timed collection of arterial blood was performed with a Masterflex infusion/withdrawal pump Fisher, Montreal, CAN from the right femoral artery catheter at a constant rate of 7.5 ml/min beginning 10 s before microsphere injection and continuing for 2 min. Myocardial blood flow was evaluated in all dogs at six different time points: 1 during baseline state before any intervention had commenced control, 2 during the final 2 min of the 5-min SCS period, 3 baseline control a2 i.e., 10 min after return to baseline conditions, 4 at the midpoint of coronary occlusion, 5 baseline control a3, i.e., 10 min after return to baseline conditions, and 6 during the final 2 min of the 5-min SCS plus 4-min coronary occlusion period.

Anatomic Risk Zone Analysis

At the end of each study, the angiographic balloon catheter was re-inflated; contrast medium was injected to verify that the balloon was positioned in the same location used earlier to induce regional myocardial ischemia. Monastral blue dye 5 ml was injected directly into the coronary artery distal to the occlusion site to identify the ischemic zone. During deep pentobarbital sodium anesthesia, cardiac arrest was induced by intravenous injection of saturated potassium chloride. The heart and left kidney were excised rapidly from the body, rinsed in saline at room temperature and then fixed in 10% buffered formaldehyde. For blood flow analysis, the right ventricle was removed and the LV including interventricular septum was cut into 6-mm slices from apex to base parallel to the atrioventricular groove. Four transverse myocardial sections beginning with the second most apical slice were employed for blood flow analysis. The LV was divided into anterior ischemic and posterior non-ischemic segments and further subdivided into endocardial, midmyocardial and epicardial portions. The outlines of each LV slice, cavity area and the area at risk, i.e., containing blue dye were traced onto acetate sheets.

Planimetry with Sigma Scan software; SPSS, California, USA was performed on these using a digitizing tablet Summagraphics II Plus interfaced with a personal computer to determine respective surface areas. The results so obtained were expressed as the area at risk indexed to total left-ventricular mass. Regional blood flow was also assessed in 4 kidney slices excluding the most polar slice that were further subdivided into medulla and cortex regions. Radioactivity in all tissue and blood reference samples was measured in a gamma-well scintillation counter Cobra. II, Canberra Packard Instruments, Montreal, CAN with standard window settings. Tissue counts were corrected for background, decay and isotope spillover; regional blood flow ml/min/g was calculated using the PCGERDA computer software Packard Instruments and expressed in Ml/min/g.

Data Analysis

Heart rate, arterial pressure, LV pressure and LV pressure-volume loops were evaluated on a beat-to-beat basis and averaged for 30 s prior to and during each intervention. Comparisons of cardiac hemodynamics and distribution of myocardial blood flow during different experimental conditions was performed using analysis of variance ANOVA with repeated measures. When a significant effect of treatment was obtained, pair wise comparisons were made using Scheffe's post-hoc test. All statistical procedures were performed using the SAS statistical software package SAS, Cary, N.C., USA; a pF0.05 was considered significant.

Results

Ten dogs entered into the study; two dogs, one during AD occlusion and one during LAD occlusion with con-current SCS went into intractable ventricular fibrillation and were excluded from the data analysis.

CardioVascular Variables

Heart rate, LV end-systolic and end-diastolic pressures and mean aortic pressure did not change during SCS. Table III LV stroke volume and ejection fraction were likewise unaffected by SCS. Monitored cardiovascular indices did not change significantly during 4 min of LAD occlusion Table III.

The decrease in LV chamber systolic and diastolic pressures was not significant presumably due to the short duration of the individual ischemic periods. Although the heart rate/LV pressure product, an index of myocardial oxygen demand, increased slightly during acute ischemia, this index did not change significantly due to large standard deviations from mean values data were not normalized. Ventricular dynamics were not significantly altered with acute LAD occlusion and concurrent SCS. Cardiac hemodynamics at the end of the experimental protocol, i.e., recovery-10 min after the final intervention was comparable to baseline values.

Regional Myocardial Blood Flow Distribution

The overall anatomic risk zone represented 21.2"5.3% mean"1 S. D. of total LV volume. Distribution of ventricular blood flow determined by radiolabeled microspheres showed that average blood flow levels decreased significantly within the ischemic zone during LAD occlusion 0.9"0.1 to 0.2"0.1 ml/min/g p-0.02. Blood flow levels were not significantly affected in the non-ischemic LV wall, the right ventricle or kidneys during LAD occlusion Table IV.

TABLE III

Summary of Cardiac Hemodynamics

| | HR | $LVP_{sys}$ | $LVP_{dias}$ | PaoM | RPP | ESV | EDV | SV |
|---|---|---|---|---|---|---|---|---|
| C1 | 107 ± 12 | 71 ± 3 | 2 ± 1 | 64 ± 4 | 7.29 ± 0.80 | 33.8 ± 2.7 | 39.7 ± 2.6 | 7.7 ± 1.1 |
| CS | 110 ± 12 | 72 ± 4 | 1 ± 1 | 63 ± 4 | 7.60 ± 0.83 | 33.3 ± 2.3 | 39.5 ± 2.7 | 7.8 ± 2.1 |
| C2 | 103 ± 16 | 70 ± 2 | 1 ± 1 | 64 ± 3 | 7.10 ± 1.05 | 29.7 ± 2.3 | 37.5 ± 3.3 | 8.9 ± 1.3 |
| CO | 122 ± 12 | 69 ± 4 | 3 ± 1 | 58 ± 4 | 8.08 ± 0.97 | 35.4 ± 2.2 | 40.1 ± 2.7 | 6.7 ± 1.4 |
| C3 | 110 ± 10 | 70 ± 4 | 3 ± 1 | 63 ± 3 | 7.32 ± 0.66 | 29.4 ± 2.9 | 35.5 ± 4.6 | 8.0 ± 2.0 |
| SCS-CO | 128 ± 13 | 70 ± 5 | 2 ± 1 | 58 ± 3 | 8.62 ± 0.89 | 35.3 ± 2.5 | 39.8 ± 2.8 | 6.9 ± 1.4 |
| Recovery | 113 ± 11 | 74 ± 4 | 1 ± 1 | 67 ± 3 | 8.22 ± 1.01 | 29.9 ± 2.1 | 35.6 ± 2.9 | 8.2 ± 1.3 |

Data are means ± S.E.M.

HR = heart rate (beats/min);

$LVP_{sys}$, $LVP_{dias}$ = systolic/diastolic pressure (mmHg);

PaoM = mean aortic pressure (mmHg);

RPP = heart rate-arterial pressure product (beats/min × mm Hg × $10^{-3}$);

ESV = end-systolic volume (ml);

EDV = end-diastolic volume (ml);

SV = stroke volume (ml/s);

CO = coronary occlusion;

SCS = spinal cord stimulation.

TABLE IV

Summary of Blood Flow Changes

| | C1 | SCS | C2 | CO | C3 | SCS-CO |
|---|---|---|---|---|---|---|
| Ischemic zone | | | | | | |
| Endocardium | 1.00 ± 0.016 | 1.02 ± 0.08 | 1.02 ± 0.27 | 0.24 ± 0.06 | 1.53 ± 0.43 | 0.28 ± 0.09 |
| Mid-myocardium | 0.80 ± 0.15 | 0.76 ± 0.12 | 0.84 ± 0.25 | 0.24 ± 0.06 | 1.29 ± 0.29 | 0.29 ± 0.06 |
| Epicardium | 0.82 ± 0.18 | 0.75 ± 0.10 | 0.90 ± 0.20 | 0.28 ± 0.08 | 1.10 ± 0.27 | 0.24 ± 0.06 |
| Non-ischemic Zone | | | | | | |
| Endocardium | 1.07 ± 1.12 | 1.07 ± 0.1 | 1.14 ± 0.25 | 1.05 ± 0.20 | 1.67 ± 0.39 | 1.04 ± 0.17 |
| Mid-myocardium | 0.91 ± 0.11 | 0.95 ± 0.11 | 1.10 ± 0.14 | 0.93 ± 0.18 | 1.32 ± 0.36 | 0.94 ± 0.19 |
| Epicardium | 0.72 ± 0.09 | 0.84 ± 0.13 | 0.84 ± 0.13 | 0.82 ± 0.18 | 1.05 ± 0.29 | 0.77 ± 0.13 |
| Right ventricle | 0.54 ± 0.07 | 0.856 ± 0.08 | 0.70 ± 0.12 | 0.78 ± 0.14 | 0.78 ± 0.14 | 0.44 ± 0.07 |

TABLE IV-continued

| | Summary of Blood Flow Changes | | | | | |
|---|---|---|---|---|---|---|
| | C1 | SCS | C2 | CO | C3 | SCS-CO |
| Kidney | | | | | | |
| Inner (medulla) | 0.29 ± 0.03 | 0.31 ± 0.04 | 0.30 ± 0.06 | 0.49 ± 0.10 | 0.49 ± 0.10 | 0.60 ± 0.07 |
| Outer (cortex) | 3.46 ± 0.36 | 3.49 ± 0.23 | 4.60 ± 1.05 | 4.88 ± 1.15 | 4.88 ± 1.15 | 3.24 ± 0.42 |

Data are means ± S.E.M. Data are expressed in ml/min/g wet weight. Abbreviatons are indicated in TABLE III.

Figure 37:
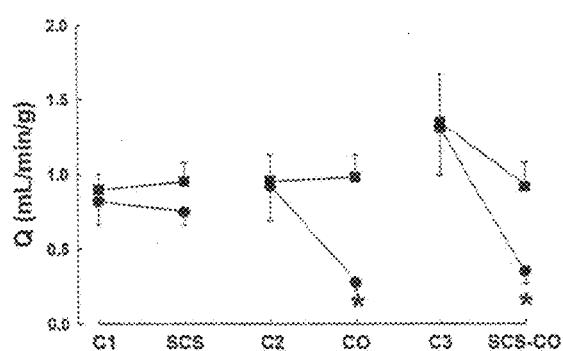
FIG. 37 shows the transmural blood flow (ml/min/g) to LV ischemic (closed spheres) and non-ischemic (closed squares) zones for each of the three baseline control conditions (C1, C2, and C3) and during the successive interventions of 5-min spinal cord stimulation (SCS), 4-min occlusion of the LAD occlusion commencing 1 min into SCS (SCS-CO). Transmural blood flow within the ischemic zone is significantly lower (*p=0.02) during both CO, and SCS-CO (p=NS between these two interventions) compared to base line.

During application of SCS concomitant with LAD occlusion, the level of blood flow reduction in the ischemic zone was similar to that which occurred during LAD occlusion alone Table IV and FIG. 37 SCS did not affect transmural blood flow distribution within the LV-free wall or the intraventricular septum (FIG. 37), or total ventricular flows. Neither did SCS affect regional blood flow in the kidneys Table IV.

Pressure-Volume Relations

Figure 38:
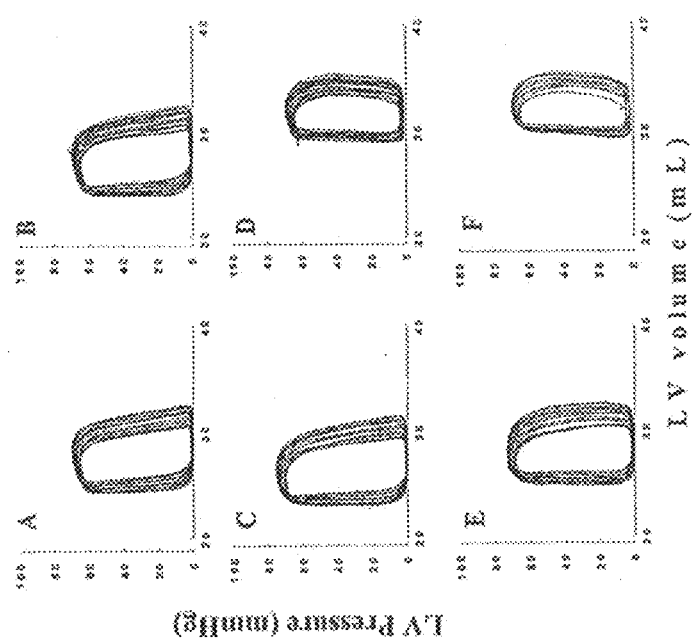
FIG. 38 shows pressure-volume (P-V) loops for the left ventricle; P-V loops obtained under basal conditions are shown in panels (A), (C) and (E) (i.e., baseline steady-state resting conditions). P-V loops obtained during SCS at 90% motor threshold (B), 4 min of LAD occlusion (D), and concurrent SCS and LAD occlusion (F) are also shown.

The LV pressure-volume loops did not change during SCS FIGS. 38(A) and (B). The LV pressure-volume loops changed immediately after the onset of LAD occlusion. The LV volumes shifted rightward, while similar peak FIG. 37. Transmural blood flow ml/min/g to LV ischemic closed spheres and non-ischemic closed squares zones for each of the three baseline control conditions C1, C2 and C3 and during the successive interventions of 5-min spinal cord stimulation SCS, 4-min occlusion of the LAD CO, and concurrent 5-min SCS plus 4 min LAD occlusion commencing 1 min into SCS SCS-CO. Transmural blood flow within the ischemic zone is significantly lower ps0.02 during both CO, and SCS-CO psNS between these two interventions compared to baseline systolic pressures were generated FIGS. 38(C) and (D). LV stroke volume and ejection fraction was reduced almost 30% compared to baseline values during the periods of local ventricular ischemia. Corresponding changes in LV pressure-volume loops were observed when the LAD was occluded concurrent with SCS FIGS. 38(E) and (F). LV stroke volume and ejection fraction was similarly diminished. Thus, SCS did not improve overall ventricular dynamics in the presence of local myocardial ischemia.

Discussion

Neuromodulation therapy is utilized to alleviate angina of cardiac origin. In order to investigate the underlying mechanisms for such therapy, we studied the potential influence of SCS on myocardial blood flow and LV dynamics in the normal canine heart. The results of this study demonstrate that electrical stimulation of the upper thoracic spinal cord does not alter either transmural distribution of blood flow within the myocardial wall or overall LV dynamics. As has been found in the past (Foreman et. al., 2000), transient focal myocardial ischemia did not alter left-ventricular chamber systolic or diastolic pressures significantly Table III. On the other hand, the LV pressure-volume loop was shifted rightward during transient occlusion of the LAD indicative of volume changes FIG. 38. Changes in LV volumes were accompanied by a significant decline in the LV ejection fraction, synonymous with altered contractile function elicited by acute coronary artery occlusion (Paulus et al., 1985; Sasayama et al., 1985; Applegate, 1991). As expected, transmural blood flow was also reduced in the ischemic zone. Application of SCS during this ischemic challenge did not further alter regional myocardial blood flow. Neither did SCS affect the rightward shift of LV pressure-volume loops induced during the ischemic challenge.

Limitations of Study

The radioactive microsphere technique for determination of regional blood flow distribution has the advantage that microspheres are trapped during the first pass through an organ with no detectable recirculation; however, the number of microspheres that can be safely injected without affecting cardiac hemodynamics is finite. Baer et al. (1984) estimated that injection of 18-27 million microspheres nine different radiolabels of 2-3 million spheres each into the left atrium had little influence on distribution of blood flow during normal coronary autoregulation or vasodilatation. In the present study systolic LV pressure and mean aortic pressure remained constant during and after microsphere injections; this indicates that these dogs were hemodynamically stable during the respective experimental protocols. It is known that radioactive microspheres have the inherent limitation that regional blood flow changes less than 10% of baseline are not readily detectable. Thus, minor changes in regional blood flow distributions between myocardial regions might not be detected. Regardless, the lack of change in measured cardiac indices during SCS suggests that the primary determinant of regional myocardial blood flow and cardiac work was not altered thereby. Coronary vascular resistance or conductance was not calculated in the present study since we did not include measurements of extravascular compressive forces or critical closing pressure; in a recent study from our laboratory we document that during autoregulation the entire coronary pressure-flow relation can shift in relation to changes in LV pressure and volume Rouleau et. al., 1999. Under steady-state conditions in the present study the endocardialrepicardial blood flow ratio was similar not during ischemia; as such, distribution of blood flow was maintained across the LV wall.

Major differences exist between the present study and some clinical studies; we used SCS, while Chauhan et al., (1994), who reported an increase in blood flow in the contralateral coronary artery, used TENS. In addition, SCS at 90% motor threshold in the anesthetized canine represents an intensity used clinically when patients anticipate more strenuous activities. Normally, stimulation intensities between 60% and 66% of paresthesia threshold are adequate to reduce anginal pain.

Clinical Implications of SCS

Pain-reducing properties of neuromodulation resulting from SCS are based on the gate theory of pain (Melzack and Wall, 1965). This theory proposes that stimulation of large afferent fibers conducting innocuous information reduce the nociceptive effects of the small afferent fibers on the activity of spinal neurons. Neuromodulation is known to stimulate neurons in the dorsal horn (Melzack and Wall, 1965; Chandler et al., 1993) and higher centers (Hautvast et al., 1997; Yakhnitsa et al., 1999). Recently we documented that the activity generated by intrinsic cardiac neurons is also suppressed by SCS, even during acute myocardial ischemic challenges (Foreman et al., 2000).

The present results are in agreement with the majority of previous clinical studies that indicate a lack of effect of SCS on overall coronary blood flow (De Landesheere et al., 1992; Hautvast et al., 1996; Sanderson et al., 1996; Norrsell et al., 1998). SCS was applied for 5 min in our study, while in most clinical studies it is maintained for much longer time periods. It is unlikely that the duration of SCS stimulation determines the effects that this intervention exerts on coronary artery blood flow (Chauhan et al., 1994). The present study was performed in canine hearts that underwent brief periods of regional ventricular ischemia. In clinical studies carried out among patients with stable angina, electrical or pharmacological i.e., dipyramidole induction of cardiac stress in the presence of neuromodulation has been shown to exert no influence on their coronary blood flow (Hautvast et al., 1996; Norrsell et al., 1998). In the present study, the canine coronary vasculature was considered to be normal in contrast to these clinical investigations in which coronary artery blood flow was assessed in patients with underlying coronary vessel disease. The primary determinant of blood flow in the normal myocardium is regional myocardial metabolic demand, the latter being very dependent on LV dynamics (Hoffman, 1987). Hemodynamic alterations are accompanied by changes in distribution of blood flow patterns across the LV wall (Dole and Bishop, 1982; Messina et al., 1985). For that reason, it is important to note that the periods of regional ventricular ischemia induced in these experiments were of short enough duration to induce minor, if any change in left-ventricular pressure Table III. It is also important to point out that the hemodynamic results obtained in the canine model may not directly apply to other animal models with different coronary collateral vascular function. However, intrinsic cardiac neuronal results derived from the canine model appear to be applicable to the porcine model and even to humans undergoing bypass surgery. Thus, the effects of regional ventricular ischemia on the intrinsic cardiac nervous system depend more on the location of the neurons and the site of ventricular injury than on species investigated. The ischemic area i.e., anatomic risk zone that was produced in these experiments was significant, being 21.2 "5.3% mean"1 S. D. of the total ventricular volume.

Ventricular ischemic zones of this magnitude are sufficient to induce fatal ventricular arrhythmias (Vegh et al., 1991; Curtis et al., 1989). In the study reported by Vegh et al. (1991), hearts were preconditioned by repeated episodes of rapid ventricular pacing; this resulted in significant cardioprotection against ischemia-induced ventricular arrhythmias. Whether SCS triggered a preconditioning response in the present experimental model is debatable. The lack of heart rate or hemodynamic effect, reflected by the similarity of the myocardial oxygen demand and myocardial blood flow data indicates that SCS may not have induced a preconditioning response. In addition, we did not observe an increase in coronary collateral flow within the ischemic myocardium. Whether preconditioning increases coronary collateral blood flow within the ischemic zone in dogs remains unclear. In the present study, ischemic zone size was not influenced by SCS. These data are in accord with the fact that SCS did not affect the LV pressure-volume relationships in addition to arterial perfusion of ventricular tissue. We cannot completely exclude the possibility that SCS redistributes blood flow between adjacent myocardial regions via the coronary collateral circulation since the microsphere technique may not reliably detect changes in blood flow at this level. Rather, these data suggest that the anti-anginal effects of SCS are induced by mechanisms other than changes in regional myocardial blood flow or LV Dynamics
Summary and Conclusions Data obtained in the present study document the fact that SCS does not affect either total myocardial blood flow or blood flow distribution across the LV wall. Neither does SCS affect the distribution of blood within the ischemic myocardium, nor that between ischemic and non-ischemic zones.

Additional studies hereinafter disclosed herein, demonstrate that (1) ischemia causes neuronal activation; (2) SCS or DCA stimulation nullifies or quenches such ischemia induced activated neurons; and (3) nullification and/or such quenching or suppressor effects on such activated neurons occur (i) prior, (ii) during, and (iii) after the cessation of SCS or DCA stimulation. Thus, SCS or DCA effectively directs the intrinsic nervous system in such a manner as to have an immediate and lasting effect on the activity of myocardial neurons and the intrinsic cardiac nervous system in general.

As mentioned previously, it is known currently that electrical excitation of the dorsal aspect of the rostral thoracic spinal cord imparts long-term therapeutic benefits to patients with angina pectoris. What is not known and is being claimed and disclosed in the present application, is that spinal cord stimulation induces short-term suppressor effects on the intrinsic cardiac nervous system. The results of the following tests show that spinal cord stimulation (SCS) induces long-term effects on the intrinsic nervous system, particularly in the presence of myocardial ischemia.

The activity generated by right atrial neurons was recorded in 10 anesthetized dogs during basal states, during prolonged (15 min) occlusion of the left anterior descending coronary artery, and during the subsequent reperfusion phase. Neuronal activity and cardiovascular indices were also monitored when the dorsal T1-T4 segments of the spinal cord were stimulated electrically (50 Hz; 0.2 ms) at an intensity 90% of motor threshold (mean 0.32 mA) for 17 min. SCS was performed before, during and after 15-min periods of regional ventricular ischemia. Occlusion of a major coronary artery, one that did not perfuse investigated neurons, resulted in their excitation. Ischemia-induced neuronal excitatory effects were suppressed (>76% from baseline) by SCS. SCS suppression of intrinsic cardiac neuronal activity persisted during the subsequent reperfusion period; after terminating 17 min of SCS, at least 20 min elapsed before intrinsic cardiac neuronal activity returned to baseline values. It is concluded that populations of intrinsic cardiac neurons are activated by inputs arising from the ischemic myocardium. Ischemia-induced activation of these neurons is nullified by SCS. The neuronal suppressor effects that SCS induces persist not only during reperfusion, but also for an extended period of time thereafter.

Introduction

High frequency, low intensity electrical stimulation of the dorsal aspect of the T1-T2 spinal cord alleviates angina pectoris in patients suffering from ischaemic heart disease (Eliasson et al., 1996; Mannheimer et al., 1993; Sanderson et al., 1992). The therapeutic effects of spinal cord stimulation on angina (SCS) can persist for hours after its termination (Jessurun et al., 1999). Accumulating evidence demonstrates that SCS is a safe anti-anginal treatment modality that does not result in increased frequency of arrhythmia formation (DeJongste et al., 1994; Eliasson et al., 1996; Hautvast et al., 1998; Mannheimer et al., 1998). However, the mechanisms whereby SCS produces its long-term effects remain unknown. Clinical studies have led to the hypothesis that SCS exerts its anti-anginal effects principally by altering the ventricular oxygen supply/demand ratio (Mannheimer et al., 1993; Sanderson et al., 1992). Mannheimer et al. (1993)

suggested that SCS reduces cardiac metabolism, thereby reducing oxygen demand and, consequently, the myocardial lactate production within the ischemic myocardium. In this regard, Hautvast et al. (1998) proposed that SCS redistributes myocardial blood flow from normal to ischaemic regions of the heart. However, in the canine model, SCS does not alter cardiac chronotropism or inotropism (as shown in the experiments above), suggesting that oxygen demand is minimally affected by such an intervention. Furthermore, SCS does not alter blood flow distribution within either the normal or ischaemic canine myocardium (also shown above).

As we show, the effects of SCS reflect changes within the CNS and/or changes in neurohumoral control of the heart. SCS modulates impulse transmission within the spinothalamic tracts of the spinal cord without blocking afferent neuronal signals arising from the ischaemic myocardium (Chandler et al., 1993). It also alters intrinsic cardiac neuronal function (show hereinabove). The intrinsic cardiac nervous system represents the final common regulator of regional cardiac function (Armour, 1991; Ardell, 2000). Its neurons are under the constant influence of central neurons, including those in the spinal cord (Gagliardi et al., 1988). Regional myocardial ischaemia results in the heterogeneous activation of the intrinsic cardiac nervous system (Armour et al., 1998). When sub-populations of intrinsic cardiac neurons become excessively activated, the cardiac electrophysiological consequences, such as the occurrence of ventricular tachycardia or ventricular fibrillation, may be devastating (Armour, 1991). Stabilization of the intrathoracic intrinsic cardiac nervous system, especially in the presence of myocardial ischaemia ameliorate the potential for cardiac electrical instability. Such a system is shown and demonstrated in the experiments outlined in the present application.

Short duration SCS (4 min) transiently suppresses the activity generated by intrinsic cardiac neurons (shown hereinabove). In a clinical setting, the anti-anginal effects of SCS persist long after its termination (Jessurun et al., 1999). The following experiments were devised to evaluate the effects of prolonged (17 min) SCS on the intrinsic cardiac nervous system in normally perfused and ischaemic hearts. These experiments were also designed to evaluate whether the neurohormonal effects that SCS imparts on the intrinsic cardiac nervous system persist not only throughout its application, but also for a time thereafter.

Materials and Methods

Animal Preparation

The Institutional Animal Care and Use Committee of Dalhousie University approved the experiments performed in the following experiments. These experiments followed the guidelines outlined by the International Association for the Study of Pain as well as the NIH Guide for the Care and Use of Laboratory Animals (National Academy Press, Washington, D C, 1996). Ten adult dogs of mixed breed, weighing between 12.5 and 26 kg (mean 19.6 kg), were used for this study. The animals were kept under standard laboratory conditions in a light-cycled environment (12 h/12 h) with free access to water at all times and to food at regular intervals.

Dogs were anesthetized in a standard manner by first administering a bolus dose of sodium thiopental (20 mg $kg^{-1}$, i.v.). Anesthesia was maintained throughout the surgery period by means of bolus doses of thiopental (5 mg $kg^{-1}$, i.v.) administered to effect every 5-10 min. Animals were intubated and then artificially ventilated using a Bird Mark VII respirator with 100% $O_2$. After completing the surgery, anesthesia was changed to alpha chloralose by first administering a dose of alpha chloralose (75 mg $kg^{-1}$, i.v.). Thereafter, repeat doses of alpha chloralose (20 mg $kg^{-1}$, i.v.) were administered, as required, during the remainder of the experiments.

The level of anesthesia was checked throughout each experiment by observing pupil reaction as well as monitoring jaw tension, heart rate and blood pressure, and by periodically checking for the withdrawal reflex by squeezing a paw. Since each bolus of alpha chloralose suppressed neuronal activity for a few minutes after its administration, these doses were administered between the interventions performed in each protocol. This anesthetic regimen produces adequate anesthesia without inordinately suppressing peripheral autonomic neural activity. Electrodes were inserted in the forelimbs and the left hind limb and connected to an Astro-Med (West Warwick, R.I.) model MT 9500 eight-channel rectilinear recorder to monitor a Lead II electrocardiogram throughout the experiments. In addition, a 12-lead electrocardiogram (ECG) strip-chart recorder (Nihon Ohden Cardiofax V model BME 7707) was employed to obtain standard lead electrocardiograms during control states and at 5-min intervals during each intervention. Heart rate and the duration of the PQ, QR and QTc intervals were analyzed during control states as well as 1, 5, 10 and 15 min after occlusions began in the absence or presence of SCS. In addition, alterations in the morphology of ST-T segments and arrhythmia formation were assessed.

Implantation of Spinal Cord Stimulation Electrodes

After induction of anesthesia, animals were placed in the prone position. The epidural space of the mid-thoracic spinal column was penetrated percutaneously with a Toughy needle (15 F). A Toughy needle has a slight angle at its tip to ease penetration between vertebral processes. Using the loss-of-resistance technique as is routinely done in a clinical setting, the tip of the Toughy needle was slowly advanced until it entered the epidural space, as visualized via A-P fluoroscopy. Once the inner cannula was removed from the Toughy needle, a four-pole catheter electrode (Medtronic QUAD Plus Model 3888; Medtronic, Minneapolis, Minn.) was introduced through the needle such that its tip could be advanced to the T1 level of the spinal column, as determined by fluoroscopy. The tip of this electrode was positioned slightly to the left of the midline, as is done in a clinical setting (Linderoth and Foreman, 1999). The rostral and caudal poles of the stimulating electrode chosen for subsequent use (inter-electrode distance of 1.5 cm) were located at the levels of the T1 and T4 vertebrae. Correct placement of the stimulating electrodes was confirmed by delivering electrical current to induce motor responses using the rostral or caudal poles as cathodes, respectively.

The rostral cathode (T1 level) and caudal anode (T4 level) of the quadripolar electrode were connected to a Grass S88 stimulator via a constant current stimulus isolation unit (Grass model CCU1 and Grass SIU5). Stimuli, delivered at 50 Hz and 0.2-ms duration, were monitored on an oscilloscope to determine the amount of current delivered. Rostral stimulation above motor threshold resulted in proximal forepaw or shoulder muscle fasciculations (or both), while caudal electrode stimulation induced contractions in the thoracic trunk. When the appropriate electrode position was confirmed, the electrode lead was covered by a Teflon protective sleeve and fixed to adjacent interspinous ligaments with a suture. Extension wires attached to the electrode leads were connected to the Grass constant current stimulator (see hereinabove). Motor responses were rechecked after the animal had been placed in the supine position to ensure that the electrodes had not moved during that maneuver.

Cardiac Instrumentation

After placing the animal on its back, a bilateral thoracotomy was made in the fifth intercostal space. The ventral pericardium was incised and retracted laterally to expose the heart and the ventral right atrial deposit of fat containing the ventral component of the right atrial ganglionated plexus. We investigated the activity generated by neurons in the right atrial ganglionated plexus because not only are they representative of those found in other atrial and in ventricular ganglionated plexuses (Armour, 1991), but they do not receive their arterial blood supply from the left ventral descending coronary artery (Huang et al., 1993). The regional arterial blood supply of these neurons and other cardiac tissues is unaffected by spinal cord stimulation (Kingma et al., in press). Thus, the blood supply of identified neurons was not affected in a significant manner by the procedures described below.

Left ventricular chamber pressure was monitored via a Cordis (Miami, Fla.) #7 French pigtail catheter that was inserted into the chamber via one femoral artery. Systemic arterial pressure was measured using a Cordis #6 French catheter placed in the descending aorta via the other femoral artery. These catheters were attached to Bentley (Irvine, Calif.) Trantec model 800 transducers.

Neuronal Recording

To minimize epicardial motion during each cardiac beat, a circular ring of stiff wire was placed gently on the fatty epicardial tissue overlying the ventral surface of the right atrium containing the right atrial ganglionated plexus (Gagliardi et al., 1988). A tungsten microelectrode (10-mm shank diameter; exposed tip of 1 mm; impedance of 9-11 MV at 1000 Hz) mounted on a micromanipulator was lowered into this fat using a microdrive. The indifferent electrode was attached to mediastinal connective tissue adjacent to the heart. The electrode tip explored this tissue at depths ranging from the surface of the fat to regions adjacent to cardiac musculature. Proximity to the atrial musculature was indicated by increases in the amplitude of the ECG artifact. Signals generated by the somata and/or proximal dendrites of intrinsic atrial neurons were differentially amplified by a Princeton Applied Research model 113 amplifier with bandpass filters set at 300 Hz to 10 kHz and an amplification range of 100-500×. The output of this amplifier, further amplified (50-200×) and filtered (bandwidth 100 Hz-2 kHz) by means of optically isolated amplifiers (Applied Microelectronics Institute, Halifax, NS, Canada), was led to a Nicolet model 207 oscilloscope and to a Grass AM8 Audio Monitor. Signals were displayed on an Astro-Med MT 9500 eight-channel rectilinear recorder along with the cardiovascular variables described above. All data were stored via a Vetter (Rebesburg, Pa.) M3000A digital tape system for later analysis. Action potentials generated by neurons in a site in the right atrial ganglionated plexus were recorded.

Individual units being identified by their amplitudes and configurations. The amplitudes of the identified action potentials varied by less than 10-50 µV over several hours; individual action potential retained the same configuration over time. Somata and/or dendrites rather than axons of passage generate individual action potentials so identified. Action potentials recorded at a given locus that displayed the same configuration and amplitude were considered to be generated by a single unit. When multiple action potentials were identified at an active site, action potentials generate by individual units were discriminated by means of a window discriminator (Hartley Instrumentation Development Laboratories, Baylor College of Medicine, Houston, Tex.).

Induction of Coronary Artery Occlusion

A silk (3-0) ligature was placed around the left anterior descending (LAD) coronary artery approximately 1.5 cm from its origin, distal to its first diagonal branch. If a relatively large number of collateral arterial branches from the apex or lateral wall were evident, ligatures were also placed around these vessels. These ligatures were led through short segments of polyethylene tubing in order to occlude these arteries later in the experiments. Since the arterial blood supply of investigated right atrial neurons arises from major branches of the right and distal circumflex coronary arteries, their blood supply remained patent during these coronary artery occlusions.

Spinal Cord Stimulation (SCS)

With the animal placed in the supine position, the intensity of the current delivered via the bipolar electrode was increased until a detectable skeletal muscle motor response was evident, as described above. This current intensity corresponds to the threshold for motor activity induction (MT). An intensity of 90% of MT was used for all subsequent stimuli as it recruits A-delta fibers and other axon populations (Linderoth and Foreman, 1999). This stimulus intensity corresponds to parameters used clinically to stimulate the thoracic spinal cord (Linderoth and Foreman, 1999). The stimulus intensity at 90% MT varied between 0.09 and 0.63 mA (mean 0.32 mA) among animals studied. Presumably the variation in current intensity at 90% MT among animals reflected slight differences in electrode position with respect to the dorsal surface of the thoracic cord. The MT was checked periodically and found to remain constant over time in individual animals.

Protocols

Figure 39:
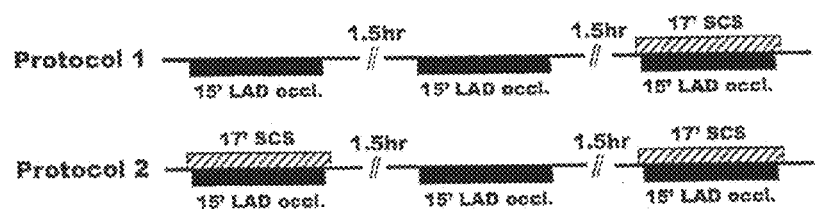
FIG. 39 shows a graphical representation of the two protocols in each group of five dogs. Note that 1.5 h was allowed to lapse between each intervention in either protocol.

Two separate protocols were applied to each of five animals, the order of their application being randomized among the 10 animals. These were devised to evaluate the long-term effects of successive 15-min periods of coronary artery occlusion performed with or without concurrent SCS. Electrical stimuli were delivered to the dorsal aspect of the thoracic spinal cord for 17-min periods. Protocol #1 began with two 15-min periods of coronary artery occlusion, with a 1.5-h interval elapsing between occlusions (FIG. 39, top panels). The coronary artery occlusion was repeated in these five animals in order to determine the reproducibility of ischaemia-induced changes in ECG morphology and intrinsic cardiac neuronal activity. After an additional 1.5-h recovery phase, 17 min of SCS (90% MT) was performed during which time a 15-min period of coronary artery occlusion was instigated 1 min after SCS began. This was followed by a 1-h period during which time neuronal activity was quantified. Thereafter, veratridine was applied to epicardial loci (see hereinbelow).

Protocol #2 was employed in the other five animals. In protocol #2, the effects of 17 min of SCS combined with 15 min of coronary artery occlusion were studied first. The coronary occlusion was initiated 1 min after beginning SCS (FIG. 34, bottom panels). After waiting for 1.5 h, a 15-min period of coronary artery occlusion was performed alone. After waiting another 1.5 h, the combined SCS and coronary artery occlusion was performed again. Protocol #2 was performed to verify the reproducibility of effects induced by SCS in the presence of ventricular ischaemia. This protocol was followed by a 1-h recovery period after which time veratridine was applied to epicardial loci.

Epicardial Application of Veratridine

Veratridine is a selective modifier of Na+ channels that excites sensory neurites associated with cardiac afferent neurons without inducing tachyphylaxis (Thompson et al., 2000). This agent (obtained from Sigma, St. Louis, Mo., USA) was dissolved in physiological Tyrode solution to make a 7.5 µM solution. Gauze squares (1×1 cm) soaked with veratridine (0.5 ml) were applied for 60-100 s to discrete epicardial loci on the right ventricular conus and the ventral surface of the left ventricle at the end of each experiment (n=10 dogs). In four animals, the effects that epicardial application of veratridine exerted on the intrinsic cardiac nervous system was also tested before the protocols described above had been performed. After removing the applied gauze, the epicardial region was flushed with normal saline for at least 30 s. Gauze squares soaked with room temperature normal saline were also applied to identify epicardial sensory fields in order to determine whether neuronal responses elicited by chemical application were due to vehicle effects or the mechanical effects elicited by gauze squares.

Data Analysis

Individual action potentials generated by the somata or dendrites of neurons within the right atrial ganglionated plexus were averaged over 30-s periods of time prior to and during each intervention. Average heart rate, left ventricular chamber systolic pressure and aortic pressure were determined concomitantly. Changes in ECG morphology induced by the protocols were assessed. When the coronary artery occlusion was performed alone, data were assessed during baseline conditions and 14 min after the occlusion began (occlusion period), as well as starting 15 s after reperfusion began (reperfusion period). When the occlusions were performed in the presence of SCS, cardiac indices and neuronal activity were assessed at five time points: (1) control period; (2) 30 s after SCS began; (3) 12 min after coronary artery occlusion began, in the presence of SCS; (4) after terminating the occlusion while the SCS persisted; and (5) within 30-60 s of terminating the SCS. Data are expressed as means±S. E. M. One-way ANOVA and paired t-test, with Bonferroni correction for multiple tests, were employed to examine grouped responses elicited during occlusion of a coronary artery alone (first occlusion) or when SCS and occlusions were performed in each protocol. Values of $P<0.05$ were used to determine significance.

Results

Identification of Active Sites

Action potentials with signal-to-noise ratios greater than 3:1 were identified in 2-3 loci within the ventral right atrial ganglionated plexus of each animal. Based on the different amplitudes and configurations of action potentials recorded at one site per animal, an average of 3.2±0.5 (range 2-6) neurons generated spontaneous activity at investigated sites during control states. Neuronal activity during basal states was usually sporadic in nature. During basal states, a few spontaneous active neurons were identified in active loci of most animals (FIG. 40), while in a few animals, a number of neurons generated spontaneous activity (FIG. 41(D)). The neuron aggregates identified in one active locus in each of the 10 investigated dogs generated, on average, 34.1±3.4 to 48.2±6.5 impulses/min (Table V).

TABLE V

Heart rate (HR), left ventricular chamber systolic pressure (LVP), aortic systolic and diastolic pressures (AP) and the activity generated by right atrial neurons recorded before (control) and during coronary artery occlusion (CAO), as well as during early reperfusion (reperfusion). These indices were also recorded when occlusion occurred during spinal cord stimulation.

| Intervention (n = 10 dogs) | HR (bpm) | LVP (mmHg) | AP (mmHg) | Neuronal activity (impulses/min) |
|---|---|---|---|---|
| Control | 134 ± 2 | 134 ± 5 | 138 ± 5/99 ± 5 | 34.1 ≠ 3.4 |
| CAO | 134 ± 2 | 136 ± 5 | 140 ± 5/99 ± 5 | 62.2 ≠ 9.5* |
| Reperfusion | 134 ± 2 | 136 ± 5 | 138 ± 5/99 ± 5 | 66.0 ≠ 13.3* |
| Control | 130 ± 3 | 137 ± 4 | 141 ± 5/99 ± 5 | 48.2 ≠ 6.5 |
| SCS | 130 ± 3 | 137 ± 4 | 141 ± 5/99 ± 6 | 15.1 ≠ 3.1* |
| SCS + CAO | 128 ± 3 | 139 ± 4 | 141 ± 5/98 ± 6 | 13.5 ≠ 2.4* |
| SCS + reperfusion | 130 ± 3 | 137 ± 4 | 141 ± 5/99 ± 5 | 15.2 ≠ 3.3* |
| Control | 131 ± 4 | 134 ± 5 | 141 ± 5/99 ± 5 | 46.8 ≠ 10.2 |

Effects of Transient Myocardial Ischaemia

Figure 42:
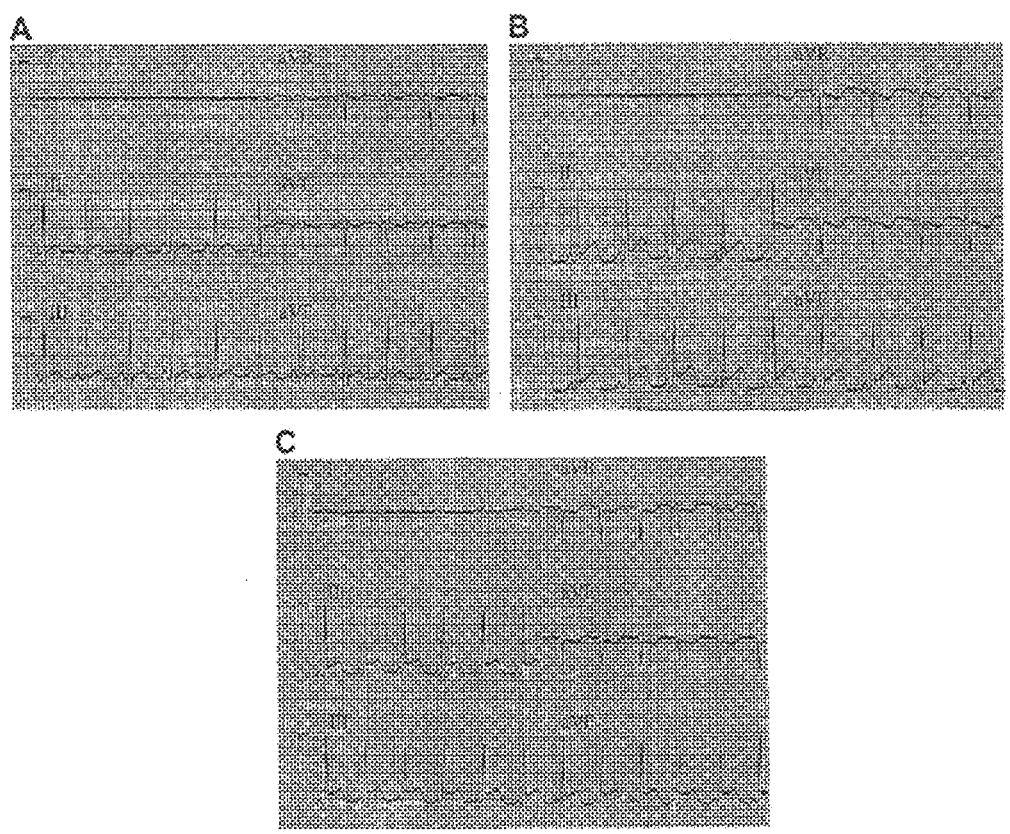
FIG. 42 shows representative ECG records obtained from one animal during control states (A), as well as a few minutes after beginning coronary artery occlusion in the presence of spinal cord stimulation (B) and at the end of occlusion while SCS was maintained (C). Note that ST segment alterations occurred throughout the period of ischaemia.

Monitored cardiac indices did not change significantly overall during coronary artery occlusion or the reperfusion period, except when cardiac arrhythmias occurred. For instance, heart rate was 134±2 beats/min (bpm) before occlusion and 130±3, 134±3, 132±2 and 134±2 bpm after 1, 5, 10 and 15 min of ischaemia, respectively. S-T segment alterations and terminal QRS slurring was evident in the ECG pattern of each animal during ischaemic episodes (FIG. 42). The ST segments remained altered (elevated or depressed by 1.0±0.2 mm) during the first 2-5 min of reperfusion. ECG patterns returned to baseline values within 20 min of reestablishing coronary artery blood flow. Short bursts of ventricular arrhythmias occurred in most animals during coronary artery occlusion. In two animals, ventricular fibrillation developed during or immediately after the first coronary artery occlusion. In those instances, the hearts were successfully defibrillated and, after 1 h, the protocol was continued. These animals did not exhibit any unusual alterations in monitored indices throughout during the rest of the protocols. The data obtained during these short bouts of arrhythmias or fibrillation was excluded from the study.

Figure 40:
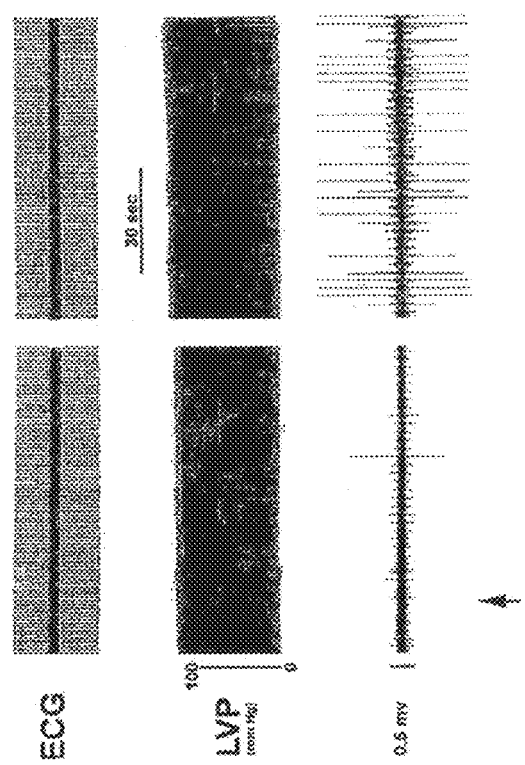
FIG. 40 shows the effects of coronary artery occlusion on the activity generate by intrinsic cardiac neurons in one animal. Following occlusion of the left anterior descending coronary artery (beginning at arrow below), the activity generated by right atrial neurons (lowest line) increased (right-hand panel). Heart rate was unaffected by this intervention, while left ventricular chamber systolic pressure (LVP) increased a little. The time between panels represents 1.5 min.

Overall, these electrophysiological data substantiate the substantial ischaemia insult that was induced by 15-min periods of left anterior descending coronary artery (LAD) occlusion. When the LAD was occluded in either protocol in the absence of SCS, the activity generated by right atrial neurons (FIG. 40). Effects of coronary artery occlusion on the activity generated by intrinsic cardiac neurons in one animal. Following occlusion of the left anterior descending coronary artery (beginning at arrow below), the activity generated by right atrial neurons (lowest line) increased (right-hand panel). Heart rate was unaffected by this intervention, while left ventricular chamber systolic pressure (LVP) increased a little. The time between panels represents 1.5 min. increased by 82% (FIG. 40; Table V). Neuronal excitation persisted through the period of occlusion. During protocol #1, the two successive 15-min periods of coronary artery occlusion separated by 1.5 h of recovery induced similar neuronal excitation. Twelve minutes after initiating the first LAD occlusion, neuronal activity was 69% greater than identified in normally perfused states (31.7±6.9 to 53.5±10.2 impulses/min; P<0.01). During the second period of coronary artery occlusion, neuronal activity increased by 95% (28.3±4.1 to 55.1±8.9 impulses/min; P<0.01). Neuronal activity began to increase within 30-45 s after coronary artery occlusion began. This occurred despite the fact that coronary artery occlusion did not interfere with the arterial blood supply to identified right atrial neurons as it arose from the right and distal circumflex coronary arteries. Furthermore, neuronal activity remained elevated not only throughout the period of occlusion but during the early reperfusion period following reestablishing coronary artery flow. Five to ten minutes after reestablishment of coronary artery flow, neuronal activity began to diminish, reaching steady state values within 15 min.

Figure 41:
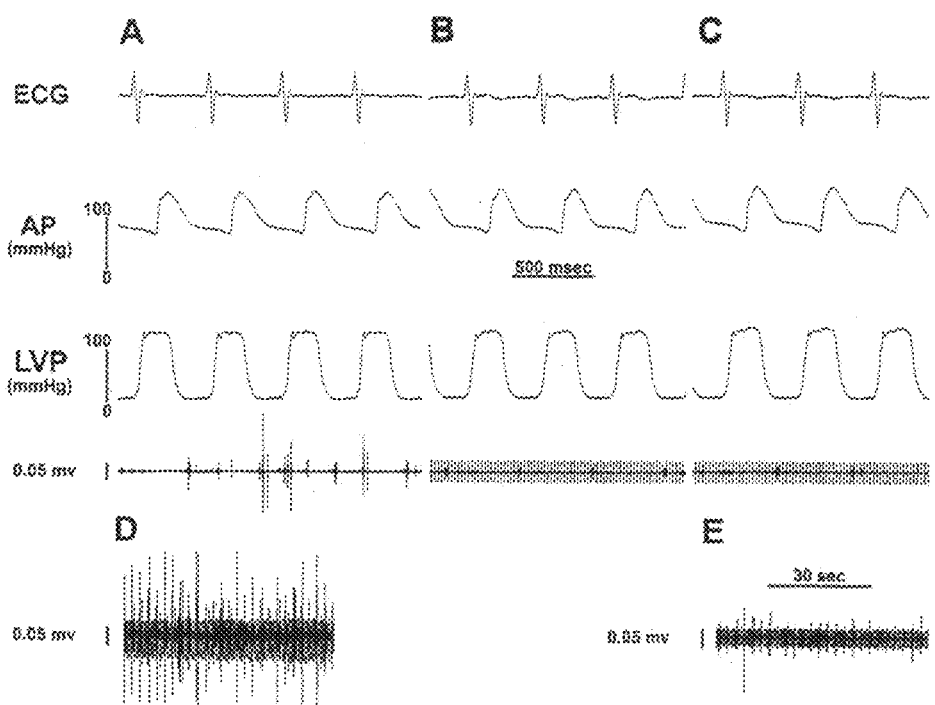
FIG. 41 shows the activity generated by intrinsic cardiac neurons in one animal during control states (panel A, lowest line) decreased when the dorsal aspect of the spinal cord was stimulated (panel B). The suppressor effects of SCS persisted during coronary artery occlusion (panel C). The electrical stimuli delivered during SCS are represented in panels B and C by regular, low signal-to-noise artifacts (note that atrial electrical artifact is recorded during each cardiac cycle as a low signal during the p wave of the ECG). The suppression of spontaneous activity generated by intrinsic cardiac neurons persisted after discontinuing SCS (panel E represents neuronal activity recorded 5 min post-SCS and 6 min post-LAD occlusion; panel D represents basal activity at same time scale obtained before commencing these interventions). ECG=electrocardiogram; AP=aortic pressure; LVP=left ventricular chamber pressure.

FIG. 41 shows the activity generated by intrinsic cardiac neurons in one animal during control states (panel A, lowest line) decreased when the dorsal aspect of the spinal cord was stimulated (panel B). The suppressor effects of SCS persisted during coronary artery occlusion (panel C). The electrical stimuli delivered during SCS are represented in panels B and C by regular, low signal-to-noise artifacts (note that atrial electrical artifact is recorded during each cardiac cycle as a low signal during the p wave of the ECG). The suppression of spontaneous activity generated by intrinsic cardiac neurons persisted after discontinuing SCS (panel E represents neuronal activity recorded 5 min post-SCS and 6 min post-LAD occlusion; panel D represents basal activity at same time scale obtained before commencing these interventions). ECG=electrocardiogram; AP=aortic pressure; LVP=left ventricular chamber pressure.

Table V shows heart rate (HR), left ventricular chamber systolic pressure (LVP), aortic systolic and diastolic pressures (AP) and the activity generated by right atrial neurons recorded before (control) and during coronary artery occlusion (CAO), as well as during early reperfusion (reperfusion). These indices were also recorded when occlusion occurred during spinal cord stimulation.

Effects of Spinal Cord Stimulation in the Presence of Myocardial Ischaemia

Figure 43:
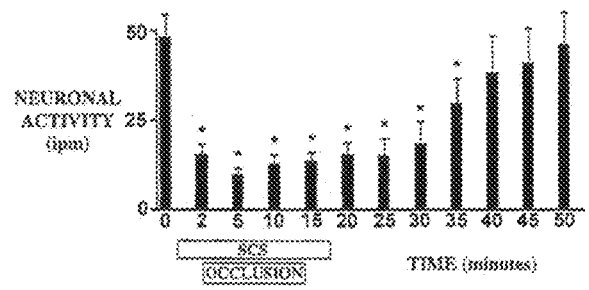
FIG. 43 shows the average neuronal activity recorded in all animals before, during and after dorsal spinal cord stimulation (SCS) delivered in the presence of coronary artery occlusion (occlusion). Note that SCS reduced neuronal activity soon after its application began. SCS also prevented enhancement in intrinsic cardiac neuronal activity normally associated with coronary artery occlusion (cf. Table V). Neuronal activity remained reduced for 17 min after terminating SCS despite the induction of myocardial ischaemia. These data were collected during application of the first SCS in protocol 2.
Figure 44:
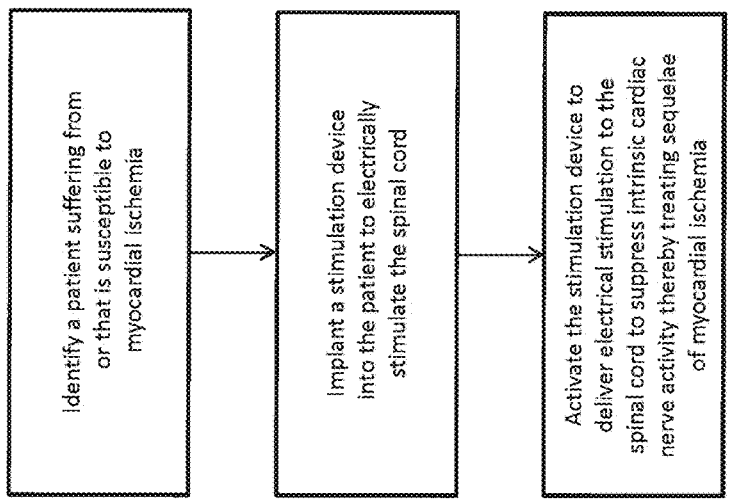
FIG. 44 is a flow chart illustrating the steps of the method of treating sequelae of myocardial ischemia in a patient discussed herein.

During normal coronary artery perfusion, SCS did not alter the ECG or monitored cardiac indices (Table V). The activity generated by identified right atrial neurons was reduced from 48.2±6.5 to 23±2.5 impulses/min within 30 s of applying electrical current to the dorsal aspect of the rostral thoracic spinal cord in hearts with normal coronary arterial blood supply (FIG. 43). After the coronary artery occlusion had been maintained for 1 min in the presence of SCS (2 min after beginning SCS), right atrial neuronal activity was reduced to 15.1±3.1 impulses/min. Thus, SCS suppressed the activity generated by intrinsic cardiac neurons not only in normally perfused hearts (FIG. 41(B)), but also in the presence of regional ventricular ischaemia (FIG. 41(C)). Furthermore, the neuronal suppressor effects of SCS persisted throughout the ischaemic periods. Monitored cardiovascular indices did not change overall when SCS was applied during coronary artery occlusion. Ischaemia-induced alterations in ECG patterns also remained throughout the period when SCS was applied concomitant with the occlusions. Neuronal activity gradually increased after discontinuing SCS such that by 20 to 25 min after terminating SCS, neuronal activity was similar statistically to that recorded during basal conditions. It increased a little thereafter (FIG. 43).

Epicardial Application of Veratridine

The activity generated by right atrial neurons increased when veratridine was applied topically to their ventricular sensory inputs. Veratridine-induced excitation of intrinsic cardiac neurons was studied both before and after application of SCS in four animals. In those cases, veratridine enhanced intrinsic cardiac neuronal activity by 124% (40.5±26.7; P<0.05) before application of SCS and by only 39% (11.8±2.5 to 16.5±4.6 impulses/min; no significant difference) after its application. When veratridine was applied to their ventricular sensory inputs after completing the protocols in all 10 dogs (following SCS and regional ventricular ischaemia), intrinsic cardiac neuronal activity increased by only 58% (25.6±5.7 to 40.6±12.5 impulses/min; P<0.05).

Figure II shows representative ECG records obtained from one animal during control states (A), as well as a few minutes after beginning coronary artery occlusion in the presence of spinal cord stimulation (B) and at the end of occlusion while SCS was maintained (C). Note that ST segment alterations occurred throughout the period of ischaemia.

Discussion

The results obtained from the experiments conducted in the present study not only confirm that spinal cord neurons can modulate the intrinsic cardiac nervous system (as discussed hereinabove), but they demonstrate that such modulation persists unabated throughout 17-min periods of stimulating the dorsal thoracic spinal cord. They also indicate that spinal cord neurons continue to exert their suppressor effects on the intrinsic cardiac nervous system long after their activation terminates. Furthermore, these data indicate that spinal cord neurons reorganize information processing within the intrinsic cardiac nervous system arising from the ischaemic myocardium, including during the reperfusion post-ischaemic phase. Finally, as indicated by the neural responses evoked by veratridine application to the ventricular epicardium, the stabilizing influence that SCS exerts on the intrinsic cardiac nervous system extends to intrinsic cardiac reflex responses evoked by activating cardiac sensory neurites associated with afferent neurons within the cardiac neuroaxis.

Given that bilateral transection of the ansae subclavia abolishes the neuro-suppressor effects that SCS imparts upon the intrinsic cardiac nervous system (as discussed hereinabove), it appears that the sympathetic nervous system is involved in the effects of SCS on the intrinsic cardiac nervous system. Activation of spinal cord neurons may inhibit intrinsic cardiac local circuit neurons in a manner similar to that which occurs when they receive increasing inputs from sympathetic efferent preganglionic neurons (Murphy et al., 1995). Based on the results obtained during application of SCS to the lumbosacral spinal cord (Linderoth and Foreman, 1999), sympathetic afferent as well as efferent axons may contribute to the suppressor effects that SCS exerts on the intrinsic cardiac nervous system.

Activation of sympathetic efferent preganglionic axons attenuates the activity generated by sub-populations of neurons within intrathoracic ganglia, including those on the heart (Armour, 1991; Murphy et al., 1995). Supramaximal stimulation of sympathetic efferent preganglionic neurons also leads to a rapid reduction in the capacity of intrathoracic sympathetic efferent neurons to influence cardiodynamics (Butler et al., 1988). It has been proposed that such suppressor effects are most likely due to inhibitory synapses within intrathoracic ganglia, including those on the heart (Armour, 1991). In accord with that, spinal cord neurons, when activated, suppress the activity generated by intrinsic cardiac neurons.

It is known that the activity generated by many intrinsic cardiac neurons increases secondary to transient ventricular ischaemia (Armour et al., 1998). Right atrial neurons are supplied by arterial blood in the sinoatrial artery arising from the right coronary artery and distal branches of the circumflex coronary artery (Huang et al., 1993). Since occlusion of the left anterior descending coronary artery does not compromise the arterial blood supply of investigated right atrial neurons (Huang et al., 1993), the effects that regional ventricular ischaemia exerted on investigated neurons were primarily the result of ischaemia-induced enhancement of ventricular sensory neurite inputs to identified neurons rather than any direct effects of ischaemia on identified somata and/or dendrites (Armour, 1991). Intrinsic cardiac neuronal activity remained elevated throughout the 15-min periods of regional ventricular ischaemia when performed in the absence of SCS. That these regional coronary artery occlusions affected the ST segments of the ECG presumably is reflective of the underlying myocardial ischaemia so induced. The processing of cardiac sensory information within the intrinsic cardiac nervous system was affected by SCS, as indicated by changed neuronal responsiveness to chemical (veratridine) activation of their ventricular sensory inputs.

Given the fact that the capacity of veratridine to affect sensory neurites associated with cardiac afferent neuron exhibits no tachyphylaxis (Thompson et al., 2000), the changed transduction properties of ventricular sensory inputs to the intrinsic cardiac nervous system is due, in part, to remodeling of the intrinsic cardiac nervous system subsequent to SCS. It should be noted that in clinical studies, the sensory effects that SCS imparts persist long after the stimulation has stopped. Patients with refractory angina pectoris continue to experience decreased episodes of pain after terminating SCS (Jessurun et al., 1999). Furthermore, the allodynia associated with neuropathic pain can be reduced for as long as 1 h after terminating SCS (Stiller et al., 1996). Application of SCS immediately prior to onset of LAD occlusion did not blunt the evolution of ischaemic-induced changes in the ECG. It is unlikely that the results obtained by SCS in a clinical setting can be ascribed to alterations in hemodynamics (Hautvast et al., 1998; Linderoth and Foreman, 1999) or coronary artery blood flow (as discussed hereinabove). This is because SCS exerts its primary effects on the intrinsic cardiac nervous system that, in turn, may influence control over regional cardiac electrical or mechanical events. These data indicate that activation of spinal cord neurons induces a conformational change in the intrinsic cardiac nervous system that persists for a considerable period of time after terminating such activation. This remodeling of the intrinsic cardiac nervous system can override excitatory inputs to it arising from the ischaemic myocardium. Thus, thoracic spinal cord neurons act to stabilize the intrinsic cardiac nervous system in the presence of ventricular ischaemia and during reperfusion. The prolonged salutary effects that SCS imparts to some patients long after it is discontinued are due, in part, to remodeling of the cardiac nervous system.

Thus it should be apparent that there has been provided in accordance with the present disclosure a detailed description, examples and data showing the SCS or DCA stimulation directly impacts the intrinsic cardiac nervous system and that such an impact can be used to modify, treat, modulate, suppress, and/or quench the neuronal activity of the intrinsic cardiac nervous system and in turn protect cardiac myocytes and preserve the electrical stability of the intrinsic cardiac nervous system and the heart itself, that fully satisfies the objectives and advantages set forth above. Although the present disclosure has been described in conjunction with specific embodiments thereof, it is evident that many alternatives, modifications, and variations will be apparent to those skilled in the art. Accordingly, it is intended to embrace all such alternatives, modifications, and variations that fall within the spirit and broad scope of the appended claims.

REFERENCES

The following references, to the extent that they provide exemplary procedural or other details supplementary to those set forth herein, are specifically incorporated herein by reference in their entirety as though set forth herein in particular.

Adamson, P. B., S. S. Hull, Jr., E. Vanoli, G. M. De Ferrari, P. Wisler, R. D. Foreman, A. M. Watanabe, and P. J. Schwartz. "Pertussis toxin-induced ADP ribosylation of inhibitor G proteins alters vagal control of heart rate in vivo", Am. J. Physiol 265 (2 Pt 2):H734-H740, 1993.

Adamson, P. B., M. H. Hu ang, E. Vanoli, R. D. Foreman, P. J. Schwartz, and S. S. Hull. "Unexpected interaction between beta-adrenergic blockade and heart rate variability before and after myocardial infarction; A longitudinal study in dogs at high and low risk for sudden cardiac death", Circulation 90: 976-382, 1994.

Adamson, P. B., E. Vanoli, S. S. Hull, R. D. Foreman, and P. J. Schwartz. "Antifibrillatory efficacy of ersentilide, a novel beta-adrenergic and lkr blocker, in conscious dogs with a healed myocardial infarction", Cardiovasc Res. 40 (1):56-63, 1998.

Allen, T. G. J. and G. Burnstock. "Intracellular studies of the electrophysiological properties of cultured intracardiac neurons of the guinea-pig", J. Physiol. 388: 349-366, 1987.

Allen, T. G. J. and G. Burnstock. "M1 and M2 Muscarinic receptors mediate excitation and inhibition of guinea-pig intracardiac neurons in culture", J. Physiol. 422: 463-480, 1990.

Allen, T. G. J., C. J. S. Hassall, and G. Burnstock. "Mammalian Intrinsic Cardiac Neurons in Cell Culture", In: Neurocardiology, edited by J. A. Armour and J. L. Ardell. New York: Oxford University Press, 1994, p. 139 164.

Ammons, W. S., R. W. Blair, and R. D. Foreman. "Vagal afferent inhibition of spinothalamic cell responses to sympathetic afferents and bradykinin in the monkey", Circ. Res. 53 (5):603-612, 1983.

Ammons, W. S., M. N. Girardot, and R. D. Foreman. "Effects of intracardiac bradykinin on T2-T5 medial spinothalamic cells", Am. Journ. Physiol 249 (2 Pt 2):R147-R152, 1985.

Anderson, C., Hole, P., Oxhoj, H. "Does pain relief with spinal cord stimulation for angina conceal myocardial infarction?", Br Heart J 1994; 71:419-421.

Andresen, M. C. "Short- and long-term determinants of baroceptor function in aged normotensive and spontaneously hypertensive rats", Circ. Res. 54: 750-759, 1984.

Applegate, R. J., 1991. "Load dependence of left ventricular diastolic Pressure-volume relations during short-term coronary artery occlusion", Circulation 83, 661-673.

Ardell, J. L., S. M. Barman, and G. L. Gebber. "Sympathetic nerve discharge in chronic spinal cat", Am. J. Physiol. 243: H1463 H1470, 1982.

Ardell, J. L. and W. C. Randall. Selective vagal innervation of sinoatrial and atrioventricular nodes in canine heart", Am. Journ. Physiol. 251: H764-H773, 1986.

Ardell, J. L., W. C. Randall, W. J. Cannon, D. C. Schmacht, and E. Tasdemiroglu. "Differential sympathetic regulation of automatic, conductile and contractile tissue in dog heart, Am. Journ. Physiol. 255: H1050-H1059, 1988.

Ardell, J. L., C. K. Butler, F. M. Smith, D. A. Hopkins, and J. A. Armour. "Activity of in vivo atrial and ventricular neurons in chronic decentralized canine hearts", Am. Journ. Physiol. 260: H713-H721, 1991.

Ardell, J. L. Structure and Function of Mammalian Intrinsic Cardiac Neurons", In Armour, J. A. and J. L. Ardell, eds. Neurocardiology. New York, Oxford University Press. 1994, 95-114.

Ardell, J. L., 2000. "Neurohumoral control of cardiac function. In: Sperelakis, N. (Ed.), Physiology and Pathophysiology of the Heart", 4th edn. Kluwer Academic Publishing, Boston, pp. 73-108, Chap. 3.

Ardell, J. L., "Neurohumoral control of cardiac function. Heart Physiology and Pathophysiology", Academic Press. 2001, 45-59.

Armour, J. A. "Physiological behavior of thoracic cardiovascular receptors", Amer. Journ. Physiol. 225:177-185, 1973.

Armour, J. A. "Instant-to-instant reflex cardiac regulation", Cardiology 61:309-328, 1976.

Armour, J. A. and J. B. Pace. "Cardiovascular effects of thoracic afferent nerve stimulation in conscious dogs", Canadian Journal of Physiology and Pharmacology. 60:1193-1199, 1982.

Armour, J. A. "Synaptic transmission in thoracic autonomic ganglia of the dog", Canadian Journal of Physiology and Pharmacology. 61:793-801, 1983.

Armour, J. A. "Synaptic transmission in chronically decentralized middle cervical and stellate ganglia of the dog", Canadian Journal of Physiology and Pharmacology 61, 1149-1155. 1983.

Armour, J. A. "Activity of in situ middle cervical ganglion neurons in dogs, using extracellular recording techniques", Canadian Journal of Physiology and Pharmacology. 63: 704-716, 1985.

Armour, J. A. "Activity of in situ stellate ganglion neurons of dogs recorded extracellularly", Canadian Journal of Physiology and Pharmacology, 64: 101-111, 1986.

Armour, J. A. "Neuronal activity recorded extracellularly in chronic decentralized in situ canine middle cervical ganglia", Canadian Journal of Physiology and Pharmacology, 64: 1038-1046, 1986.

Armour, J. A. "Neuronal activity recorded extracellularly in chronically decentralized in situ canine middle cervical ganglia", Canadian Journal of Physiology and Pharmacology 64, 1038-1046. 1986.

Armour, J. A. "Cardiac effects of electrically induced intrathoracic autonomic reflexes", Canadian Journal of Physiology and Pharmacology. 66: 714-720, 1988.

Armour, J. A. and R. D. Janes. "Neuronal activity recorded extracellularly from in situ mediastinal ganglia", Canadian Journal of Physiology and Pharmacology. 66: 119-127, 1988.

Armour, J. A. "Anatomy and function of the intrathoracic neurons regulating the mammalian heart", In Zucker, I. H. and J. P. Gilmore, eds. Reflex control of the circulation. Boca Raton, Fla., CRC Press. 1991, 1-37.

Armour, J. A. "Intrinsic cardiac neurons", J. Cardiov. Electrophysiol. 2: 331-341, 1991.

Armour, J. A. "Peripheral Autonomic Neurnal Interactions in Cardiac Regulation", In Armour, J. A. and J. L. Ardell, eds. Neurocardiology. New York, Oxford University Press. 1994, 219-244.

Armour, J. A. "Histamine-sensitive intrinsic cardiac and intrathoracic extracardiac neurons influence cardiodynamics", American Journal Physiology 270, R906-R913. 1996.

Armour, J. A. "Comparative effects of enodthelin and neurotensin on intrinsic cardiac neurons in situ", Peptides 17, 1047-1052. 1999.

Armour, J. A. "Myocardial ischemia and the cardiac nervous system", Cardiovascular Research 41, 41-54. 1999.

Armour, J. A., Collier, K., Kember, G., and Ardell, J. L. Differential selectivity of cardiac neurons in separate intrathoracic autonomic ganglia, American Journal Physiology 274, R939-R949. 1998.

Armour, J. A. and D. A. Hopkins. "Activity of canine in situ left atrial ganglion neurons", Am. J. Physiol. 259: H1207-H1215, 1990.

Armour, J. A. and D. A. Hopkins. "Activity of in vivo ventricular neurons", Am. J. Physiol. 258: H326-H336, 1990.

Armour, J. A., Huang, M. H., Pelleg, A., and Sylven, C. "Responsiveness of in situ canine nodose ganglion cardiac afferent neurons to epicardial mechanoreceptor and/or chemoreceptor stimuli" Cardiovascular Research 28, 1218-1225. 1994.

Armour, J. A., Huang, M. H., and Smith, F. M. "Peptidergic modulation of in situ canine intrinsic cardiac neurons", Peptides 14, 191-202. 1993.

Armour, J. A., Murphy, D. A., Yuan, B. X., MacDonald, S., and Hopkins, D. A. "Anatomy of the human intrinsic cardiac nervous system", The Anatomical Record 297, 289-298. 1997.

Armour, J. A., B. X. Yuan, and C. K. Butler. "Cardiac responses elicited by peptide administration to canine intrinsic cardiac neurons", Peptides 11: 753-761, 1990.

Arora, R. C., J. L. Ardell, and J. A. Armour. "Cardiac denervation and cardiac function", Curr. Interv. Cardiol. Rep. 2: 188-195, 2000.

Augustinsson, L. E., Linderoth, B., Mannheimer, C., Eliasson, T. "Spinal cord stimulation in cardiovascular disease", In: Gildenberg P, editor Neurosurgery clinics of North America, 1995, pp. 157-165.

Augustinsson, L. E., Linderoth, B., Eliasson, T., Mannheimer, C. "Spinal cord stimulation in peripheral vascular disease and angina pectoris", In: Gildenberg P, Tasker R, editors, Textbook of stereotactic and functional neurosurgery, NY: McGraw-Hill, 1997, pp. 1973-1978.

Baan, J., van der Velde, E. T., de Bruin, H. G., Smeenk, G. J., Koops, J., van Dijk, A. D., Temmerman, D., Senden, J., Buis, B., 1984. "ontinuousmeasurement of left ventricular volume in animals and humans by conductance catheter", Circulation 70, 812-823.

Baer, R. W., Payne, B. D., Verrier, E. D., Vlahakes, G. J., Molodowitch, D., Uhlig, P. N., Hoffman, J. I. E., 1984. "Increased number of myocardial blood flow measurements with radionuclide-labeled microspheres, Am. J. Physiol. 246, H418-H434.

Baker, D. G., H. M. Coleridge, J. C. Coleridge, and T. Nerdrum. "Search for a cardiac nociceptor: stimulation by bradykinin of sympathetic afferent nerve endings in the heart of the cat", J. Physiol 306:519-536, 1980.

Baluk, P. and G. Gabella. "Some intrinsic neurons of the guinea-pig heart contain substance P", Neurosci. Lett. 104: 269-273, 1989.

Baluk, P. and G. Gabella. "Some parasympathetic neurons in the guinea-pig heart express aspects of the catecholaminergic phenotype in vivo", Cell Tissue Res. 261: 275-285, 1990.

Barron, K. W., J. E. Croom, C. A. Ray, M. J. Chandler, and R. D. Foreman. "Spinal integration of antidromic mediated cutaneous vasodilation during dorsal spinal cord stimulation in the rat", Neurosci. Lett. 260 (3):173-176, 1999.

Bartfai, T., lverfeldt, K., and Fisone, G. "Regulation and the release of coexisting neurotransmitters", Ann. Rev. Pharmacol. Toxicol. 28, 285-310. 1988.

Beau, Scott L., Hand, Dwight E., Schuessler, Richard B., Bromberg, Burt I., Kwon, Brian, Boineau, John P., and Saffitz, Jeffrey E. "Relative Densities of Muscarinic Cholinergic and B-adrenergic receptors in the canine sinoatrial node and their relation to sites of pacemaker activity", Circulation Research 77, 957-963. 1995.

Besson, J. M. and A. Chaouch. "Peripheral and spinal mechanisms of nociception", Physiol Rev. 67 (1):67-186, 1987.

Billman G. E., Schwartz P. J., Stone H. L. "The effects of daily exercise on susceptibility to sudden cardiac death", Circulation 1984; 69:1182-1189.

Blair, R. W., R. N. Weber, and R. D. Foreman. "Responses of thoracic spinothalamic neurons to intracardiac injection of bradykinin in the monkey", Circ. Res. 51 (1):83-94, 1982.

Blair, R. W., W. S. Ammons, and R. D. Foreman. "Responses of thoracic spinothalamic and spinoreticular cells to coronary artery occlusion", J. Neurophysiol. 51 (4):636-648, 1984.

Blair, R. W., and R. D. Foreman. "Activation of feline spinal neurones by potentiated ventricular contractions and other mechanical cardiac stimuli", J. Physiol 404:649-667, 1988.

Blomquist, T. M., D. V. Priola, and A. M. Romero. "Source of intrinsic innervation of canine ventricles: a functional study", Am. J. Physiol., 252: H638-H644, 1987.

Bluemel, K. M., R. D. Wurster, W. C. Randall, M. J. Duff, and M. F. O'Toole. "Parasympathetic postganglionic pathways to the sinoatrial node", Am. J. Physiol. 259: H1504-H1510, 1990.

Bosnjak, Z. and Kampine, J. P. "Cardiac sympathetic afferent cell bodies are located in the peripheral nervous system of the cat", Circulation Research 64, 554-562. 1989.

Brink, M., de Gasparo, M., Rogg, H., Whitebread, S., and Bullock, G. "Localization of Angiotensin II Receptor Subtypes in the Rabbit Heart", Journal Molecular and Cellular Cardiology 27, 459-470. 1995.

Brodde, Otto-Erich. "Beta-adrenoceptors in cardiac disease", Pharmac. Ther. 60, 405-430. 1993.

Brodde, O.-E. and H.-R. Zerkowski. "Neural control of cardiac myocyte function", In Armour, J. A. and J. L. Ardell, eds. Neurocardiology. New York, Oxford University Press. 1994, 193-218.

Brown, A. M. "Excitation of afferent cardiac sympathetic nerve fibres during myocardial ischaemia", J. Physiol 190 (1):35-53, 1967.

Brown, A. M. "Cardiac reflexes", In Berne, R. M., N. Sperelakis, and S. R. Geiger, eds. Handbook of Physiology, The Cardiovascular System, Section 2, Vol. 1, The Heart. Bethesda, American Physiological Society (Williams and Wilkins). 1979, 677-689.

Brown, P. B., H. R. Koerber, and R. P. Yezierski. "Crosscorrelation analysis of connectivities among cat lumbosacral dorsal horn cells", J. Neurophysiol. 42 (5):1199-1211, 1979.

Burnstock G., Wood J. N. "Purinergic receptors: their role in nociception and primary afferent neurotransmission", Cur Opinion Biol 1996; 6:526-532.

Burton, H. and A. D. Loewy. "Descending projections from the marginal cell layer and other regions of the monkey spinal cord", Brain Res. 116 (3):485-491, 1976.

Butler, C. K., Watson-Wright, W. M., Wilkinson, M., Johnston, D. E., Armour, J. A., 1988. "Cardiac effects produced by long-term stimulation of acutely decentralized thoracic autonomic ganglia and cardiac nerves: implications for inter-neuronal interactions within the thoracic autonomic nervous system", Can. J. Physiol. Pharmacol. 66, 175-184.

Butler, C. K., F. M. Smith, R. Cardinal, D. A. Murphy, D. A. Hopkins, and J. A. Armour. "Cardiac responses to electrical stimulation of discrete loci in canine atrial and ventricular ganglionated plexi", Am. J. Physiol. 259: H1365-H1373, 1990.

Butler, C. K., F. M. Smith, J. Nicholson, and J. A. Armour. "Cardiac effects induced by chemically activated neruons in canine intrathoracic ganglia", Am. J. Physiol. 259: H1108-H1117, 1990.

Butler, C. K., Watson-Wright, W. M, Wilkinson, M., Johnston, D. E., and Armour, J. A. "Cardiac effects produced by long-term stimulation of acutely decentralized thoracic autonomic ganglia and cardiac nerves: implications for inter-neuronal interactions within the thoracic autonomic nervous system", Canadian Journal of Physiology and Pharmacology 66, 175-184. 1988.

Canteras, N. S., S. Chiavegatto, L. E. Valle, and L. W. Swanson. "Severe reduction of rat defensive behavior to a predator by discrete hypothalamic chemical lesions", Brain Res. Bull. 44 (3):297-305, 1997.

Cao, J.-M., L. S. Chen, B. H. KenKnight, T. Ohara, M.-H. Lee, J. Tsai, W. W. Lai, H. S. Karagueuzian, P. L. Wolf, M. C. Fishbein, and P.-S. Chen. "Nerve sprouting and sudden cardiac death", Circ. Res. 86: 816-821, 2000.

Cao, J.-M., M. C. Fishbein, J. B. Han, W. W. Lai, A. C. Lai, T.-J. Wu, L. Czer, P. L. Wolf, T. A. Denton, P. Shintaku, P.-S. Chen, and L. S. Chen. "Relationship between regional hyperinnervation and ventricular arrhythmia", Circulation 101: 1960-1969, 2000.

Carstens, E. and D. L. Trevino. "Anatomical and physiological properties of ipsilaterally projecting spinothalamic neurons in the second cervical segment of the cat's spinal cord", J. Comp Neurol. 182 (1):167-184, 1978.

Casati, R., F. Lombardi, and A. Malliani. "Afferent sympathetic unmyelinated fibres with left ventricular endings in cats", J. Physiol 292:135-148, 1979.

Chahine R, L. Olivia, H. Lockwell and R. Nadeau. "Oxygen-free radicals and myocardial nerve fiber endings", Exp. Toxic Path. 46:403-408, 1994.

Chandler, M. J., S. F. Hobbs, D. C. Bolser, and R. D. Foreman. "Effects of vagal afferent stimulation on cervical spinothalamic tract neurons in monkeys", Pain 44 (1):81-87, 1991.

Chandler, M. J., T. J. Brennan, D. W. Garrison, K. S. Kim, P. J. Schwartz, and R. D. Foreman. "A mechanism of cardiac pain suppression by spinal cord stimulation: implications for patients with angina pectoris", Eur. Heart J. 14 (1):96-105, 1993.

Chandler, M. J., J. Zhang, and R. D. Foreman. "Vagal, sympathetic and somatic sensory inputs to upper cervical (C1-C3) spinothalamic tract neurons in monkeys", J. Neurophysiol. 76 (4):2555-2567, 1996.

Chandler, M. J., J. Zhang, C. Qin, Y. Yuan, and R. D. Foreman. "Intrapericardiac injections of algogenic chemicals excite primate C1-C2 spinothalamic tract neurons", Am. J. Physiol Regul. Integr. Comp Physiol 279 (2): R560-R568, 2000.

Chang, Y., S. R. Stover, and D. B. Hoover. "Regional localization and abundance of calcitonin gene-related peptide receptors in guinea pig hearts", J. Mol. Cell. Cardiol. 33: 745-754, 2001.

Chapleau, M. W., Cunningham, J. T., Sullivan, M. J., Wachtel, R. E., and Abboud, F. M. "Structural versus functional modulation of the arterial baroreflex", Hypertension 26, 341-347. 1995.

Chauhan, A., Mullins, P. A., Thuraisingham, S. I., Taylor, G., Petch, M. C., Schofield, P. M., 1994. "Effect of transcutaneous electrical nerve stimulation on coronary blood flow", Circulation 89, 921-926.

Cardinal, R., P. Savard, J. A. Armour, R. Nadeau, D. L. Carson, and A. R. LeBlanc. "Mapping of ventricular tachycardia induced by thoracic neural stimulation in dogs", Canadian Journal of Physiology and Pharmacology. 64 (4):411-418, 1986.

Cardinal, R., B. J. Scherlag, M. Vermeulen, and J. A. Armour. "Distinct activation patterns of idioventricular rhythms and sympathetically-induced ventricular tachycardias in dogs with atrioventricular block" Pacing Clin. Electrophysiol. 15 (9):1300-1316, 1992.

Cardinal, R., R. Nadeau, C. Laurent, G. Boudreau, and J. A. Armour. "Reduced capacity of cardiac efferent sympathetic neurons to release noradrenaline and modify cardiac function in tachycardia-induced canine heart failure", Can. J. Physiol Pharmacol. 74 (9):1070-1078, 1996.

Chen, P.-S., L. S. Chen, B. Sharifi, H. S. Karagueuzian, and M. C. Fishbein. "Sympathetic nerve sprouting, electrical remodeling and the mechanisms of sudden cardiac death", Cardiov. Res. 50: 409-416, 2001.

Cheng, Z., Powley, T. L., Schwaber, J. S., and Doyle, F. J. "Vagal afferent innervation of the atria of the rat heart reconstructed with confocal microscopy", The Journal of Comparative Neurology (381), 1-17. 1997.

Cole, C. R., E. H. Blackstone, F. J. Pashkow, C. E. Snader, and M. S. Lauer. "Heart-rate recovery immediately after exercise as a predictor of mortality", N. Engl. J. Med. 341 (18):1351-1357, 1999.

Coyle, J. T., M. E. Molliver, and M. J. Kuhar. "In situ injection of kainic acid: a new method for selectively lesioning neural cell bodies while sparing axons of passage", J. Comp Neurol. 180 (2):301-323, 1978.

Craig, Jr., A. D., and D. N. Tapper. "Lateral cervical nucleus in the cat: functional organization and characteristics", J. Neurophysiol. 41 (6):1511-1534, 1978.

Croom, J. E., Foreman, R. D., Chandler, M. J., and Barron, K. W. "Cutaneous vasodilation during dorsal column stimulation is mediated by dorsal roots and CGRP", American Journal Physiology 272, H950-H957. 1997.

Crowe, R. and G. Burnstock. "Fluorescent histochemical localization of quinacrine-postive neurons in the guinea-pig and rabbit atrium", Cardiov. Res. 16: 384-390, 1982.

Curtis, M. J., Hearse, D. J., 1989. "Reperfusion-induced arrhythmias are critically dependent upon occluded zone size: relevance to the mechanism of arrhythmogenesis", J. Mol. Cell Cardiol. 21, 625-637.

Dalsgaard, C. J., A. Franco-Cereceda, A. Saria, J. M. Lundberg, E. Theodorsson-Norheim, and T. Hokfelt. "Distribution and origin of substance P- and neuropeptide Y-immunoreactive nerves in the guinea-pig heart", Cell Tissue Res. 243: 477-485, 1986.

Darvesh, S., D. M. Nance, D. A. Hopkins and J. A. Armour. "Distribution of neuropeptide immunoreactivity in intact and chronically decentralized middle cervical and stellate ganglia of dogs", J. Autonomic Nerv. Syst., 21: 167-180, 1987.

Dávila-Garcia, M. I., J. L. Musachio, D. C. Perry, Y. Xiao, A. Horti, E. D. London, R. F. Dannals, and K. J. Kellar. "[125I]IPH, an epibatidine analog, binds with high affinity to neuronal nicotinic cholinergic receptors", J. Pharmacol. Exp. Ther. 445-451, 1997.

Della, N. G., R. E. Papka, J. B. Furness, and M. Costa. "Vasoactive intestinal peptide-like immunoreactivity in nerves associated with the cardiovascular system of guinea-pigs", Neurosci. 9: 605-619, 1983.

De Ferrari, G. M., M. Mantica, E. Vanoli, S. S. Hull, Jr., and P. J. Schwartz. "Scopolamine increases vagal tone and vagal reflexes in patients after myocardial infarction", J. Am. Coll. Cardiol. 22 (5):1327-1334, 1993.

DeJongste, M. J. L., Haaksma, J., Hautvast, R. W., Hillege, H. L., Meyler, P. W, Staal, M. J., Sanderson, J. E., Lie, K. I., 1994a. "Effects of spinal ord stimulation on daily life myocardial ischemia in patients with severe coronary artery disease. A prospective ambulatory ECG study", Br. Heart J. 71, 413-418.

DeJongste, M. J. L., Hautvast, R. W. M., Hillege, H., Lie, K. I., 1994b. "Efficacy of spinal cord stimulation as an adjuvant therapy for intractable angina pectoris: a prospective randomized clinical study", J. Am. Coll. Cardiol. 23, 1592-1597.

DeJongste, M. J., Nagelkerke, D., Hooyschuur, C. M. Journe, H. L. Meyler P. W. Staal M J, De Jonge P., Lie, K. I. "Stimulation characteristics, complications, and efficacy of spinal cord stimulation systems in patients with refractory angina: a prospective feasability study", Pacing Clin Electrophysiol 1994; 17:1751-1760.

De Landsheere, C., Mannheimer, C., Habets, A., Guillaume, M., Bourgeois, I., Augustinsson, L.-E., Eliasson, T., Lamotte, D., Kulbertus, H., Rigo, P., 1992. "Effect of spinal cord stimulation on regional myocardial perfusion assessed by positron emission tomography", Am. J. Cardiol. 69, 1143-1149.

Dole, W. P., Bishop, V. S., 1982. "Influence of autoregulation and capacitance on diastolic coronary artery pressure-flow relationships in the dog", Circ. Res. 51, 261-270.

Eblen-Zajjur, A. A., and J. Sandkuhler. "Synchronicity of nociceptive and non-nociceptive adjacent neurons in the spinal dorsal horn of the rat: stimulus-induced plasticity", Neuroscience 76 (1):39-54, 1997.

Eliasson, T., Augustinsson, L. E., and Mannheimer, C. "Spinal cord stimulation in severe angina pectoris: Presentation of current studies, indications and clinical experience", Pain 65, 169-179. 1996.

Eliasson, T., Mannheimer, C., Waagstein, F., Andersson, B., Berg, C. H., Augustinsson, L. E., Hedner, T., and Larsson, G. "Myocardial turnover of endogenous opoids and CGRP in the human heart and the effects of spinal cord stimulation", Cardiology 89, 170-177. 1998.

Ellison, J. P. and R. G. Hibbs. "An ultrastructural study of mammalian cardiac ganglia", J. Mol. Cell. Cardiol. 8: 89-101, 1976.

Euchner-Wamser, S. T. Meller, and G. F. Gebhart. "A model of cardiac nociception in chronically instrumented rats: behavioral and electrophysiological effects of pericardial administration of algogenic substances", Pain 58 (1):117-128, 1994.

Farrell, D. M., C. C. Wei, J. Tallaj, J. L. Ardell, J. A. Armour, G. R. Hageman, W. E. Bradley, and L. J. Dell'Italia. "Angiotensin II modulates catecholamine release into interstitial fluid of canine ventricle in vivo", Am. J. Physiol. Heart Circ. Physiol. 281: H813-H822, 2001.

Farrell, D. M., C. C. Wei, J. L. Ardell, J. A. Armour, G. R. Hageman, W. E. Bradley and L. J. Dell'Italia. "Angiotensin II modulates norepinephrine release into the interstitial fluid of the canine myocardium in vivo", Am. J. Physiol., in press, 2001.

Farrell, T. G., O. Odemuyiwa, Y. Bashir, T. R. Cripps, M. Malik, D. E. Ward, and A. J. Camm. "Prognostic value of baroreflex sensitivity testing after acute myocardial infarction", Br. Heart J. 67 (2):129-137, 1992.

Fee, J. D., W. C. Randall, R. D. Wurster, and J. L. Ardell. "Selective ganglionic blockade of vagal inputs to sinoatrial and/or atrioventricular regions", J. Pharmacol. Exp. Ther. 242: 1006-1012, 1987.

Ferrer, E. Lopez, R. Blanco, R. Rivera, J. Krupinski, and E. Marti. "Differential c-Fos and caspase expression following kainic acid excitotoxicity", Acta Neuropathol. (Berl) 99 (3):245-256, 2000.

Flink, R., and J. Westman. "Different neuron populations in the feline lateral cervical nucleus: a light and electron microscopic study with the retrograde axonal transport technique", J. Comp Neurol. 250 (3):265-281, 1986.

Flink, R. and B. A. Svensson. "Fluorescent double-labelling study of ascending and descending neurones in the feline lateral cervical nucleus", Exp. Brain Res. 62 (3):479-485, 1986.

Foreman, R. D. "Spinal cord neuronal regulation of the cardiovascular system", In Armour, J. A. and J. L. Ardell, eds. Neurocardiology. New York, Oxford University Press. 1994, 245-276.

Foreman, R. D. "Mechanisms of cardiac pain", Annu. Rev. Physiol. 61, 143-167. 1999.

Foreman, R. D., R. W. Blair, H. R. Holmes, and J. A. Armour. "Correlation of ventricular mechanosensory neurite activity with myocardial sensory field deformation", Am. J. Physiol 276 (4 Pt 2):R979-R989, 1999.

Foreman, R. D., R. W. Blair, H. R. Holmes and J. A. Armour. "Correlation of activity generated by sympathetic afferent ventricular mechanosensory neurites with sensory field deformation in the normal and ischemic myocardium", Am. J. Physiol., 276: R976-R989, 1999.

Foreman, R. D., B. Linderoth, J. L. Ardell, K. W. Barron, M. J. Chandler, S. S. Hull, G. J. TerHorst, M. J. L. DeJongste, and J. A. Armour. "Modulation of intrinsic cardiac neurons by spinal cord stimulation: implications for therapeutic use in angina pectoris", Cardiov. Res. 47: 367-375, 2000.

Fu, Q. G., M. J. Chandler, D. L. McNeill, and R. D. Foreman. "Vagal afferent fibers excite upper cervical neurons and inhibit activity of lumbar spinal cord neurons in the rat", Pain 51 (1):91-100, 1992.

Furukawa, Y., D. W. Wallick, M. D. Carlson, and P. J. Martin. "Cardiac electrical responses to vagal stimulation of fibers to discrete cardiac regions", Am. J. Physiol. 258: H1112-H1118, 1990.

Furukawa, Y., D. W. Wallick, P. J. Martin, and M. N. Levy. "Chronotropic and dromotropic responses to stimulation of intracardiac sympathetic nerves to sinoatrial or atrioventricular nodal region in anesthetized dogs", Circ. Res. 66: 1391-1399, 1990.

Gagliardi, M., W. C. Randall, D. Bieger, R. D. Wurster, D. A. Hopkins, and J. A. Armour. "Activity of in vivo canine cardiac plexus neurons", Am. J. Physiol. 255: H789-H800, 1988.

Gebber, G. L., S. Zhong and Y. Paitel. "Bispectral analysis of complex patterns of sympathetic nerve discharge", Am. J. Physiol. 271: R1173-R1185, 1996.

Glickstein, S. B., E. V. Golanov, and D. J. Reis. "Intrinsic neurons of fastigial nucleus mediate neurogenic neuroprotection against excitotoxic and ischemic neuronal injury in rat", J. Neurosci. 19 (10):4142-4154, 1999.

Grill, H. J., M. I. Friedman, R. Norgren, G. Scalera, and R. Seeley. "Parabrachial nucleus lesions impair feeding response elicited by 2,5-anhydro-D-mannitol", Am. J. Physiol 268 (3 Pt 2):R676-R682, 1995.

Gu, J., J. M. Polak, J. M. Allen, W. M. Huang, M. N. Sheppard, K. Tatemoto, and S. R. Bloom. "High concentrations of a novel peptide neuropeptide Y, in the innervation of mouse and rat heart", J. Histochem. Cytochem. 32: 467-472, 1984.

Hancock, J. C., D. B. Hoover, and M. W. Hougland. "Distribution of muscarinic receptors and acetylcholinesterase in the rat heart", J. Auton. Nerv. Syst. 19: 59-66, 1987.

Harding, S. E., L. A. Brown, D. G. Wynne, C. H. Davies, and P. A. Poole Wilson. "Mechanisms of β adrenoceptor desensitization in the failing human heart", Cardiov. Res. 28: 1451 1460, 1994.

Hassall, C. J. S. and G. Burnstock. "Intrinsic neurons and associated cells of the guinea-pig heart in culture", Brain Res. 364: 102-113, 1986.

Hassall, C. J. S. and G. Burnstock. "Immunocytochemical localization of neuropeptide Y and 5 hydroxytryptamine in a subpopulation of amine handling intracardiac neurons that do not contain dopamine β hydroxylase in tissue culture", Brain Res. 422: 74 82, 1987.

Hautvast, R. W., Blanksma, P. K., DeJongste, M. J., Pruim, J., Van der Wall, E. E., Vaalberg, W., Lie, K. I., 1996. "Effect of spinal cord stimulation on myocardial blood flow assessed by positron emission tomography in patients with refractory angina pectoris", Am. J. Cardiol. 77, 462-467.

Hautvast, R. W. M., Ter Horst, G. J., DeJong, B. M., DeJongste, M. J., Blanksma, P. K., Paans, A. M., Korf, J., 1997. "Relative changes in regional cerebral blood flow during spinal cord stimulation in patients with refractory angina pectoris", Eur. J. Neurosci. 9, 1178-1183.

Hautvast, R. W., DeJongste, M. J. L., Staal, M. J., Van Gilst, V. H., and Lie, K. I. "Spinal cord stimulation in chronic intractable angina pectoris: a randomized, controlled efficacy study", American Heart Journal 136, 114-120. 1998.

Herrera, D. G., and H. A. Robertson. "Activation of c-fos in the brain", Prog Neurobiol. 50 (2-3):83-107, 1996.

Hillarp, N.-A., "Peripheral autonomic mechanisms", In: Handbook of Physiology, Section I: Neurophysiology. ed. J. Field, American Physiological Society, Washington, 1960, pp 979-1006.

Hobbs, S. F., U. T. Oh, M. J. Chandler, and R. D. Foreman. "Cardiac and abdominal vagal afferent inhibition of primate T9-S1 spinothalamic cells", Am. J. Physiol 257 (4 Pt 2):R889-R895, 1989.

Hobbs, S. F., M. J. Chandler, D. C. Bolser, and R. D. Foreman. "Segmental organization of visceral and somatic input onto C3-T6 spinothalamic tract cells of the monkey", J. Neurophysiol. 68 (5):1575-1588, 1992.

Hoffman, J. I. E., 1987. "A critical view of coronary reserve", Circulation 75 . Suppl. l, 1-6.

Holland, R. P. and H. Brooks. "TQ-ST segment mapping: Critical review and analysis of current concepts", Am. J. Cardiol. 40: 110-129, 1977.

Hoover, D. B. and J. C. Hancock. "Distribution of substance P binding sites in guinea-pig heart and pharmacological effects of substance P", J. Auton. Nerv. Syst. 23: 189-197, 1988.

Hoover, D. B., R. H. Baisden, and S. X. Xi Moy. "Localization of Muscarinic Receptor mRNAs in Rat Heart and Intrinsic Cardiac Ganglia by In Situ Hybridization", Circ. Res. 75: 813 820, 1994.

Hoover, D. B., Y. Chang, J. C. Hancock, and L. Zhang. "Actions of tachykinins within the heart and their relevance to cardiovascular disease", Jpn. J. Pharmacol. 84: 367-373, 2000.

Hopkins, D. A. and Armour, J. A. "Ganglionic distribution of afferent neurons innervating the canine heart and physiological identified cardiopulmonary nerves", Journal of the Autonomic Nervous System 26, 213-222. 1989.

Hopkins, D. A. and H. H. Ellenberger. "Cardiorespiratory neurons in the medulla oblongata: input and output relationships", In Armour, J. A. and J. L. Ardell, eds. Neurocardiology. New York, Oxford University Press. 1994, 277-308.

Hopkins, D. A., S. MacDonald, D. A. Murphy, and J. A. Armour. "Pathology of intrinsic cardiac neurons from ischemic human hearts", Anat Rec 259: 424-436, 2000.

Horackova, M. and J. A. Armour. "Role of peripheral autonomic neurones in maintaining adequate cardiac function", Cardiov. Res. 30: 326 335, 1995.

Horackova, M. and Armour, J. A. "ANG II modifies cardiomyocyte function via extracardiac and intracardiac neurons: in situ and in vitro studies", American Journal Physiology 272, R766-R775. 1997.

Horackova, M., J. A. Armour and Z. Byczko. "Multiple neurochemical coding of intrinsic cardiac neurons in whole-mount guinea-pig atria; confocal microscopic study" Cell Tissue Res., 297: 409-421, 1999.

Huang, B., T. El-Sherif, M. Gidh-Jain, D. Qin, and N. El-Sherif. "Alterations of sodium channel kinetics and gene expression in the postinfarction remodeled myocardium", J. Cardiov. Electrophysiol. 12: 226-238, 2001.

Huang H S, Pan H, Stahl G L, Longhurst J C. "Ischemia- and reperfusion-sensitive cardiac sympathetic afferents: influence of $H_2O_2$ and hydroxyl radicals", Am. J. Physiol. 1995:269:H888-H901.

Huang H S, Stahl G L, Longhurst J C. "Cardiac-cardiovascular reflexes induced by hydrogen peroxide in cats", Am J. Physiol 1995; 268:H2114-2124.

Huang, M. H., J. L. Ardell, B. D. Hanna, S. G. Wolf, and J. A. Armour. "Effects of transient coronary artery occlusion on canine intrinsic cardiac neuronal activity", Integ. Physiol. Behav. Sci. 28: 5-21, 1993.

Huang, M. H., F. M. Smith, and J. A. Armour. "Amino acids modify activity of canine intrinsic cardiac neurons involved in cardiac regulation", Am. J. Physiol. 264: H1275-H1282, 1993.

Huang, M. H., F. M. Smith, and J. A. Armour. "Modulation of in situ canine intrinsic cardiac neuronal activity by nicotinic, muscarinic and β-adrenergic agonists", Am. J. Physiol. 265: R659-R669, 1993.

Huang, M. H., C. Sylven, A. Pelleg, F. M. Smith, and J. A. Armour. "Modulation of in situ canine intrinsic cardiac neuronal activity by local applied adenosine, ATP or their analogs", Am. J. Physiol. 265: R914-R922, 1993.

Huang, M. H., Wolf, S. G., and Armour, J. A. "Ventricular arrhythmias induced by chemically modified intrinsic cardiac neurones", Cardiovascular Research 28, 636-642. 1994.

Huang, M. H., C. Sylvén, M. Horackova and J. A. Armour. "Ventricular sensory neurons in canine dorsal root ganglia: effects of adenosine and substance P", Am. J. Physiol., 269: R318-R324, 1995.

Huang, M. H., Negoescu, R. M., Horackova, M., Wolf, S. G., and Armour, J. A. "Polysensory response characteristics of dorsal root ganglion neurons that may serve sensory functions during myocardial ischemia", Cardiovascular Research 32, 503-515. 1996.

Hull S S Jr, Evans E, Vanoli E, Adamson P B, Yeo C, Albert D E, Stramba-Babiale M, Foreman R D, Schwartz P J: "Heart Rate Variability Before and After Myocardial Infarction in Dogs at High and Low risk for sudden cardiac death", J Am Coll Cardiol 1990; 16; 978-985.

Hull S S Jr, Vanoli E, Adamson P B, Verrier R L, Foreman R D, Schwartz P J. "Exercise training confers anticipatory protection from sudden death during acute myocardial ischemia", Circulation 1994; 89:548-552.

Hull, S. S., E. Vanoli, P. B. Adamson, G. M. De Ferrari, R. D. Foreman, and P. J. Schwartz. "Do increases in markers of vagal activity imply protection from sudden cardiac death? The case of scopolamine", Circulation 91: 2516-2519, 1995.

Jacobowitz, D. "Histochemical studies of the relationship of chromaffin cells and adrenergic nerves fibers to the cardiac ganglia of several species", J. Pharmacol. Exp. Ther. 158: 227-240, 1967.

Jacobowitz, D., T. Cooper, and H. B. Barner. "Histochemical and chemical studies of the localization of adrenergic and cholinergic nerves in normal and denervated cat hearts", Circ. Res. 20: 289-298, 1967.

Jakobs, K. H., Minuth, M., Bauer, S., Grandt, R., Greiner, C., and Zubin, P. "Dual regulation of adenylate cyclase. A signal transduction mechanism of membrane receptors", Basic Res. Cardiol. 81, 1-9. 1986.

Jessurun, G. A. J., Meeder, J. G., and DeJongste, M. J. L. "Pain Review 4", 89-99. 1997.

Jessurun, G. A., Tio, R. A., DeJongste, M. J. L., Hautvast, R. W., Den Heijer, P., Crijns, H. J., 1998. "Coronary blood flow dynamics during transcutaneous electrical stimulation for stable angina pectoris associated with severe narrowing of one major coronary artery", Am. J. Cardiol. 82, 921-926.

Jessurun, G. A., DeJongste, M. J. L., Hautvast, R. W., Tio, R. A., Brouwer, J., vanLelieveld, S., Crijns, H. J., 1999. "Clinical follow-up after cessation of chronic electrical neuromodulation in patients with sever coronary artery disease: a prospective randomized controlled study on putative involvement of sympathetic activity", Pacing Clin. Electrophysiol. 22, 1432-1439.

Katchanov G, Xu J, Clay A, Pelleg A. "Electrophysiological-anatomical correlates of ATP-triggered vagal reflex in the dog. IV. Role of LV vagal afferents", Am J Physiol 1997; 272:H1898-H1903.

Katz, D. M., and H. J. Karten. "Substance P in the vagal sensory ganglia. Localization in cell bodies and pericellular arborizations", J. Comp. Neurol. 193:549-564, 1980.

Kember, G. C., G. A. Fenton, K. Collier and J. A. Armour. "Stochastic resonance in a hysteretic population of cardiac neurons", Physical Rev. E, 61: 1816-1824, 2000.

Kember, G. C., G. A. Fenton, J. A. Armour and N. Kalyaniwalla. "A competition model for aperiodic stochastic resonance in a Fitz-Hugh Nagumo model of cardiac sensory neurons", Physical Rev. E, 63: 041911, 1-6, 2001.

Kingma Jr., J. G., Armour, J. A., Rouleau, J. R., 1994. "Chemical modulation of in situ cardiac neurones influences myocardial blood flow in the anesthetized dog. Cardiovasc", Res. 28, 1403-1406.

Kingma, J. G., B. Linderoth, J. L. Ardell, J. A. Armour, M. J. L. DeJongste, and R. D. Foreman. "Neuromodulation therapy does not influence blood flow distribution or left-ventricular dynamics during acute myocardial ischemia", Autonomic Neuroscience: Basic and Clinical 91: 47-54, 2001.

Kléber, A. G., M. J. Janse, M. J. L. van Capelle, and D. Durrer. "Mechanisms and time course of T-Q and S-T segment changes during acute regional myocardial ischemia in the pig heart determined by extracellular and intracellular recording", Circ. Res. 42: 603-613, 1978.

Kleiger, R. E., J. P. Miller, J. T. Bigger, Jr., and A. J. Moss. "Decreased heart rate variability and its association with increased mortality after acute myocardial infarction", Am. J. Cardiol. 59 (4):256-262, 1987.

Kocsis, B. "Basis for differential coupling between rhythmic discharges of sympathetic efferent nerves", Amer. J. Physiol. 267, R1008-R1019, 1994.

Kocsis, B., T, Karlsson and B. G. Wallin. "Cardiac- and noncardiac-related coherence between sympathetic drives to muscles of different hind limbs", Am. J. Physiol. 276: R1608-R1616, 1999.

Kompa, A. R., Molenaar, P., and Summers, R. J. "Effect of chemical sympathectomy on (−)-isoprenaline-induced changes in cardiac beta-adrenoceptor subtypes in the guinea-pig and rat", Journal Autonomic Pharmacology 14, 411-423. 1994.

Kovacs, K. J. "c-Fos as a transcription factor: a stressful (re)view from a functional map", Neurochem. Int. 33 (4):287-297, 1998.

Kumada, T., K. Gallagher, A. Battler, F. White, W. S. Kemper, and J. Jr. Ross. "Comparison of post-pacing and exercise-induced myocardial dysfunction during collateral development in conscious dogs", Circulation 65: 1178-1185, 1982.

Kuntz, A. "The Autonomic Nervous System", Philadelphia, Lea and Febiger. 1934.

Kuo, D. C., J. J. Oravitz, and W. C. DeGroat. "Tracing of afferent and efferent pathways in the left inferior cardiac nerve of the cat using retrograde and transganglionic transport of horseradish peroxidase", Brain Res. 321 (1):111-118, 1984.

Kuypers, F. A., R. A. Lewis, M. Hua, M. A. Schott, D. Discher, J. D. Ernst, and B. H. Lubin. "Detection of altered membrane phospholipid asymmetry in subpopulations of human red blood cells using fluorescently labeled annexin V", Blood 87 (3):1179-1187, 1996.

La Rovere, M. T., J. T. Bigger, F. Marcus, A. Mortara, and P. J. Schwartz. "ATRAMI (Autonomic Tone and Reflexes After Myocardial Infarction)", Lancet 351: 478-484, 1998.

La Rovere M. T., Specchia G, Mortara A, Schwartz P J: "Baroreflex sensitivity, clinical correlates and cardiovascular mortality among patients with a first myocardial infarction: a prospective study", Circulation 1988; 78:816-24.

La Rovere, M. T., G. D. Pinna, S. H. Hohnloser, F. I. Marcus, A. Mortara, R. Nohara, J. T. Bigger, Jr., A. J. Camm, and P. J. Schwartz. "Baroreflex Sensitivity and Heart Rate Variability in the Identification of Patients at Risk for Life-Threatening Arrhythmias: Implications for Clinical Trials"< Circulation 103 (16):2072-2077, 2001.

Lathrop, D. A. and P. M. Spooner. "On the neural connection", J. Cardiov. Electrophysiol. 12: 841-844, 2001.

Laurent, C. E., R. Cardinal, G. Rousseau, M. Vermeulen, C. Bouchard, M. Wilkinson, J. A. Armour, and M. Bouvier. "Functional desensitization to isoproterenol without reducing cAMP production in canine failing cardiocytes", Am. J. Physiol Regul. Integr. Comp Physiol 280 (2): R355-R364, 2001.

Levett, J. M., Murphy, D. A., McGuirt, A. S., Ardell, J. L., and Armour, J. A. "Cardiac augmentation can be maintained by continuous exposure of intrinsic cardiac neurons to a beta-adrenergic agonist or angiotensinII", J. Surg. Res. 66, 167-173.1996.

Levitzki, Alexander. "Regulation of adenylate cyclase by hormones and G-proteins", FEBS Letters 211(2), 113-118. 1987.

Levy, M. N. and M. R. Warner. "Parasympathetic Effects on Cardiac Function", In Armour, J. A. and J. L. Ardell, eds. Neurocardiology. Oxford University Press. 1994, 53-76.

Lewis, C. D., G. L. Gebber, P. D. Larsen and S. M. Barman. "Long-term correlations in the spike trains of medullary sympathetic neurons", J. Neurophysiol. 85: 1614-1623, 2001.

Li, B. H., A. C. Spector, and N. E. Rowland. "Reversal of dexfenfluramine-induced anorexia and c-Fos/c-Jun expression by lesion in the lateral parabrachial nucleus", Brain Res. 640 (1-2):255-267, 1994.

Linden, R. J. and C. T. Kappagoda. "Atrial Receptors", Cambridge Univ. Press, Cambridge, England, 1982.

Linderoth, B., Fedorcsak I, Meyerson, B. A. "Peripheral vasodilatation after spinal cord stimulation: animal studies of putative effector mechanisms", Neurosurgery 1991; 28:187-195.

Linderoth, B., L. Gunasekera, and B. A. Meyerson. "Effects of sympathectomy on skin and muscle microcirculation during dorsal column stimulation: animal studies", Neurosurgery 29 (6):874-879, 1991.

Linderoth, B., P. Herregodts, and B. A. Meyerson. "Sympathetic mediation of peripheral vasodilation induced by spinal cord stimulation: animal studies of the role of cholinergic and adrenergic receptor subtypes" Neurosurgery 35 (4):711-719, 1994.

Linderoth, B., and R. D. Foreman. "Physiology of spinal cord stimulation. Review and update", Neuromodulation 2: 150-164, 1999.

Lombardi, F., Bella P. Della, R. Casati, and A. Malliani. "Effects of intracoronary administration of bradykinin on the impulse activity of afferent sympathetic unmyelinated fibers with left ventricular endings in the cat", Circ. Res. 48 (1):69-75, 1981.

Lundberg, J. M., A. Franco-Cereceda, X. Hua, T. Hokfelt, and J. A. Fisher. "Co-existance of substance P and calcitonin gene-related peptide-like immunoreactivities in sensory nerves in relation to cardiovascular and bronchoconstrictor effects of capsaicin", Eur. J. Pharmacol. 108: 315-319, 1985.

Macdonald R L, Skerrit J H, Werz M A. "Adenosine Agonists Reduce Voltage-Dependent Calciumconductance of Mouse Sensory Nuerones in Cell Culture", J PHYSIOL LOND 1986; 370:75-90.

Maixner, W., K. B. Touw, M. J. Brody, G. F. Gebhart, and J. P. Long. "Factors influencing the altered pain perception in the spontaneously hypertensive rat", Brain Res. 237 (1):137-145, 1982.

Maixner, W., and A. Randich. "Role of the right vagal nerve trunk in antinociception", Brain Res. 298 (2):374-377, 1984.

Malik M, Camm A. J. "Components of heart rate variability: what they really mean and what they really measure", Am J Cardiol 1993; 72:821-822.

Malliani, A., G. Recordati, and P. J. Schwartz. "Nervous activity of afferent cardiac sympathetic fibres with atrial and ventricular endings", J. Physiol 229 (2):457-469, 1973.

Malliani, A. "Cardiovascular sympathetic afferent fibers", Rev. Physiol. Biochem. Pharmacol. 94:11-74, 1982.

Mannheimer, C., Carlsson, C.-A., Emanuelsson, H., Vendin, A., Waagstein, F., Wilhelmsson, C., 1985. "The effects of transcutaneous electric nerve stimulation in patients with severe angina pectoris", Circulation 71, 308-316.

Mannheimer, C., Eliasson, T., Andersson, B., Berg, C. H., Augustinsson, L. E., Emanuelsson, H., and Waagstein, F. "Effects of spinal cord stimulation in angina pectoris induced by pacing and possible mechanisms of action", British Medical Journal 307, 477-480. 1993.

Mannheimer, C., Eliasson, T., Augustinsson, L. E., Blomstrand, C., Emanuelsson, H., Larsson, S., Norrsell, H., and Hjalmarsson, A. "Electrical stimulation versus coronary bypass surgery in severe angina pectoris", The ESBY study. Circulation 97, 1157-1163. 1998.

Massari, V. J., Johnson, T. A., and Gatti, P. J. "Cardiotopic organization of the nucleus ambiguus? An anatomical and physiological analysis of neurons regulating atrioventicular conduction", Brain Research 679, 227-240. 1995.

Matsushita, M. "Ascending propriospinal afferents to area X (substantia grisea centralis) of the spinal cord in the rat", Exp. Brain Res. 119 (3):356-366, 1998.

McGuirt, A. S., Schmacht, D. C., and Ardell, J. L. "Autronomic interactions for control of atrial rate are maintained after SA nodal parasympathectomy", American Journal Physiology 272, H2525-H2533. 1997.

McLennan, H., and D. Lodge. "The antagonism of amino acid-induced excitation of spinal neurones in the cat", Brain Res. 169 (1):83-90, 1979.

Meller, S. T., and G. F. Gebhart. "A critical review of the afferent pathways and the potential chemical mediators involved in cardiac pain", Neuroscience 48 (3):501-524, 1992.

Melssen, W. J., and W. J. Epping. "Detection and estimation of neural connectivity based on crosscorrelation analysis", Biol. Cybern. 57 (6):403-414, 1987.

Melzack, R., Wall, P. D., 1965. "Pain mechanisms: a new theory", Science 150, 971-979.

Messina, L. M., Hanley, F. L., Uhlig, P. N., Baer, R. W., Grattan, M. T., Hoffman, J. I. E., 1985. "Effects of pressure gradients between branches of the left coronary artery on the pressure axis intercept and the shape of steady state circumflex pressure-flow relations in dogs" Circ. Res. 56, 11-19.

Middlekauff, H. R., S. A. Rivkees, H. E. Raybould, B. Bitticaca, J. I. Goldhaber and J. N. Weiss. "Localization and functional effects of adenosine A1 receptors on cardiac vagal afferents in adult rats", Am. J. Physiol. 274: H441-H447, 1998.

Miller, K. E., V. D. Douglas, A. B. Richards, M. J. Chandler, and R. D. Foreman. "Propriospinal neurons in the C1-C2 spinal segments project to the L5-51 segments of the rat spinal cord", Brain Res. Bull. 47 (1):43-47, 1998.

Miwa, H., T. Fuwa, K. Nishi, and Y. Mizuno. "Effects of the globus pallidus lesion on the induction of c-Fos by dopaminergic drugs in the striatum possibly via pallidostriatal feedback loops", Neurosci. Lett. 240 (3):167-170, 1998.

Mobilia, G., Zuin, G., Zanco, P., DiPede, F., Pinato, G., Neri, G., Cargnel, S., Ravile, A., Ferlin, G., Buchberger, R., 1998. "Effects of spinal cord stimulation on regional myocardial blood flow in patients with refractory angina. A positron emission tomography study", G. Ital. Cardiol. 28, 1113-1119.

Molander, C., Q. Xu, C. Rivero-Melian, and G. Grant. "Cytoarchitectonic organization of the spinal cord in the rat: II. The cervical and upper thoracic cord", J. Comp Neurol. 289 (3):375-385, 1989.

Molenaar, I., A. Rustioni, and H. G. Kuypers. "The location of cells of origin of the fibers in the ventral and the lateral funiculus of the cat's lumbo-sacral cord", Brain Res. 78 (2):239-254, 1974.

Molenaar, I. and H. G. Kuypers. "Cells of origin of propriospinal fibers and of fibers ascending to supraspinal levels. A HRP study in cat and rhesus monkey", Brain Res. 152 (3):429-450, 1978.

Moravec, M., A. Courtalon, and J. Moravec. "Intrinsic neurosecretory neurons of the rat heart atrioventricular junction: possibility of local neuromuscular feed back loops", J. Mol. Cell. Cardiol. 18: 357-367, 1986.

Moravec, M. and J. Moravec. "Intrinsic innervation of the atrioventricular junction of the rat heart", Am. J. Anat. 171: 307-319, 1984.

Moravec, M. and J. Moravec. "Adrenergic neurons and short proprioceptive feedback loops involved in the integration of cardiac function in the rat", Cell Tissue Res. 258: 381-385, 1989.

Moravec, M., Moravec, J., and Forsgren, W. G. "Catecholaminergic and peptidergic nerve components of intramural ganglia in the rat heart", Cell and Tissue Research 262, 315-327. 1990.

Murphy, D. A., O'Blenes, S., Nassar, B. A., and Armour, J. A. "Effects of acutely raising intrathoracic pressure on cardiac sympathetic efferent neuron function", Cardiovascular Research 30, 716-724. 1995.

Murphy, D. A., G. W. Thompson, J. L. Ardell, R. McCraty, R. S. Stevenson, V. E. Sangalang, R. Cardinal, M. Wilkinson, S. Craig, F. M. Smith, J. G. Kingma, and J. A. Armour. "The heart reinnervates after transplantation", Ann. Thorac. Surg. 69 (6):1769-1781, 2000.

Nadeau, R., D. Lamontagne, R. Cardinal, J. de Champlain, and J. A. Armour. "Coronary sinus norepinephrine concentrations during ventricular tachycardia induced by left stellate ganglion stimulation in dogs", Can. J. Physiol Pharmacol. 66 (4):419-421, 1988.

Norrsell, H., Eliasson, T., Albertsson, P., Augustinsson, L.-E., Emanuelsson, H., Eriksson, P., Mannheimer, C., 1998. "Effects of spinal cord stimulation on coronary blood flow velocity", Coron. Artery Dis. 9, 273-278.

Nozdrachev, A. D. and A. G. Pogorelov. "Extracellular recording of neuronal activity of the cat heart ganglia", J. Auton. Nerv. Syst. 6: 73-81, 1982.

Oldfield, B. J., and E. M. McLachlan. "Localization of sensory neurons traversing the stellate ganglion of the cat", J. Comp Neurol. 182 (4 Pt 2):915-922, 1978.

Oppenheimer, S. M. and D. A. Hopkins. "Suprabulbar neuronal regulation of the heart", In Armour, J. A. and J. L. Ardell, eds. Neurocardiology. New York, Oxford University Press. 1994, 309-342.

Page P. L., N. Dandan, P. Savard, R. Nadeau, J. A. Armour, and R. Cardinal. "Regional distribution of atrial electrical changes induced by stimulation of extracardiac and intracardiac neural elements", J. Thorac. Cardiovasc Surg. 109 (2):377-388, 1995.

Paintal, A. S. "A study of right and left atrial receptors", J. Physiol. 120: 596-610, 1953.

Parati, G., J. P. Saul, M. Dr Rienzo, and G. Mancia. "Spectral analysis of blood pressure and heart rate variability in evaluating cardiovascular regulation: a critical appraisal", Hypertension 25: 1276-1286, 1995.

Paulus, W. J., Grossman, W., Serizawa, T., Bourdillon, P. D., Pasipoularides, A., Mirsky, I., 1985. "Different effects of two types of ischemia on myocardial systolic and diastolic function", Am. J. hysiol. Heart. Circ. Physiol. 248, H719-H728.

Pauza, D. H., Skripka, V., Pauziene, N., and Stropus, R. "Anatomical study of the neural ganglionated plexus in the canine right atrium: Implications for selective denervation and electrophysiology in the sinoatrial node in dog", The Anatomical Record 255, 271-294. 1999.

Pelleg, A. "Cardiac cellular electrophysiologic actions of adenosine and adenosine trisphosphate", Am. Heart J. 110: 688-693, 1985.

Perkel, D. H., G. L. Gerstein, and G. P. Moore. "Neuronal spike trains and stochastic point processes", I. The single spike train. Biophys. J. 7 (4):391-418, 1967.

Perkel, D. H., G. L. Gerstein, and G. P. Moore. "Neuronal spike trains and stochastic point processes", II. Simultaneous spike trains. Biophys. J. 7 (4):419-440, 1967.

Pinto, J. M. and P. A. Boyden. "Electrical remodeling in ischemia and infarction", Cardiov. Res. 42: 284-297, 1999.

Plecha, D. M., Randall, W. C., Geis, G. S., and Wurster, R. D. "Localization of vagal preganglionic somata controlling sinoatrial and atrioventricular nodes", American Journal Physiology 255, R703-R708. 1988.

Poree, L. R., and L. P. Schramm. "Role of cervical neurons in propriospinal inhibition of thoracic dorsal horn neurons", Brain Res. 599 (2):302-308, 1992.

Potter, E. "Presynaptic inhibition of cardiac vagal postganglionic nerves by neuropeptide Y", Neurosci. Lett. 83: 101-106, 1987.

Priola, D. V. and H. A. Spurgeon. "Cholinergic sensitivity of the denervated canine heart", Circ. Res. 41: 600-606, 1977.

Qin, C., M. J. Chandler, K. E. Miller, and R. D. Foreman. "Chemical activation of cervical cell bodies: effects on responses to colorectal distension in lumbosacral spinal cord of rats", J. Neurophysiol. 82 (6):3423-3433, 1999.

Qin, C., M. J. Chandler, K. E. Miller, and R. D. Foreman. "Responses and afferent pathways of superficial and deeper c(1)-c(2) spinal cells to intrapericardial algogenic chemicals in rats", J. Neurophysiol. 85 (4):1522-1532, 2001.

Randall, D. C., Brown, D. R., Li, S. G., Olmstead, M. E., Kilgore, J. M., Sprinkle, A. G., Randall, W. C., and Ardell, J. L. "Ablation of posterior atrial ganglionated plexus potentiates sympathetic tachycardia to behavioral stress", American Journal Physiology 275, R779-R787. 1998.

Randall, W. C., Armour, J. A., Geis, G. S., and Lippincott, D. B. "Regional cardiac distribution of sympathetic nerves", Federation Proceedings 31, 1199-1208. 1972.

Randall, W. C., J. L. Ardell, D. Calderwood, M. Milosavljevic, and S. C. Goyal. "Parasympathetic ganglia innervating the canine atrioventricular nodal region", J. Auton. Nerv. Syst. 16: 311-323, 1986.

Randall, W. C., J. L. Ardell, R. D. Wurster, and M. Milosavljevic. "Vagal postganglionic innervation of the canine sinoatrial node", J. Auton. Nerv. Syst. 20: 13-23, 1987.

Randall, W. C. and J. L. Ardell. "Functional anatomy of the cardiac efferent innervation", In Kulbertus, H. E. and G. Franck, eds. Neurocardiology. Mount Kisco, N.Y., Futura Publishing Co., Inc. 1988, 3-24.

Randall, W. C. and J. L. Ardell. "Nervous Control of the Heart: Anatomy and Pathophysiology", In Zipes, D. P. and J. Jalife, eds. Cardiac Electrophysiology: From Cell to Bedside. Philadelphia, W.B. Saunders Company. 1990, 291-299.

Randall, W. C. Efferent sympathetic innervation of the heart In Armour, J. A. and J. L. Ardell, eds. Neurocardiology. New York, N.Y., Oxford University Press. 1994, 77-94.

Randich, A., and W. Maixner. Interactions between cardiovascular and pain regulatory systems Neurosci. Biobehay. Rev. 8 (3):343-367, 1984.

Randich, A., and S. A. Aicher. Medullary substrates mediating antinociception produced by electrical stimulation of the vagus Brain Res. 445 (1):68-76, 1988.

Randich, A., and G. F. Gebhart. Vagal afferent modulation of nociception Brain Res. Brain Res. Rev. 17 (2):77-99, 1992.

Randich, A. Neural substrates of pain and analgesia Arthritis Care Res. 6 (4):171-177, 1993.

Ranson, S. W. "Afferent paths for visceral reflexes", Physiol. Rev. 1: 477-522, 1921.

Ren, K., A. Randich, and G. F. Gebhart. "Vagal afferent modulation of a nociceptive reflex in rats: involvement of spinal opioid and monoamine receptors", Brain Res. 446 (2):285-294, 1988.

Ren, K., A. Randich, and G. F. Gebhart. "Vagal afferent modulation of spinal nociceptive transmission in the rat", J. Neurophysiol. 62 (2):401-415, 1989.

Ren, K., A. Randich, and G. F. Gebhart. "Electrical stimulation of cervical vagal afferents. I. Central relays for modulation of spinal nociceptive transmission", J. Neurophysiol. 64 (4):1098-1114, 1990.

Ren, K., A. Randich, and G. F. Gebhart. "Effects of electrical stimulation of vagal afferents on spinothalamic tract cells in the rat", Pain 44 (3):311-319, 1991.

Riley, D. A. "Effects of neuropeptides on heart rate in dogs: comparison of VIP, PHI, NPY, CGRP, and NT", American Journal Physiology 255, H311-H317. 1988.

Robb, J. S. "Comparative Basic Cardiology", Grune & Stratton, New York, 1965.

Roudenok, V., L. Gutjar, V. Antipova, and Y. Rogov. "Expression of vasoactive intestinal polypeptide and calcitonin gene-related peptide in human stellate ganglia after acute myocardial infarction", Ann. Anat. 183: 341-344, 2001.

Rouleau, J. R., Simard, D., Kingma Jr., J. G., 1999. "Myocardial blood flow regulation relative to left ventricle pressure and volume in anesthetized dogs", Can. J. Physiol. Pharmacol. 77, 902-908.

Rowe, Brian P., Saylor, David L., and Speth, Robert C. "Analysis of Angiotensin II Receptor Subtypes in Individual Rat Brain Nuclei", Neuroendocrinology 55, 563-573. 1992.

Rowell, R. B. "Human Cardiovascular Control", New York, Oxford University Press. 1993.

Saito, Kazuto, Potter, William Z., and Saavedra, Juan M. "Quantitative autoradiography of ▫-adrenoceptors in the cardiac vagus ganglia of the rat", European Journal of Pharmacology 153, 289-293. 1988.

Sanderson, J. E., Brooksby, P., Waterhouse, D., Palmer, R. B., and Neubauer, K. "Epidural spinal electrical stimulation for severe angina: a study of its effects on symptoms, exercise tolerance and degree of ischemia", European Heart J. 13, 628-633. 1992.

Sanderson, J. E., Ibrahim, B., Waterhouse, D., and Palmer, R. B. "Spinal cord stimulation for intractable angina: long term clinical outcome and safety", European Heart Journal 15, 810-814. 1994.

Sanderson, J. E., Woo, K. S., Chung, H. K., Chan, W. W., Tse, L. K., White, H., 1996. "The effect of transcutaneous electrical nerve stimulation on coronary and systemic hemodynamics in syndrome X", Coron. Artery Dis. 7, 547-552.

Sandkuhler, J., B. Stelzer, and Q. G. Fu. "Characteristics of propriospinal modulation of nociceptive lumbar spinal dorsal horn neurons in the cat", Neuroscience 54 (4):957-967, 1993.

Sandkuhler, J., and A. A. Eblen-Zajjur. "Identification and characterization of rhythmic nociceptive and non-nociceptive spinal dorsal horn neurons in the rat", Neuroscience 61 (4):991-1006, 1994.

Sandkuhler, J., and A. A. Eblen-Zajjur. "Identification and characterization of rhythmic nociceptive and non-nociceptive spinal dorsal horn neurons in the rat", Neuroscience 61 (4):991-1006, 1994.

Sandkuhler, J., A. Eblen-Zajjur, Q. G. Fu, and C. Forster. "Differential effects of spinalization on discharge patterns and discharge rates of simultaneously recorded nociceptive and non-nociceptive spinal dorsal horn neurons", Pain 60 (1):55-65, 1995.

Sandkuhler, J. "Neurobiology of spinal nociception: new concepts", Prog Brain Res. 110:207-224, 1996.

Sasayama, S., Nonogi, H., Miyazaki, S., Sakurai, T., Kawai, C., Eiho, S., Kuwahara, M., 1985. "Changes in diastolic properties of the regional myocardium during pacing-induced ischemia in human subjects", J. Am. Coll. Cardiol. 5, 599-606.

Savard, P., R. Cardinal, R. A. Nadeau, and J. A. Armour. "Epicardial distribution of ST segment and T wave changes produced by stimulation of intrathoracic ganglia or cardiopulmonary nerves in dogs", J. Auton. Nerv. Syst. 34 (1):47-57, 1991.

Schaper, W. "The Pathophysiology of Myocardial Perfusion", Amsterdan, N.Y., Oxford, Elsevier/North-Holland Biomedical Press. 1979.

Schmidt, H. H. H. W., Schurr, C., Hedler, L., and Majewski, M. "Local modulation of noradrenaline release in vivo: presynaptic β2-adrenoceptors and endogenous adrenaline", J. Cardiovascul. Pharmacol. 6(4), 641-649. 1984.

Schoebel, F. C., Frazier, 0. H., Jessurun, G. A. J., DeJongste, M. J. L., Kadipasaoglu, K. A., Heintzen, M. P., Jax, T. W., Cooley, D. A., Strauer, B. E., and Leschke, M. "Refractory angina pectoris in end-stage coronary artery disease: evolving therapeutic concepts", American Heart Journal 134, 587-602. 1997.

Schramm, L. P., and R. H. Livingstone. "Inhibition of renal nerve sympathetic activity by spinal stimulation in rat", Am. J. Physiol 252 (3 Pt 2):R514-R525, 1987.

Schwartz, P. J., M. Pagani, F. Lombardi, A. Malliani, and A. M. Brown. "A cardiocardiac sympathovagal reflex in the cat", Circ. Res. 32 (2):215-220, 1973.

Schwartz, P. J., R. D. Foreman, H. L. Stone, and A. M. Brown. "Effect of dorsal root section on the arrhythmias associated with coronary occlusion", Am. J. Physiol 231 (3):923-928, 1976.

Schwartz, P. J., G. E. Billman, and H. L. Stone. "Autonomic mechanisms in ventricular fibrillation induced by myocardial ischemia during exercise in dogs with a healed myocardial infarction: an experimental preparation for sudden cardiac death", Circulation 69: 780-790, 1984.

Schwartz, P. J., E. Vanoli, M. Stramba-Badiale, G. M. De Ferrari, G. E. Billman, and R. D. Foreman. "Autonomic mechanisms and sudden death. New insights from analysis of baroreceptor reflexes in conscious dogs with and without myocardial infarction", Circulation 78: 969-979, 1988.

Schwartz, P. J., M. T. La Rovere, and E. Vanoli. "Autonomic nervous system and sudden cardiac death. Experimental basis and clinical observations for post-myocardial infarction risk stratification", Circulation 85: 177-191, 1992.

Schwartz, P. J., and M. T. La Rovere. "ATRAMI: a mark in the quest for the prognostic value of autonomic markers. Autonomic Tone and Reflexes After Myocardial Infarction", Eur. Heart J. 19 (11):1593-1595, 1998.

Seabrook, G. R., L. A. Fieber, and D. J. Adams. "Neurotransmission in neonatal rat cardiac ganglion in situ", Am. J. Physiol. 259: H997-H1005, 1990.

Selyanko, A. A. "Membrane properties and firing characteristics of rat cardiac neurons in vitro", J. Auton. Nerv. Syst. 39: 181-190, 1982.

Selyanko, A. A. and V. I. Skok. "Synaptic transmission in rat cardiac neurones", J. Auton. Nerv. Syst. 39: 191-200, 1992.

Sgambato, V., N. Maurice, M. J. Besson, A. M. Thierry, and J. M. Deniau. "Effect of a functional impairment of corticostriatal transmission on cortically evoked expression of c-Fos and zif 268 in the rat basal ganglia", Neuroscience 93 (4):1313-1321, 1999.

Shvalev, V. N. and Sosunov, A. A. "A light and electron microscopic study of cardiac ganglia in mammals", Z Mikrosk Anat Forsch 99, 676-694. 1985.

Skok V. "Physiology of Autonomic Ganglia", Tokyo: I. Shoin, Ltd., 1973.

Smith, F. M., D. A. Hopkins, and J. A. Armour. "Electrophysiological properties of in vitro intrinsic cardiac neurons in the pig (Sus scrofa)", Brain Res. Bull. 28: 715-725, 1992.

Smith, F. M., A. S. McGuirt, D. B. Hoover, J. A. Armour, and J. L. Ardell. "Chronic decentralization of the heart differentially remodels canine intrinsic cardiac neuron muscarinic receptors", Am. J. Physiol. Heart Circ. Physiol. in press, 2001.

Smith, F. M., A. S. McGuirt, J. Leger, J. A. Armour, and J. L. Ardell. "Effects of chronic cardiac decentralization on functional properites of canine intracardiac neurons in vitro", Am. J. Physiol. Regulatory Integrative Comp. Physiol. in press, 2001.

Smith M L, Thames M D. "Cardiac receptors: discharge characteristics and reflex effects", In: Armour J A, Ardell J L, eds. Neurocardiology. New York: Oxford University Press, 1994:19-52.

Smith, M. V., A. V. Apkarian, and C. J. Hodge, Jr. "Somatosensory response properties of contralaterally projecting spinothalamic and nonspinothalamic neurons in the second cervical segment of the cat", J. Neurophysiol. 66 (1):83-102, 1991.

Steedman, W. M., and S. Zachary. "Characteristics of background and evoked discharges of multireceptive neurons in lumbar spinal cord of cat", J. Neurophysiol. 63 (1):1-15, 1990.

Sternini, C. and N. Brecha. "Distribution and colocalization of neuropeptide Y- and tyrosine hydroxylase-like immunoreactivity in the guinea-pig heart", Cell Tissue Res. 241: 93-102, 1985.

Stiller, C. O., Cui, J.-G., O'Conner, W. T., Brodin, E., Meyerson, B. A., Linderoth, B., 1996. "Release of GABA in the dorsal horn and suppression of tactile allodynia by spinal cord stimulation in mononeuropathic rats", Neurosurgery 39, 367-375.

Summers, Roger J., McMartin, Lynne R., Kompa, Andrew R., Gu, Xinhua, and Molenaar, Peter. "Signalling pathways in cardiac failure", Clinical and Experimental Pharmacology and Physiology 22, 874-876. 1995.

Sylven, C. Angina pectoris. "Clinical characteristics, neurophysiological and molecular mechanisms", Pain 36, 145-167. 1989.

Tanaka, S., K. W. Barron, M. J. Chandler, B. Linderoth, and R. D. Foreman. "Low intensity spinal cord stimulation may induce cutaneous vasodilation via CGRP release", Brain Res. 896 (1-2):183-187, 2001.

Tejani-Butt, S. M. "[3H]Nisoxetine: A radioligand for quantitation of norepinephrine uptake sites by autoradiography or by homogenate binding", Journal Pharmacology and Experimental Therapeutics 260, 427-436. 1992.

Thies, R. and R. D. Foreman. "Descending inhibition of spinal neurons in the cardiopulmonary region by electrical stimulation of vagal afferent nerves", Brain Res. 207 (1):178-183, 1981.

Thompson, G. W., Hoover, D. B., Ardell, J. L., and Armour, J. A. "Canine intrinsic cardiac neurons involved in cardiac regulation possess NK1, NK2 and NK3 receptors", American Journal Physiology 275, R1683-R1689. 1998.

Thompson, G. W., K. Collier, J. L. Ardell, G. Kember, and J. A. Armour. "Functional interdependence of neurons in a single canine intrinsic cardiac ganglionated plexus", J. Physiol 528: 561-571, 2000.

Thompson, G. W., M. Horackova and J. A. Armour. "Chemotransduction properties of nodose ganglion cardiac afferent neurons in guinea-pigs", Am. J. Physiol., 279: R433-R439, 2000.

Thoren, P. "Characteristics of left ventricular receptors with nonmedullated vagal afferents in cats", Circulation Research 40, 415-421. 1977.

Thorén, P. "Role of cardiac vagal c-fibers in cardiovascular control", Rev. Physiol. Biochem. Pharmacol. 86: 1-94, 1979.

Uchida, Y., and S. Murao. "Afferent sympathetic nerve fibers originating in left atrial wall", Am. J. Physiol 227 (4): 753-758, 1974.

Uchida, Y., and S. Murao. "Excitation of afferent cardiac sympathetic nerve fibers during coronary occlusion", Am. J. Physiol 226 (5):1094-1099, 1974.

Urban, L. and R. E. Papka. "Origin of small primary afferent substance P-immunoreactive nerve fibers in the guinea-pig heart", J. Auton. Nerv. Syst. 12: 321-331, 1985.

Vance, W. H., and R. C. Bowker. "Spinal origins of cardiac afferents from the region of the left anterior descending artery", Brain Res. 258: 96-100, 1983.

Van der Velde, E. T., Burkhoff, D., Steendijk, P., Karsdon, J., Sagawa, K., Baan, J., 1991. "Nonlinearity and load sensitivity of end-systolic pressure-volume relation of canine left ventricle in vivo", Circulation 83, 315-327.

Vanoli, E., G. M. DeFerrari, M. Stramba-Badiale, S. S. Hull, R. D. Foreman, and P. J. Schwartz. "Vagal stimulation and prevention of sudden death in conscious dogs with a healed myocardial infarction", Circ. Res. 68: 429-435, 1991.

Vanoli, E. and P. B. Adamson. "Baroreflex sensitivity: methods, mechanisms and prognostic value", PACE 17: 434-445, 1994.

Vanoli, E., S. S. Hull, Jr., P. B. Adamson, R. D. Foreman, and P. J. Schwartz. "K+ channel blockade in the prevention of ventricular fibrillation in dogs with acute ischemia and enhanced sympathetic activity", J. Cardiovasc Pharmacol. 26 (6):847-854, 1995.

Vanoli, E., P. B. Adamson, Lin Ba, G. D. Pinna, R. Lazzara, and W. C. Orr. "Heart rate variability during specific sleep stages. A comparison of healthy subjects with patients after myocardial infarction", Circulation 91 (7):1918-1922, 1995.

Vegh, A., Szekeres, L., Parratt, J. R., 1991. "Transient ischemia induced by rapid cardiac pacing results in myocardial preconditioning", Cardiovasc. Res. 25, 1051-1053.

Verburgh, C. A., J. Voogd, H. G. Kuypers, and H. P. Stevens. "Propriospinal neurons with ascending collaterals to the dorsal medulla, the thalamus and the tectum: a retrograde fluorescent double-labeling study of the cervical cord of the rat", Exp. Brain Res. 80 (3):577-590, 1990.

Warner, M. R. and M. N. Levy. "Neuropeptide Y as a putative modulator of the vagal effects on heart rate", Circ. Res. 64: 882-889, 1989.

Warner, M. R., P. D. Senanayake, C. M. Ferrario, and M. N. Levy. "Sympathetic stimulation-evoked overflow of norepinephrine and neuropeptide Y from the heart", Circ. Res. 69: 455-465, 1991.

Watson-Wright, W., G. Boudreau, R. Cardinal, and J. A. Armour. "Beta 1- and beta 2-adrenoceptor subtypes in canine intrathoracic efferent sympathetic nervous system regulating the heart", Am. J. Physiol 261 (5 Pt 2):R1269-R1275, 1991.

Watson-Wright, W. M., M. Wilkinson, D. E. Johnstone, R. Cardinal, and J. A. Armour. "Prolonged supramaximal stimulation of canine efferent sympathetic neurons induces desensitization of inotropic responses without a change in myocardial beta-adrenergic receptors", Can. J. Cardiol. 8 (2):177-186, 1992.

Watson-Wright, W. M., M. Wilkinson, R. Cardinal, G. Boudreau, and J. A. Armour. "Minimal modification of canine ventricular myocyte cell surface beta adrenoceptors despite desensitisation of ventricular function during exogenous beta adrenoceptor challenge", Cardiovasc Res. 28 (5):680-683, 1994.

Weber, R. N., R. W. Blair, and R. D. Foreman. "Effects of cardiac administration of bradykinin on thoracic spinal neurons in the cat", Exp. Neurol. 78 (3):703-715, 1982.

Wei, F., R. Dubner, and K. Ren. "Nucleus reticularis gigantocellularis and nucleus raphe magnus in the brain stem exert opposite effects on behavioral hyperalgesia and spinal Fos protein expression after peripheral inflammation", Pain 80 (1-2):127-141, 1999.

Weihe, E., M. Reinecke, and W. G. Forssman. "Distribution of vasoactive intestinal polypeptide-like immunoreactivity in the mammalian heart: Interrelation with neurotensin- and substance P-like immunoreactive nerves", Cell Tissue Res. 236: 527-540, 1984.

Weinreich, D., G. M. Koschorke, B. J. Undem and G. E. Taylor. "Prevention of the excitatory actions of bradykinin by inhibition of PGI2 formation in nodose neurones of the guinea-pig", J. Physiol. 483:735-746, 1995.

Wharton, J. and S. Gulbenkian. "Peptides in the mammalian cardiovascular system", Experientia 43: 821-832, 1987.

Wharton, J., J. M. Polak, L. Gordon, N. R. Banner, D. R. Springall, M. Rose, A. Khagani, J. Wallwork, and M. H. Yacoub. "Immunohistochemical demonstration of human cardiac innervation before and after transplantation", Circ. Res. 66: 900-912, 1990.

White, J. C. "Cardiac pain: Anatomic pathways and physiologic mechanisms", Circ. 16: 644-655, 1954.

Wijffels, M., C. Kirchhof, R. Dorland, J. Power, and M. A. Allessie. "Electrical remodeling due to atrial fibrillation in chronically instrumented conscious goats. Roles of neurohumoral changes, ischemia, atrial stretch and high rate of electrical activation", Circulation 96: 3710-3720, 1997.

Wilkinson, M., A. Giles, J. A. Armour, and R. Cardinal. "Ventricular, but not atrial, M2-muscarinic receptors increase in the canine pacing-overdrive model of heart failure", Can. J. Cardiol. 12 (1):71-76, 1996.

Wilson, Stephen K. "Peripheral Alpha-1 and Alpha-2 Adrenergic Receptors in Three Models of Hypertension in Rats: An In Vitro Autoradiography Study", Journal Pharmacology and Experimental Therapeutics 256, 801-810. 1991.

Xi-Moy, S. X., W. C. Randall, and R. D. Wurster. "Nicotinic and muscarinic synaptic transmission in canine intracardiac ganglion cells innervating the sinoatrial node", J. Auton. Nerv. Syst. 42: 201-214, 1993.

Xi, X., W. C. Randall, and R. D. Wurster. "Morphology of intracellularly labeled canine intracardiac ganglion cells", J. Comp. Neurol. 314: 396-402, 1991.

Xi, X., W. C. Randall, and R. D. Wurster. "Intracellular recording of spontaneous activity of canine intracardiac ganglion cells", Neurosci. Lett. 128: 129-132, 1993.

Xi, X., J. X. Thomas, W. C. Randall, and R. D. Wurster. "Intracellular recordings from canine intracardiac ganglion cells", J. Auton. Nerv. Syst. 32: 177-182, 1991.

Xu, Z. J. and D. J. Adams. "a adrenergic modulation of ionic currents in cultured parasympathetic neurons from rat intracardiac ganglia", J. Neurophysiol. 69: 1060 1070, 1993.

Yakhnitsa, V., Linderoth, B., Meyerson, B. A., 1999. "Spinal cord stimulation attenuates dorsal horn neuronal hyperexcitability in a rat model of mononeuropathy", Pain 79, 223-233.

Ye, F., S. Zangenehpour, and A. Chaudhuri. "Light-induced down-regulation of the rat class 1 dynein-associated protein robl/LC7-like gene in visual cortex", J. Biol. Chem. 275 (35):27172-27176, 2000.

Yuan, B. X., J. L. Ardell, D. A. Hopkins, and J. A. Armour. "Differential cardiac responses induced by nicotine sensitive canine atrial and ventricular neurones", Cardiovasc. Res. 27: 760-769, 1993.

Yuan, B. X., J. L. Ardell, D. A. Hopkins, and J. A. Armour. "Differential cardiac responses induced by nicotine sensitive canine atrial and ventricular neurons", Cardiov. Res. 27: 760-769, 1993.

Yuan, B. X., Ardell, J. L., Hopkins, D. A., Losier, A. M., and Armour, J. A. "Gross and microscopic anatomy of the canine intrinsic cardiac nervous system", The Anatomical Record 239, 75-87. 1994.

Zhang, J., M. J. Chandler, and R. D. Foreman. "Thoracic visceral inputs use upper cervical segments to inhibit lumbar spinal neurons in rats", Brain Res. 709 (2):337-342, 1996.

Zhang, J., M. J. Chandler, K. E. Miller, and R. D. Foreman. "Cardiopulmonary sympathetic afferent input does not require dorsal column pathways to excite C1-C3 spinal cells in rats", Brain Res. 771 (1):25-30, 1997.

Zimmermann, M. "Encoding in dorsal horn interneurons receiving noxious and non noxious afferents", J. Physiol (Paris) 73 (3):221-232, 1977.

Zoubina, E. V. and P. G. Smith. "Sympathetic hyperinnervation of the uterus in the estrogen receptor alpha knockout mouse", Neurosci. 103: 237-244, 2001.

Zucker, I. H., W. Wang, M. Brandle, and H. D. Schultz. "Baroreflex and cardiac reflex control of the circulation in pacing-induced heart failure", In Spinale, F. G., ed. Pathophysiology of Tachycardia-Induced Heart Failure. Armonk, N.Y., Futura Publishing Company. 1996, 193-226.

Zucker I. H. "Reflex Control of the Circulation in Heart Failure", In: Shepherd J. T., Vatner S. F., eds. Nervous Control of the Heart. Amsterdam: Harwood Academic Publishers, 1996:357-378.

What is claimed is:

1. A method of treating heart failure in a patient, comprising the steps of:
   identifying a patient susceptible to or suffering from heart failure;
   implanting a stimulation device into the identified patient to electrically stimulate the spinal cord, wherein the stimulation device comprises a plurality of electrodes and a generator in which at least one electrode is placed near the spinal cord at a selected site, wherein the selected site is selected from one spinal cord location selected from the list consisting of C1 spinal segment, C2 spinal segment, and T1-T4 spinal segments;
   activating the stimulation device to deliver electrical stimulation to the spinal cord on a chronic basis such that the electrical stimulation induces beneficial remodeling of intrinsic cardiac nerve system activity by stabilizing adrenergic neurons thereby providing cardioprotection, wherein activating the stimulation device comprises applying stimulation pulses to the selected site at a high frequency of at least 50 Hz and at a sufficiently high amplitude to activate A-delta fibers.

* * * * *